(12) United States Patent
Petter et al.

(10) Patent No.: US 8,309,685 B2
(45) Date of Patent: *Nov. 13, 2012

(54) HCV PROTEASE INHIBITORS AND USES THEREOF

(75) Inventors: Russell C. Petter, Stow, MA (US); Juswinder Singh, Ashland, MA (US); Arthur F. Kluge, Lincoln, MA (US); Deqiang Niu, Lexington, MA (US); Lixin Qiao, Tewksbury, MA (US); Shomir Ghosh, Brookline, MA (US)

(73) Assignee: Celgene Avilomics Research, Inc., Bedford, MA (US)

( * ) Notice: Subject to any disclaimer, the term of this patent is extended or adjusted under 35 U.S.C. 154(b) by 510 days.

This patent is subject to a terminal disclaimer.

(21) Appl. No.: 12/497,103

(22) Filed: Jul. 2, 2009

(65) Prior Publication Data

US 2010/0069294 A1    Mar. 18, 2010

Related U.S. Application Data

(63) Continuation-in-part of application No. 12/339,680, filed on Dec. 19, 2008.

(60) Provisional application No. 61/016,110, filed on Dec. 21, 2007, provisional application No. 61/016,473, filed on Dec. 23, 2007, provisional application No. 61/060,371, filed on Jun. 10, 2008, provisional application No. 61/098,668, filed on Sep. 19, 2008.

(51) Int. Cl.
*C07K 5/08* (2006.01)

(52) U.S. Cl. ...................................................... 530/331

(58) Field of Classification Search .................... 530/331
See application file for complete search history.

(56) References Cited

U.S. PATENT DOCUMENTS

| | | | |
|---|---|---|---|
| 6,018,020 A | 1/2000 | Attwood et al. |
| 6,211,338 B1 | 4/2001 | Malcolm et al. |
| 6,642,204 B2 | 11/2003 | Llinas-Brunet et al. |
| 6,727,267 B2 | 4/2004 | Jaen et al. |
| 6,800,434 B2 | 10/2004 | Saksena et al. |
| 6,825,347 B2 | 11/2004 | Carpino et al. |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,894,072 B2 | 5/2005 | Arasappan et al. |
| 6,908,901 B2 | 6/2005 | Bailey et al. |
| 6,914,122 B2 | 7/2005 | Venkatraman et al. |
| 6,919,423 B2 | 7/2005 | Llinas-Brunet |
| 6,995,174 B2 | 2/2006 | Wang et al. |
| 7,041,698 B2 | 5/2006 | Ripka et al. |
| 7,091,184 B2 | 8/2006 | Llinas-Brunet et al. |
| 7,122,627 B2 | 10/2006 | Priestley et al. |
| 7,132,504 B2 | 11/2006 | Scola et al. |
| 7,135,462 B2 | 11/2006 | Scola et al. |
| 7,148,347 B2 | 12/2006 | Brandenburg et al. |
| 7,189,844 B2 | 3/2007 | Gallou et al. |
| 7,208,600 B2 | 4/2007 | Cottrell et al. |
| 7,253,160 B2 | 8/2007 | Njoroge et al. |
| 7,273,851 B2 | 9/2007 | Miao et al. |
| 7,273,885 B2 | 9/2007 | Pitlik et al. |
| 7,309,708 B2 | 12/2007 | Tu et al. |
| 7,323,447 B2 | 1/2008 | Sin et al. |
| 7,402,568 B2 | 7/2008 | Or et al. |
| 7,449,479 B2 | 11/2008 | Wang et al. |
| 7,470,664 B2 | 12/2008 | Holloway et al. |
| 7,491,794 B2 | 2/2009 | Blatt et al. |
| 7,582,605 B2 | 9/2009 | Moore et al. |
| 7,605,126 B2 | 10/2009 | Niu et al. |
| 7,635,683 B2 | 12/2009 | Gai et al. |
| 7,662,779 B2 | 2/2010 | Sun et al. |
| 7,687,459 B2 | 3/2010 | Niu et al. |
| 2003/0064499 A1 | 4/2003 | Houghton et al. |
| 2004/0162318 A1 | 8/2004 | Saha et al. |
| 2004/0180815 A1 | 9/2004 | Nakajima et al. |
| 2004/0265917 A1 | 12/2004 | Benjamin et al. |
| 2005/0014136 A1 | 1/2005 | Depla et al. |
| 2005/0020503 A1 | 1/2005 | Llinas-Brunet et al. |
| 2005/0053617 A1 | 3/2005 | Depla et al. |
| 2005/0143316 A1 | 6/2005 | Tu et al. |
| 2005/0267018 A1 | 12/2005 | Blatt et al. |
| 2005/0267151 A1 | 12/2005 | Busacca et al. |
| 2006/0019905 A1 | 1/2006 | Bailey et al. |
| 2006/0046956 A1 | 3/2006 | Sannigrahi et al. |
| 2006/0121563 A1 | 6/2006 | Prassler et al. |
| 2006/0122123 A1 | 6/2006 | Chaudhary et al. |
| 2006/0142204 A1 | 6/2006 | Halfon et al. |
| 2006/0183694 A1 | 8/2006 | Sin et al. |
| 2006/0199773 A1 | 9/2006 | Sausker et al. |
| 2006/0205638 A1 | 9/2006 | Busacca et al. |
| 2006/0258868 A1 | 11/2006 | Bailey et al. |
| 2006/0276405 A1 | 12/2006 | Albrecht |

(Continued)

FOREIGN PATENT DOCUMENTS

| | | |
|---|---|---|
| WO | WO 03099274 | 5/2003 |
| WO | WO 2004/033425 | 4/2004 |
| WO | WO 2005037214 | 10/2004 |
| WO | WO 2005/051980 | 6/2005 |
| WO | WO-2005/095403 | 10/2005 |
| WO | WO-2006/007700 | 1/2006 |
| WO | WO-2006/026352 | 3/2006 |
| WO | WO-2006/122188 | 11/2006 |
| WO | WO-2006/130607 | 12/2006 |
| WO | WO-2006/130666 | 12/2006 |
| WO | WO-2007/009227 | 1/2007 |
| WO | WO-2007/016441 | 2/2007 |
| WO | WO 2007015787 | 2/2007 |
| WO | WO-2007/089618 | 8/2007 |
| WO | WO-2007/131966 | 11/2007 |
| WO | WO 2007131966 | 11/2007 |
| WO | WO-2008/005511 | 1/2008 |

(Continued)

OTHER PUBLICATIONS

Alberti, A. et al., J. Hepatology 31., (Suppl. 1): 17-24, 1999.
Blight, K.J. et al., Antiviral Ther. 3, Suppl. 3: 71-81, 1998.

(Continued)

*Primary Examiner* — David Lukton
(74) *Attorney, Agent, or Firm* — Choate Hall & Stewart LLP; Andrea L. C. Robidoux; John P. Rearick

(57) ABSTRACT

The present invention provides compounds, pharmaceutically acceptable compositions thereof, and methods of using the same.

36 Claims, 23 Drawing Sheets

U.S. PATENT DOCUMENTS

| | | | |
|---|---|---|---|
| 2006/0276406 | A1 | 12/2006 | Gupta et al. |
| 2006/0276407 | A1 | 12/2006 | Albrecht et al. |
| 2006/0281688 | A1 | 12/2006 | Zhang et al. |
| 2006/0281689 | A1 | 12/2006 | Malcolm |
| 2006/0287248 | A1 | 12/2006 | Malcolm |
| 2007/0004635 | A1 | 1/2007 | Albrecht et al. |
| 2007/0010431 | A1 | 1/2007 | Malcolm et al. |
| 2007/0010455 | A1 | 1/2007 | Hewawasam et al. |
| 2007/0021351 | A1 | 1/2007 | White et al. |
| 2007/0027071 | A1 | 2/2007 | Holloway et al. |
| 2007/0054842 | A1 | 3/2007 | Blatt et al. |
| 2007/0054864 | A1 | 3/2007 | Graupe et al. |
| 2007/0072809 | A1 | 3/2007 | Cho et al. |
| 2007/0099825 | A1 | 5/2007 | D'Andrea et al. |
| 2007/0224167 | A1 | 9/2007 | Emini et al. |
| 2007/0237818 | A1 | 10/2007 | Malcolm et al. |
| 2007/0243166 | A1 | 10/2007 | Llinas-Brunet et al. |
| 2008/0032936 | A1 | 2/2008 | Gai et al. |
| 2008/0119461 | A1 | 5/2008 | Sin et al. |
| 2008/0152619 | A1 | 6/2008 | Sin et al. |
| 2009/0081636 | A1 | 3/2009 | Huang |
| 2009/0176858 | A1 | 7/2009 | Niu et al. |
| 2009/0180981 | A1 | 7/2009 | Niu et al. |
| 2009/0274656 | A1 | 11/2009 | Wang et al. |
| 2009/0306085 | A1 | 12/2009 | Petter et al. |
| 2010/0041591 | A1 | 2/2010 | Niu et al. |
| 2010/0041674 | A1 | 2/2010 | Niu et al. |
| 2010/0074890 | A1 | 3/2010 | Hagel et al. |

FOREIGN PATENT DOCUMENTS

| | | |
|---|---|---|
| WO | WO-2008/051477 | 5/2008 |
| WO | WO-2008/057208 | 5/2008 |
| WO | WO-2008/057209 | 5/2008 |
| WO | WO-2008/112108 | 9/2008 |
| WO | WO-2009/047264 | 4/2009 |

OTHER PUBLICATIONS

Hepatitis C Support Project, "HCV: Genotype & Quasispecies", Version 2.0, pp. 1-3, Feb. 2006.
Huang, J.F. et al., J Viral Hepatitis 13(6): 396-401, 2006.
Hung, C.H. et al., J Viral Hepatitis 13(6): 409-414, 2006.
International Search Report PCT/US08/87725 mailed Feb. 23, 2009.
International Search Report PCT/US08/87736 mailed Feb. 23, 2009.
International Search Report PCT/US10/40473 mailed Aug. 30, 2010.
International Search Report PCT/US10/40474 mailed Aug. 30, 2010.
Liverton N. et al., J. Am. Chem. Soc., 130 (14), 4607-4609, 2008.
Lin et al., The Journal of Biological Chemistry, vol. 279, No. 17, Issue of Apr. 23, 17508-17514, 2004.
Lohmann V et al., J. Virol., 77:3007-3019, 2003.
McCauley, J.A. et al., *Angew. Chem. Int. Ed.*, 47, 9104-7, 2008.
Moradpour, D. et al., Eur. J. Gastroenterol. Hepatol., 11, 1199-1202, 1999.
Ontoria, et al., J. Med. Chem., 47, 6443-6446, 2004.
Raboisson, et al., Bioorganic & Medical Chemistry Letters (2008), doi:10.1016/j.bmcl.2008.07.088.
Ronn, et al., The 229th ACS National Meeting, in San Diego, CA, Mar. 13-17, 2005.
Ronn, et al., Bioorganic & Medical Chemistry 14 (2006) 544-559.
Ronn, et al., Bioorganic & Medical Chemistry 15 (2007) 4057-4068.
Ronn, Digital Comprehensive Summaries of Uppsala Dissertations from the Faculty of Pharmacy 53, "Design and Synthesis of Inhibitors Targeting the Hepatitis C Virus NS3 Protease", 2007, 1-80.
Rostovtsev et al., Angew. Chem. Int. Ed., 41, 2596-99, 2002.
Simmonds et al., Hepatology, vol. 42, No. 4, 962-973, 2005.
Sun et al., Bioconjugate Chem., 17, 52-57, 2006.
Walker, M.A. et al., DDT 4: 518-29, 1999.
Weiland, O., FEMS Microbiol. Rev. 14: 279-88, 1994.
Lamarre et al., "An NS3 protease inhibitor with antiviral effects in humans infected with hepatitis C virus" Nature 186-189, 314 (2004).
Llinas-Brunet et al., "Structure-activity study on a novel series of macrocyclic inhibitors of the hepatitis C virus NS3 protease leading to the discovery of BILN 2061" J. Med. Chem. 47:1605-1608 (2004).
McCauley et al., "Bismacrocyclic Inhibitors of Hepatitis C NS3/4a Protease" Angew. Chem. Int. Ed. 47:1-5 (2008).
Raboisson et al., "Structure-activity relationship study on a novel series of cyclopentane-containing macrocyclic inhibitors of the hepatitis C virus NS3/4A protease leading to the discovery of TMC435350" Bioorganic & Medical Chemistry Letters (2008), 4853-4858.
Rönn, Digital Comprehensive Summaries of Uppsala Dissertations from the Faculty of Pharmacy 53, "Design and Synthesis of Inhibitors Targeting the Hepatitis C Virus NS3 Protease", 2007, 1-80.
Rönn et al., "Evaluation of a diverse set of potential P1 carboxylic acid bioisosteres in hepatitis C virus NS3 protease inhibitors" Bioorganic & Medical Chemistry 15 (2007) 4057-4068.
Rönn et al., "Exploration of acyl sulfonamides as carboxylic acid replacements in protease inhibitors of the hepatitis C virus full-length NS3" Bioorganic & Medical Chemistry 14 (2006) 544-559.
Ronn et al., "Novel C-terminal Functionalities in Hepatitis C Virus NS3 Protease Inhibitors" The 229th ACS National Meeting, in San Diego, CA, Mar. 13-17, 2005.
Seiwert et al., "Preclinical characteristics of the hepatitis C virus NS3/4A protease inhibitor ITMN-191 (R7227)" Antimicrob Agents Chemother. 52(12):4432-4441 (2008).
Supplementary European Search Report for Application No. EP 08865122 mailed Apr. 17, 2012.
Supplementary European Search Report for Application No. EP 08864666 mailed Apr. 17, 2012.

Compound I-3 Contacted with A156S

Compound I-3 Contacted with A156T

Compound I-3 Contacted with D168A

Compound I-3 Contacted with D168V

Compound I-7 Contacted with Wild-type HCV Protease

Compound I-8 Contacted with Wild-type HCV Protease

Compound I-4 Contacted with Wild-type HCV Protease

Compound I-9 Contacted with Wild-type HCV Protease

Compound I-12 Contacted with Wild-type HCV Protease

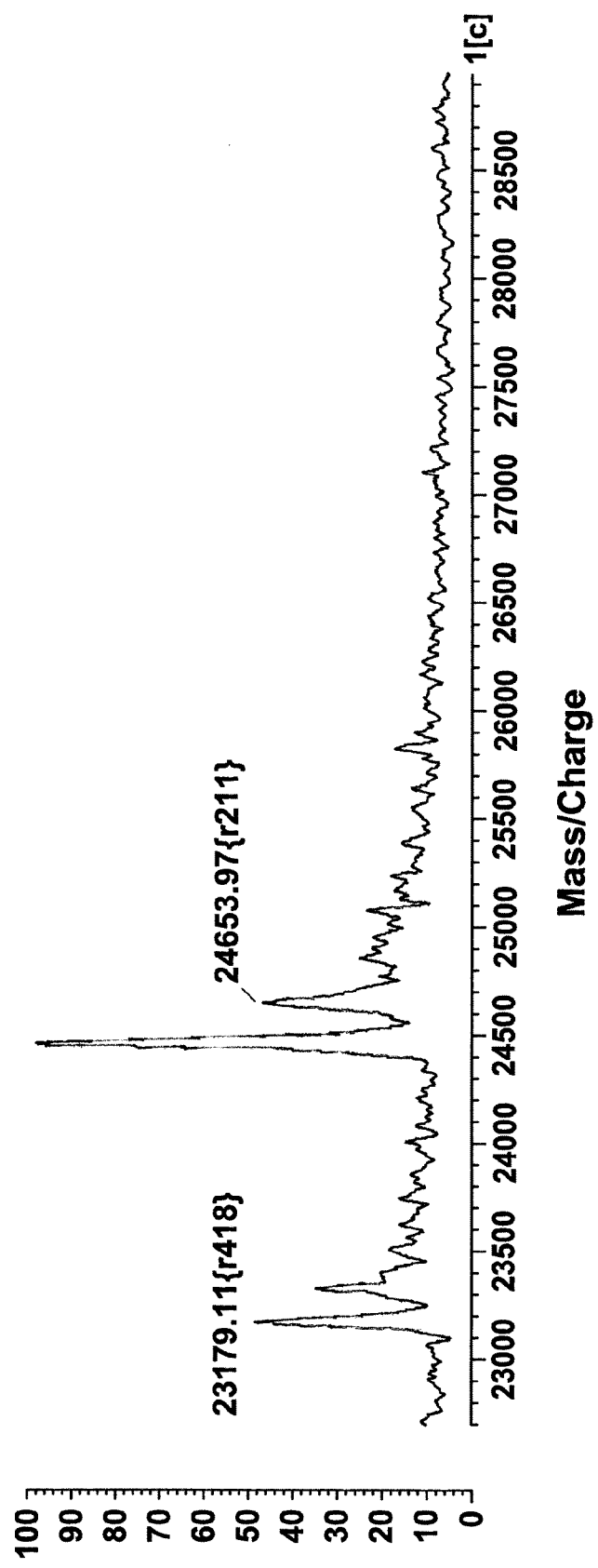
FIG. 11-A Comparison of I-3 (Irreversible) and $I^R$-3 (Reversible)

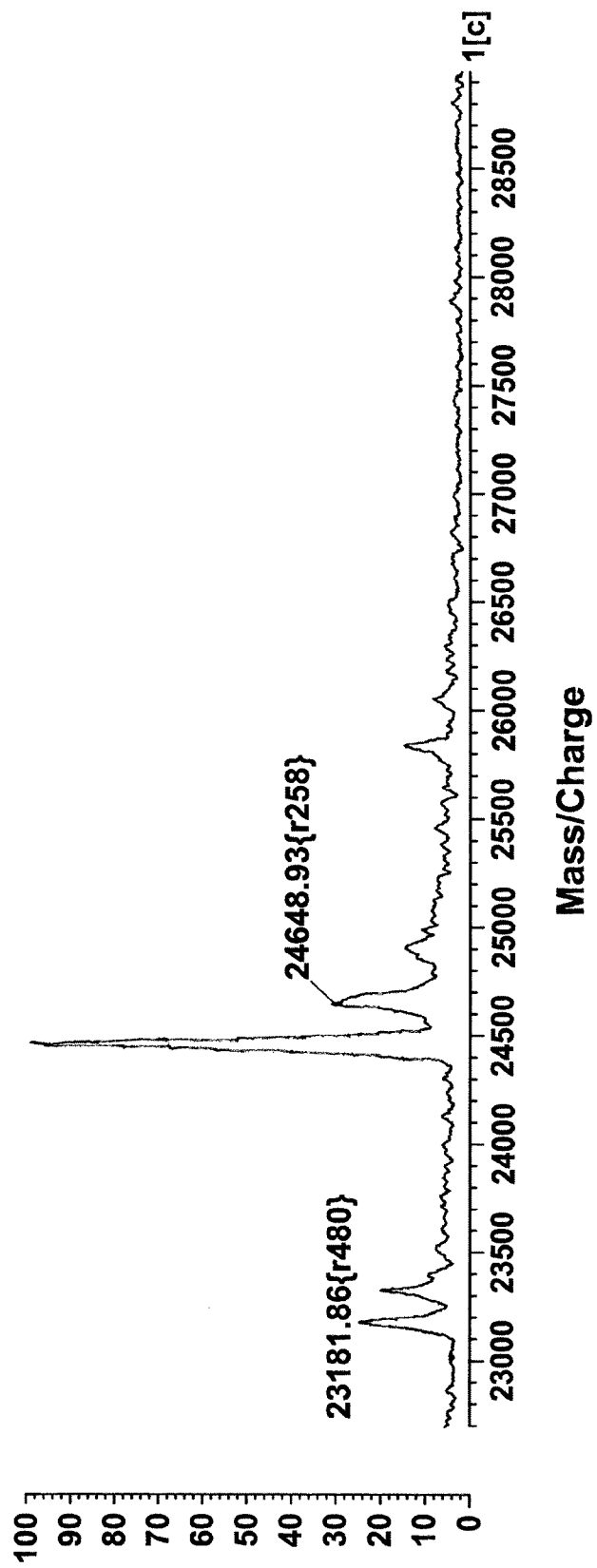
FIG. 11-B
Comparison of I-3 (Irreversible) and I^R-3 (Reversible)

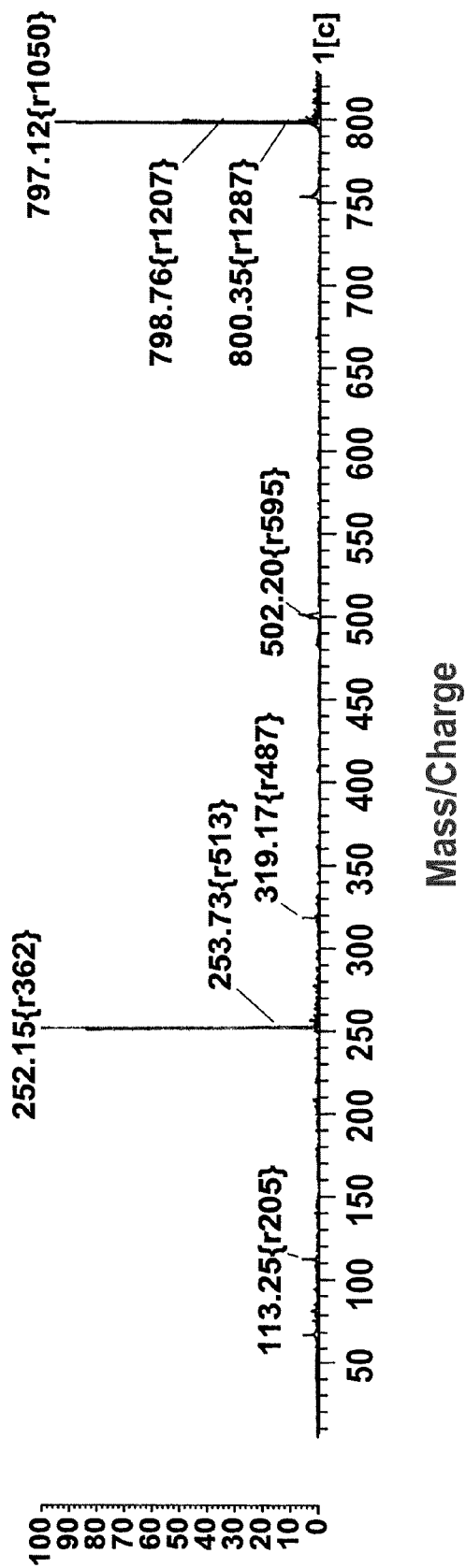
FIG. 12-A

Compound I-75 Contacted with Wild-type HCV Protease

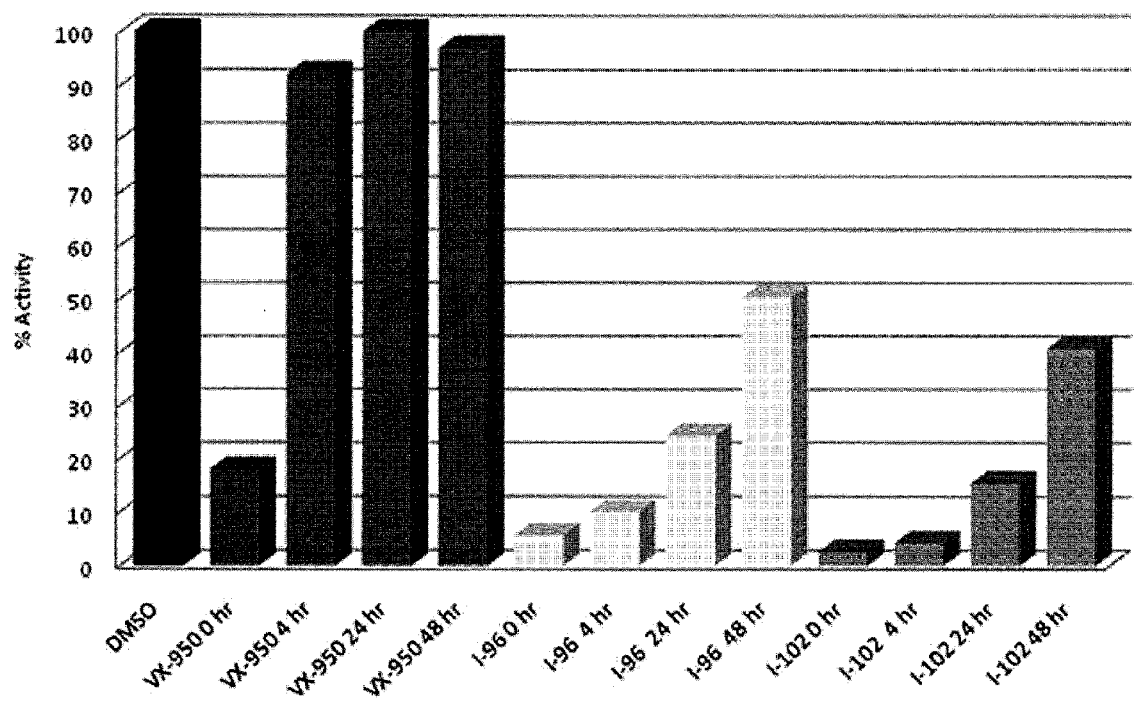
Figure 17-A
Washout Experiment in WT Replicon

HCV PROTEASE INHIBITORS AND USES THEREOF

CROSS-REFERENCE TO RELATED APPLICATIONS

The present application is a continuation-in-part of U.S. Ser. No. 12/339,680, filed Dec. 19, 2008, which claims priority to U.S. provisional application Ser. No. 61/016,110, filed Dec. 21, 2007, U.S. provisional application Ser. No. 61/016,473, filed Dec. 23, 2007, U.S. provisional application Ser. No. 61/060,371, filed Jun. 10, 2008, and U.S. provisional application Ser. No. 61/098,668, filed Sep. 19, 2008, the entirety of each of which is hereby incorporated by reference.

TECHNICAL FIELD OF THE INVENTION

The present invention relates to compounds useful as inhibitors of HCV protease. The invention also provides pharmaceutically acceptable compositions comprising compounds of the present invention and methods of using said compositions in the treatment of various disorders.

In accordance with 37 CFR 1.52(e)(5), a Sequence Listing in the form of a text file (entitled "Sequence Listing.txt," created on Oct. 5, 2009, and 19 kilobytes) is incorporated herein by reference in its entirety.

BACKGROUND OF THE INVENTION

It is estimated that over 170 million people worldwide are infected with the Hepatitis C virus (HCV). With an estimated human sero-prevalence of 3% globally, HCV is the major cause for most cases of non-A, non-B hepatitis, (Alberti, A. et al., J. Hepatology 31., (Suppl. 1): 17-24, 1999). While the symptoms of acute hepatitis subside in some patients, at least 85% of HCV infections become chronic, and 20% of those infected develop liver cirrhosis. There is less than a 50% survival rate at four years post cirrhosis diagnosis. Chronic HCV infection is also associated with increased incidence of hepatocellular carcinoma.

HCV is a positive-stranded RNA virus whose genome encodes a polyprotein of approximately 3000 amino acids. This precursor protein is processed into at least 10 viral structural and nonstructural proteins: C, E1, E2, p7, NS2, NS3, NS4A, NS4B, NS5A, and NS5B (Blight, K. J., et al., Antiviral Ther. 3, Suppl. 3: 71-81, 1998). HCV nonstructural (NS) proteins are derived by proteolytic cleavage of the polyprotein and are presumed to provide the essential catalytic machinery for viral replication.

NS3 is an approximately 68 Kda protein, and has both an N-terminal serine protease domain and an RNA-dependent ATPase domain at its C-terminus. It has been shown that the NS4A protein serves as a co-factor for the serine protease activity of NS3. NS3 functions as a proteolytic enzyme that cleaves sites liberating other nonstructural proteins necessary for HCV replication and is a viable therapeutic target for antiviral chemotherapy.

No vaccines are available for HCV, and the established therapy of interferon treatment is effective in only 15-20% of patients (Weiland, O., FEMS Microbiol. Rev. 14: 279-88, 1994), and has significant side effects (Walker, M. A., et al., DDT 4: 518-29, 1999; Moradpour, D., et al., Eur. J. Gastroenterol. Hepatol. 11: 1199-1202, 1999). While the current standard of care, pegylated interferon a in combination with ribavirin, is more efficacious and appears to decrease hepatocellular carcinoma in patients with HCV-related cirrhosis (Hung, C. H., et al., J Viral Hepatitis 13(6): 409-414, 2006), this treatment has also been shown to produce side effects such as thyroid dysfunction (Huang, J. F., et al., J Viral Hepatitis 13(6): 396-401, 2006).

The poor prognosis for patients suffering from HCV infection and the current lack of effective, approved treatments, highlights the overwhelming need for new inhibitors of HCV NS3 protease.

SUMMARY OF THE INVENTION

It has now been found that compounds of this invention, and pharmaceutically acceptable compositions thereof, are effective as inhibitors of HCV protease. Such compounds have the general formula I:

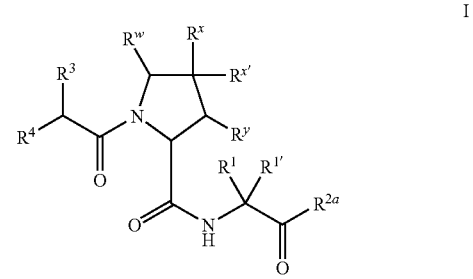

I or a pharmaceutically acceptable salt thereof, wherein $R^1$, $R^{1'}$, $R^{2a}$, $R^3$, $R^4$, $R^w$, $R^x$, $R^{x'}$, and $R^y$ are as defined herein.

Compounds of the present invention, and pharmaceutically acceptable compositions thereof, are useful for treating a variety of diseases, disorders or conditions, associated with HCV. Such diseases, disorders, or conditions include those described herein.

Compounds provided by this invention are also useful for the study of HCV protease in biological and pathological phenomena; the study of intracellular signal transduction pathways mediated by HCV protease; and the comparative evaluation of new HCV protease inhibitors.

BRIEF DESCRIPTION OF THE DRAWINGS

FIGS. 11-11B depict a mass spectroscopic analysis of HCV NS3/4A wild type in the presence of test compound I-3 as compared to its reversible counterpart, compound I^R-3 and compared to no test compound.

Figure 12:
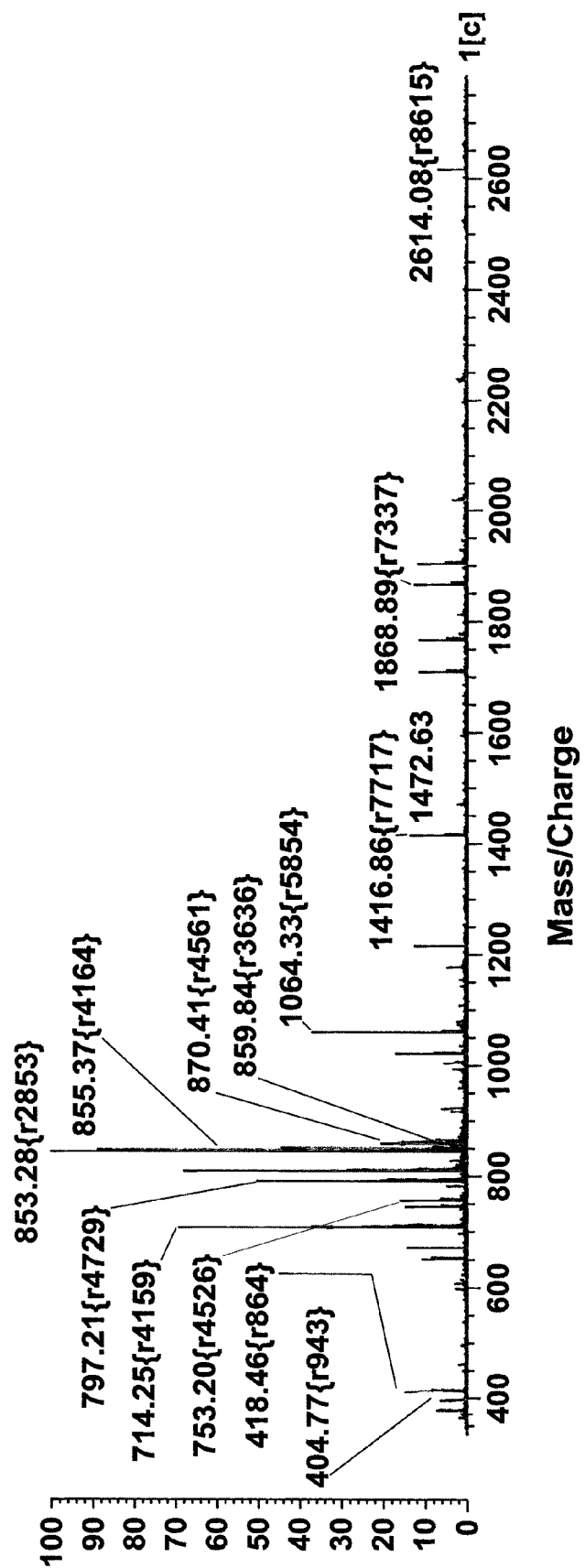

FIGS. 12-12A depict a mass spectroscopic analysis of HCV NS3/4A wild type after tryptic digest in the presence of test compound I-3.

Figure 13:
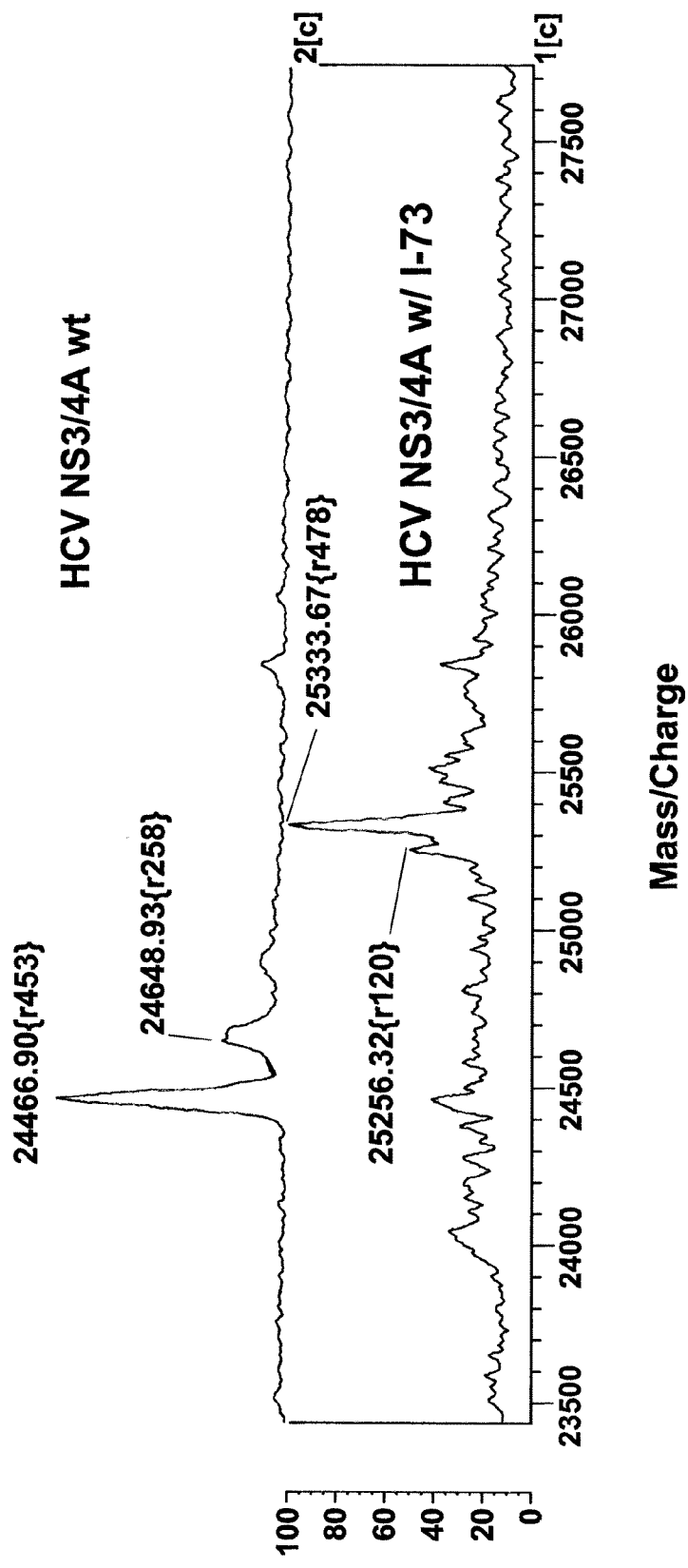

FIG. 13 depicts a mass spectroscopic analysis of HCV NS3/4A wild type in the presence of test compound I-73.

Figure 14:
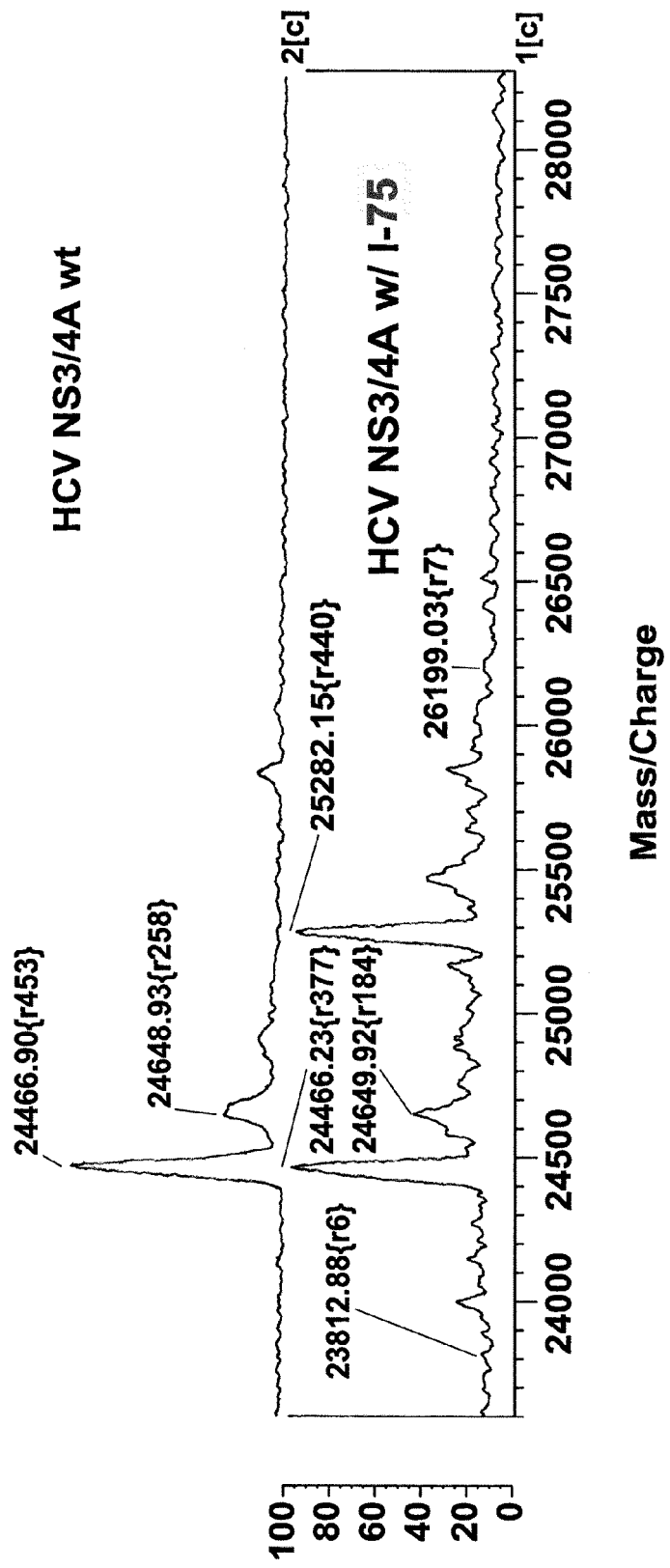

FIG. 14 depicts a mass spectroscopic analysis of HCV NS3/4A wild type in the presence of test compound I-75.

Figure 15:
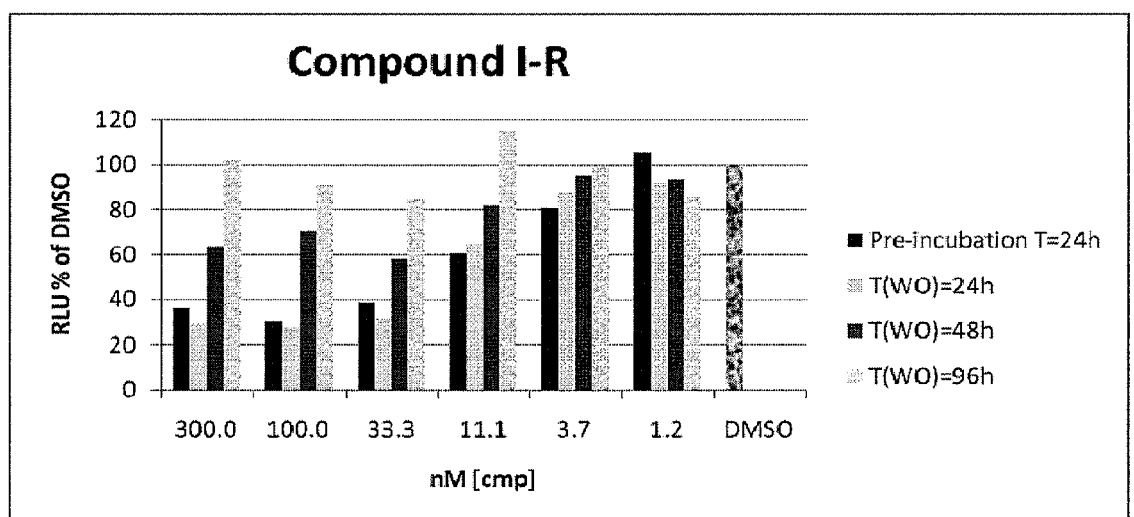
Figure 16:
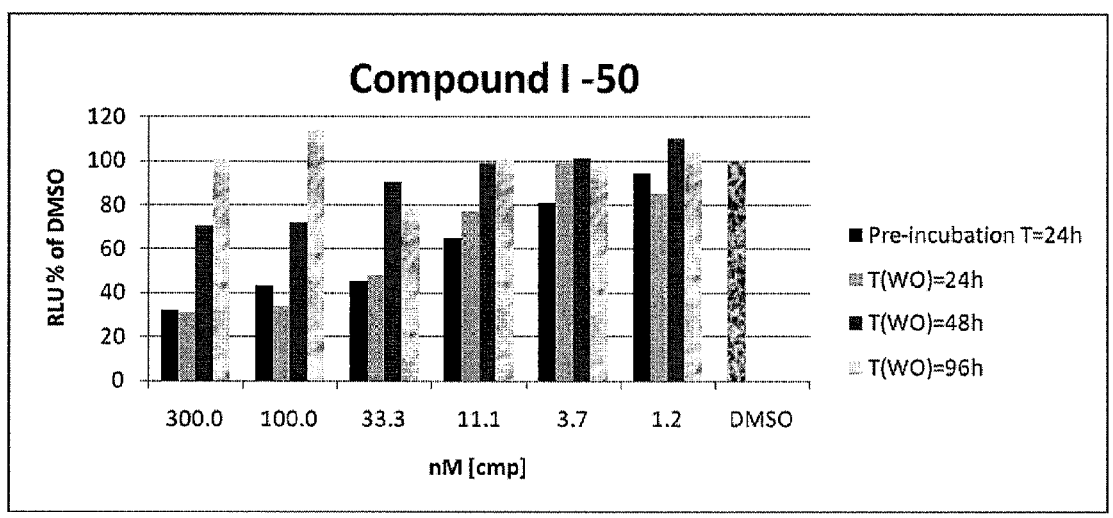

FIGS. 15 and 16 depicts luciferase activity, using a replicon assay, in the presence of varying concentrations of two HCV protease inhibitors, compound I-R and compound I-50, at 24 h, 48 h and 96 h. Compound I-R is a non-covalent inhibitor whereas compound I-50 is an irreversible covalent inhibitor. Despite differences in the mechanism of action of the two compounds on the protease, the replicon assay shows similar results, due to the indirect nature of the assay readout.

Figure 17:
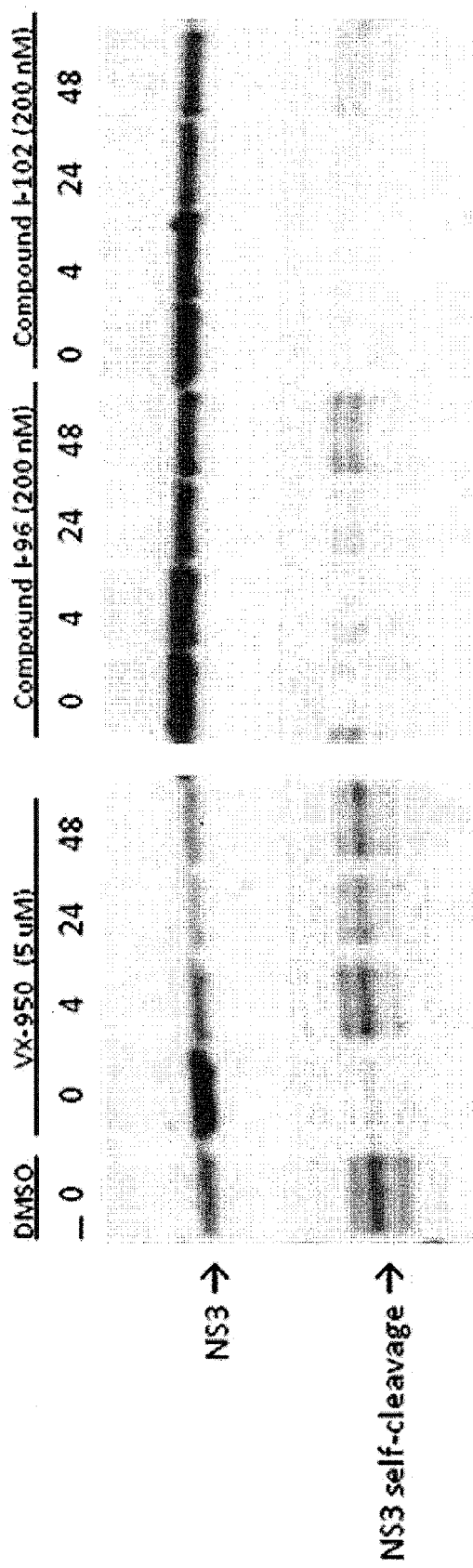

FIGS. 17-17A depict two irreversible covalent inhibitors (compounds I-96 and I-102) of NS3 protease which demonstrate prolonged inhibition of NS3 protease activity in the wild-type replicon cells, as measured by self-cleavage, after the compounds are removed. Compounds are incubated with replicon cells for 16 hours and then removed (time 0). Even up to 48 hours after removal of covalent NS3 inhibitors, NS3 self-cleaving activity is inhibited by at least 50%, whereas a reversible drug shows virtually complete return of activity in as little as 4 hours after drug removal.

Figure 18:
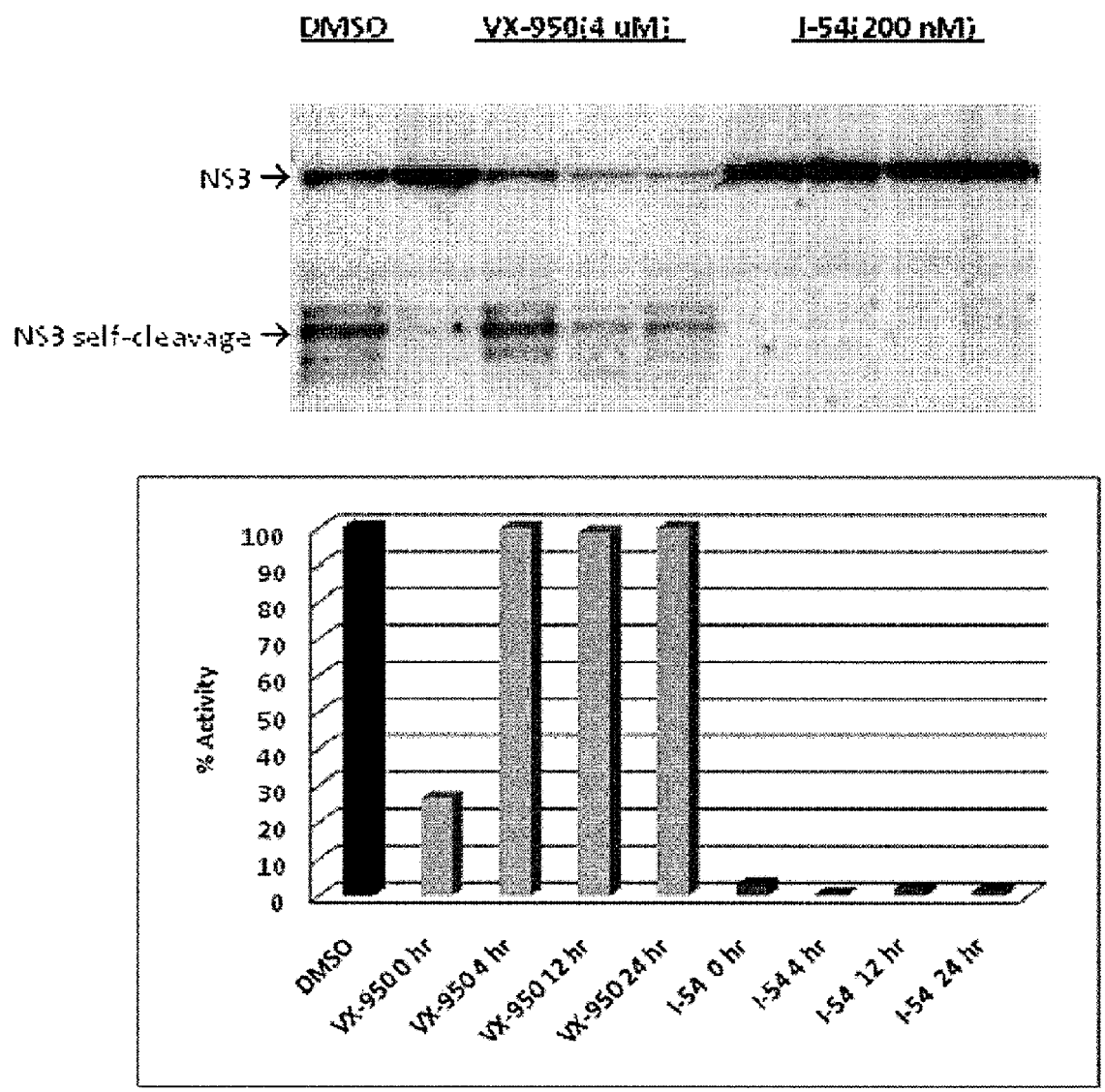

FIG. 18 depicts another covalent inhibitor of NS3 protease which demonstrates prolonged inhibition of NS3 protease activity in the wild-type replicon cells, as measured by self-cleavage, up to 24 hours after the compound is removed. The irreversible covalent inhibitor I-54 demonstrates virtually complete inhibition up to 24 hours after compound removal whereas the reversible drug shows complete return of activity in as little as 4 hours after drug removal.

Figure 19:
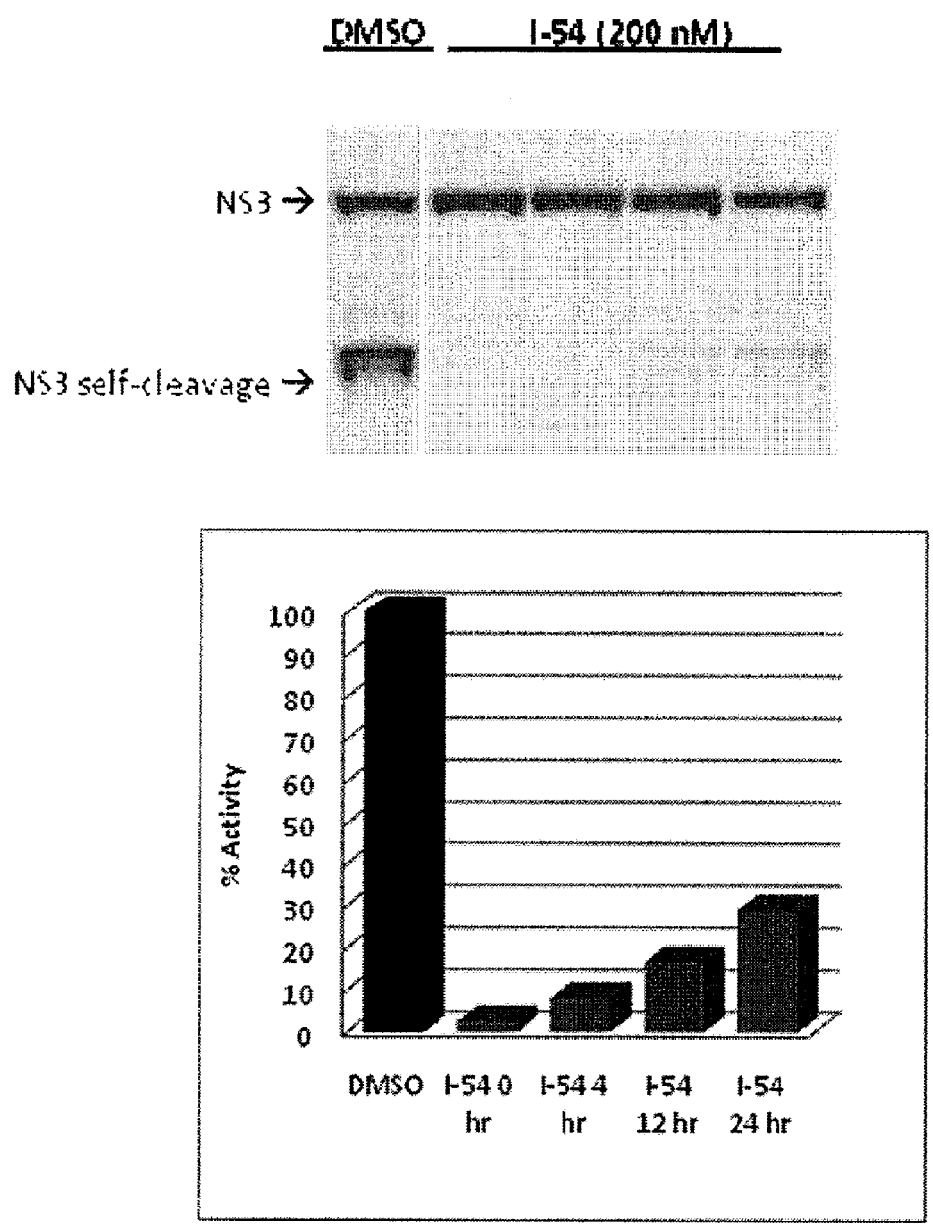

FIG. 19 depicts a covalent protease inhibitor I-54 which demonstrates prolonged inhibition of NS3 protease activity in modified replicon system where the NS3 protease contains a clinically observed mutation that alters an amino acid from arginine to lysine at position 155 (R155K). This mutation results in clinical drug resistance to protease inhibitors. FIG. 19 depicts that, even with this mutation, irreversible covalent drugs can inhibit activity from the mutant protease for at least 24 hours after compound removal.

DETAILED DESCRIPTION OF CERTAIN EMBODIMENTS

1. General Description of Compounds of the Invention:

In certain embodiments, the present invention provides a compound of formula I:

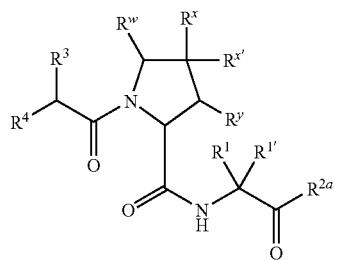

I or a pharmaceutically acceptable salt thereof, wherein:
$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^{21}$ is —OH or —NHSO$_2$R$^2$;

$R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted $C_{1-6}$ aliphatic, or:

two R on the same nitrogen atom are taken together with the nitrogen to form a 4-7 membered heterocyclic ring having 1-2 heteroatoms independently selected from nitrogen, oxygen, or sulfur;

$R^3$ is a warhead group, or:

$R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group; or $R^3$ and a ring formed by $R^1$ and $R^{1'}$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group;

$R^w$ is hydrogen or an optionally substituted group selected from $C_{1-6}$ aliphatic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur: or $R^w$ and $R^x$ are taken together to form an optionally substituted $C_{3-7}$ membered ring having 0-2 heteroatoms indepentently selected from nitrogen, oxygen or sulfur, or:

$R^w$ and $R^y$ are taken together to form an optionally substituted $C_{3-7}$ membered ring having 0-2 heteroatoms indepentently selected from nitrogen, oxygen or sulfur;

$R^x$ is -T-R$^z$, wherein:

T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and $R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^{x'}$ is hydrogen, or $R^{x'}$ and $R^x$ are taken together with their intervening atoms to form an optionally substituted spiro-fused 5-7 membered ring having 0-2 heteroatoms independently selected from nitrogen, oxygen, or sulfur;

$R^y$ is hydrogen, or $R^x$ and $R^y$ are taken together to form an optionally substituted $C_{3-7}$ membered ring having 0-2 heteroatoms independently selected from nitrogen, oxygen or sulfur;

$R^4$ is H, —NHC(O)R$^5$, —NHC(O)OR$^6$

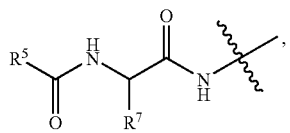

a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur;

each $R^5$ is independently —$N(R)_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

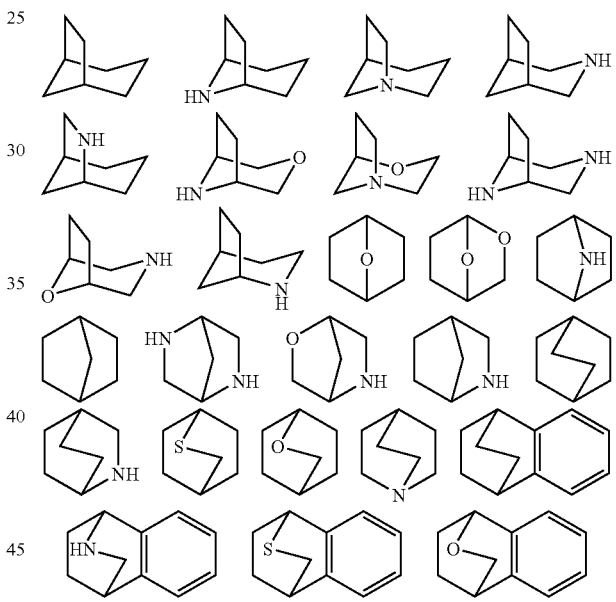

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-18}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

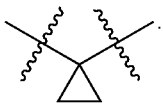

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the phrase "natural amino acid side-chain group" refers to the side-chain group of any of the 20 amino acids naturally occuring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to the side-chain group of amino acids not included in the list of 20 amino acids naturally occuring in proteins, as described above. Such amino acids include the D-isomer of any of the 20 naturally occuring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$; —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently Cl$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^3$, of a provided compound comprises one or more deuterium atoms.

As used herein, the term "irreversible" or "irreversible inhibitor" refers to an inhibitor (i.e. a compound) that is able to be covalently bonded to HCV protease in a substantially non-reversible manner. That is, whereas a reversible inhibitor is able to bind to (but is generally unable to form a covalent bond with) HCV protease, and therefore can become dissociated from the HCV protease an irreversible inhibitor will remain substantially bound to HCV protease once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to HCV protease once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with HCV protease, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein.

As used herein, the term "inhibitor" is defined as a compound that binds to and/or inhibits HCV protease with measurable affinity. In certain embodiments, an inhibitor has an IC$_{50}$ and/or binding constant of less about 50 μM, less than about 1 μM, less than about 500 nM, less than about 100 nM, less than about 10 nM, or less than about 1 nM.

A compound of the present invention may be tethered to a detectable moiety. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4', 5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in HCV protease activity between a sample comprising a compound of the present invention, or composition thereof, and HCV protease, and an equivalent sample comprising HCV protease, in the absence of said compound, or composition thereof.

3. Description of Exemplary Compounds:

In certain embodiments, the present invention provides a compound of formula I:

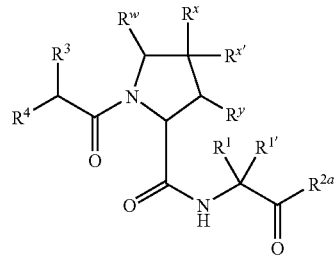

or a pharmaceutically acceptable salt thereof, wherein:

$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^{2a}$ is —OH or —NHSO$_2$R$^2$;

$R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted $C_{1-6}$ aliphatic, or:

two R on the same nitrogen atom are taken together with the nitrogen to form a 4-7 membered heterocyclic ring having 1-2 heteroatoms independently selected from nitrogen, oxygen, or sulfur;

$R^3$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and each R$^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN; or $R^3$ and $R^1$ are taken together with their intervening atoms to form an optionally substituted saturated or unsaturated 12-18 membered ring having 2-6 heteroatoms independently selected from nitrogen oxygen, or sulfur, wherein the ring formed thereby comprises -L-Y; or $R^3$ and a ring formed by $R^1$ and $R^{1'}$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group;

$R^w$ is hydrogen or an optionally substituted group selected from $C_{1-6}$ aliphatic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur: or $R^w$ and $R^x$ are taken together to form an optionally substituted $C_{3-7}$ membered ring having 0-2 heteroatoms indepentently selected from nitrogen, oxygen or sulfur, or:

$R^w$ and $R^y$ are taken together to form an optionally substituted $C_{3-7}$ membered ring having 0-2 heteroatoms indepentently selected from nitrogen, oxygen or sulfur;

$R^x$ is -T-$R^z$, wherein:

T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and $R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^{x'}$ is hydrogen, or $R^{x'}$ and $R^x$ are taken together with their intervening atoms to form an optionally substituted spirofused 5-7 membered ring having 0-2 heteroatoms independently selected from nitrogen, oxygen, or sulfur;

$R^y$ is hydrogen, or $R^x$ and $R^y$ are taken together to form an optionally substituted $C_{3-7}$ membered ring having 0-2 heteroatoms independently selected from nitrogen, oxygen, or sulfur;

$R^4$ is H, —NHC(O)$R^5$, —NHC(O)O$R^6$,

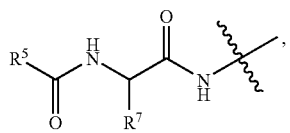

a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur;

each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, L is a covalent bond.

In certain embodiments, L is a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

In certain embodiments, L is a bivalent $C_{1-8}$ saturated or unsaturated, straight or branched, hydrocarbon chain. In certain embodiments, L is —CH$_2$—.

In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.

In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, —O—, —N(R)—, or —C(O)—.

In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.

In some embodiments, L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent $C_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent $C_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —CH$_2$C(O)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH$_2$OC(O)CH=CHCH$_2$—, —CH$_2$—OC(O)CH=CH—, or —CH(CH=CH$_2$)OC(O)CH=CH—.

In certain embodiments, L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-, wherein each R is independently hydrogen or optionally substituted $C_{1-6}$ aliphatic.

In certain embodiments, L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —O—.

Exemplary L groups include —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$OC(=O)C≡C—.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R). Exemplary L groups include —NHC(O)-cyclopropylene-SO$_2$— and —NHC(O)— cyclopropylene-.

As defined generally above, Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, NO$_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and, Z is hydrogen or $C_{1-6}$ aliphatic optionally substituted with oxo, halogen, NO$_2$, or CN.

In certain embodiments, Y is hydrogen.

In certain embodiments, Y is $C_{1-6}$ aliphatic optionally substituted with oxo, halogen, NO$_2$, or CN. In some embodiments, Y is $C_{2-6}$ alkenyl optionally substituted with oxo, halogen, NO$_2$, or CN. In other embodiments, Y is $C_{2-6}$ alkynyl optionally substituted with oxo, halogen, NO$_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, NO$_2$, or CN. Such Y groups include —CH$_2$F, —CH$_2$Cl, —CH$_2$CN, and —CH$_2$NO$_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above and described herein.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above and described herein. Exemplary such rings are epoxide and oxetane rings, wherein each ring is substituted with 1-2 $R^e$ groups, wherein each $R^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

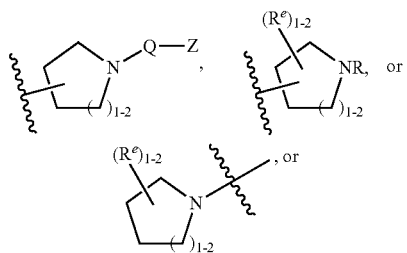

wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein. In certain embodiments, Y is

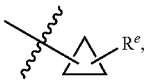

wherein $R^e$ is as defined above and described herein. In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined above and described herein. In certain embodiments, Y is

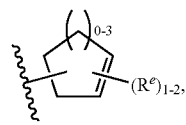

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

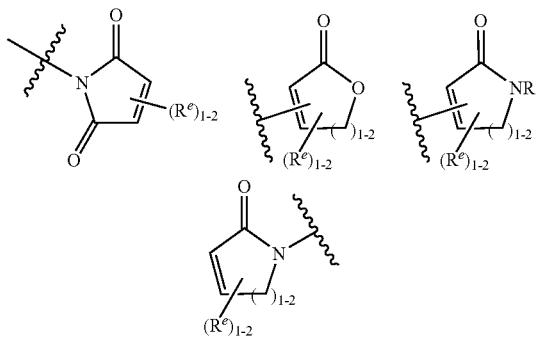

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

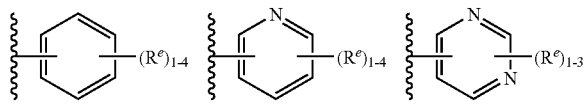

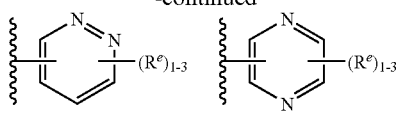

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

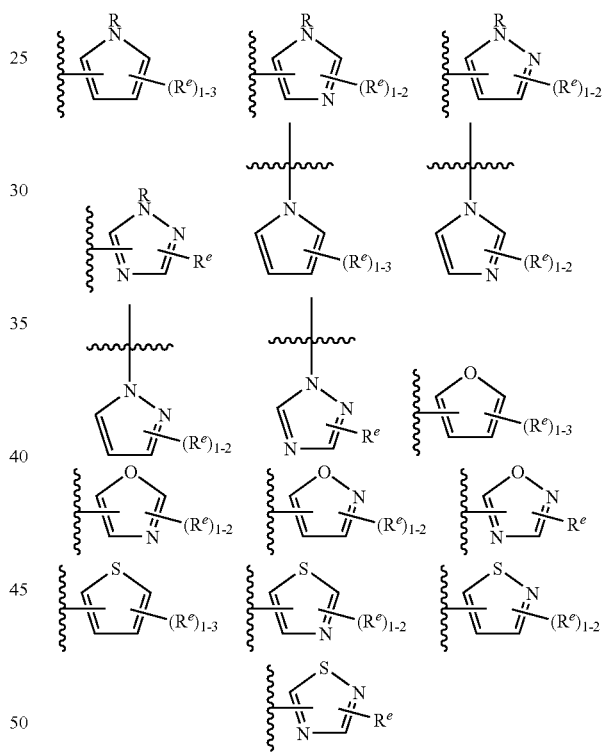

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH=$CH_2$ or —C(O)CH=$CH_2$.

In certain embodiments, each $R^e$ is independently selected from from oxo, $NO_2$, CN, fluoro, chloro, —NHC(O)CH=$CH_2$, —C(O)CH=$CH_2$, —$CH_2$CH=$CH_2$, —CδCH, —C(O)O$CH_2$Cl, —C(O)O$CH_2$F, —C(O)O$CH_2$CN, —C(O)$CH_2$Cl, —C(O)$CH_2$F, —C(O)$CH_2$CN, or —$CH_2$C(O)$CH_3$.

In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:

(a) L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—; and Y is hydrogen or $C_{1-6}$ aliphatic optionally substituted with oxo, halogen, $NO_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (d) L is a bivalent $C_{2-8}$ straight or branched, hydrocarbon chain wherein L has at least one double bond and at least one methylene unit of L is replaced by —C(O)—; and Y is hydrogen or $C_{1-6}$ aliphatic optionally substituted with oxo, halogen, $NO_2$, or CN; or (e) L is a bivalent $C_{2-8}$ straight or branched, hydrocarbon chain wherein L has at least one double bond and at least one methylene unit of L is replaced by —OC(O)—; and Y is hydrogen or $C_{1-6}$ aliphatic optionally substituted with oxo, halogen, $NO_2$, or CN; or (f) L is —NRC(O)CH=CH—, —NRC(O)CH=CH$CH_2$N($CH_3$)—, —NRC(O)CH=CH$CH_2$O—, —$CH_2$NRC(O)CH=CH—, —NR$SO_2$CH=CH—, —NR$SO_2$CH=CH$CH_2$—, —NRC(O)(C=$N_2$)—, —NRC(O)(C=$N_2$)C(O)—, —NRC(O)CH=CH$CH_2$N($CH_3$)—, —NR$SO_2$CH=CH—, —NR$SO_2$CH=CH$CH_2$—, —NRC(O)CH=CH$CH_2$O—, —NRC(O)C(=$CH_2$)$CH_2$—, —$CH_2$NRC(O)—, —$CH_2$NRC(O)CH=CH—, —$CH_2$$CH_2$NRC(O)—, or —$CH_2$NRC(O)cyclopropylene-; wherein R is H or optionally substituted $C_{1-6}$ aliphatic; and Y is hydrogen or $C_{1-6}$ aliphatic optionally substituted with oxo, halogen, $NO_2$, or CN; or (g) L is —NHC(O)CH=CH—, —NHC(O)CH=CH$CH_2$N($CH_3$)—, —NHC(O)CH=CH$CH_2$O—, —$CH_2$NHC(O)CH=CH—, —NH$SO_2$CH=CH—, —NH$SO_2$CH=CH$CH_2$—, —NHC(O)(C=$N_2$)—, —NHC(O)(C=$N_2$)C(O)—, —NHC(O)CH=CH$CH_2$N($CH_3$)—, —NH$SO_2$CH=CH—, —NH$SO_2$CH=CH$CH_2$—, —NHC(O)CH=CH$CH_2$O—, —NHC(O)C(=$CH_2$)$CH_2$—, —$CH_2$NHC(O)—, —$CH_2$NHC(O)CH=CH—, —$CH_2$$CH_2$NHC(O)—, or —$CH_2$NHC(O)cyclopropylene-; and Y is hydrogen or $C_{1-6}$ aliphatic optionally substituted with oxo, halogen, $NO_2$, or CN; or (h) L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (i) L is a bivalent $C_{2-8}$ straight or branched, hydrocarbon chain wherein L has at least one triple bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, or —C(O)O—, and Y is hydrogen or $C_{1-6}$ aliphatic optionally substituted with oxo, halogen, $NO_2$, or CN; or (j) L is —C≡C—, —C≡CCH₂N(isopropyl)-, —NHC(O)C≡CCH₂CH₂—, —CH₂—C≡C—CH₂—, —C≡CCH₂O—, —CH₂C(O)C≡C—, —C(O)C≡C—, or —CH₂OC(=O)C≡C—; and Y is hydrogen or C$_{1-6}$ aliphatic optionally substituted with oxo, halogen, NO$_2$, or CN; or (k) L is a bivalent C$_{2-8}$ straight or branched, hydrocarbon chain wherein one methylene unit of L is replaced by cyclopropylene and one or two additional methylene units of L are independently replaced by —NRC(O)—, —C(O)NR—, —N(R)SO₂—, —SO₂N(R)—, —S—, —S(O)—, —SO₂—, —OC(O)—, or —C(O)O—; and Y is hydrogen or C$_{1-6}$ aliphatic optionally substituted with oxo, halogen, NO$_2$, or CN; or (l) L is a covalent bond and Y is selected from:
  (i) C$_{1-6}$ alkyl substituted with oxo, halogen, NO$_2$, or CN;
  (ii) C$_{2-6}$ alkenyl optionally substituted with oxo, halogen, NO$_2$, or CN; or
  (iii) C$_{2-6}$ alkynyl optionally substituted with oxo, halogen, NO$_2$, or CN; or
  (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or
  (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or
  (vi)

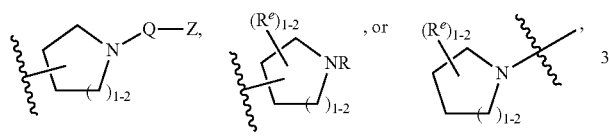

wherein each R, Q, Z, and R$^e$ is as defined above and described herein; or
  (vii) a saturated 3-6 membered carbocyclic ring, wherein said ring is substituted with 1-4 R$^e$ groups, wherein each R$^e$ is as defined above and described herein; or
  (viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or
  (ix) a partially unsaturated 3-6 membered carbocyclic ring, wherein said ring is substituted with 1-4 R$^e$ groups, wherein each R$^e$ is as defined above and described herein; or
  (x)

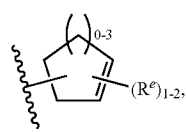

wherein each R$^e$ is as defined above and described herein; or
  (xi) a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein; or
  (xii)

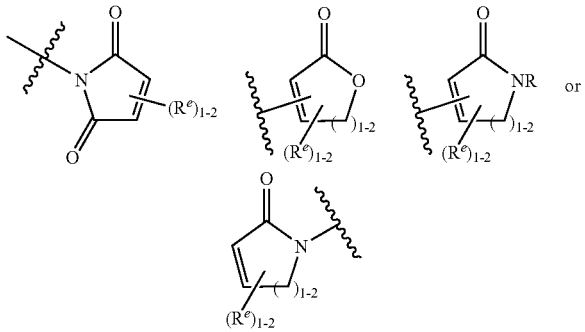

wherein each R and R$^e$ is as defined above and described herein; or
  (xiii) a 6-membered aromatic ring having 0-2 nitrogens wherein said ring is substituted with 1-4 R$^e$ groups, wherein each R$^e$ group is as defined above and described herein; or
  (xiv)

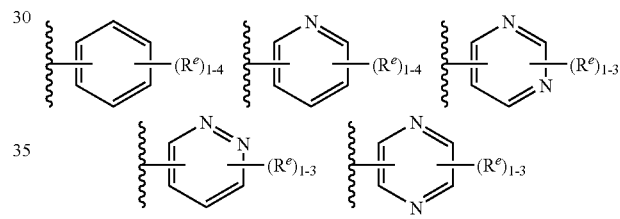

wherein each R$^e$ is as defined above and described herein; or
  (xv) a 5-membered heteroaryl ring having 1-3 heteroatoms independently selected from nitrogen, oxygen, or sulfur, wherein said ring is substituted with 1-3 R$^e$ groups, wherein each R$^e$ group is as defined above and described herein: or
  (xvi)

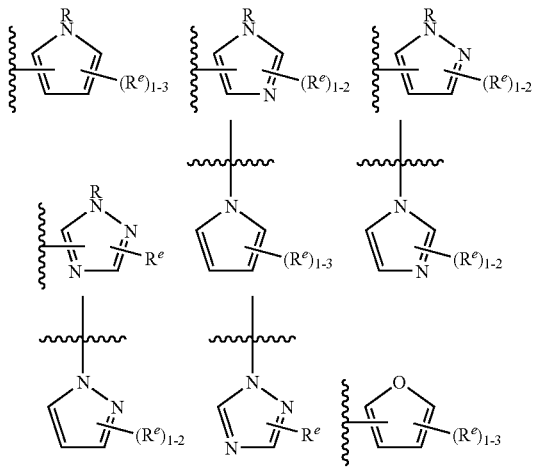

-continued

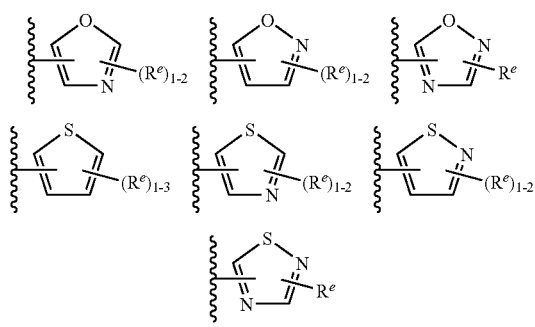

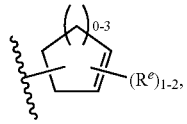

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:
(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or
(vi)

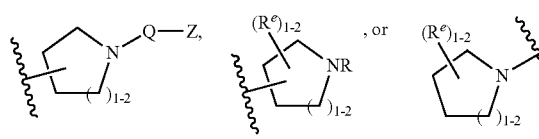

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or (x)

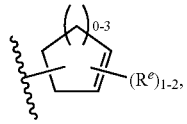

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or
(xii)

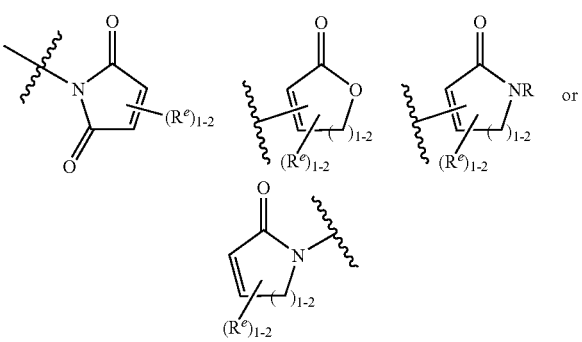

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or
(xiv)

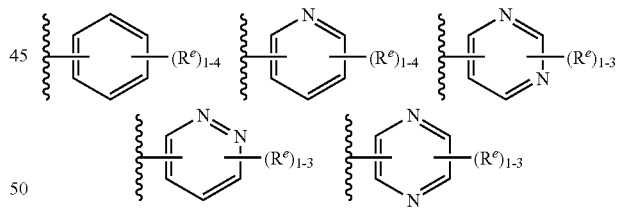

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or
(xvi)

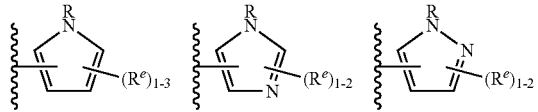

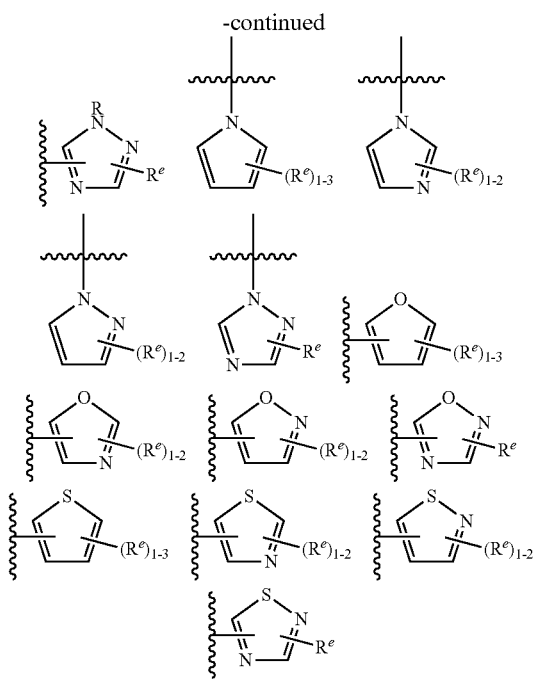

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(n) L is —N(R)C(O)— and Y is selected from:
(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or
(vi)

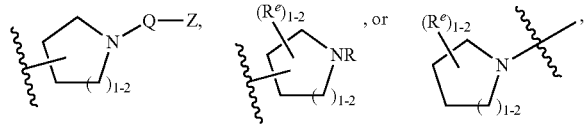

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or
(x)

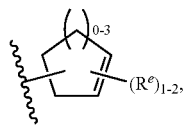

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or
(xii)

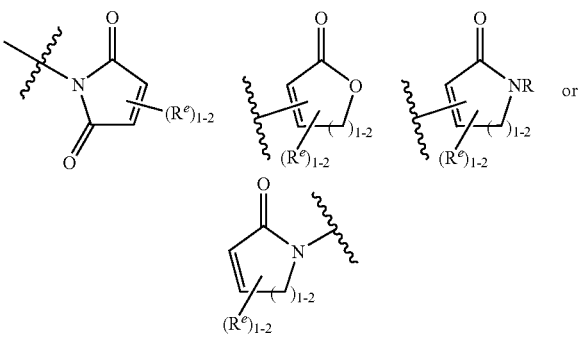

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or
(xiv)

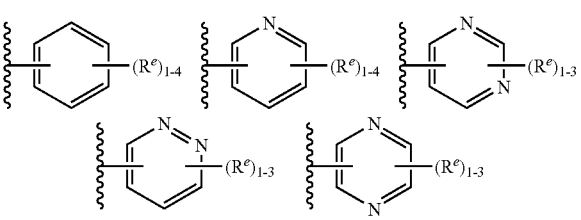

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or '(xvi)

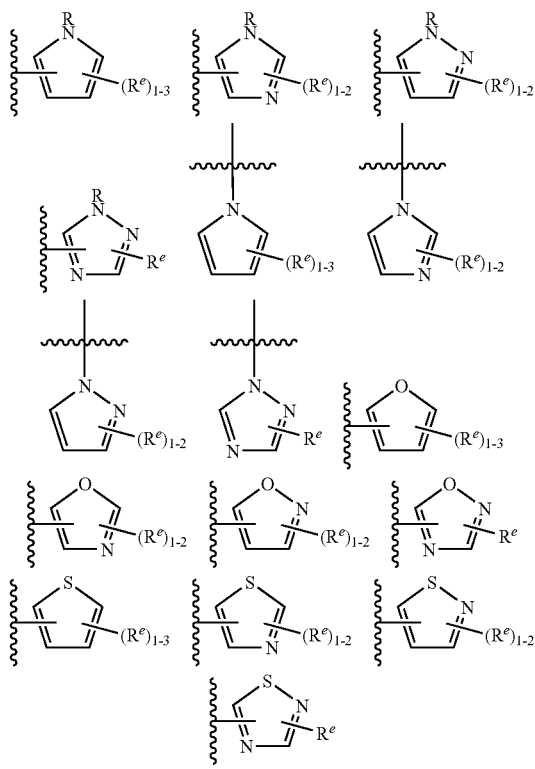

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;
(o) L is a bivalent $C_{1-8}$ saturated or unsaturated, straight or branched, hydrocarbon chain; and Y is selected from:
(i) $C_{1-6}$ alkyl substituted with oxo, halogen, $NO_2$, or CN;
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or
(vi)

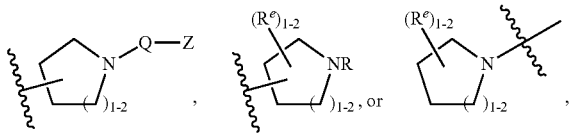

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or
(x)

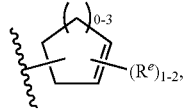

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or
(xii)

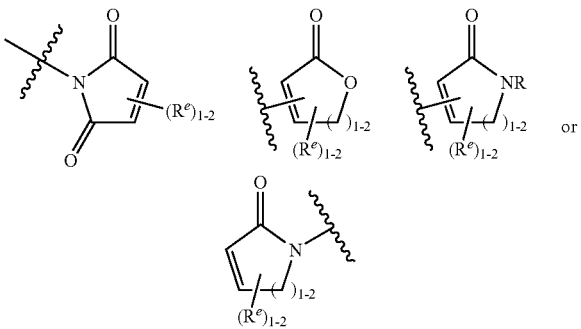

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or
(xiv)

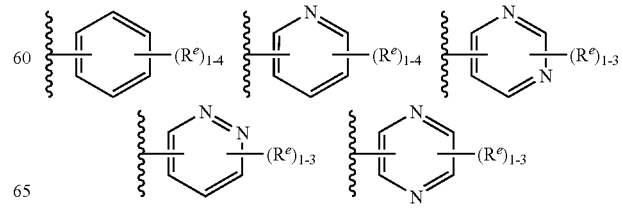

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or
(xvi)

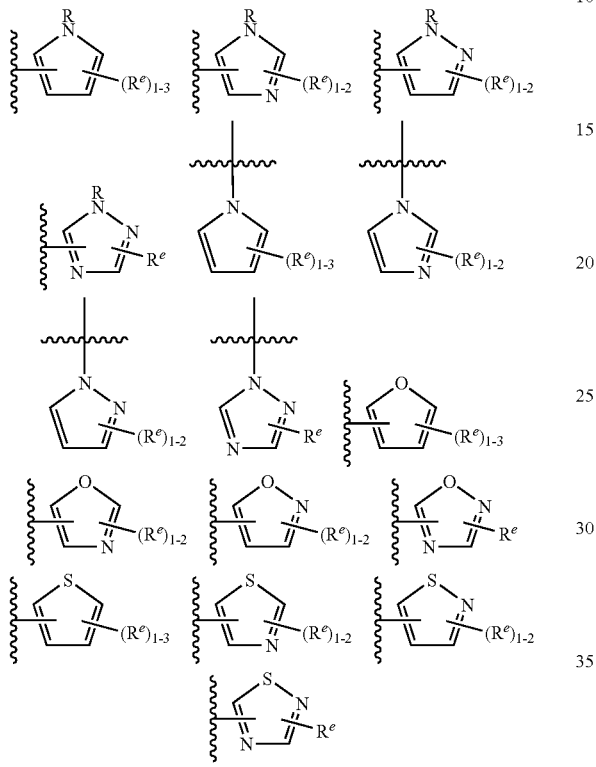

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;
(p)L is a covalent bond, —CH$_2$—, —NH—, —C(O)—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—; and Y is selected from:
(i) C$_{1-6}$ alkyl substituted with oxo, halogen, NO$_2$, or CN; or
(ii) C$_{2-6}$ alkenyl optionally substituted with oxo, halogen, NO$_2$, or CN; or
(iii) C$_{2-6}$ alkynyl optionally substituted with oxo, halogen, NO$_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatoms selected from oxygen or nitrogen wherein said ring is substituted with 1-4 $R^e$ groups, wherein each $R^e$ is as defined above and described herein; or (vi)

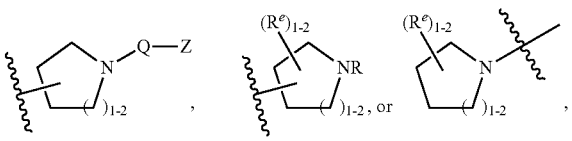

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or
(x)

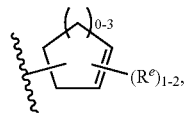

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or
(xii)

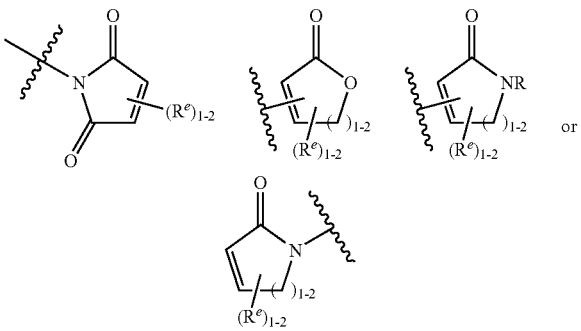

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or (xiv)

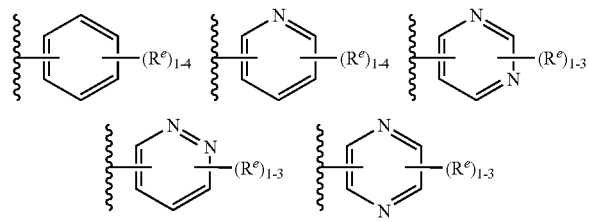

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

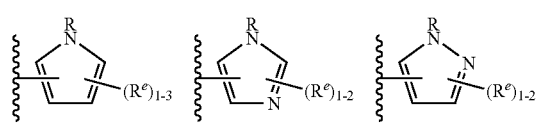

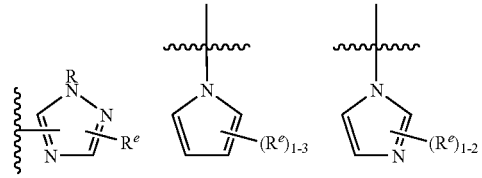

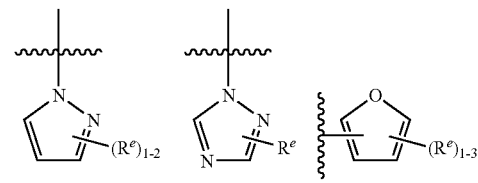

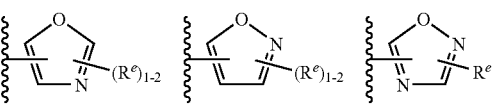

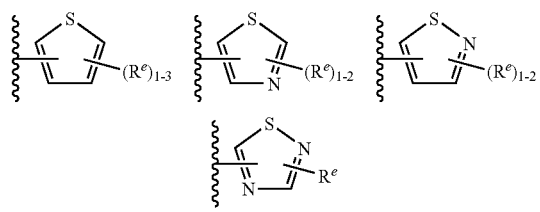

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

In certain embodiments, the Y group of formula I is selected from those set forth in Table 1, below, wherein each wavy line indicates the point of attachment to the rest of the molecule.

TABLE 1

Exemplary Y Groups of Formula I:

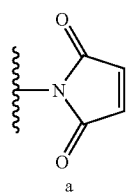

a

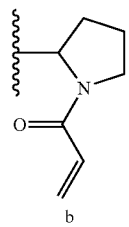

b

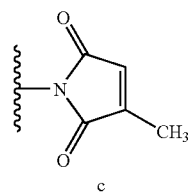

c

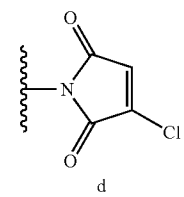

d

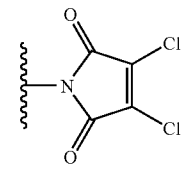

e

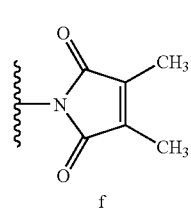

f

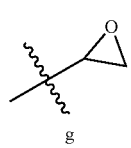

g

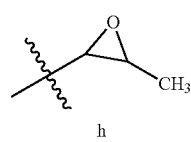

h

TABLE 1-continued
Exemplary Y Groups of Formula I:
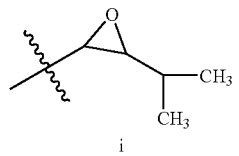
i
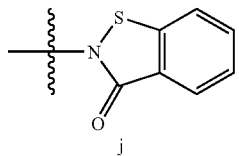
j
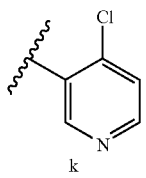
k
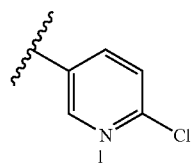
l
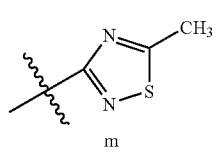
m
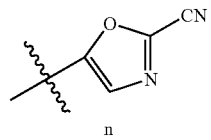
n
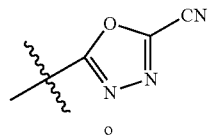
o
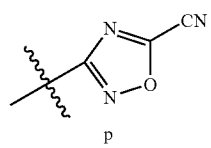
p
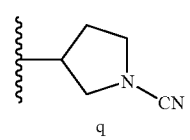
q
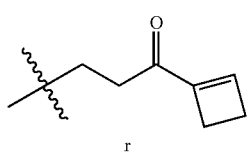
r
TABLE 1-continued
Exemplary Y Groups of Formula I:
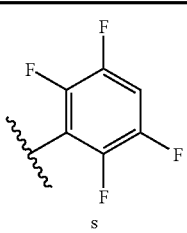
s
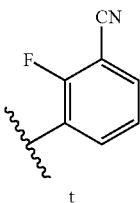
t
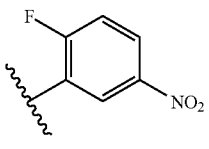
u
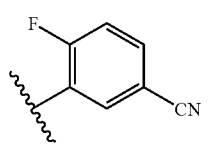
v
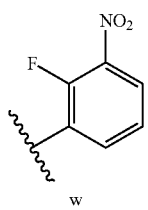
w
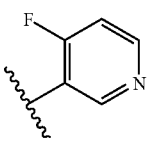
x
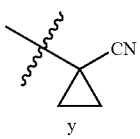
y
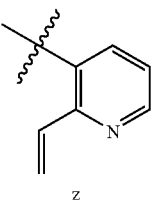
z TABLE 1-continued
Exemplary Y Groups of Formula I:
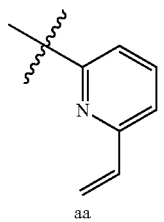
aa
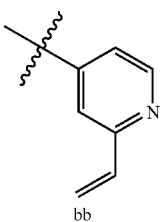
bb
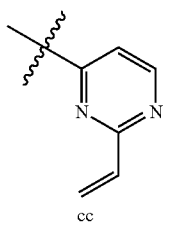
cc
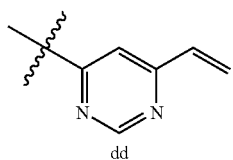
dd
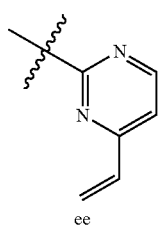
ee
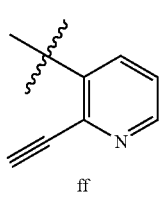
ff
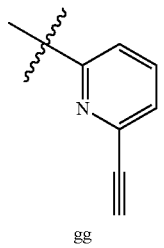
gg
TABLE 1-continued
Exemplary Y Groups of Formula I:
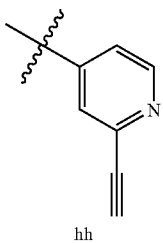
hh
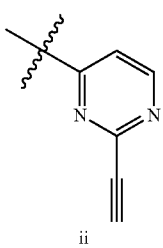
ii
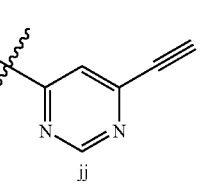
jj
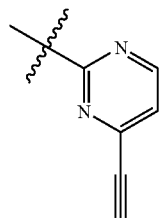
kk
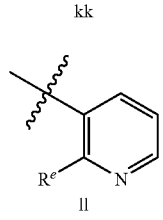
ll
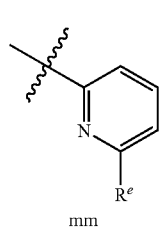
mm
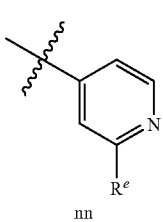
nn TABLE 1-continued
Exemplary Y Groups of Formula I:
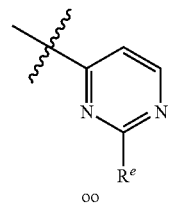
oo
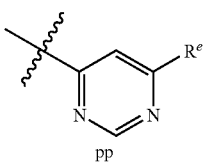
pp
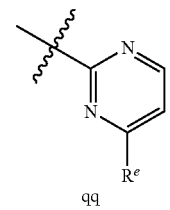
qq
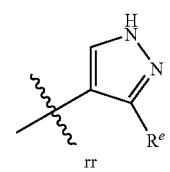
rr
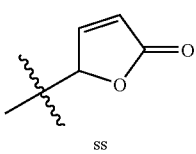
ss
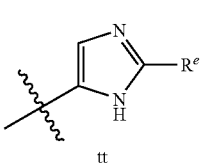
tt
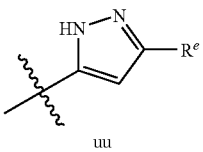
uu
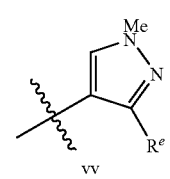
vv
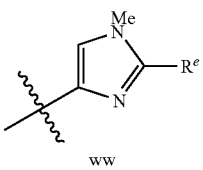
ww
TABLE 1-continued
Exemplary Y Groups of Formula I:
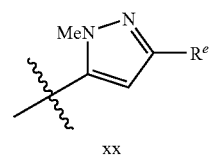
xx
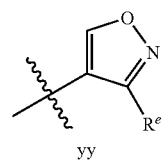
yy
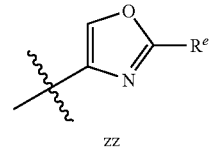
zz
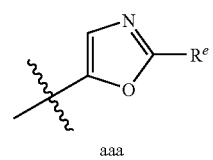
aaa
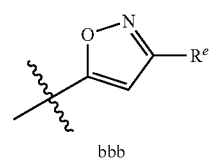
bbb
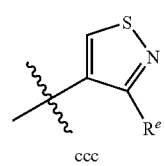
ccc
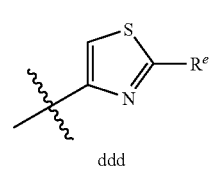
ddd
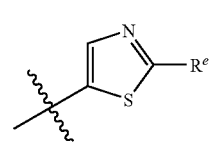
eee
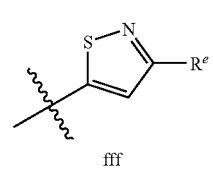
fff TABLE 1-continued
Exemplary Y Groups of Formula I:
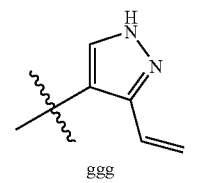
ggg
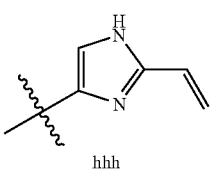
hhh
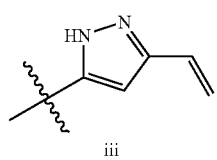
iii
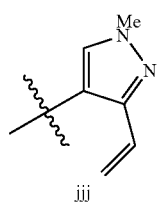
jjj
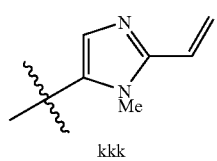
kkk
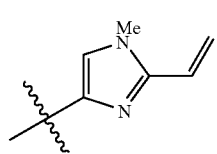
lll
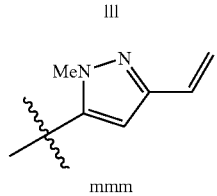
mmm
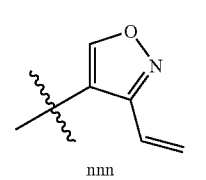
nnn
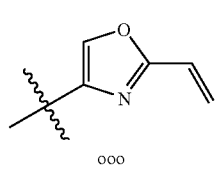
ooo
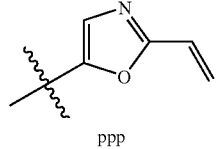
ppp
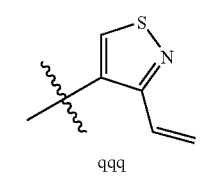
qqq
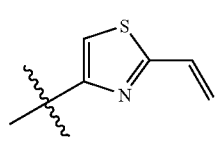
rrr
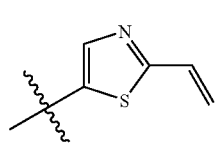
sss
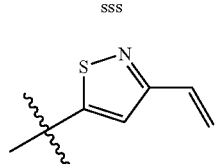
ttt
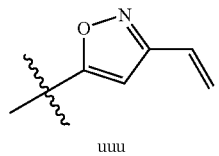
uuu
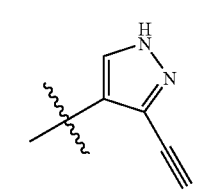
vvv
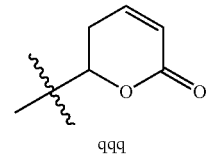
qqq
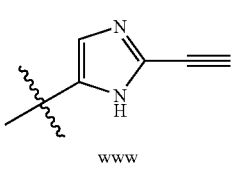
www

TABLE 1-continued
Exemplary Y Groups of Formula I:
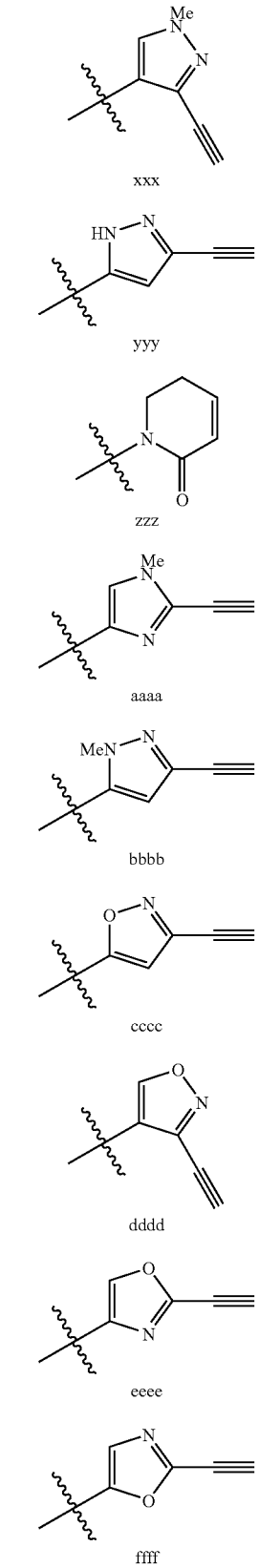
xxx
yyy
zzz
aaaa
bbbb
cccc
dddd
eeee
ffff
TABLE 1-continued
Exemplary Y Groups of Formula I:
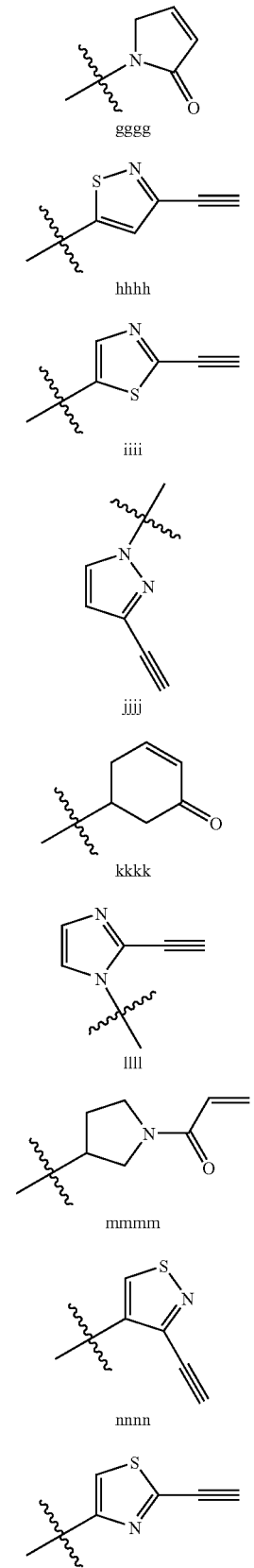
gggg
hhhh
iiii
jjjj
kkkk
llll
mmmm
nnnn TABLE 1-continued Exemplary Y Groups of Formula I:

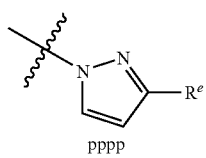
pppp

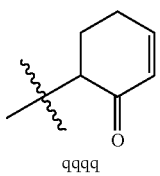
qqqq

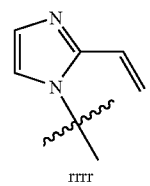
rrrr

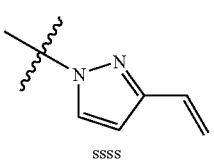
ssss

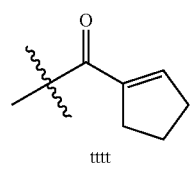
tttt

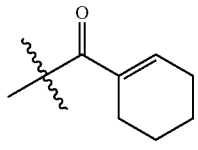
uuuu

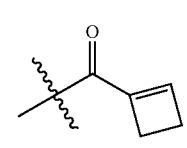
vvvv

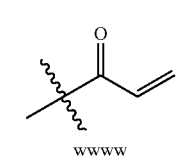
wwww

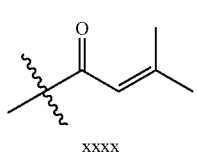
xxxx

TABLE 1-continued

Exemplary Y Groups of Formula I:

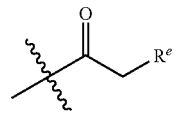
yyyy

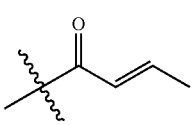
zzzz

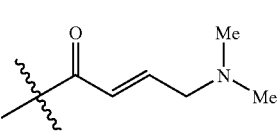
aaaaa

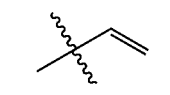
bbbbb

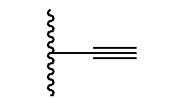
ccccc

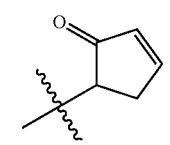
ddddd wherein each $R^e$ is independently a suitable leaving group, $NO_2$, CN, or oxo.

In certain embodiments, the $R^3$ group of formula I is selected from those set forth in Table 2, below, wherein each wavy line indicates the point of attachment to the rest of the molecule.

TABLE 2

Exemplary $R^3$ Groups:

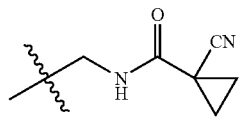
a

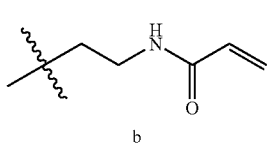
b

TABLE 2-continued
Exemplary R³ Groups:
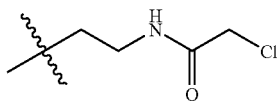
c
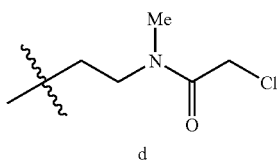
d
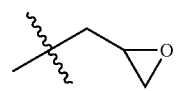
e
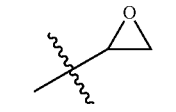
f
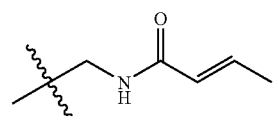
g
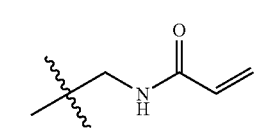
h
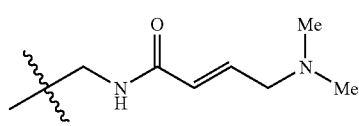
i
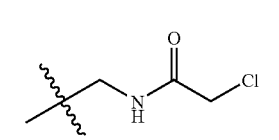
j
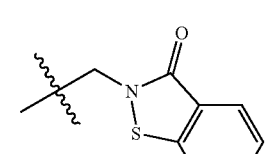
k
TABLE 2-continued
Exemplary R³ Groups:
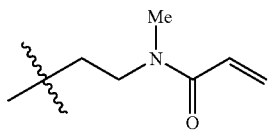
l
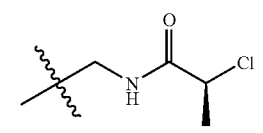
m
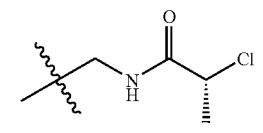
n
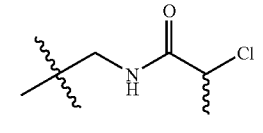
o
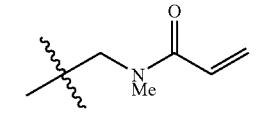
p
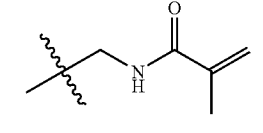
q
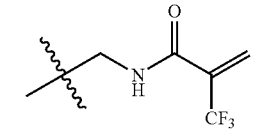
r
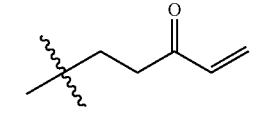
s
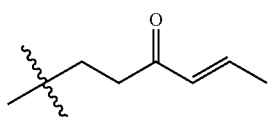
t TABLE 2-continued Exemplary R³ Groups:

u, v, w, x, y, z, aa, bb, cc, dd, ee, ff, gg, hh, ii

TABLE 2-continued
Exemplary R³ Groups:
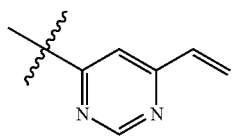
jj
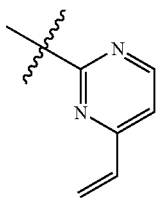
kk
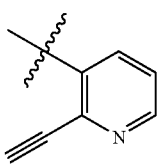
ll
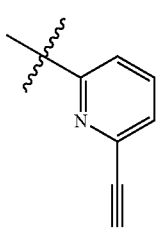
mm
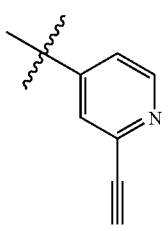
nn
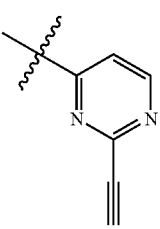
oo
TABLE 2-continued
Exemplary R³ Groups:
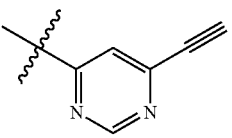
pp
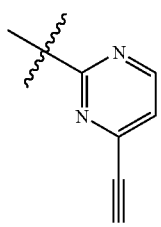
qq
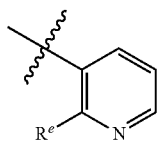
rr
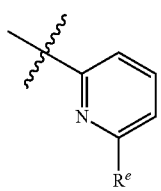
ss
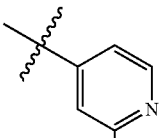
tt
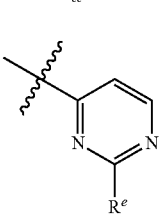
uu
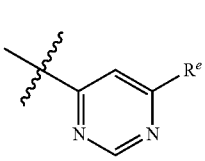
vv TABLE 2-continued
Exemplary R³ Groups:
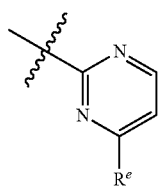
ww
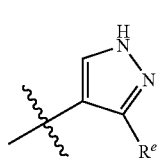
xx
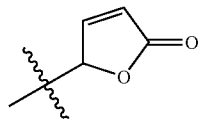
yy
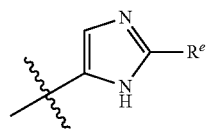
zz
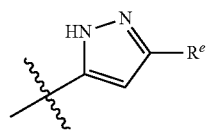
aaa
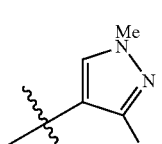
bbb
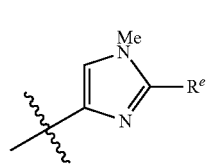
ccc
TABLE 2-continued
Exemplary R³ Groups:
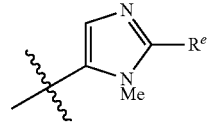
ddd
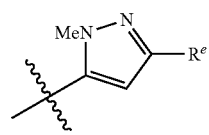
eee
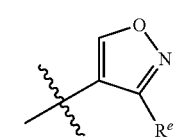
fff
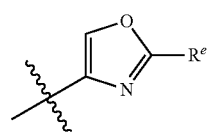
ggg
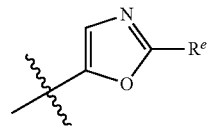
hhh
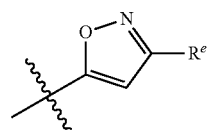
iii
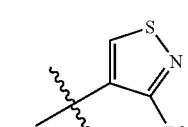
jjj
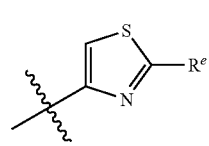
kkk TABLE 2-continued
Exemplary R³ Groups:
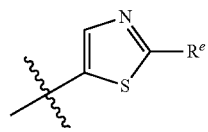
lll
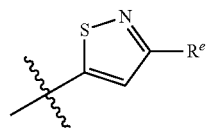
mmm
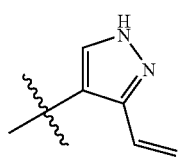
nnn
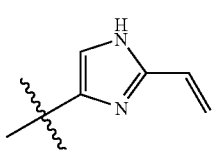
ooo
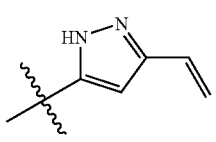
ppp
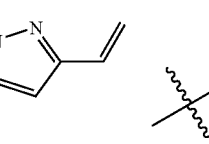
qqq
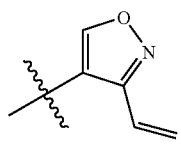
rrr
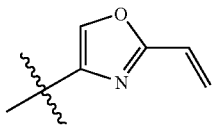
sss
TABLE 2-continued
Exemplary R³ Groups:
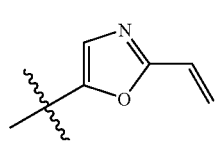
ttt
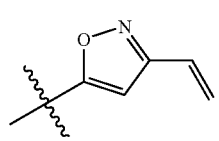
uuu
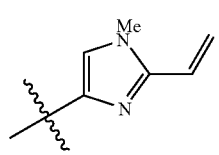
vvv
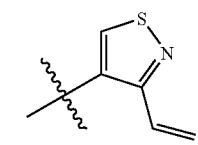
www
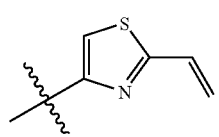
xxx
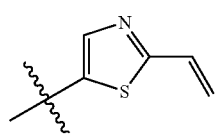
yyy
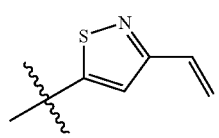
zzz
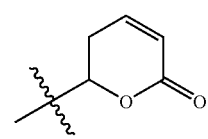
aaaa TABLE 2-continued
Exemplary R³ Groups:
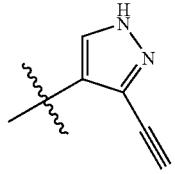
bbbb
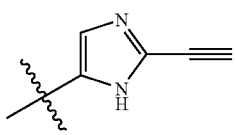
cccc
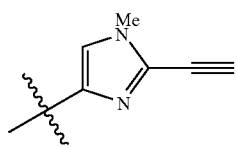
dddd
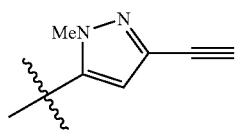
eeee
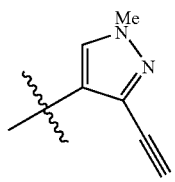
ffff
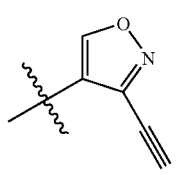
gggg
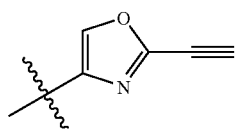
hhhh
TABLE 2-continued
Exemplary R³ Groups:
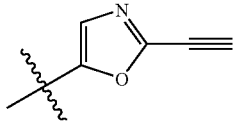
iiii
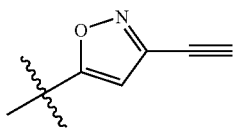
jjjj
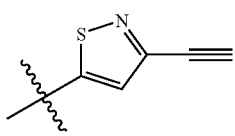
kkkk
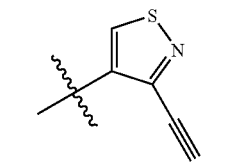
llll
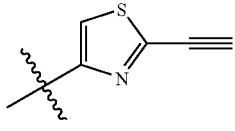
mmmm
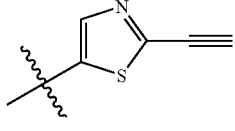
nnnn
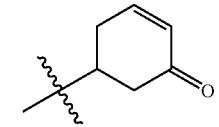
oooo
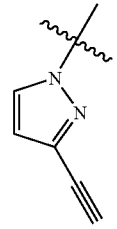
pppp TABLE 2-continued
Exemplary R³ Groups:
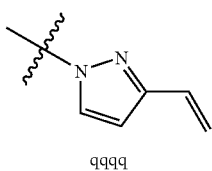
qqqq
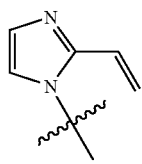
rrrr
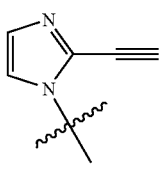
ssss
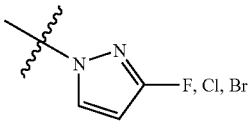
tttt
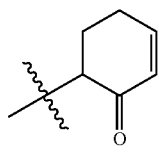
uuuu
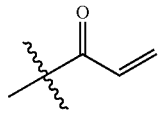
vvvv
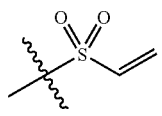
wwww
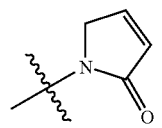
xxxx
TABLE 2-continued
Exemplary R³ Groups:
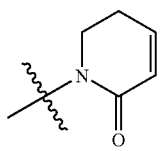
yyyy
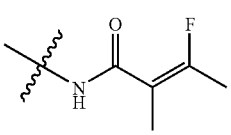
zzzz
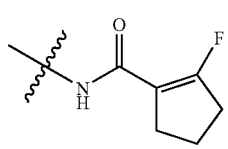
aaaaa
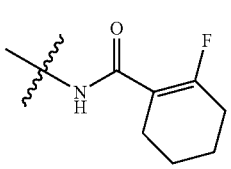
bbbbb
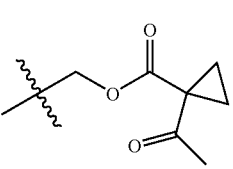
ccccc
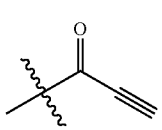
ddddd
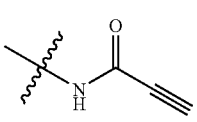
eeeee
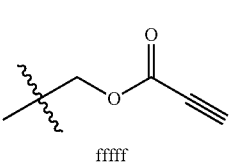
fffff TABLE 2-continued Exemplary R³ Groups:

ggggg hhhhh iiiii jjjjj kkkkk lllll mmmmm nnnnn ooooo ppppp qqqqq rrrrr sssss ttttt uuuuu vvvvv wwwww TABLE 2-continued
Exemplary R³ Groups:
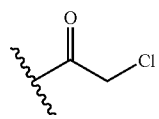
xxxxx
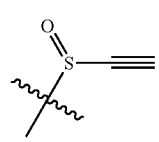
yyyyy
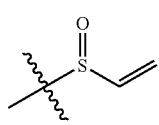
zzzzz
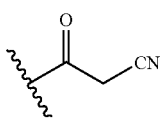
aaaaaa
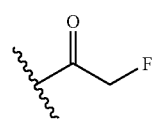
bbbbbb
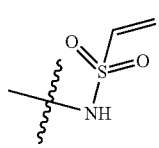
cccccc
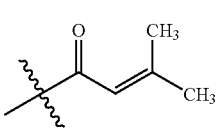
dddddd
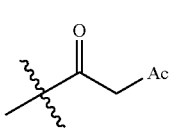
eeeeee
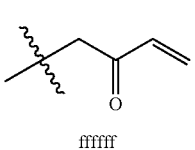
ffffff
TABLE 2-continued
Exemplary R³ Groups:
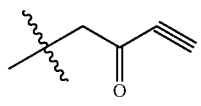
gggggg
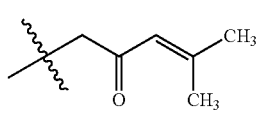
hhhhhh
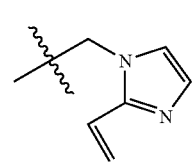
iiiiii
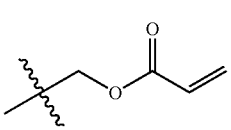
jjjjjj
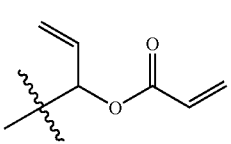
kkkkkk
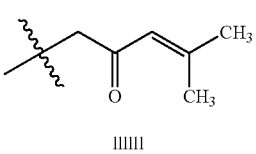
llllll
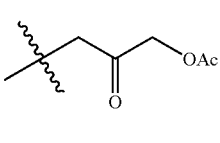
mmmmmm
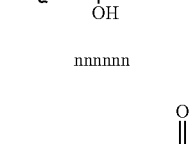
nnnnnn
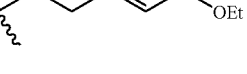
oooooo TABLE 2-continued Exemplary R³ Groups:

pppppp qqqqqq rrrrrr ssssss tttttt uuuuuu vvvvvv wwwwww xxxxxx yyyyyy zzzzzz a1 b1 c1 d1 e1

TABLE 2-continued

Exemplary $R^3$ Groups:

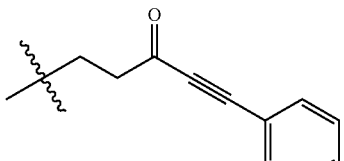

f1

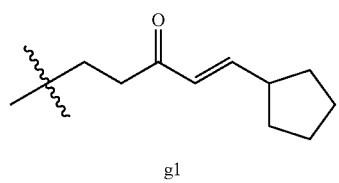

g1

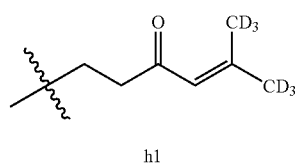

h1

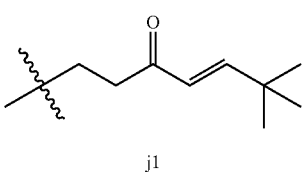

j1

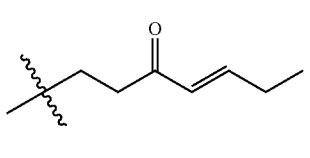

k1

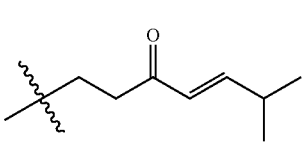

m1

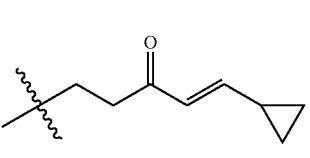

n1

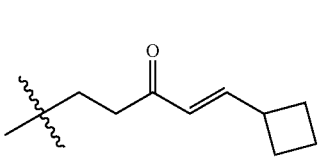

o1

TABLE 2-continued

Exemplary $R^3$ Groups:

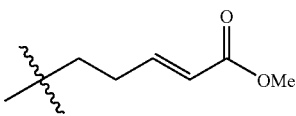

p1

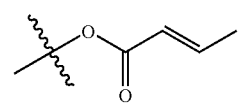

q1

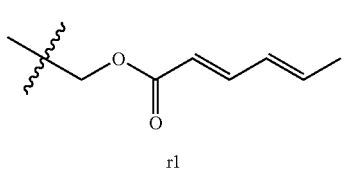

r1 wherein each $R^e$ is independently a suitable leaving group, $NO_2$, CN, or oxo.

In certain embodiments, the $R^x$ group of formula I is -T-$R^z$ and $R^x$ is hydrogen. In certain embodiments, the T group of formula I is a covalent bond. In certain embodiments, T is a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—.

In certain embodiments, T is a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—, wherein the atom of T attached to the proline ring of formula I is carbon, oxygen, or sulfur.

In some embodiments, the T group of formula I is $C_{1-4}$ bivalent hydrocarbon chain wherein one or two methylene units of T are optionally and independently replaced by —O—, —S—, —N(R)—, or —C(O)—. In other embodiments, T is —O—CH$_2$—. In other embodiments, T is —O—. In some embodiments, T is —S—.

In some embodiments, T is not a valence bond when $R^z$ is a 5-10 membered monocyclic or bicyclic heteroaryl ring or a 4-7 membered heterocyclic ring as defined herein.

In some embodiments, T is a $C_{2-3}$ bivalent hydrocarbon chain wherein one or two methylene units of T are optionally and independently replaced by —O—, —S—, —N(R)—, or —C(O)—. In some embodiments, T is —CH$_2$C(O)—, —OC(O)—, or —NHC(O)—. In certain embodiments, T is —OC(O)— and $R^z$ is an 8-10 membered bicyclic ring having at least one nitrogen.

In some embodiments, T is —O— or —O—(CH$_2$)$_{1-2}$— and $R^z$ is an optionally substituted group selected from $C_{1-6}$ aliphatic, 6-10 membered monocyclic or bicyclic aryl, 5-10 membered monocyclic or bicyclic heteroaryl having 1-4 heteroatoms independently selected from nitrogen, oxygen, or sulfur. In some embodiments, T is —O— or —CH$_2$— and $R^z$ is an optionally substituted group selected from 6-10 membered monocyclic or bicyclic aryl, 5-10 membered monocyclic or bicyclic heteroaryl having 1-4 heteroatoms independently selected from nitrogen, oxygen, or sulfur. In some embodiments, T is —O—CH$_2$— and R$^z$ is phenyl. In other embodiments, T is a covalent bond and R$^z$ is

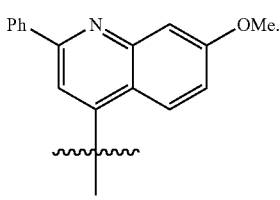

In certain embodiments, T is —OC(O)— and R$^z$ is

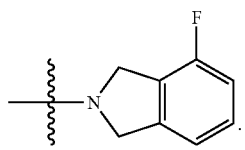

In some embodiments, T is a covalent bond or —O—. In certain embodiments, R$^z$ is

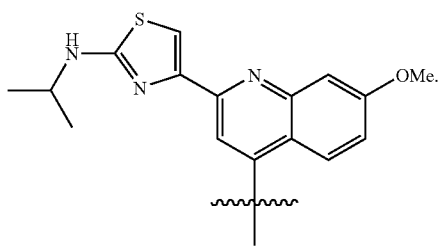

In certain embodiments, R$^z$ is

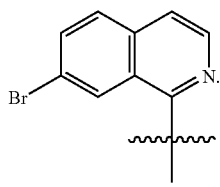

In certain embodiments, R$^z$ is

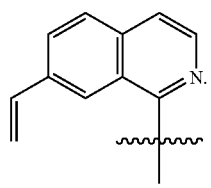

In certain embodiments, R$^z$ is

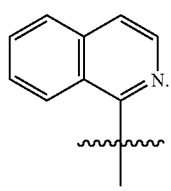

In certain embodiments, R$^z$ is

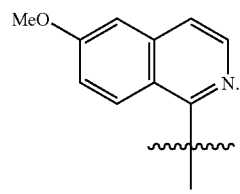

In certain embodiments, the R$^x$ and R$^{x'}$ groups of formula I are taken together to form an optionally substituted spiro-fused 5-7 membered ring having 0-2 heteroatoms independently selected from nitrogen, oxygen, or sulfur. In some embodiments, R$^x$ and R$^{x'}$ are taken together to form a spiro-fused 5-6 membered ring having 1-2 heteroatoms selected from —O— and —S—. In other embodiments, R$^x$ and R$^{x'}$ are taken together to form:

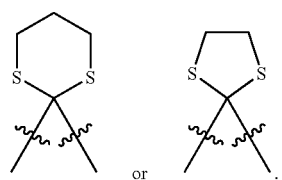

In certain embodiments, the R$^1$ and R$^{1'}$ groups of formula I are independently hydrogen or optionally substituted C$_{1-6}$ aliphatic. In some embodiments, R$^1$ is hydrogen and R$^{1'}$ is C$_{1-4}$ aliphatic. In other embodiments, R$^1$ is hydrogen and R$^{1'}$ is n-propyl.

In certain embodiments, the R$^1$ and R$^{1'}$ groups of formula I are taken together to form an optionally substituted 3-7 membered carbocyclic ring. In some embodiments, the R$^1$ and R$^{1'}$ groups of formula I are taken together to form an optionally substituted cyclopropyl ring. In some embodiments, the R$^1$ and R$^{1'}$ groups of formula I are taken together to form a cyclopropyl ring substituted with ethyl or vinyl.

In some embodiments, R$^4$ is H, —NHC(O)R$^5$, —NHC(O)OR$^6$,

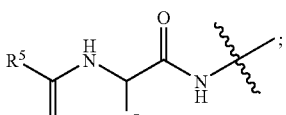

or R$^4$ and R$^x$ are taken together with their intervening atoms to form an optionally substituted, saturated or unsaturated 16-22 membered ring having 2-6 heteroatoms independently selected from nitrogen, oxygen, or sulfur.

In certain embodiments, the R$^4$ group of formula I is —NHC(O)R$^5$. In some embodiments, the R$^4$ group of formula I is —NHC(O)OR$^6$. In other embodiments, the R$^4$ group of formula I is

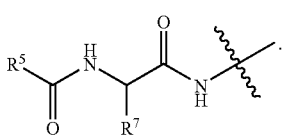

In certain embodiments, the $R^4$ group of formula I is hydrogen.

In some embodiments, when $R^4$ is —NHC(O)$R^5$, $R^5$ is $C_{1-6}$ aliphatic or an optionally substituted group selected from a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In some embodiments, when $R^4$ is —NHC(O)O$R^6$, $R^6$ is $C_{1-6}$ aliphatic or an optionally substituted group selected from a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In some embodiments, the R group of formula I is an amino acid side-chain group. In some embodiments, the $R^4$ group of formula I is an unnatural amino acid side-chain group. In some embodiments, the $R^4$ group of formula I is an aliphatic unnatural amino acid side-chain group. In some embodiments, the $R^4$ group of formula I is an unnatural amino acid side-chain group of alanine substituted with one, two, or three $R^o$ groups, wherein each $R^o$ is as defined above. In some embodiments, the $R^4$ group of formula I is an unnatural amino acid side-chain group of threonine substituted with one, two, or three $R^o$ groups, wherein each $R^o$ is as defined above. In some embodiments, $R^o$ is methyl.

In some embodiments, the $R^4$ group of formula I is a natural amino acid side-chain group.

In certain embodiments, the $R^4$ group of formula I is the natural amino acid side-chain group of alanine (i.e., $R^4$ is methyl). In some embodiments, the $R^4$ group of formula I is the natural amino acid side-chain group of D-alanine. In some embodiments, the $R^4$ group of formula I is the natural amino acid side-chain group of L-alanine.

In other embodiments, the $R^4$ group of formula I is the natural amino acid side-chain group of valine. In some embodiments, the $R^4$ group of formula I is the natural amino acid side-chain group of D-valine. In some embodiments, the $R^4$ group of formula I is the natural amino acid side-chain group of L-valine.

In some embodiments, the $R^4$ group of formula I consists of a mixture of amino acid side-chain groups in both the D- and L-configuration. Such $R^4$ groups are referred to herein as "D,L-mixed amino acid side-chain groups." In some embodiments, the ratio of D- to L-amino acid side-chain groups is selected from any of 6:1, 5:1, 4:1, 3:1, 2:1, 1:1, 1:2, 1:3, 1:4; 1:5, and 1:6. Thus, in certain embodiments, the $R^4$ group of formula I is a D,L-mixed alanine side-chain group. In other embodiments, the $R^4$ group of formula I is a D,L-mixed valine side-chain group.

While not wishing to be bound by any particular theory, it is believed that for compounds of formula I, having an amino acid side-chain group in the D-configuration is useful in allowing a compound to adopt an orientation conducive to binding HCV protease.

In certain embodiments, the $R^5$ and $R^7$ groups of formula I are independently optionally substituted groups selected from optionally substituted group selected from $C_{1-6}$ aliphatic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur. In some embodiments, $R^5$ is an optionally substituted 5-10 membered heteroaryl having 1-4 heteroatoms independently selected from nitrogen, oxygen, or sulfur, and $R^7$ is an optionally substituted $C_{1-6}$ aliphatic group. In some embodiments, $R^5$ is

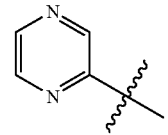

and $R^7$ is cyclohexyl.

In certain embodiments, $R^x$ and $R^{x'}$ are taken together to form an optionally substituted spiro-fused 5-7 membered ring having 0-2 heteroatoms independently selected from nitrogen, oxygen, or sulfur. In some embodiments, $R^x$ and $R^{x'}$ are taken together to form a spiro-fused 5-6 membered ring having 1-2 heteroatoms selected from —O— and —S—. In other embodiments, $R^x$ and $R^{x'}$ are taken together to form:

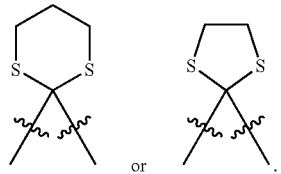

In certain embodiments, the $R^w$ group of formula I is hydrogen or an optionally substituted group selected from $C_{1-6}$ aliphatic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur. In some embodiments, $R^w$ and $R^x$ are taken together to form an optionally substituted $C_{3-7}$ membered ring having 0-2 heteroatoms indepentently selected from nitrogen, oxygen or sulfur. In other embodiments, $R^w$ and $R^y$ are taken together to form an optionally substituted $C_{3-7}$ membered ring having 0-2 heteroatoms indepentently selected from nitrogen, oxygen or sulfur.

In certain embodiments, the $R^w$ group of formula I is hydrogen. In other embodiments, the $R^w$ group of formula I is optionally substituted $C_{1-6}$ aliphatic.

In certain embodiments, the $R^{2a}$ group of formula I is —OH. In other embodiments, the $R^{2a}$ group of formula I is —NHSO$_2$R$^2$, wherein $R^2$ is as defined above and described herein. Thus, the present invention provides a compound of formula I-a or I-b:

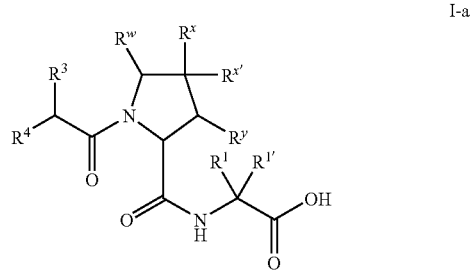

I-a

I-b

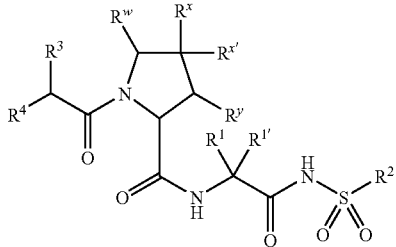

or a pharmaceutically acceptable salt thereof, wherein each of $R^1$, $R^{1'}$, $R^2$, $R^3$, $R^4$, $R^w$, $R^x$, $R^{x'}$, and $R^y$ is as defined above for formula I and described in classes and subclasses above and herein.

In certain embodiments, the $R^2$ group of formula I-b is $-N(R)_2$. In other embodiments, the $R^2$ group of formula I-b is an optionally substituted group selected from $C_{3-7}$ cycloalkyl, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur. In certain embodiments, $R^2$ is $C_{3-7}$ cycloalkyl or 6-10 membered aryl. In some embodiments, $R^2$ is optionally substituted 6-10 membered aryl. In some embodiments, $R^2$ is phenyl. In certain embodiments, $R^2$ is cyclopropyl.

In certain embodiments, $R^2$ is selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the $R^3$ group of formula I is a warhead group. In some embodiments, the $R^3$ and $R^1$ groups of formula I are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group. In some embodiments, $R^3$ and a ring formed by $R^1$ and $R^{1'}$ are taken together with their intervening atoms to form an optionally substituted saturated or unsaturated 12-18 membered ring having 2-6 heteroatoms independently selected from nitrogen oxygen, or sulfur, wherein the ring formed thereby comprises a warhead group.

As defined generally above, the ring formed by the $R^3$ and $R^1$ groups of formula I comprises a warhead group. As used herein, the phrase "comprises a warhead group" means that the ring formed by $R^3$ and $R^1$ is either substituted with a warhead group or has such a warhead group incorporated within the ring. For example, the ring formed by $R^3$ and $R^1$ may be substituted with an -L-Y warhead group, wherein such groups are as described herein. Alternatively, the ring formed by $R^3$ and $R^1$ has the appropriate features of a warhead group incorporated within the ring. For example, the ring formed by $R^3$ and $R^1$ may include one or more units of unsaturation and optional substituents and/or heteroatoms which, in combination, result in a moiety that is capable of covalently modifying HCV protease in accordance with the present invention. In certain embodiments, the ring formed by $R^3$ and $R^1$ is optionally substituted at the α-, β-, γ-, or δ-position with respect to the carbon to which $R^4$ is attached.

It will be appreciated that when $R^3$ and $R^1$ are taken together with their intervening atoms to form an optionally substituted saturated or unsaturated 12-18 membered ring having 2-6 heteroatoms independently selected from nitrogen oxygen, or sulfur, such compounds include those wherein $R^3$ and a ring formed by $R^1$ and and $R^{1'}$ are taken together.

Exemplary compounds of formula I wherein $R^3$ and a ring formed by $R^1$ and $R^{1'}$ are taken together include those of formula I-c-1, I-c-2, I-c-3, I-c-4, I-c-5-, and I-c-6:

I-c-1

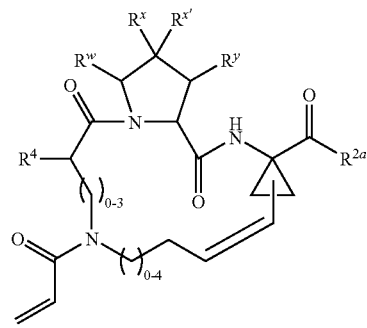

I-c-2

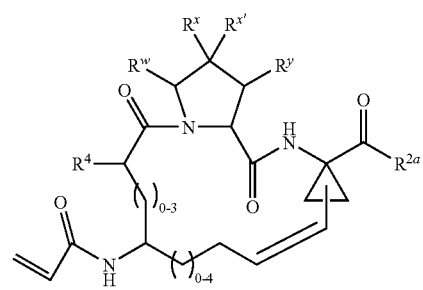

I-c-3

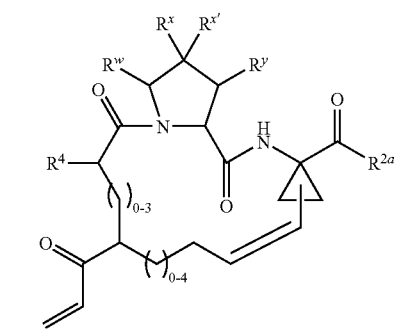

I-c-4

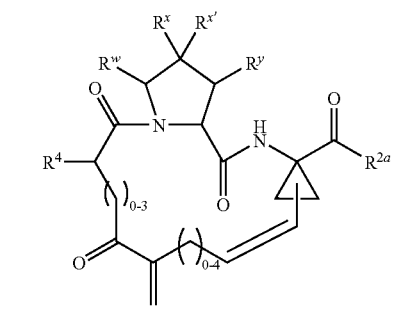

I-c-5

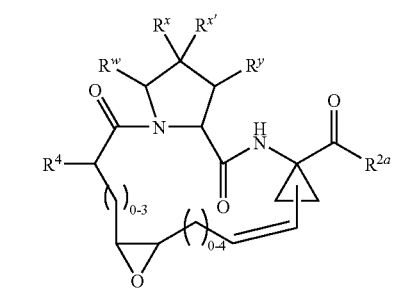

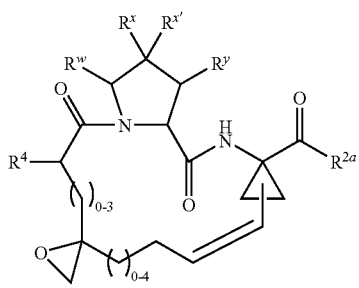

I-c-6 or a pharmaceutically acceptable salt thereof, wherein each of $R^{2a}$, $R^4$, $R^w$, $R^x$, $R^{x'}$, and $R^y$ is as defined above and described in classes and subclasses herein. It will be appreciated that, although formulae I-c-1, I-c-2, I-c-3, I-c-4, I-c-5, and I-c-6 depict a cyclopropyl ring formed by $R^1$ and $R^{1'}$, this group is depicted for the purposes of exemplification and therefore other $R^1$ and $R^{1'}$ groups, as described herein, are contemplated.

Exemplary such compounds include those set forth in Table 3, infra.

While compounds of formulae I-c-1, I-c-2, I-c-3, I-c-4, I-c-5, and I-c-6 are depicted as having (Z)-double bond stereochemistry in the macrocyclic ring, it will be understood that, in certain embodiments, compounds of formulae I-c-1, I-c-2, I-c-3, I-c-4, I-c-5, and I-c-6 may be provided having (E)-double bond stereochemistry in the macrocylic ring. In some embodiments, mixtures of both stereoisomers are provided. In other embodiments, compounds of formulae I-c-1, I-c-2, I-c-3, I-c-4, I-c-5, and I-c-6 may be treated under suitable conditions to saturate the double bond.

In certain embodiments, $R^1$ and $R^{1'}$ are taken together to form an optionally substituted 3-7 membered carbocyclic ring. In some embodiments, such compounds are of formula I-d:

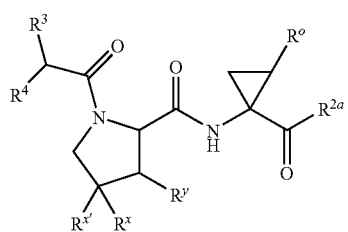

I-d or a pharmaceutically acceptable salt thereto, wherein each $R^{2a}$, $R^3$, $R^4$, $R^o$, $R^x$, $R^{x'}$, and $R^y$ is as defined in formula I and described in classes and subclasses above and herein.

In some embodiments, $R^o$ is an optionally substituted group selected from $C_{1-6}$ aliphatic. In some embodiments, $R^o$ is ethyl. In other embodiments, $R^o$ is vinyl.

Exemplary $R^3$ groups of formula I-d include those described above and herein, as well as those depicted in Table 3, below.

In certain embodiments, $R^4$ and $R^x$ are taken together with their intervening atoms to form an optionally substituted, saturated or unsaturated 16-22 membered ring having 2-6 heteroatoms independently selected from nitrogen, oxygen, or sulfur. In some embodiments, $R^4$ and $R^x$ are taken together with their intervening atoms to form an optionally substituted, unsaturated 18-22 membered ring having 3-5 heteroatoms independently selected from nitrogen, oxygen, or sulfur. In some embodiments, the ring formed by $R^4$ and $R^x$ is substituted with one or more $R^m$ groups, wherein each occurrence of $R^m$ is independently halogen, —$OR^o$; —CN; —SCN; —$SR^o$; —$SOR^o$; —$SO_2R^o$; —$NO_2$; —$N(R^o)_2$; —$NHC(O)R^o$, or an optionally substituted group selected from the group consisting of $C_{1-6}$ aliphatic and $C_{3-7}$ cycloalkyl. In certain embodiments, the present invention provides compounds of formula I-e or I-f:

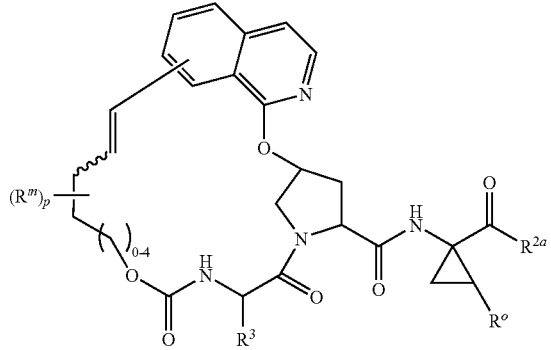

I-e

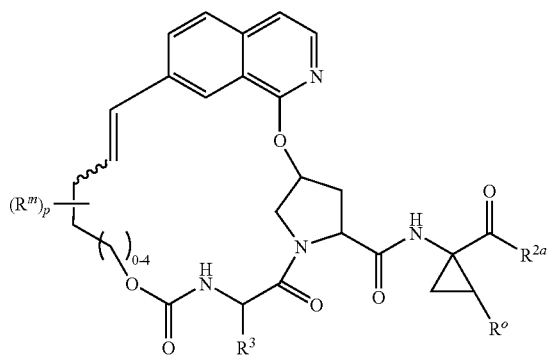

I-f or a pharmaceutically acceptable salt thereof, wherein each $R^{2a}$, $R^3$, and $R^o$ is as defined in formula I and described in classes and subclasses above and herein;

p is an integer from 1 to 6, inclusive; and each occurrence of $R^m$ is independently halogen, —$OR^o$; —CN; —$N(R^o)_2$; or an optionally substituted group selected from the group consisting of $C_{1-6}$ aliphatic and $C_{3-7}$ cycloalkyl.

In some embodiments, p is 1. In some embodiments, p is 2.

In certain embodiments, $R^m$ is $C_{1-6}$ aliphatic. In some embodiments, $R^m$ is methyl.

In some embodiments, $R^o$ is an optionally substituted group selected from $C_{1-6}$ aliphatic. In some embodiments, $R^o$ is ethyl. In other embodiments, $R^o$ is vinyl.

Exemplary $R^3$ groups of formulae I-e and I-f include those described herein and depicted in Table 3, below.

While compounds of formulae I-e and I-f are depicted as having either (Z) or (E) double bond stereochemistry in the macrocyclic ring, it will be understood that, in certain embodiments, compounds of formulae I-e and I-f may be provided having (E)-double bond stereochemistry in the macrocyclic ring. In certain embodiments, compounds of formulae I-e and I-f may be provided having (Z)-double bond stereochemistry in the macrocylic ring. In some embodiments, mixtures of both stereoisomers are provided. In other embodiments, compounds of formulae I-e and I-f may be treated under suitable conditions to saturate the double bond, thereby forming a compound of formula I-g or I-h:

I-g

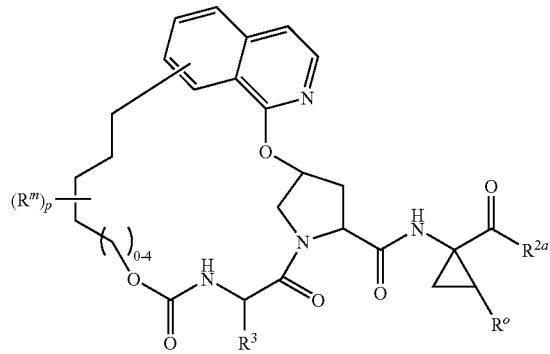

I-h

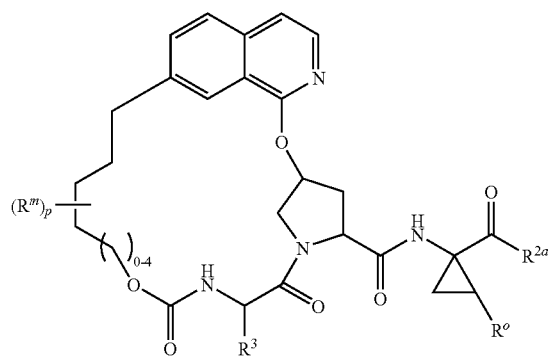

or a pharmaceutically acceptable salt thereof.

In certain embodiments, $R^4$ and $R^x$ are taken together as described above, and $R^3$ and a ring formed by $R^1$ and $R^{1'}$ are taken together as described above, to form novel bismacrocyclic compounds. In certain embodiments, the ring formed by $R^4$ and $R^x$ is substituted with one or more $R^m$ groups as described above for formulae I-e and I-f. In some embodiments, the macrocyclic ring formed by $R^3$ and a ring formed by $R^1$ and $R^{1'}$ is substituted with an -L-Y warhead group to provide a compound of formula I-j or I-k:

I-j

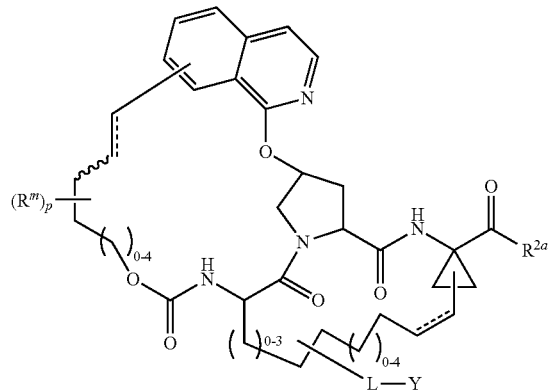

I-k

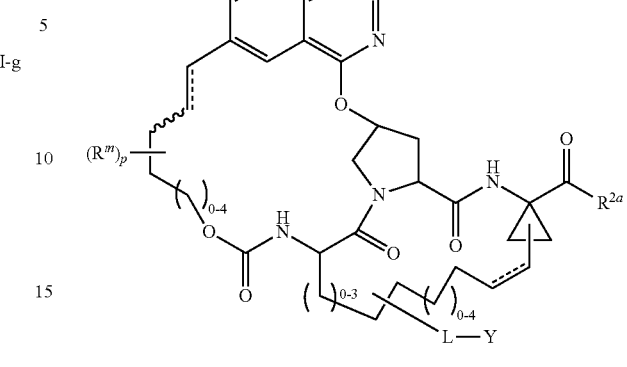

or a pharmaceutically acceptable salt thereof; wherein each ---independently represents a single or double bond. Methods of preparing such compounds, in addition to those described herein for the synthesis of other macrocycles and compounds incorporating a warhead, include those described by McCauley, J. A. et al., *Angew. Chem. Int. Ed.,* 2008, 47, pp. 9104-7.

In some embodiments, a methylene unit of the macrocyclic ring formed by $R^3$ and a ring formed by $R^1$ and $R^{1'}$ is replaced by an L-Y moiety to provide a compound of formula I-m or I-n:

I-m

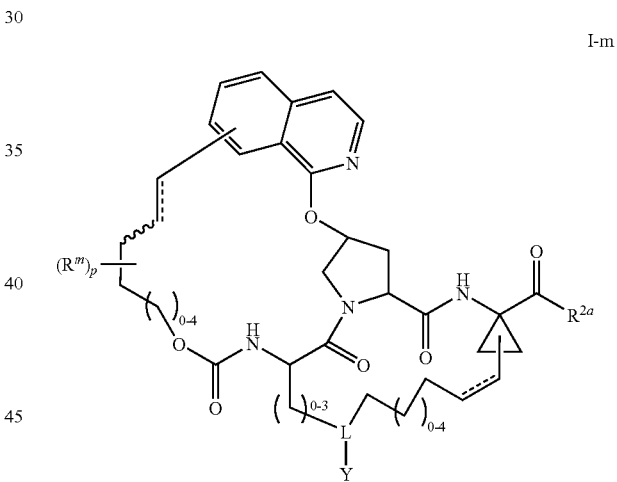

I-n

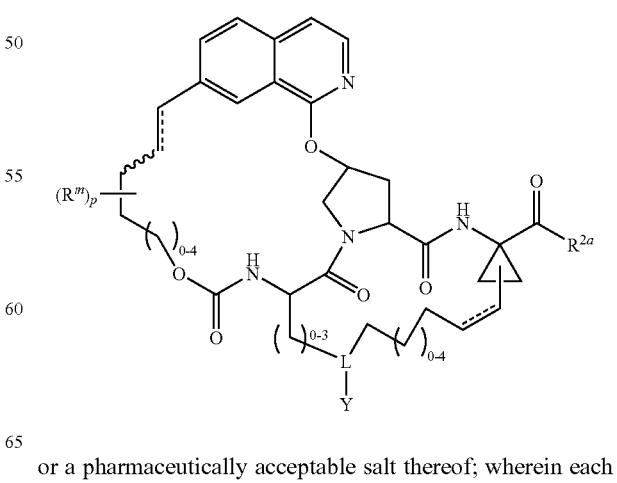

or a pharmaceutically acceptable salt thereof; wherein each ---independently represents a single or double bond.

In certain embodiments, the present invention provides a compound of formula II-a or II-b:

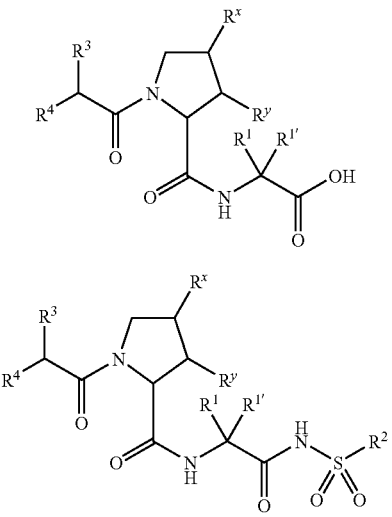

or a pharmaceutically acceptable salt thereof, wherein:
$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
$R^2$ is —$N(R)_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
$R^3$ is a warhead group;
$R^x$ is -T-$R^z$, wherein:
T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and
$R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
$R^y$ is hydrogen or $R^x$ and $R^y$ are taken together to form an optionally substituted $C_{3-7}$ membered carbocycle;
$R^4$ is H, —NHC(O)$R^5$, —NHC(O)O$R^6$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur;
each $R^5$ is independently —$N(R)_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and
$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the present invention provides a compound of formula II-a or II-b, or a pharmaceutically acceptable salt thereof, wherein each of $R^1$, $R^{1'}$, $R^2$, $R^3$, $R^4$, $R^x$, and $R^y$ is as defined above and wherein:
$R^3$ is -L-Y, wherein:
L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;
Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and
each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:
Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and
Z is hydrogen or $C_{1-6}$ aliphatic optionally substituted with oxo, halogen, NO$_2$, or CN.

In certain embodiments, the $R^1$, $R^{1'}$, $R^2$, $R^3$, $R^4$, $R^x$, and $R^y$ groups of formulae II-a and II-b are as described above for formula I and described in classes and subclasses above and herein.

In some embodiments, the $R^1$ and $R^{1'}$ groups of formulae II-a and II-b are taken together to form an optionally substituted 3-7 membered carbocyclic ring. In other embodiments, $R^1$ and $R^{1'}$ are taken together to form an optionally substituted cyclopropyl ring.

In certain embodiments, the $R^2$ group of formula II-b is —$N(R)_2$ or an optionally substituted group selected from $C_{3-7}$ cycloalkyl or 6-10 membered aryl. In some embodiments, $R^2$ is —$N(R)_2$ or an optionally substituted group selected from $C_{3-5}$ cycloalkyl or 6-8 membered aryl. In some embodiments, $R^2$ is —$N(R)_2$ and R is methyl. In some embodiments, $R^2$ is cyclopropyl. In other embodiments, $R^2$ is phenyl.

In certain embodiments, the $R^x$ groups of formulae II-a and II-b is -T-$R^z$, T is a covalent bond or a $C_{1-6}$ bivalent hydrocarbon chain wherein one or two methylene units of T are optionally and independently replaced by —O—, and $R^z$ is an optionally substituted group selected from 6-10 membered monocyclic or bicyclic aryl, 5-10 membered monocyclic or bicyclic heteroaryl having 1-4 heteroatoms independently selected from nitrogen, oxygen, or sulfur. In some embodiments, T is —CH$_2$— and R$^z$ is phenyl. In other embodiments, T is a covalent bond and R$^z$ is

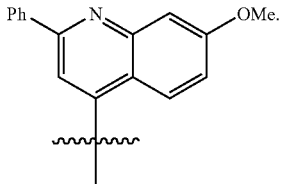

In some embodiments, T is a covalent bond or is —O—. In certain embodiments, R$^z$ is

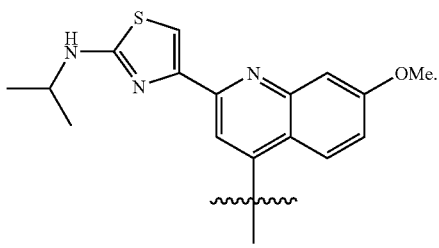

In certain embodiments, R$^z$ is

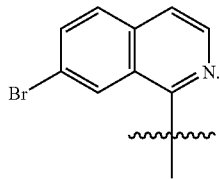

In certain embodiments, R$^z$ is

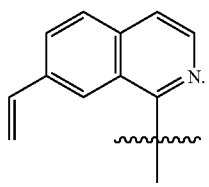

In certain embodiments, R$^z$ is

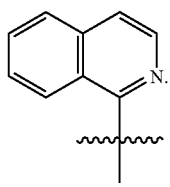

In certain embodiments, R$^z$ is

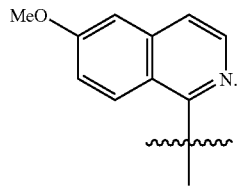

In certain embodiments, the R$^4$ group of formulae II-a and II-b is —NHC(O)OR$^6$, wherein R$^6$ is an optionally substituted group selected from C$_{1-6}$ aliphatic. In some embodiments, R$^6$ is cyclopentyl. In other embodiments, R$^6$ is t-butyl.

In certain embodiments, R$^4$ is —NHC(O)R$^5$, wherein R$^5$ is independently —N(R)$_2$ or an optionally substituted group selected from C$_{1-6}$ aliphatic. In some embodiments, R$^5$ is —N(R)$_2$ and each R is independently hydrogen or optionally substituted C$_{1-6}$ aliphatic. In some embodiments, R$^5$ is —N(R)$_2$ and each R is independently hydrogen or t-butyl.

In certain embodiments, the present invention provides a compound of formula III-a or III-b:

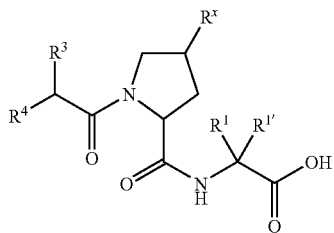

III-a

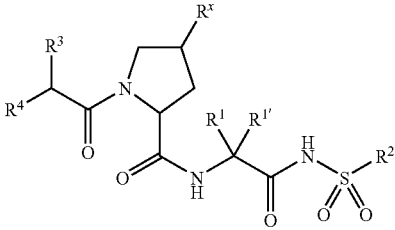

III-b or a pharmaceutically acceptable salt thereof, wherein:
R$^1$ and R$^{1'}$ are independently hydrogen or optionally substituted C$_{1-6}$ aliphatic, or R$^1$ and R$^{1'}$ are taken together to form an optionally substituted 3-7 membered carbocyclic ring;
R$^2$ is —N(R)$_2$ or an optionally substituted group selected from C$_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted C$_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
R$^3$ is a warhead group;
R$^x$ is -T-R$^z$, wherein:
T is a covalent bond or a C$_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and R$^z$ is hydrogen or an optionally substituted group selected from C$_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

R$^4$ is H, —NHC(O)OR$^6$, a natural or unnatural amino acid side-chain group; or R$^4$ and R$^x$ are taken together with their intervening atoms to form an optionally substituted, saturated or unsaturated 16-22 membered ring having 2-6 heteroatoms independently selected from nitrogen, oxygen, or sulfur; and R$^6$ is an optionally substituted group selected from C$_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the present invention provides a compound of formula III-a or III-b or a pharmaceutically acceptable salt thereof, wherein each of R$^1$, R$^{1'}$, R$^2$, R$^3$, R$^4$, and R$^x$ is as defined above and wherein:

R$^3$ is -L-Y, wherein:
L is a covalent bond or a bivalent C$_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, C$_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and each R$^e$ is independently selected from -Q-Z, oxo, NO$_2$, halogen, CN, a suitable leaving group, or a C$_{1-6}$ aliphatic optionally substituted with oxo, halogen, NO$_2$, or CN, wherein:
Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and
Z is hydrogen or C$_{1-6}$ aliphatic optionally substituted with oxo, halogen, NO$_2$, or CN.

In certain embodiments, each of the R$^1$, R$^{1'}$, R$^2$, R$^3$, R$^4$, and R, groups of formulae III-a and III-b is as described above and described in classes and subclasses above and herein.

In certain embodiments, the R$^2$ group of formula III-b is —N(R)$_2$ or an optionally substituted group selected from C$_{3-7}$ cycloalkyl or 6-10 membered aryl. In some embodiments, R$^2$ is —N(R)$_2$ or an optionally substituted group selected from C$_{3-5}$ cycloalkyl or 6-8 membered aryl. In some embodiments, R$^2$ is —N(R)$_2$ and R is methyl. In some embodiments, R$^2$ is cyclopropyl.

In certain embodiments, the R$^x$ group of formulae III-a and III-b is -T-R$^z$, T is a covalent bond or a C$_{1-6}$ bivalent hydrocarbon chain wherein one or two methylene units of T are optionally and independently replaced by —O—, and R$^z$ is an optionally substituted group selected from 6-10 membered monocyclic or bicyclic aryl, 5-10 membered monocyclic or bicyclic heteroaryl having 1-4 heteroatoms independently selected from nitrogen, oxygen, or sulfur. In some embodiments, T is —CH$_2$— and R$^z$ is phenyl. In other embodiments, T is a covalent bond and R$^z$ is

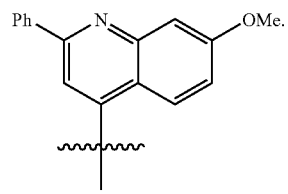

In some embodiments, T is a covalent bond or is —O—. In certain embodiments, R$^z$ is

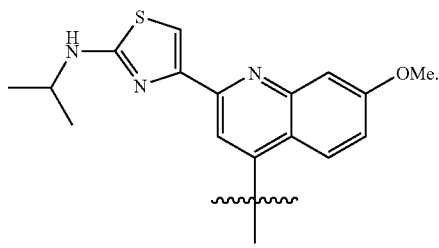

In certain embodiments, R$^z$ is

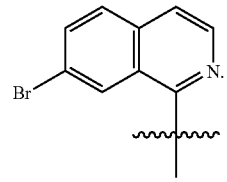

In certain embodiments, R$^z$ is

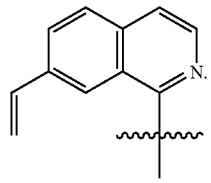

In certain embodiments, R$^z$ is

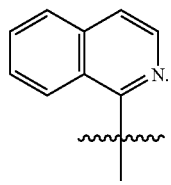

In certain embodiments, $R^z$ is

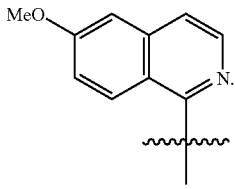

In certain embodiments, the $R^4$ group of formulae III-a and III-b is —NHC(O)OR$^6$, wherein $R^6$ is an optionally substituted group selected from $C_{1-6}$ aliphatic. In some embodiments, $R^6$ is cyclopentyl. In other embodiments, $R^6$ is t-butyl.

In certain embodiments, the present invention provides a compound of formula IV-a or IV-b:

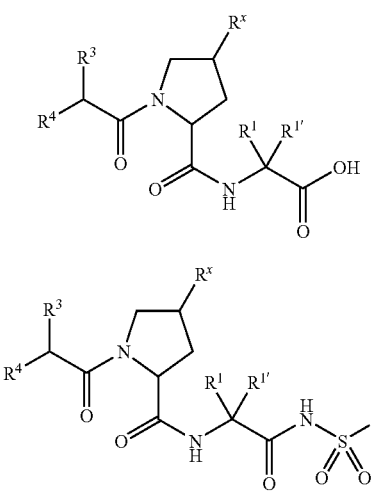

or a pharmaceutically acceptable salt thereof, wherein:
$R^1$ and $R^{1'}$ are taken together to form an optionally substituted 3-7 membered carbocyclic ring;
$R^2$ is an optionally substituted group selected from $C_{3-7}$ cycloalkyl, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
$R^3$ is a warhead group;
$R^x$ is -T-$R^z$, wherein:
T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and
$R^z$ is an optionally substituted group selected from 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
$R^4$ is H, —NHC(O)OR$^6$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur; and $R^6$ is an optionally substituted group selected from $C_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the present invention provides a compound of formula IV-a or IV-b or a pharmaceutically acceptable salt thereof, wherein each of $R^1$, $R^{1'}$, $R^2$, $R^3$, $R^4$, and $R^x$ is as defined above and wherein:
L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;
Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and
each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:
Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and
Z is hydrogen or $C_{1-6}$ aliphatic optionally substituted with oxo, halogen, NO$_2$, or CN.

In certain embodiments, each of the $R^1$, $R^{1'}$, $R^2$, $R^3$, $R^4$, and $R^x$ groups of formula IV is as described above for formula I and in classes and subclasses above and herein.

In certain embodiments, the $R^1$ and $R^{1'}$ groups of formulae IV-a and IV-b are taken together to form an optionally substituted 3-7 membered carbocyclic ring. In some embodiments, such compounds are of formula IV-c and IV-d:

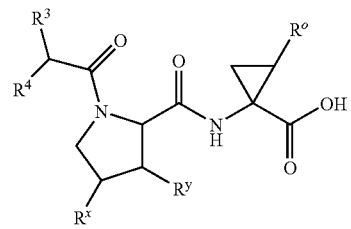

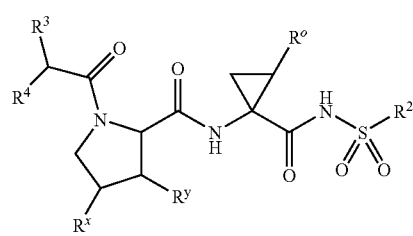

or a pharmaceutically acceptable salt thereof, wherein each of $R^2$, $R^3$, $R^4$, $R^x$, $R^y$, and $R^o$ is described above for formulae IV-a and IV-b and described in classes and subclasses above and herein.

In some embodiments, $R^o$ is an optionally substituted group selected from $C_{1-6}$ aliphatic. In some embodiments, $R^o$ is ethyl. In other embodiments, $R^o$ is vinyl.

As generally defined above in formulae IV-a and IV-b, $R^4$ is —NHC(O)OR$^6$. In some embodiments, $R^6$ is an optionally substituted group selected from $C_{1-6}$ aliphatic or 6-10 membered aryl. In other embodiments, $R^6$ is $C_{1-4}$ aliphatic. In other embodiments, $R^6$ is t-butyl.

In certain embodiments, the present invention provides a compound of formula V-a and V-b:

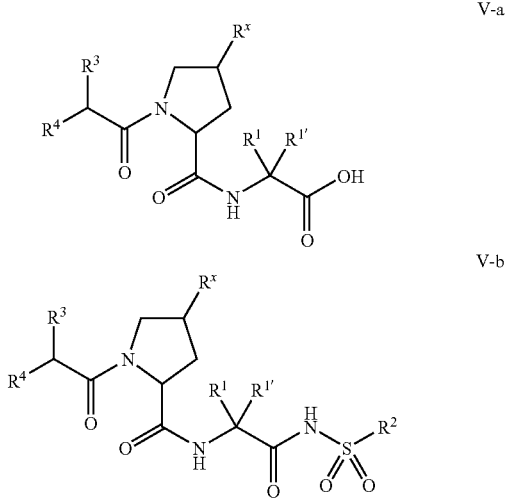

or a pharmaceutically acceptable salt thereof, wherein:

$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;

$R^2$ is —N(R)$_2$;

each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;

$R^3$ is a warhead group;

$R^x$ is -T-R$^z$, wherein:
T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and $R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^4$ is H, —NHC(O)OR$^6$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur; and $R^6$ is an optionally substituted group selected from $C_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the present invention provides a compound of formula V-a or V-b, or a pharmaceutically acceptable salt thereof, wherein each of $R^1$, $R^{1'}$, $R^2$, $R^3$, $R^4$, and $R^x$ is as defined above and wherein:

$R^3$ is -L-Y, wherein:
L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and each R$^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN.

In certain embodiments, the $R^1$, $R^{1'}$, $R^2$, $R^3$, $R^4$, and $R^x$ groups of formulae V-a and V-b are as described above and in classes and subclasses above and herein.

In certain embodiments, the $R^1$ and $R^{1'}$ groups of formula V are taken together to form an optionally substituted 3-7 membered carbocyclic ring. In some embodiments, such compounds are of formula V-c and V-d:

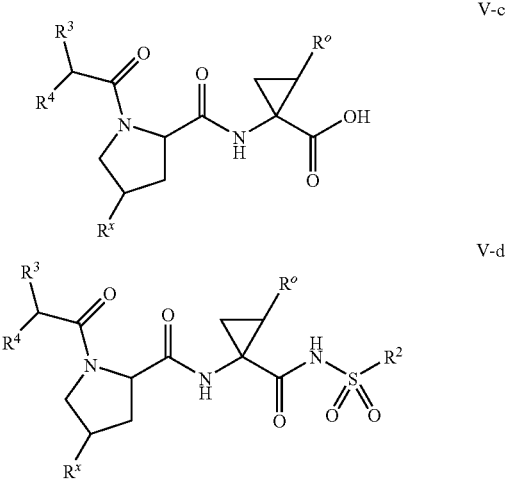

or a pharmaceutically acceptable salt thereof, wherein each of $R^2$, $R^3$, $R^4$, $R^o$, and $R^x$ are defined in formulae V-a and V-b and described in classes and subclasses above and herein.

In some embodiments, $R^o$ is an optionally substituted group selected from $C_{1-6}$ aliphatic. In other embodiments, $R^o$ is vinyl.

As generally defined in formulae V-a and V-b, $R^4$ is —NHC(O)$OR^6$. In certain embodiments, $R^6$ is an optionally substituted group selected from $C_{1-6}$ aliphatic. In some embodiments, $R^6$ is cyclopentyl.

As generally defined in formulae V-a and V-b, $R^2$ is —N(R)$_2$, wherein each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur. In certain embodiments, R is optionally substituted $C_{2-4}$ aliphatic. In some embodiments, R is methyl.

In certain embodiments, the present invention provides a compound of formula VI-a or VI-b:

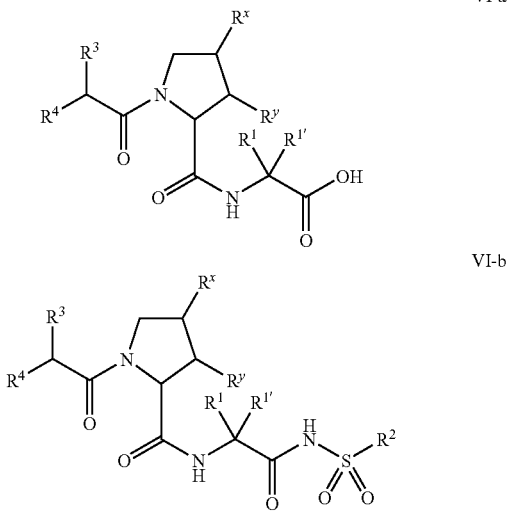

VI-a

VI-b or a pharmaceutically acceptable salt thereof, wherein:
$R^1$ and $R^{1'}$ are taken together to form an optionally substituted 3-7 membered carbocyclic ring;
$R^2$ is an optionally substituted group selected from $C_{3-7}$ cycloalkyl, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
$R^3$ is a warhead group;
$R^x$ and $R^y$ are taken together to form an optionally substituted $C_{3-7}$ membered carbocycle;
$R^4$ is H, —NHC(O)$R^5$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur; and
$R^5$ is —N(R)$_2$.

In certain embodiments, the present invention provides a compound of formula VI-a or VI-b, or a pharmaceutically acceptable salt thereof, wherein each of $R^2$, $R^3$, $R^4$, $R^x$, and $R^y$ are defined above and wherein:
$R^3$ is -L-Y, wherein:
  L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;
  Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and
  each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:
    Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and
    Z is hydrogen or $C_{1-6}$ aliphatic optionally substituted with oxo, halogen, NO$_2$, or CN.

In certain embodiments, the $R^1$, $R^{1'}$, $R^2$, $R^3$, $R^4$, $R^x$, and $R^y$ groups of formula VI are as described above for formula I and in classes and subclasses above and herein.

As defined generally for formulae VI-a and VI-b, $R^4$ is —NHC(O)$R^5$ and $R^5$ is —N(R)$_2$, wherein each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;

In certain embodiments, each R is independently hydrogen or optionally substituted $C_{1-6}$ aliphatic. In other embodiments, each R is independently hydrogen t-butyl.

In certain embodiments, the present invention provides a compound of formula VII-a or VII-b:

VII-a

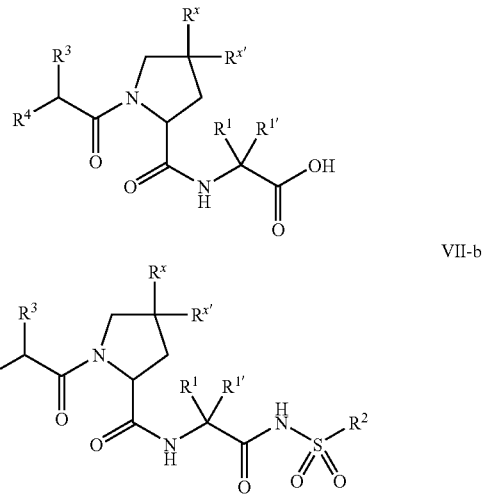

VII-b or a pharmaceutically acceptable salt thereof, wherein:
$R^1$ and $R^{1'}$ are independently hydrogen or optionally substituted $C_{1-6}$ aliphatic;
$R^2$ is an optionally substituted group selected from $C_{3-7}$ cycloalkyl, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;

R$^3$ is a warhead group;

R$^{x'}$ and R$^x$ are taken together with their intervening atoms to form an optionally substituted spiro-fused 5-7 membered ring having 0-2 heteroatoms independently selected from nitrogen, oxygen, or sulfur;

R$^4$ is H,

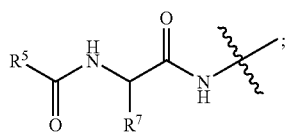

a natural or unnatural amino acid side-chain group; or R$^4$ and R$^x$ are taken together with their intervening atoms to form an optionally substituted, saturated or unsaturated 16-22 membered ring having 2-6 heteroatoms independently selected from nitrogen, oxygen, or sulfur;

R$^5$ is an optionally substituted group selected from C$_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and R$^7$ is an optionally substituted group selected from C$_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

In certain embodiments, the present invention provides a compound of formula VII-a or VII-b, or a pharmaceutically acceptable salt thereof, wherein each of R$^1$, R$^{1'}$, R$^2$, R$^3$, R$^4$, R$^x$, and R$^{x'}$ are defined above and wherein:

R$^3$ is -L-Y, wherein:

L is a covalent bond or a bivalent C$_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)—O—, —S—, —SO—, —SO$_2$—, —C(=S)—, —C(=NR)—, —N=N—, or —C(=N$_2$)—;

Y is hydrogen, C$_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and each R$^e$ is independently selected from -Q-Z, oxo, NO$_2$, halogen, CN, a suitable leaving group, or a C$_{1-6}$ aliphatic optionally substituted with oxo, halogen, NO$_2$, or CN, wherein:

Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or C$_{1-6}$ aliphatic optionally substituted with oxo, halogen, NO$_2$, or CN.

In certain embodiments, the R$^1$, R$^{1'}$, R$^2$, R$^3$, R$^x$, and R$^{x'}$ groups of formulae VII-a and VII-b are as described above for formula I and in classes and subclasses above and herein.

In certain embodiments, the R$^5$ group of formulae VII-a and VII-b is an optionally substituted 5-10 membered heteroaryl ring having 1-4 heteroatoms independently selected from nitrogen, oxygen, or sulfur. In some embodiments, R$^5$ is an optionally substituted 6 membered heteroaryl ring having 1-2 nitrogens. In certain embodiments, R$^5$ is piperazinyl.

In certain embodiments, the R$^7$ group of formulae VII-a and VII-b is an optionally substituted C$_{1-6}$ aliphatic group. In some embodiments, R$^7$ is a branched C$_{1-5}$ alkyl group. In other embodiments, R$^7$ is cyclopentyl or cyclohexyl.

In certain embodiments, the R$^x$ and R$^{x'}$ groups of formulae VII-a and VII-b are taken together to form an optionally substituted spiro-fused 5-7 membered ring having 0-2 heteroatoms independently selected from nitrogen, oxygen, or sulfur. In some embodiments, R$^x$ and R$^{x'}$ are taken together to form a spiro-fused 5-6 membered ring having 1-2 heteroatoms selected from —O— and —S—. In other embodiments, R$^x$ and R$^{x'}$ are taken together to form:

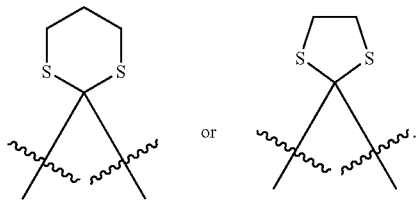

As described above and herein, in certain embodiments, the R$^4$ group for compounds of formula I is hydrogen. In certain embodiments, the present invention provides a compound of formula VIII-a or VIII-b:

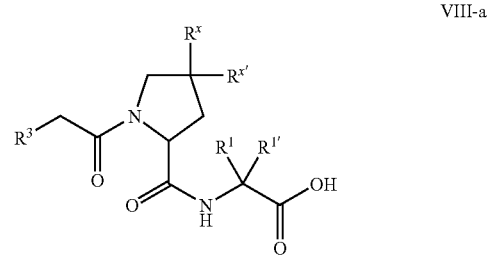

VIII-a

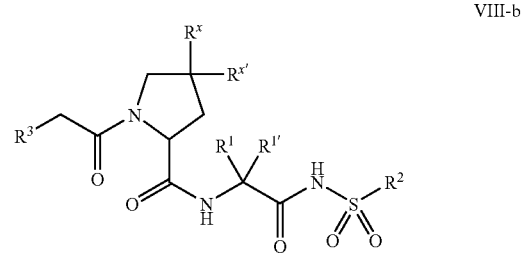

VIII-b wherein each of the R$^1$, R$^{1'}$, R$^2$, R$^3$, R$^x$, and R$^{x'}$ groups is as defined for formula I above and described in classes and subclasses herein.

Exemplary compounds of formula I are set forth in Table 3 below.
TABLE 3
Exemplary Compounds of Formula I
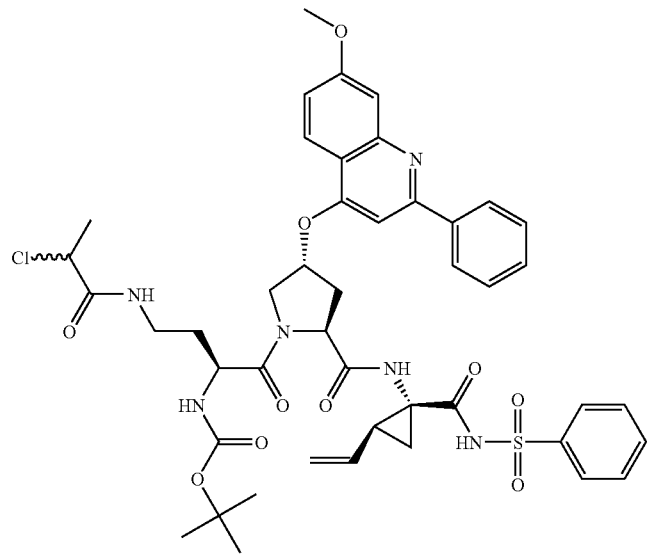
I-1
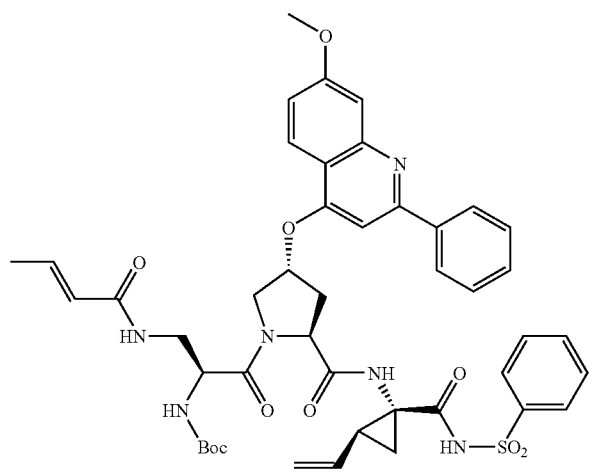
I-2

TABLE 3-continued
Exemplary Compounds of Formula I
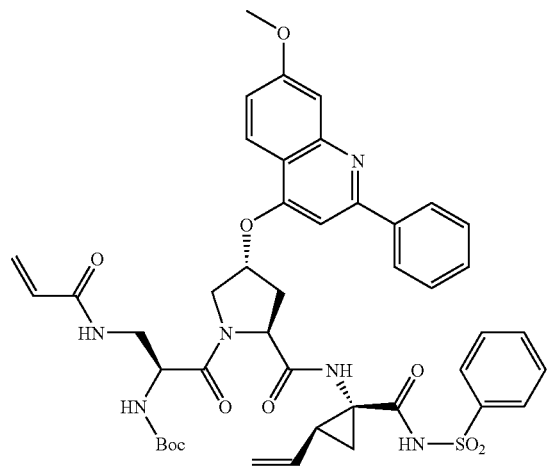
I-3
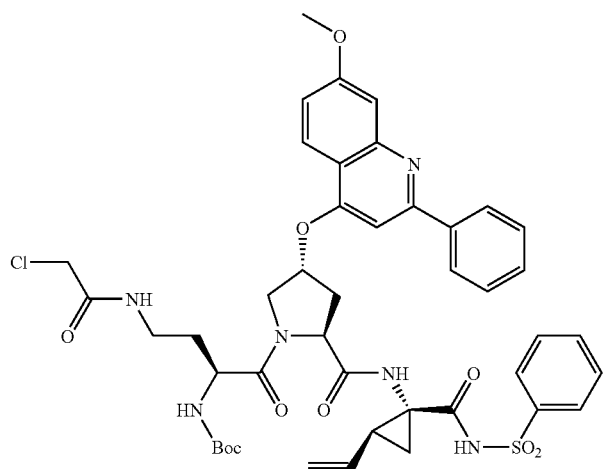
I-4
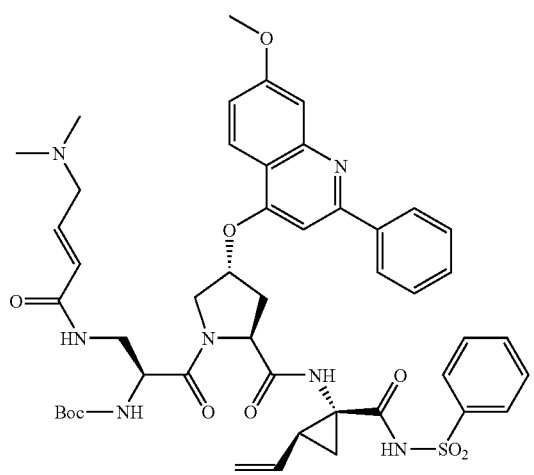
I-5

TABLE 3-continued
Exemplary Compounds of Formula I
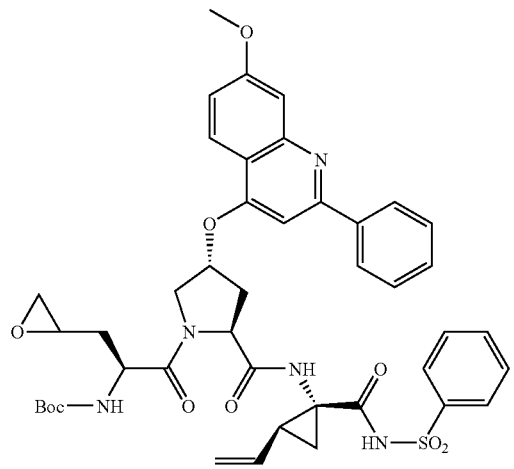
I-6
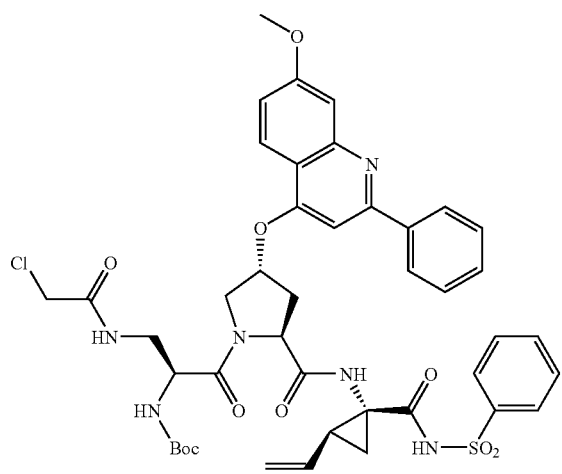
I-7
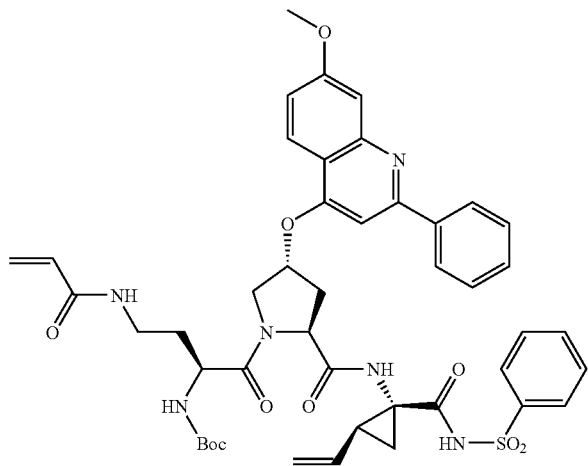
I-8

TABLE 3-continued
Exemplary Compounds of Formula I
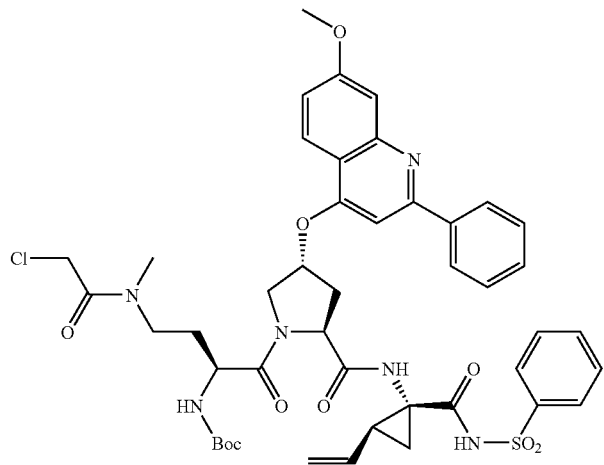
I-9
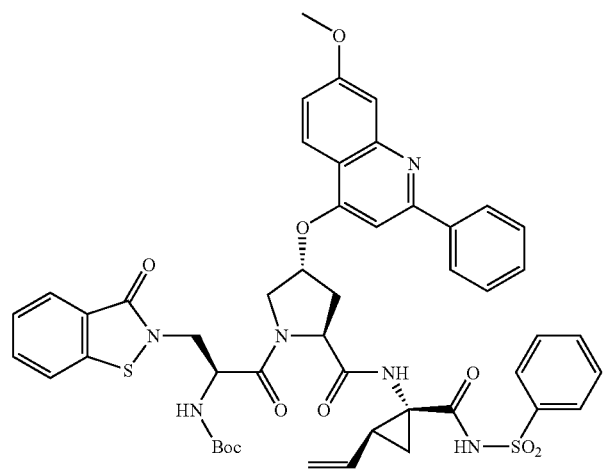
I-10
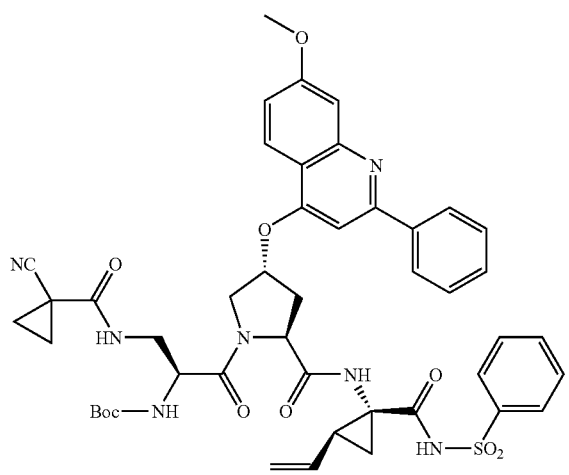
I-11

TABLE 3-continued
Exemplary Compounds of Formula I
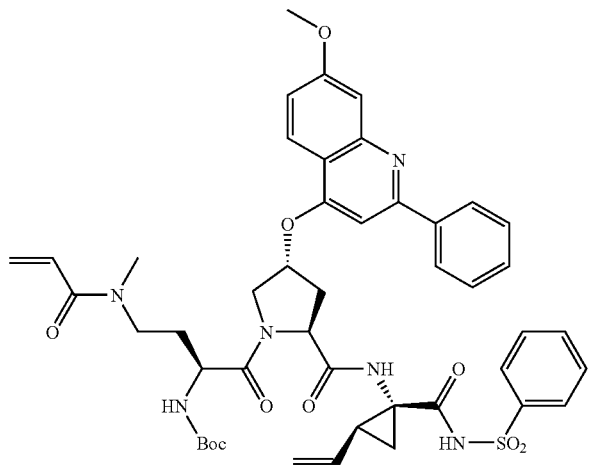
I-12
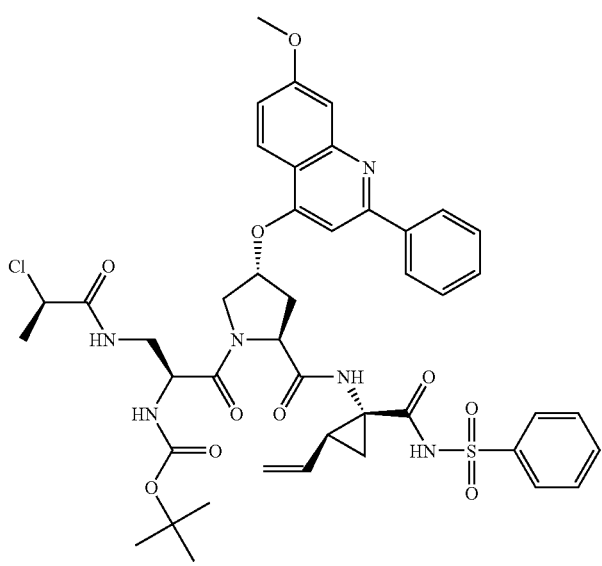
I-13
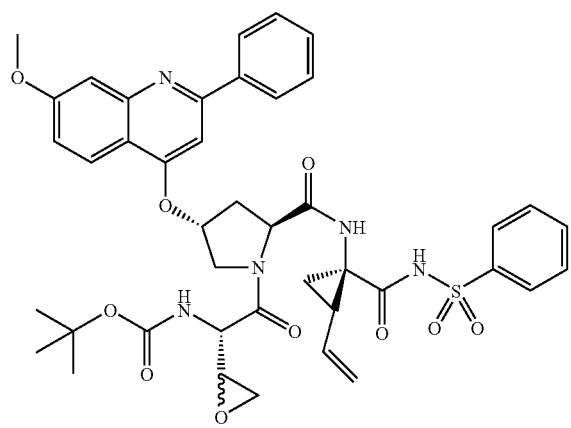
I-14

TABLE 3-continued
Exemplary Compounds of Formula I
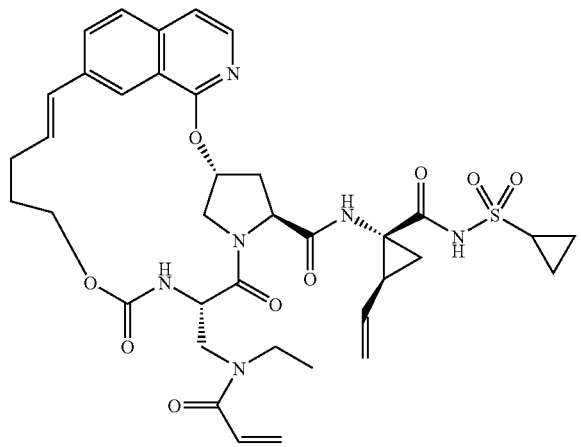
I-15
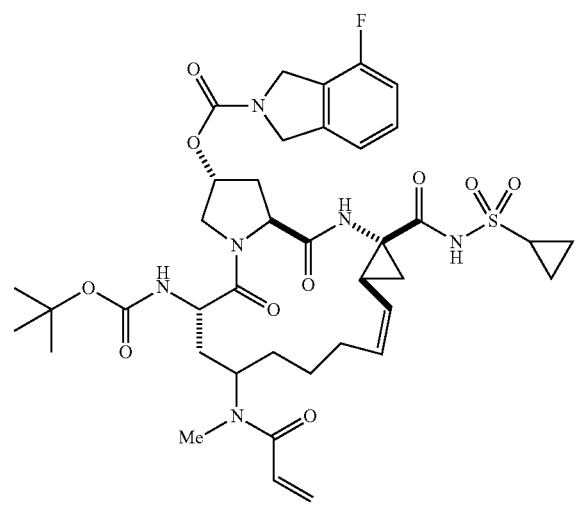
I-16
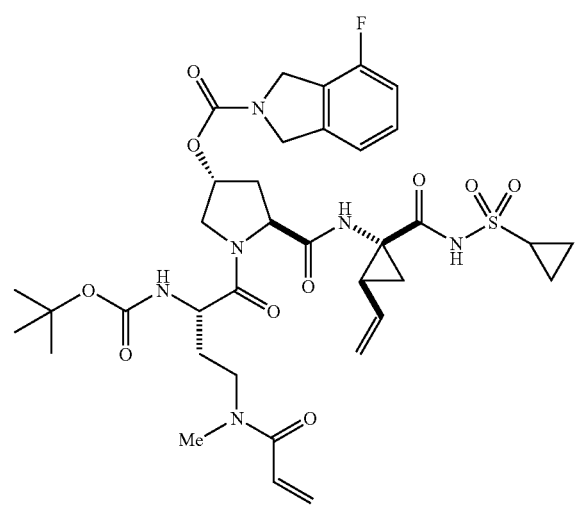
I-17

TABLE 3-continued
Exemplary Compounds of Formula I
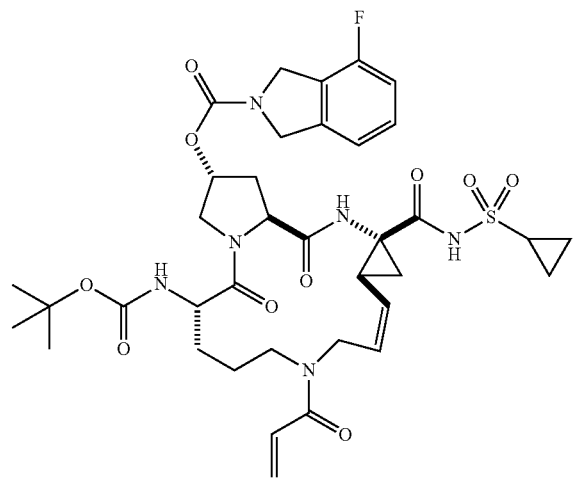
I-18
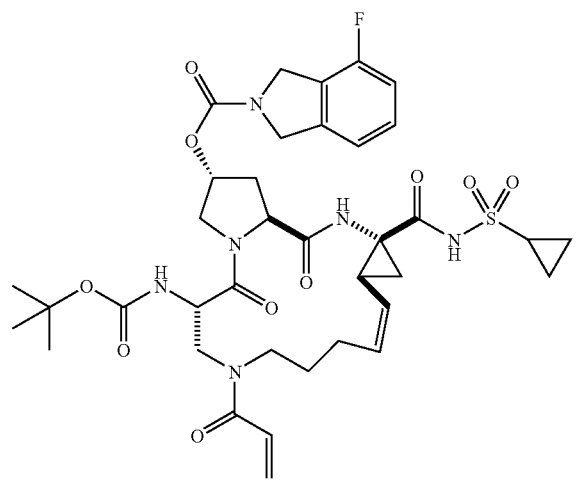
I-19

TABLE 3-continued
Exemplary Compounds of Formula I
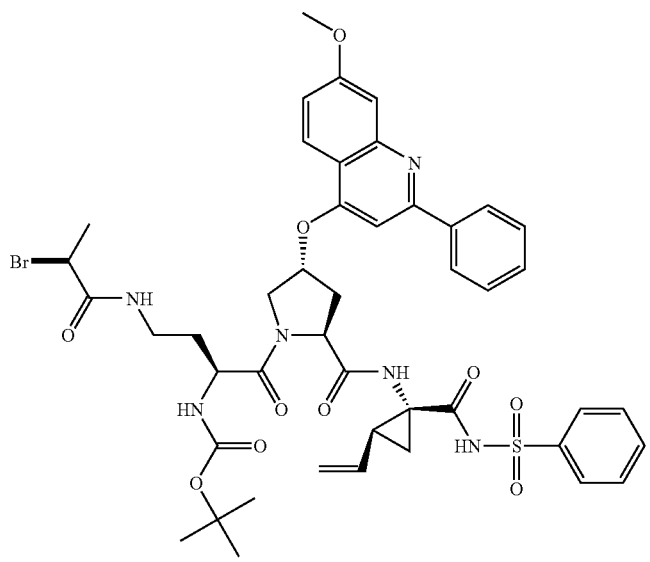
I-20
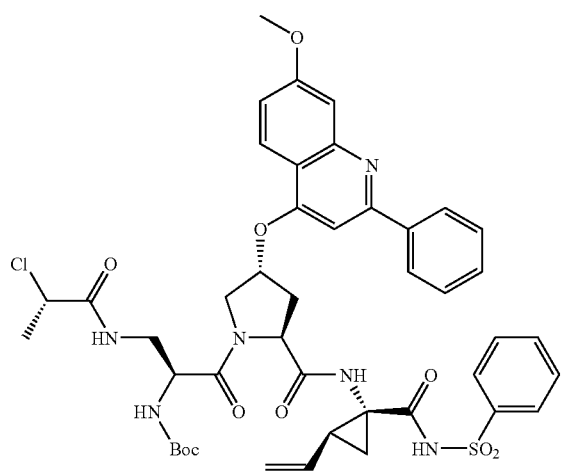
I-21

TABLE 3-continued
Exemplary Compounds of Formula I
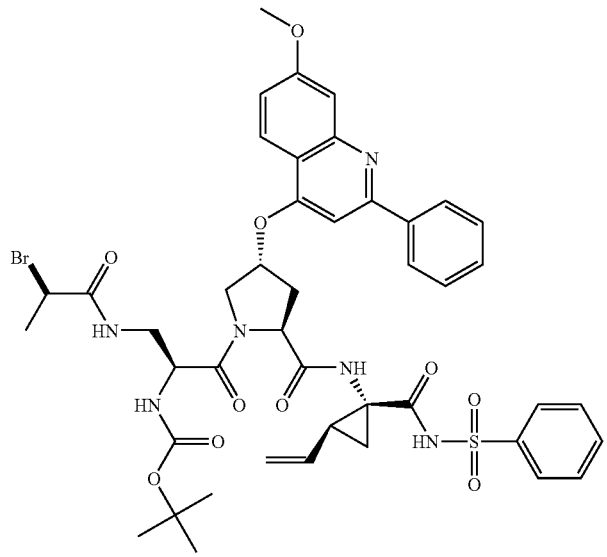
I-22
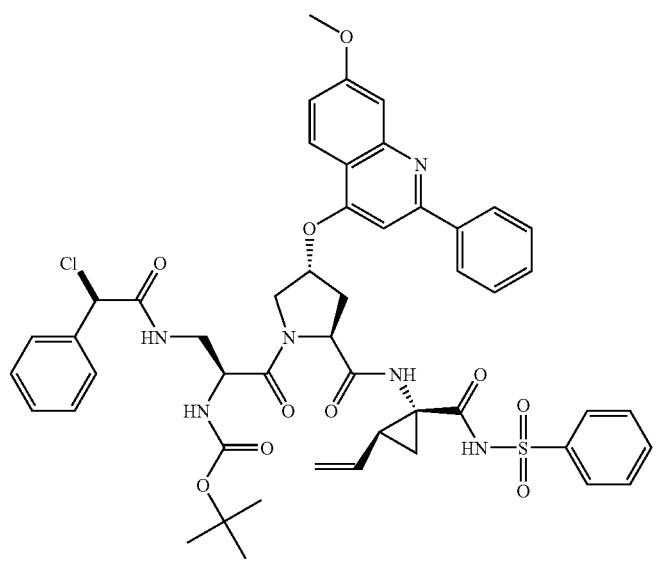
I-23

TABLE 3-continued
Exemplary Compounds of Formula I
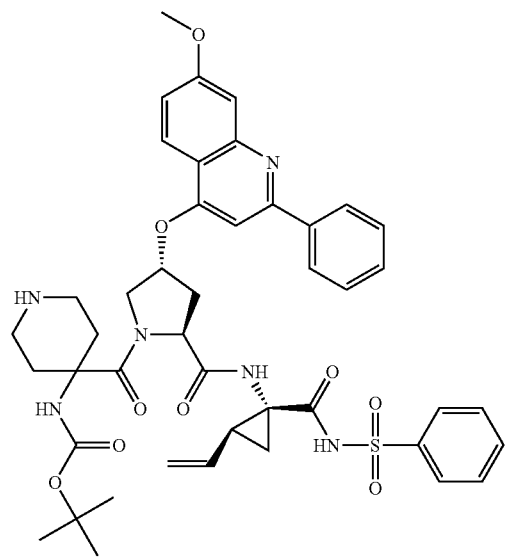
I-24
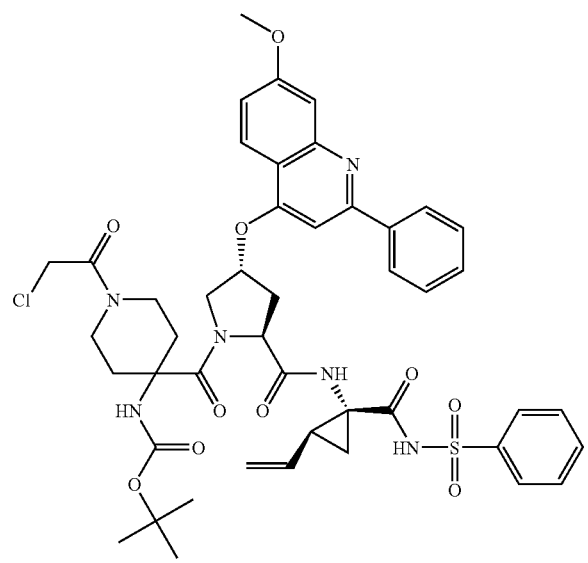
I-25

TABLE 3-continued
Exemplary Compounds of Formula I
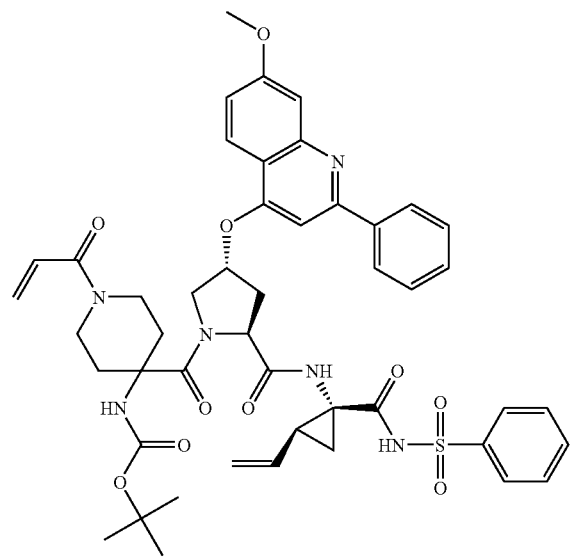
I-26
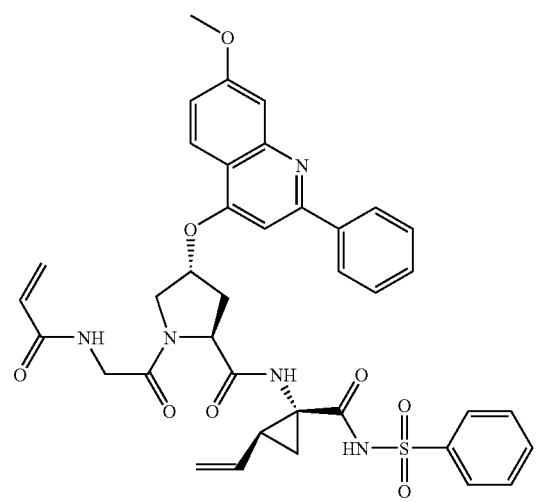
I-27

TABLE 3-continued
Exemplary Compounds of Formula I
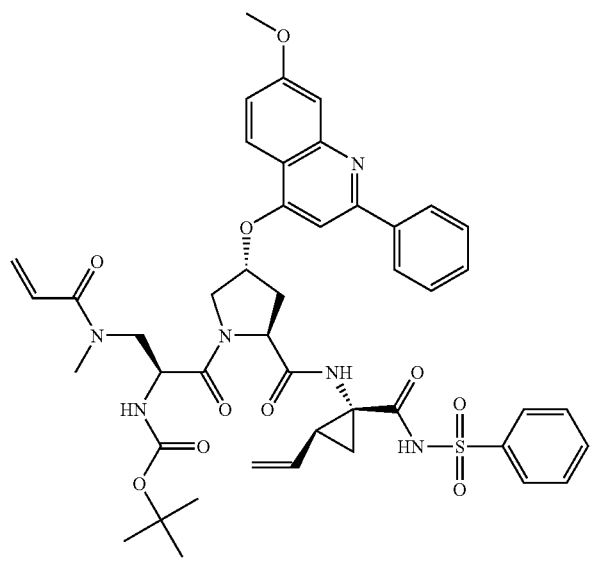
I-28
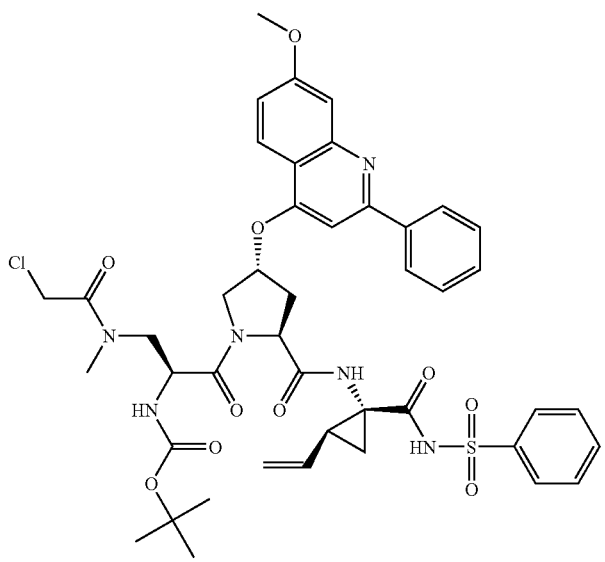
I-29

TABLE 3-continued
Exemplary Compounds of Formula I
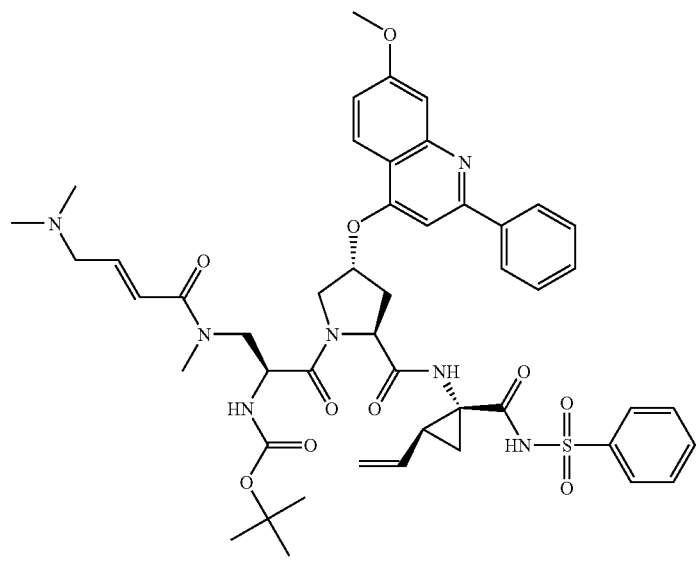
I-30
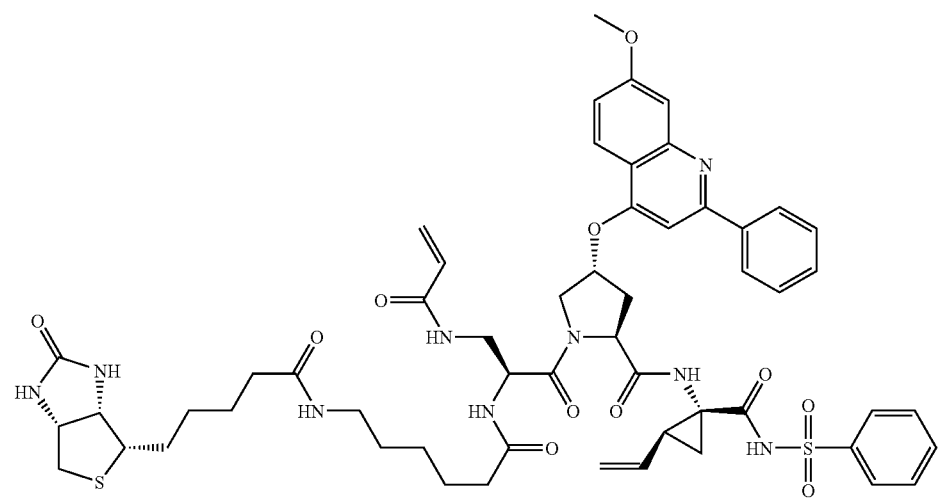
I-31

TABLE 3-continued
Exemplary Compounds of Formula I
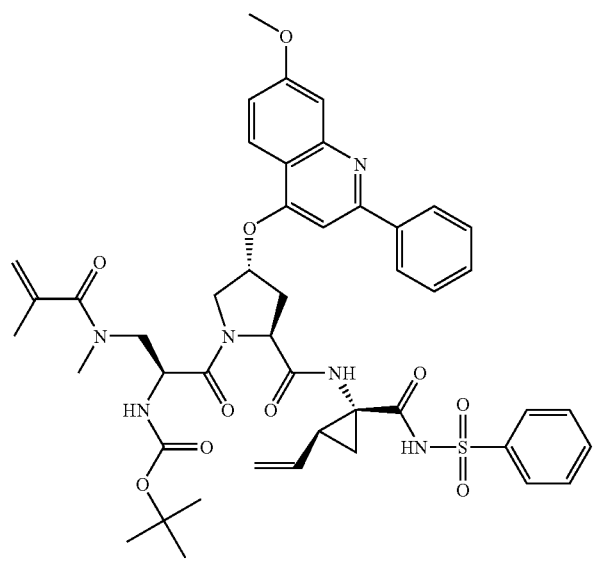
I-32
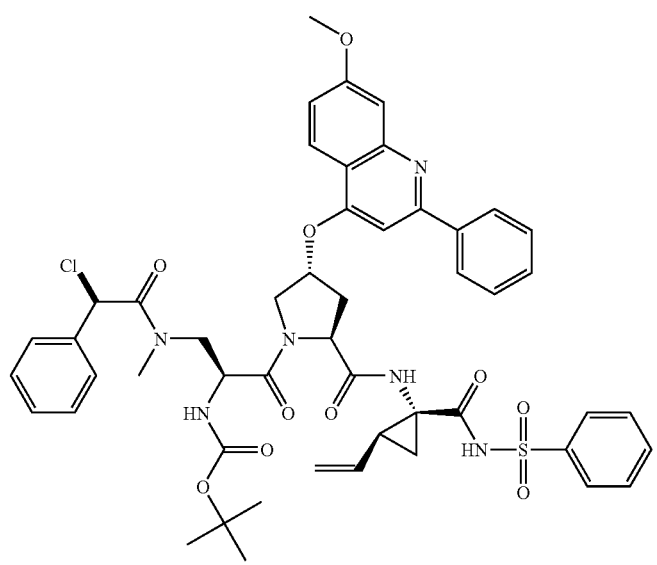
I-33

TABLE 3-continued
Exemplary Compounds of Formula I
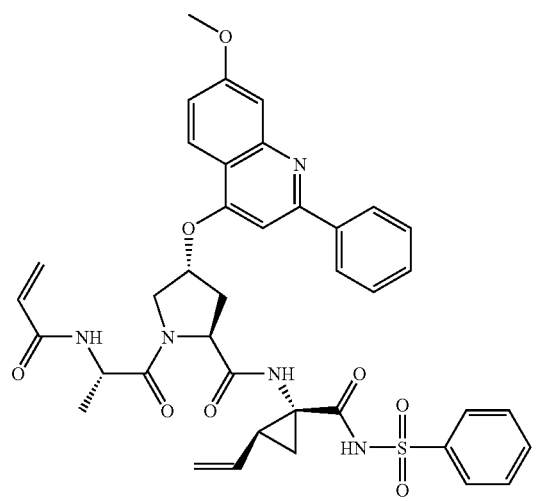
I-34
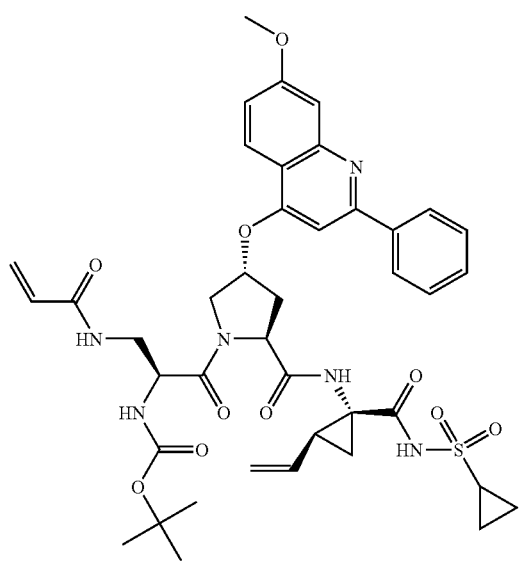
I-35

TABLE 3-continued
Exemplary Compounds of Formula I
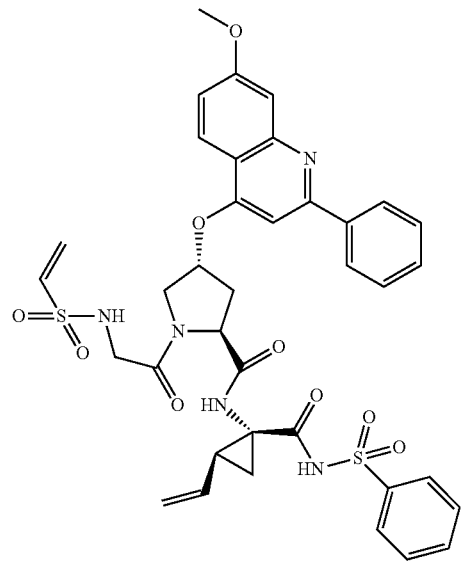
I-36
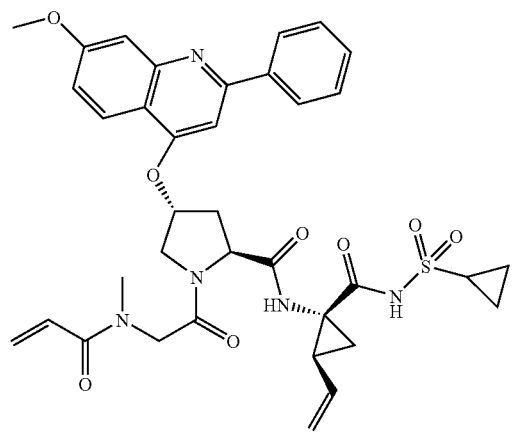
I-37

TABLE 3-continued
Exemplary Compounds of Formula I
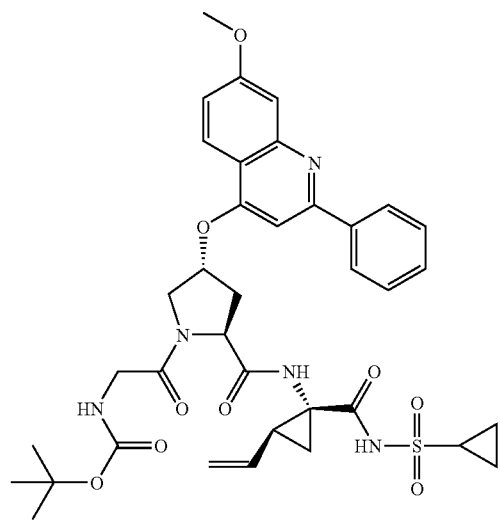
I-38
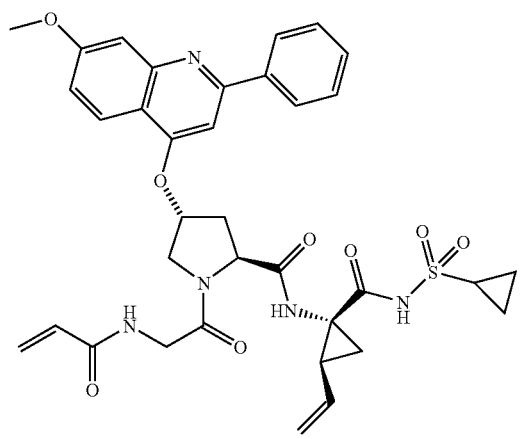
I-39

TABLE 3-continued
Exemplary Compounds of Formula I
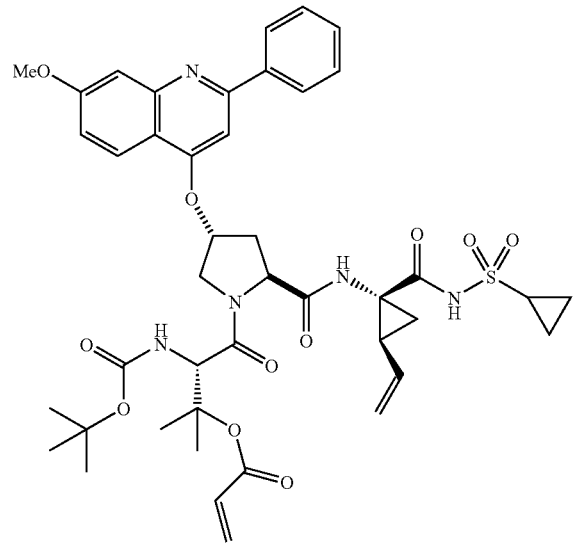
I-40
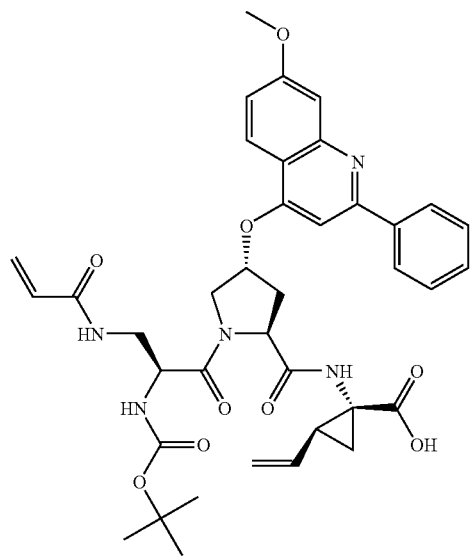
I-41

TABLE 3-continued
Exemplary Compounds of Formula I
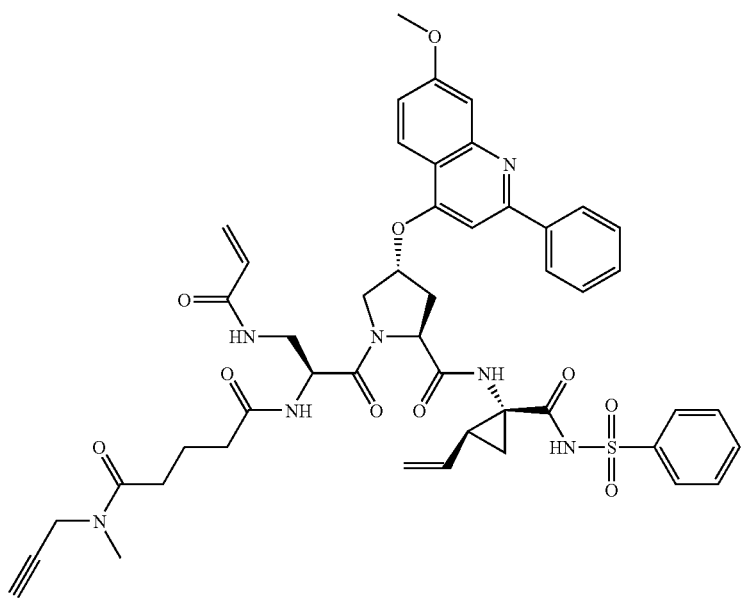
I-42
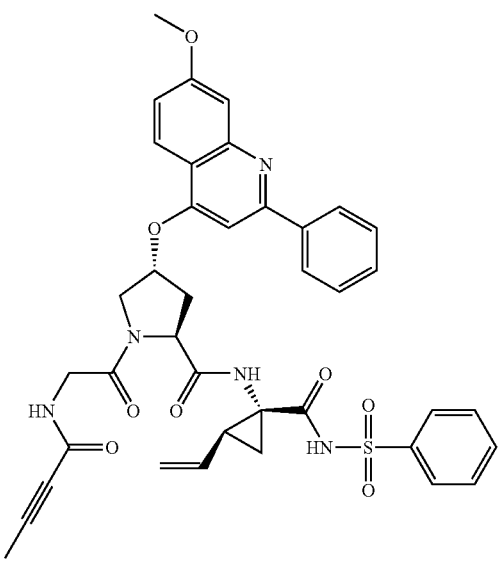
I-43

TABLE 3-continued
Exemplary Compounds of Formula I
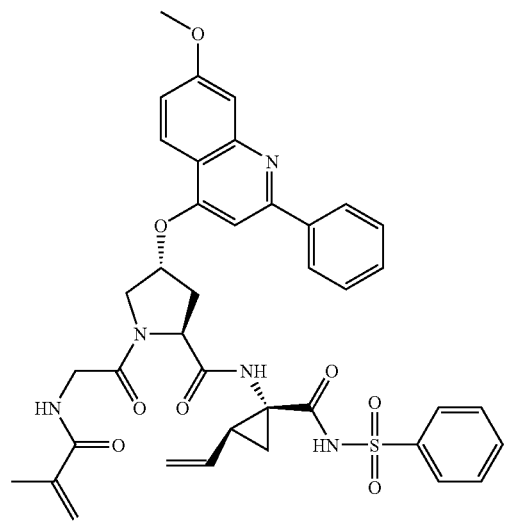
I-44
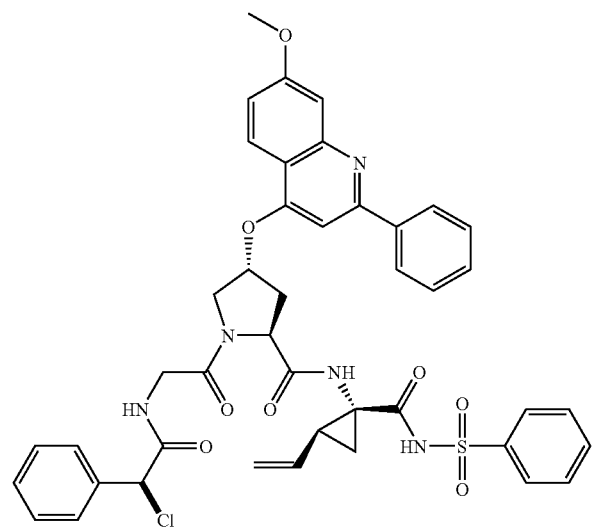
I-45

TABLE 3-continued
Exemplary Compounds of Formula I
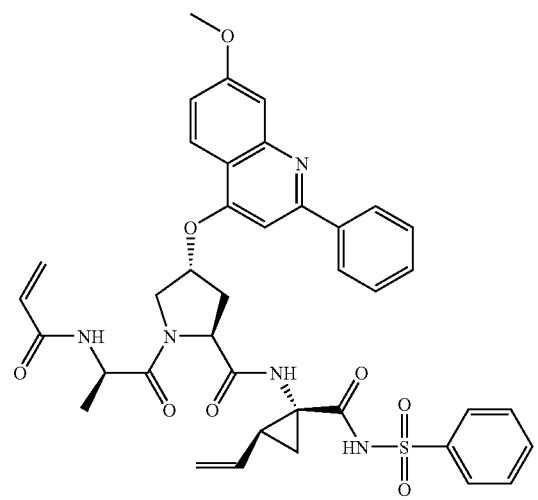
I-46
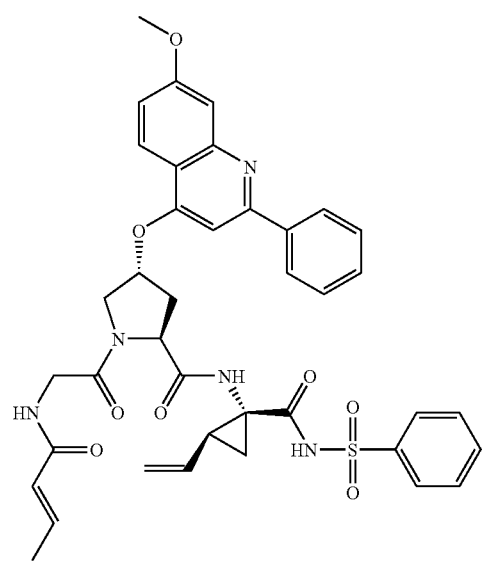
I-47

TABLE 3-continued
Exemplary Compounds of Formula I
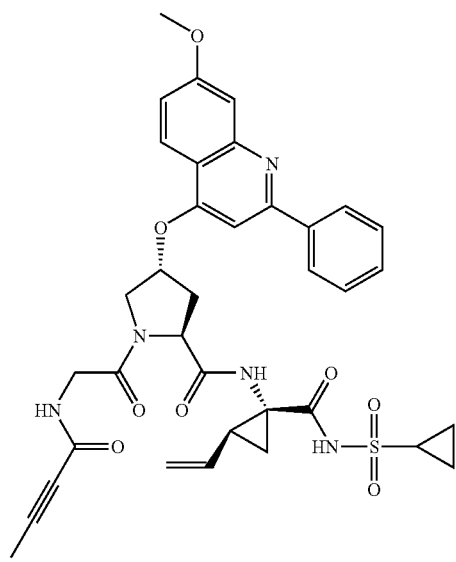
I-48
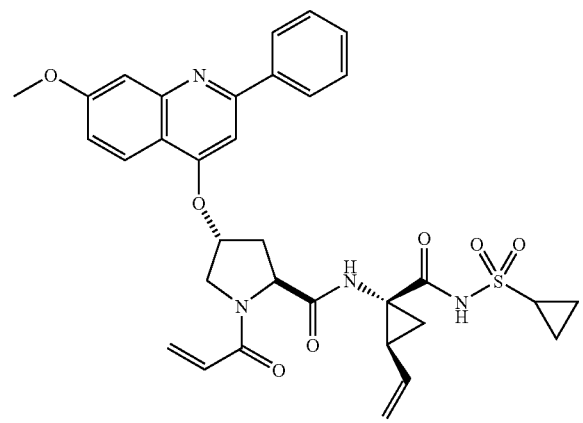
I-49

TABLE 3-continued
Exemplary Compounds of Formula I
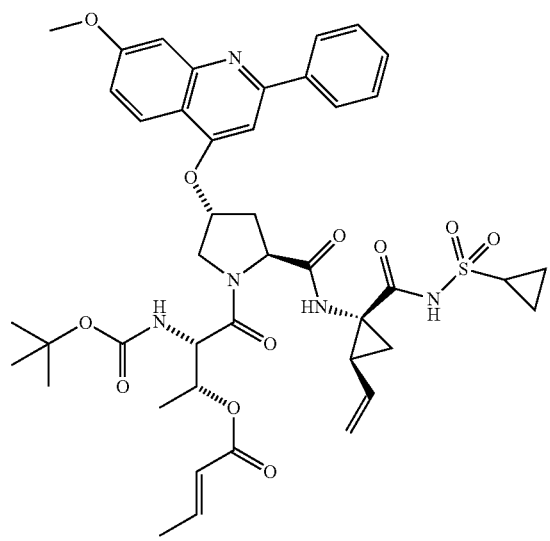
I-50
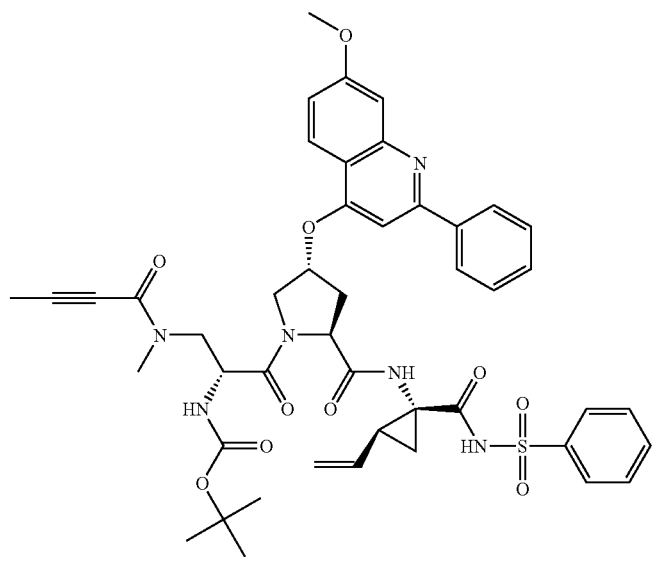
I-51

TABLE 3-continued
Exemplary Compounds of Formula I
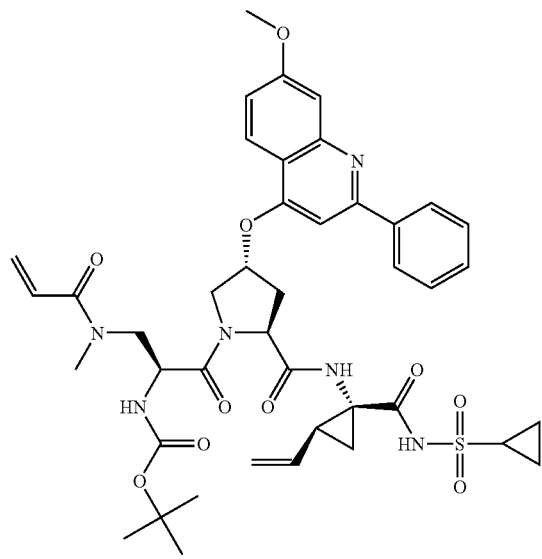
I-52
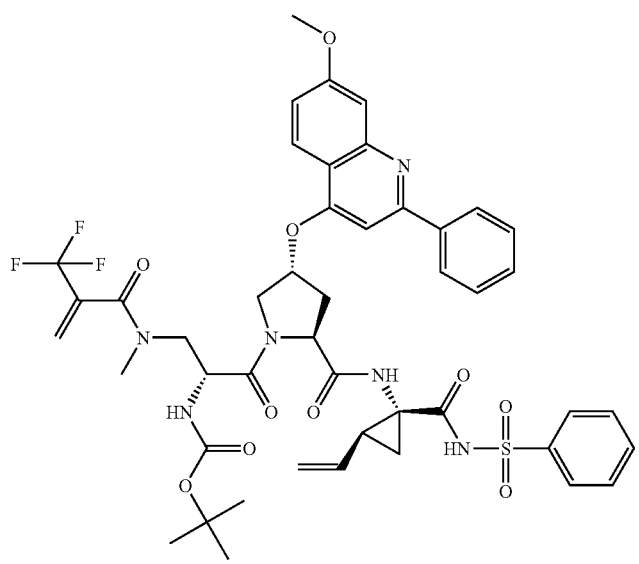
I-53

TABLE 3-continued
Exemplary Compounds of Formula I
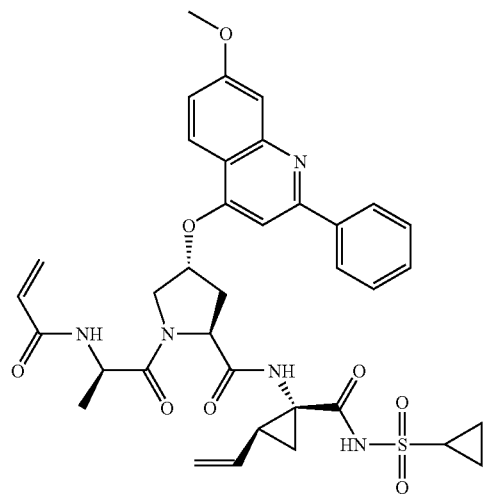
I-54
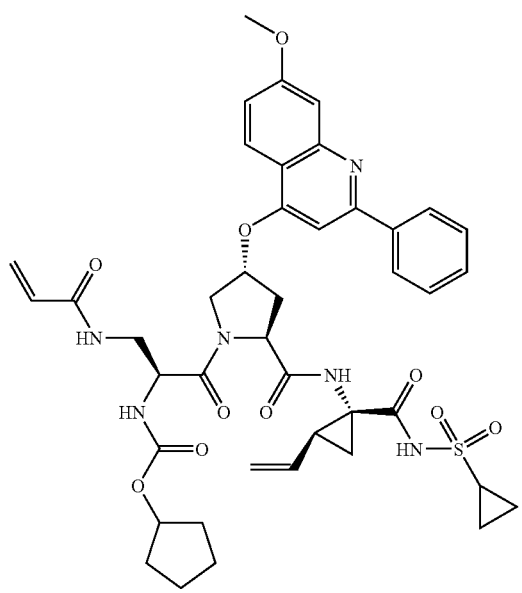
I-55

TABLE 3-continued
Exemplary Compounds of Formula I
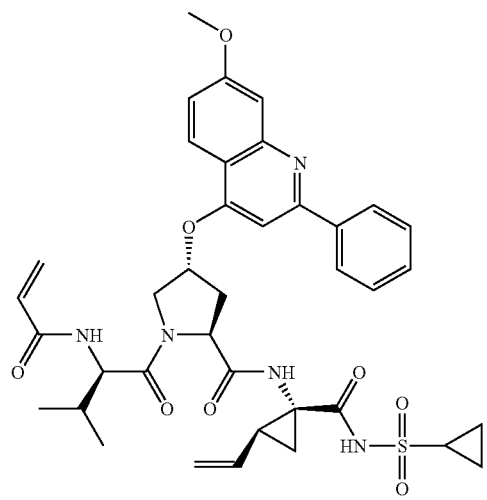
I-56
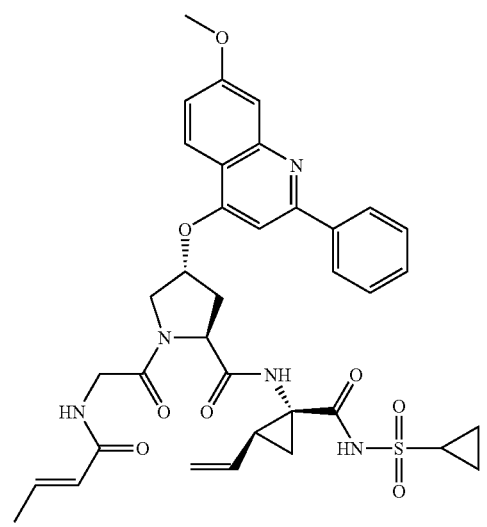
I-57

TABLE 3-continued
Exemplary Compounds of Formula I
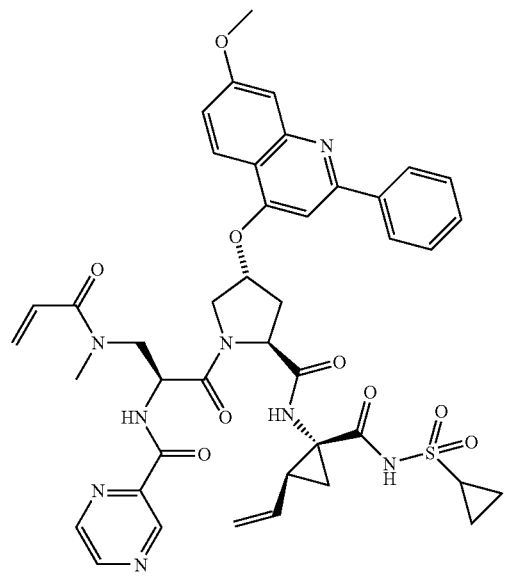
I-58
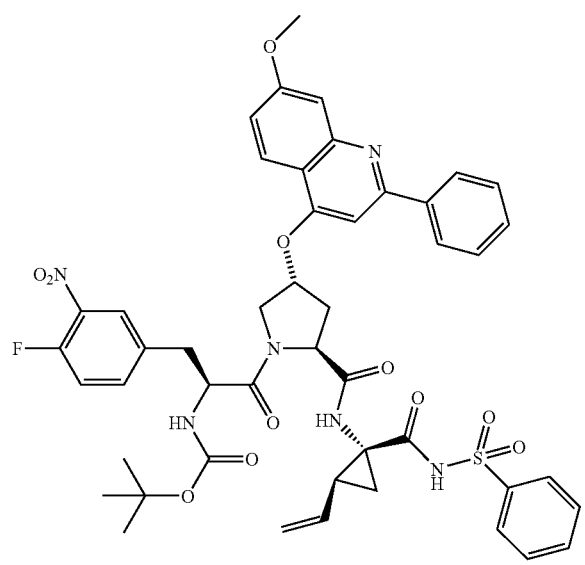
I-59

TABLE 3-continued
Exemplary Compounds of Formula I
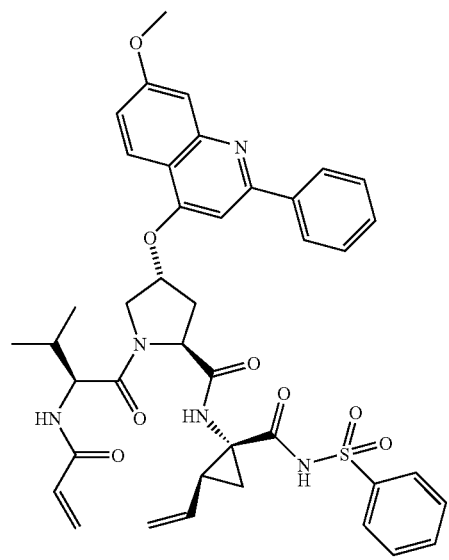
I-60
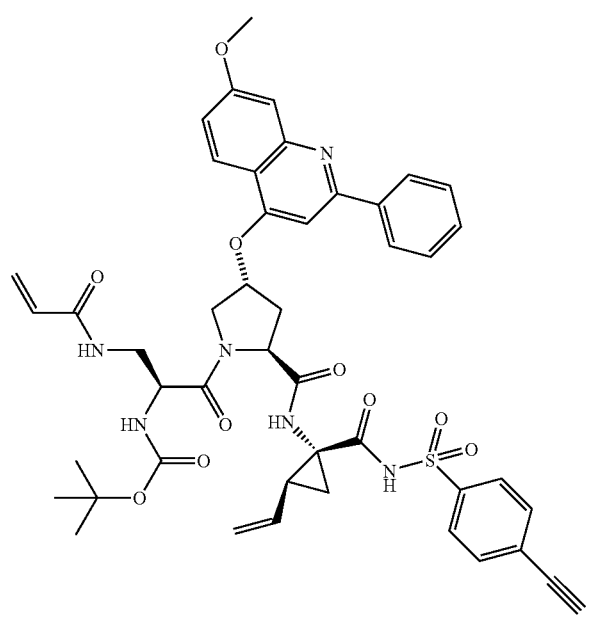
I-61

TABLE 3-continued
Exemplary Compounds of Formula I
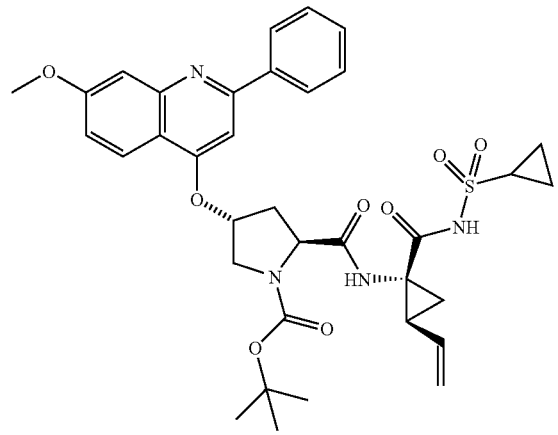
I-62
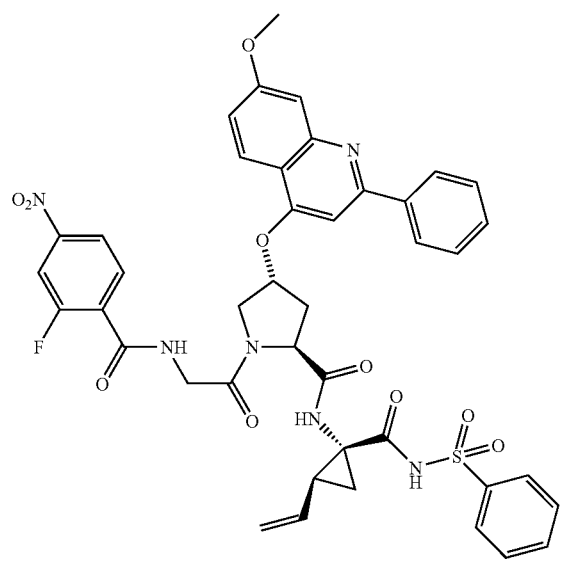
I-63

TABLE 3-continued
Exemplary Compounds of Formula I
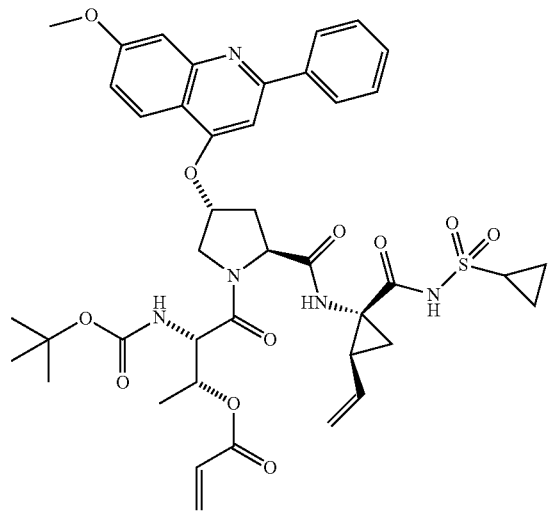
I-64
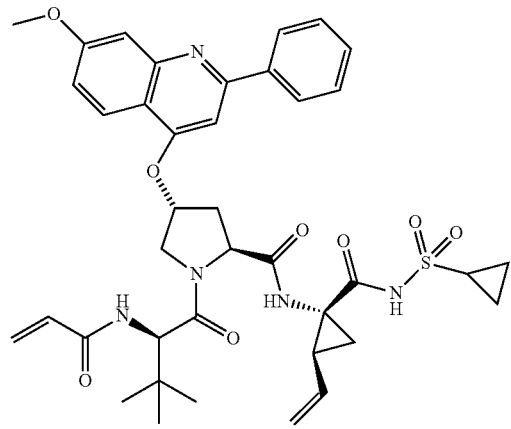
I-65
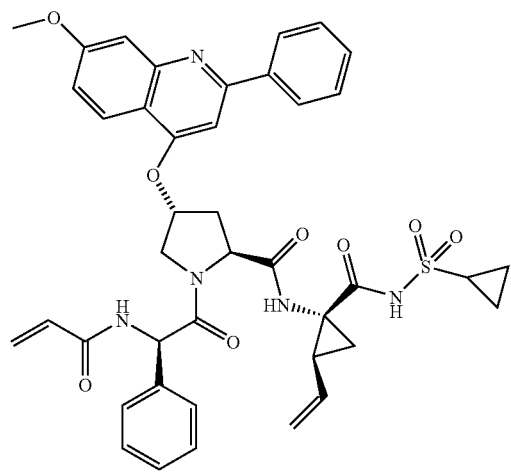
I-66

TABLE 3-continued
Exemplary Compounds of Formula I
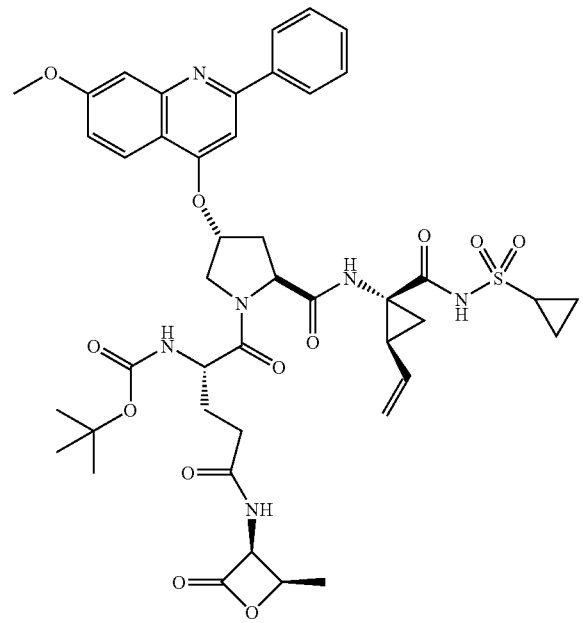
I-67
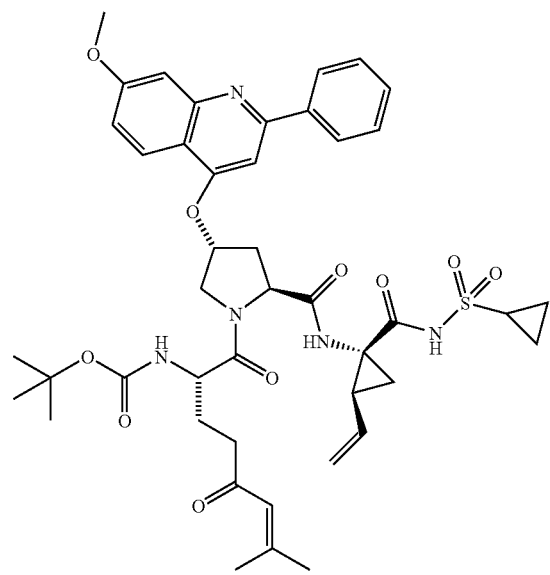
I-68

TABLE 3-continued
Exemplary Compounds of Formula I
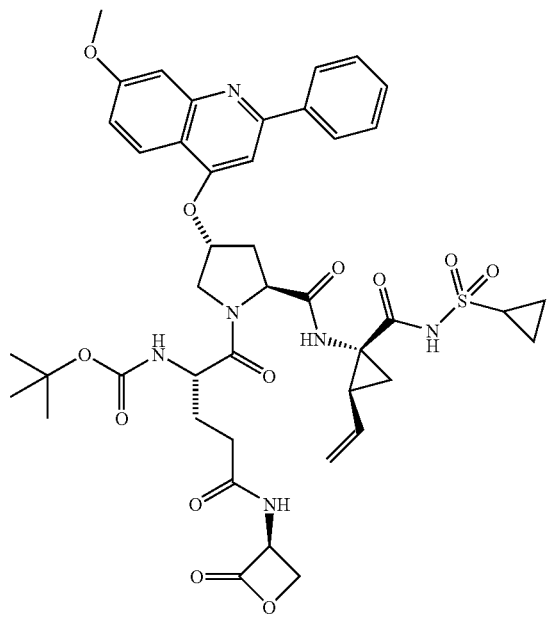
I-69
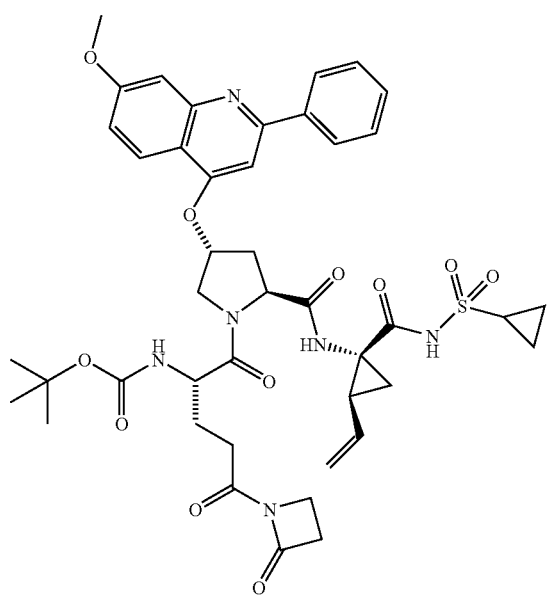
I-70

TABLE 3-continued
Exemplary Compounds of Formula I
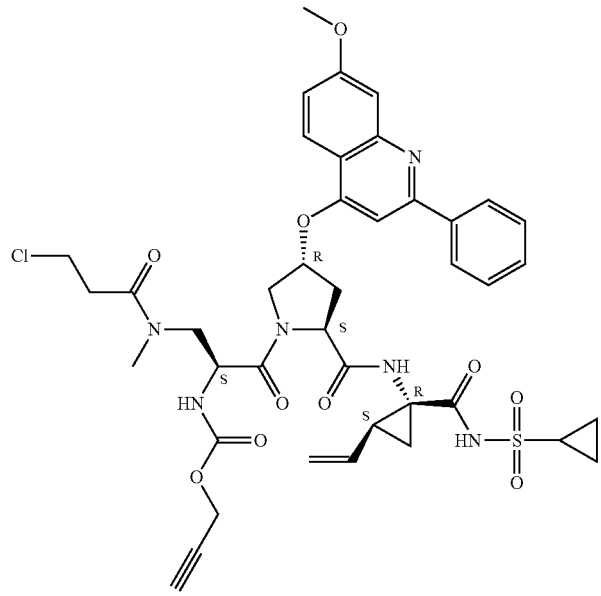
I-71
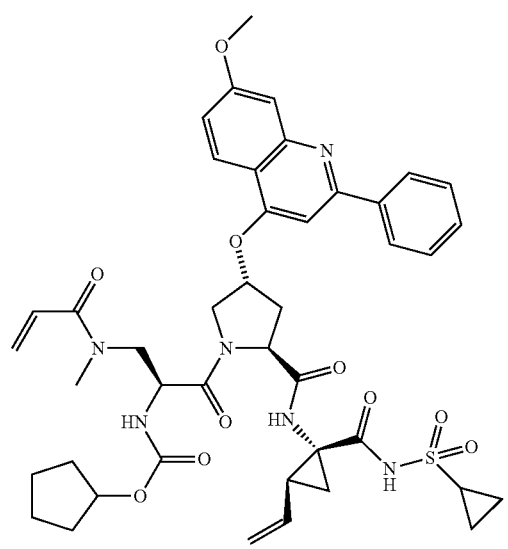
I-72

TABLE 3-continued
Exemplary Compounds of Formula I
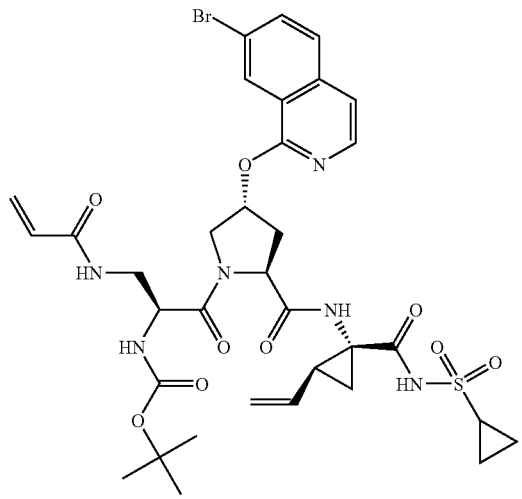
I-73
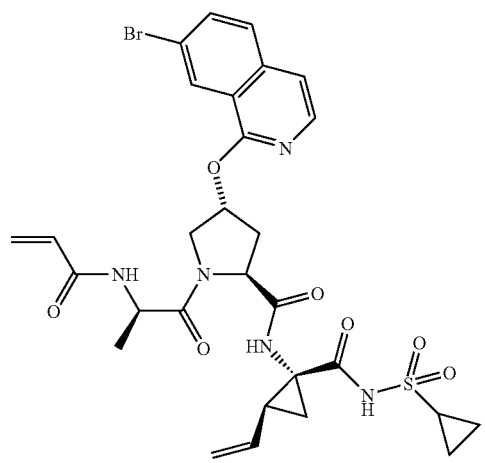
I-74
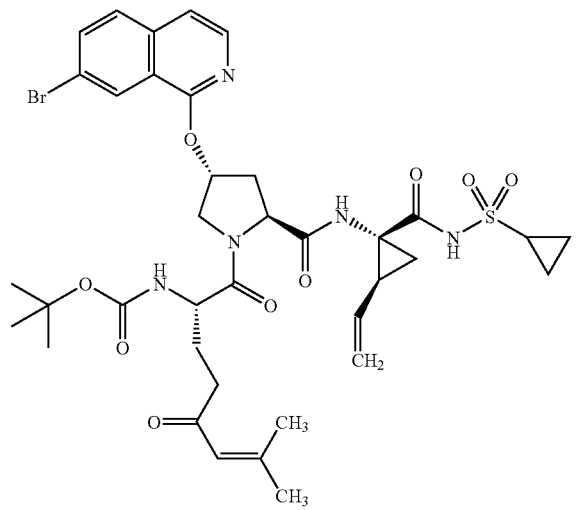
I-75

TABLE 3-continued
Exemplary Compounds of Formula I
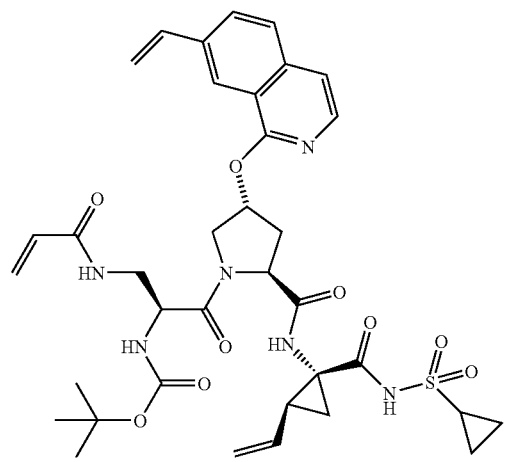
I-76
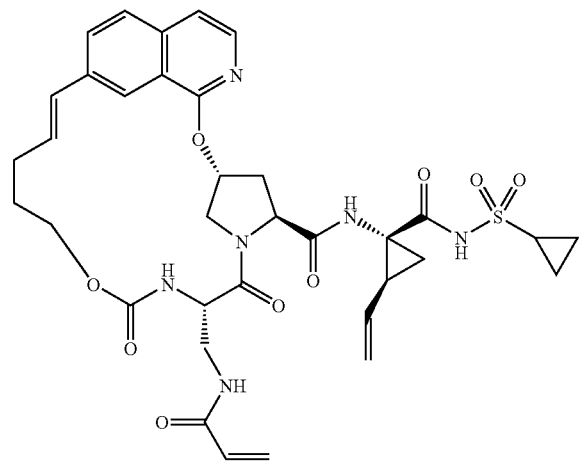
I-77

TABLE 3-continued
Exemplary Compounds of Formula I
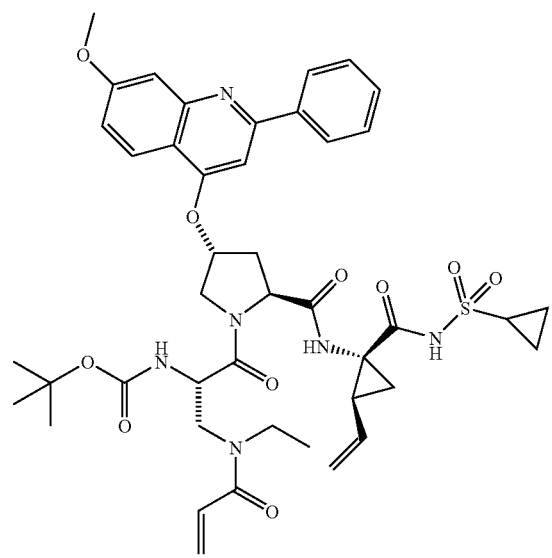
I-78
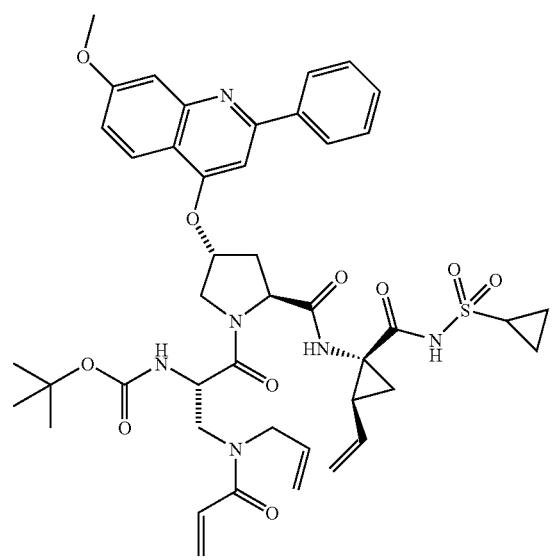
I-79

TABLE 3-continued
Exemplary Compounds of Formula I
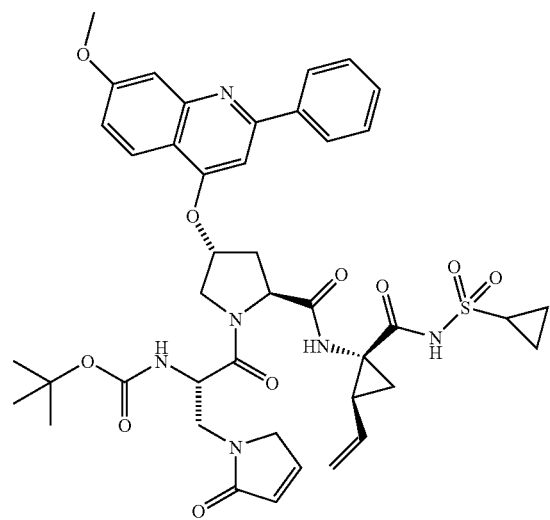
I-80
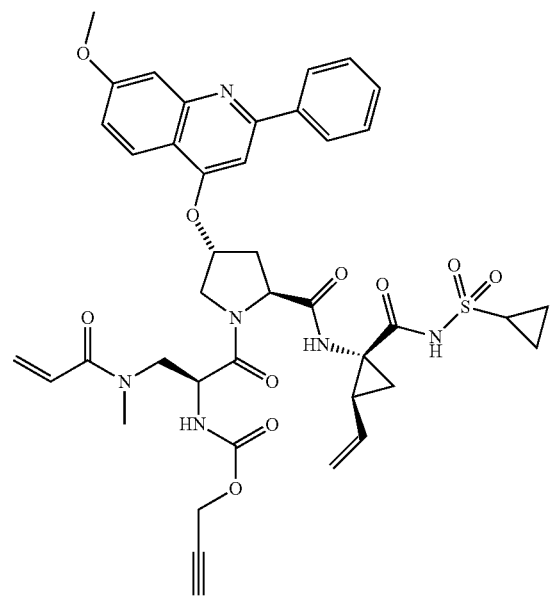
I-81

TABLE 3-continued
Exemplary Compounds of Formula I
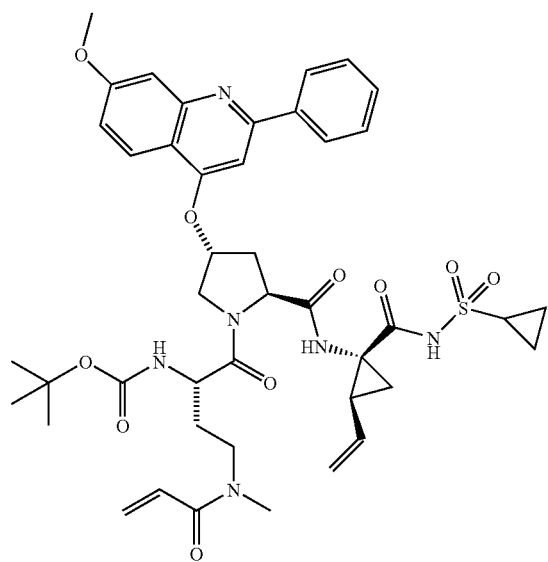
I-82
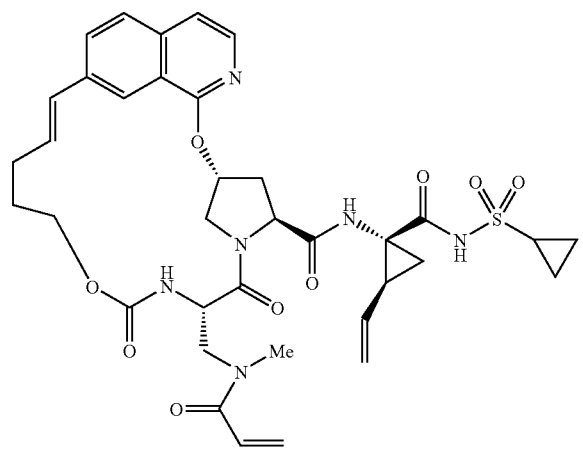
I-83

TABLE 3-continued
Exemplary Compounds of Formula I
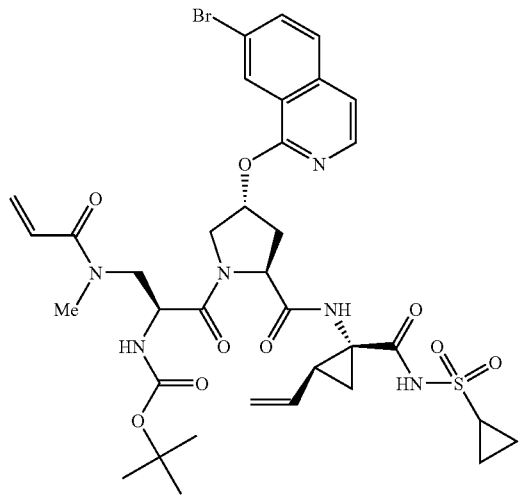
I-84
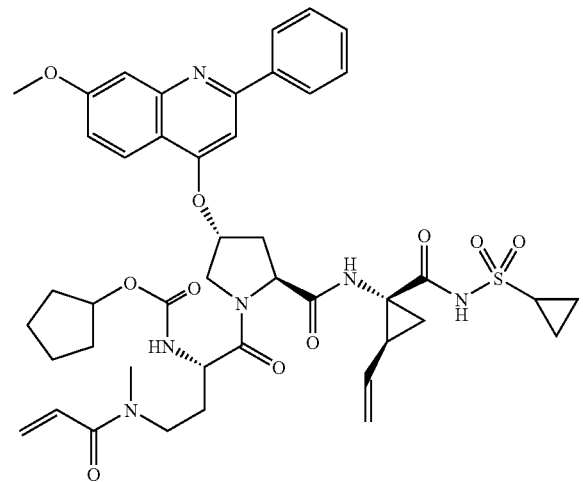
I-85

TABLE 3-continued
Exemplary Compounds of Formula I
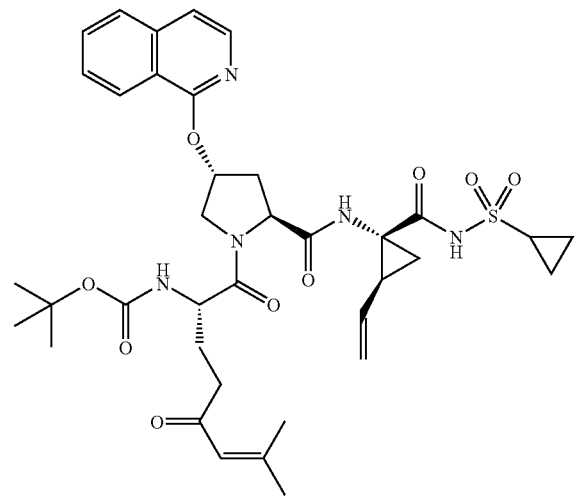
I-86
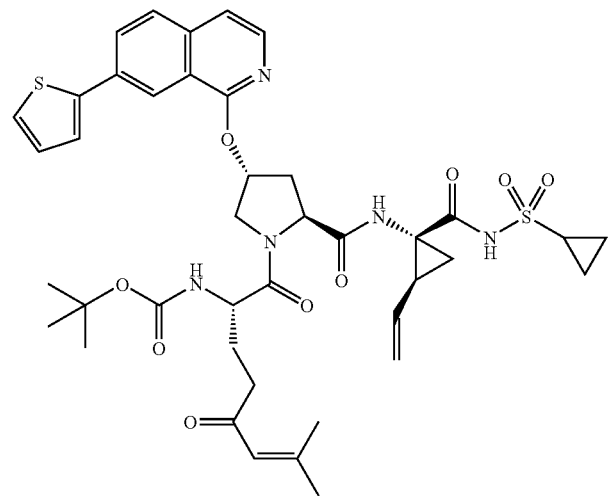
I-87

TABLE 3-continued
Exemplary Compounds of Formula I
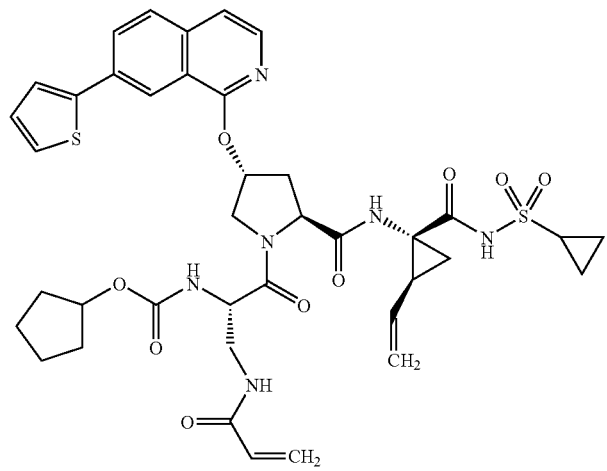
I-88
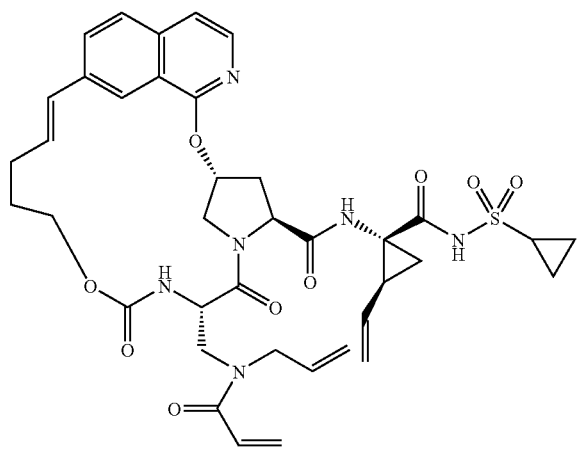
I-89
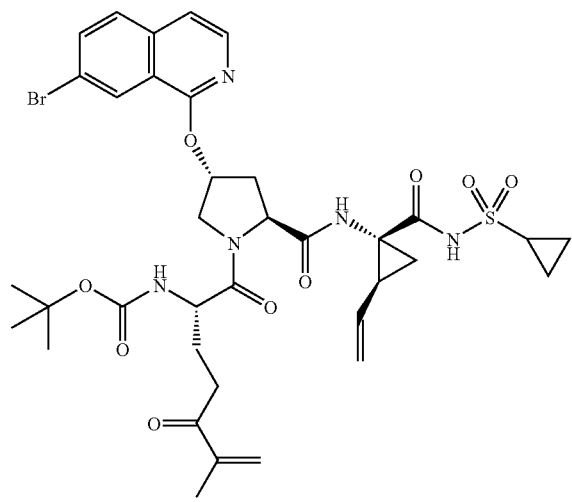
I-90

TABLE 3-continued
Exemplary Compounds of Formula I
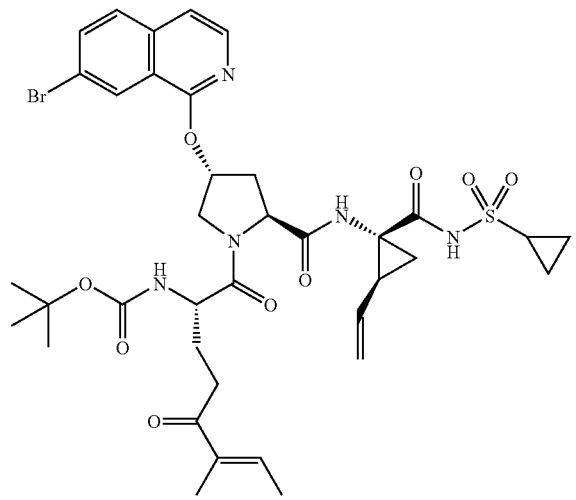
I-91
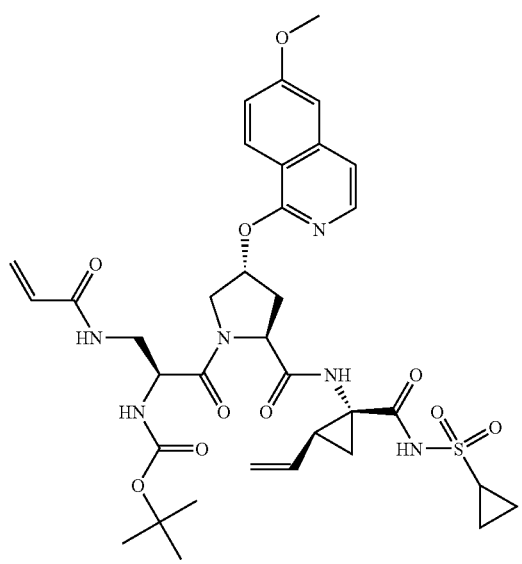
I-92

TABLE 3-continued
Exemplary Compounds of Formula I
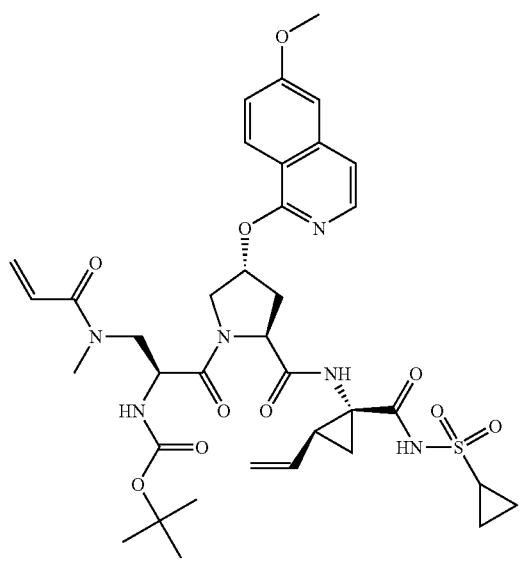
I-93
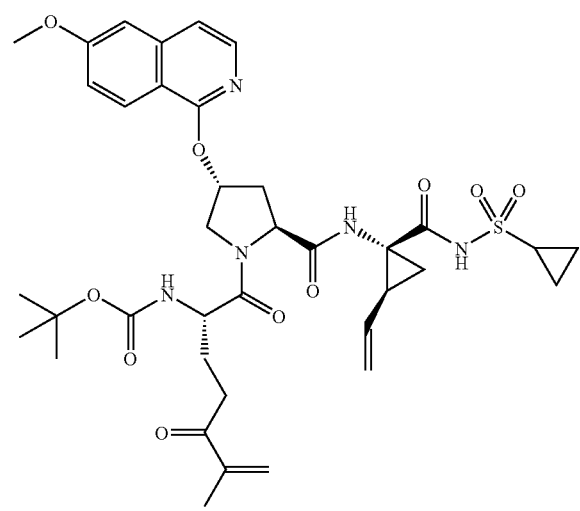
I-94

TABLE 3-continued
Exemplary Compounds of Formula I
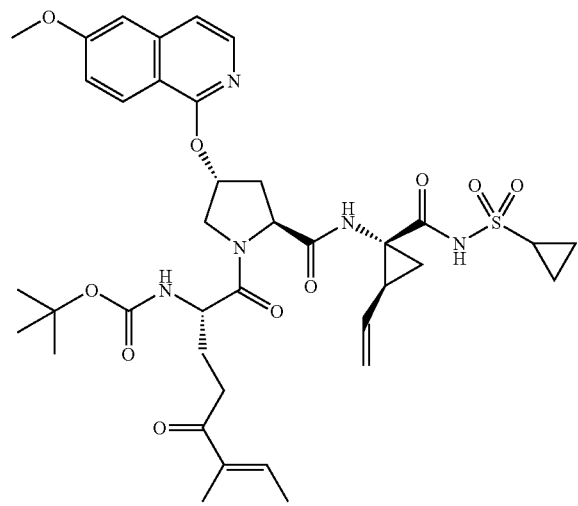
I-95
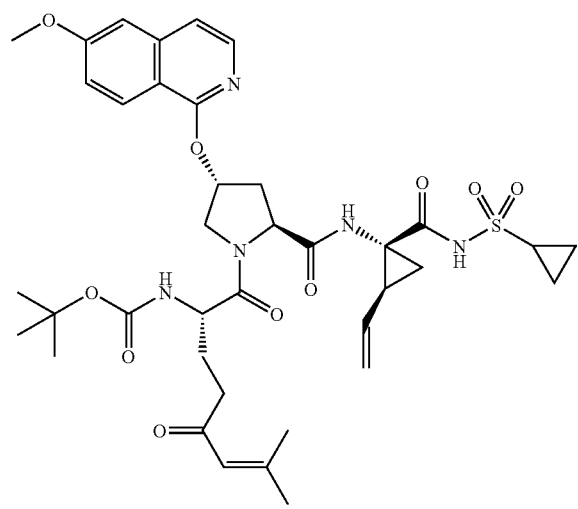
I-96

TABLE 3-continued
Exemplary Compounds of Formula I
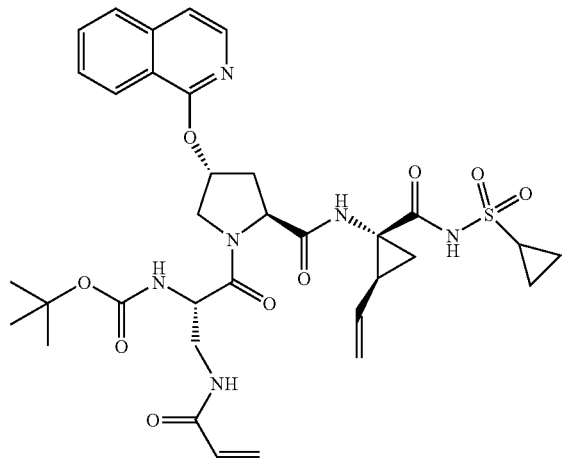
I-97
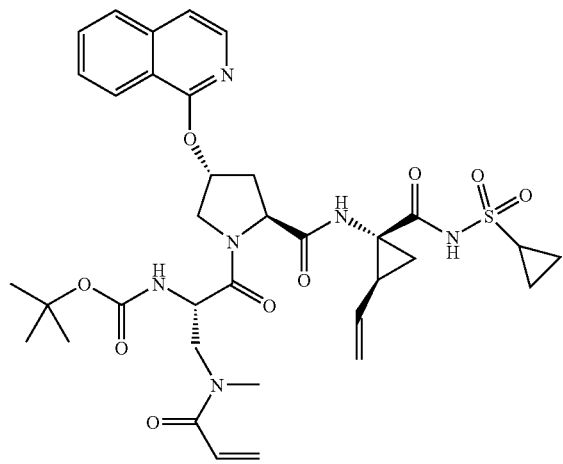
I-98
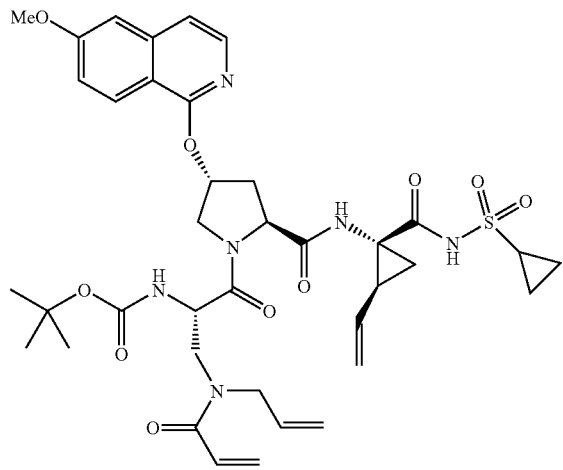
I-99

TABLE 3-continued
Exemplary Compounds of Formula I
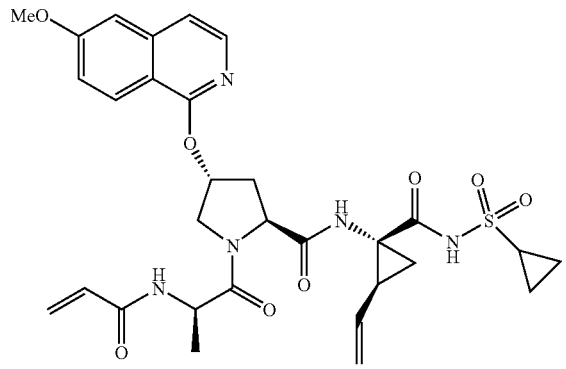
I-100
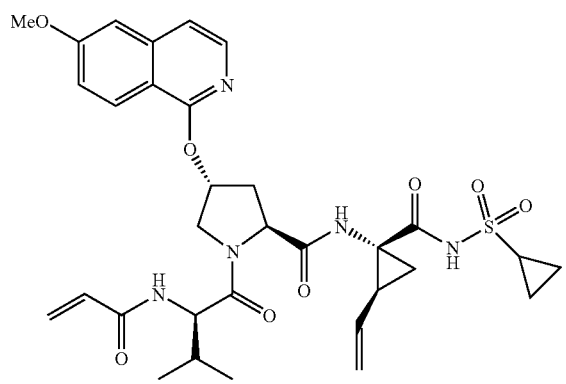
I-101
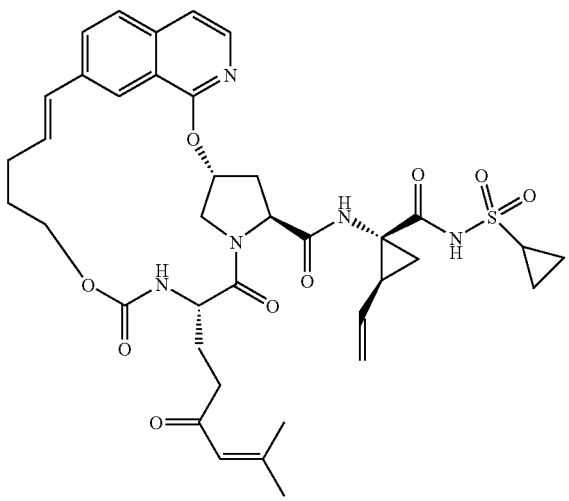
I-102

TABLE 3-continued
Exemplary Compounds of Formula I
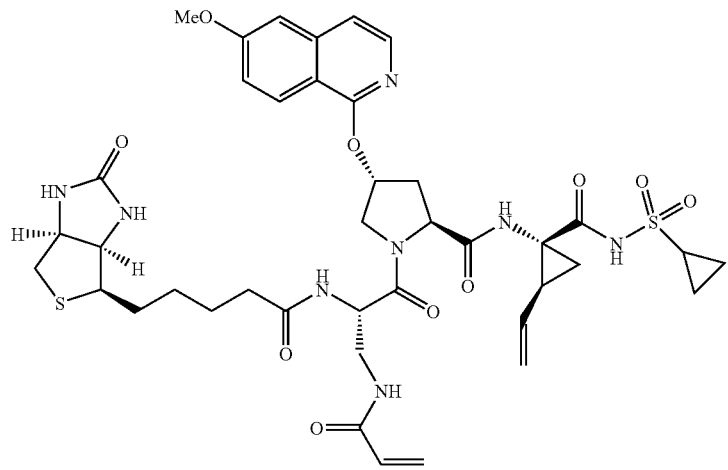
I-103
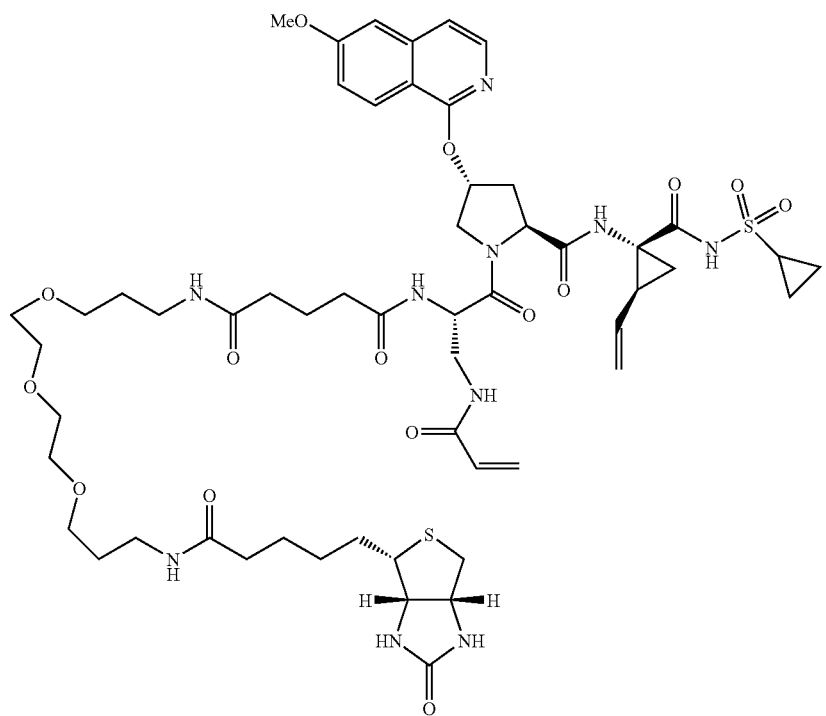
I-104

TABLE 3-continued
Exemplary Compounds of Formula I
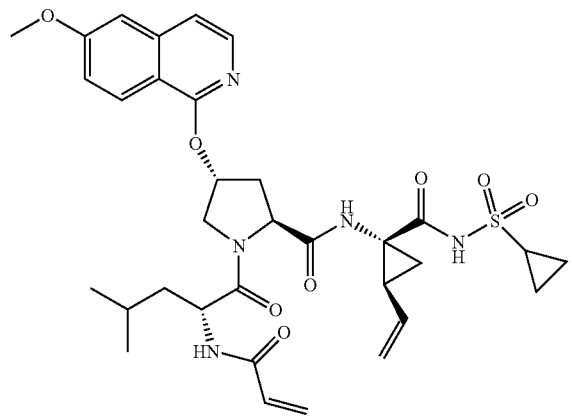
I-105
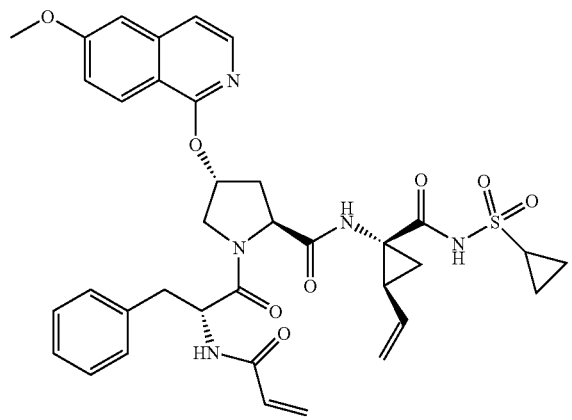
I-106
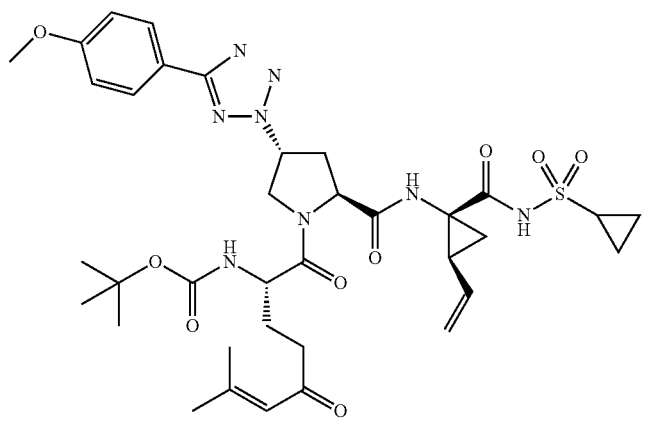
I-107

TABLE 3-continued
Exemplary Compounds of Formula I
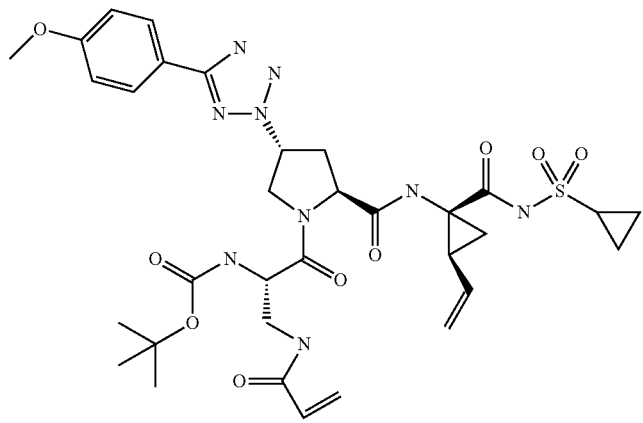
I-108
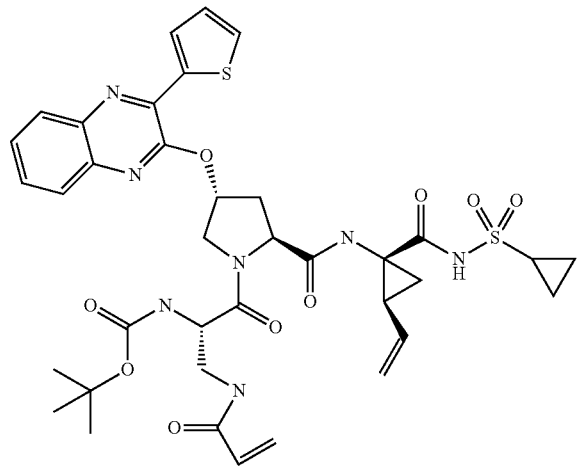
I-109
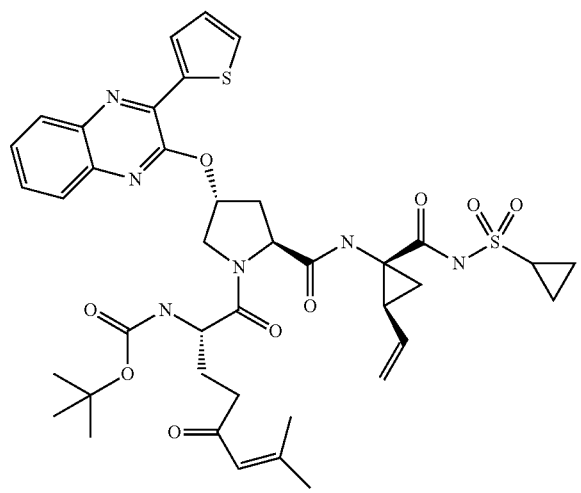
I-110

TABLE 3-continued
Exemplary Compounds of Formula I
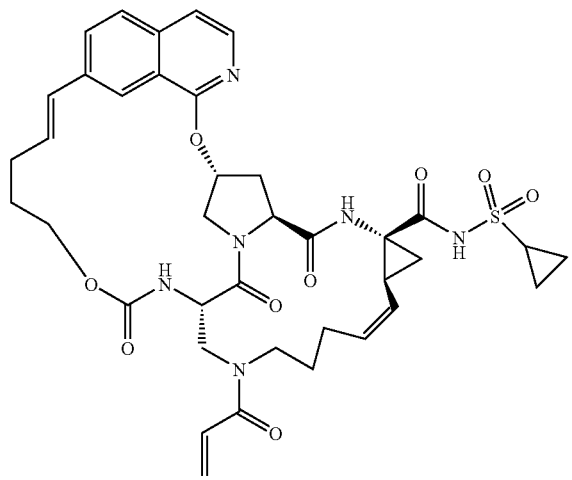
I-111
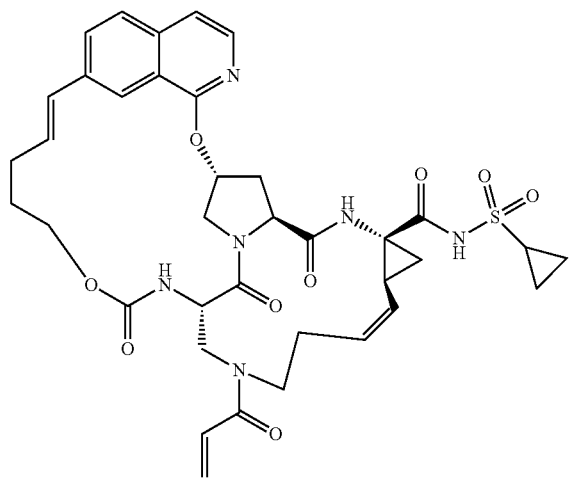
I-112

TABLE 3-continued
Exemplary Compounds of Formula I
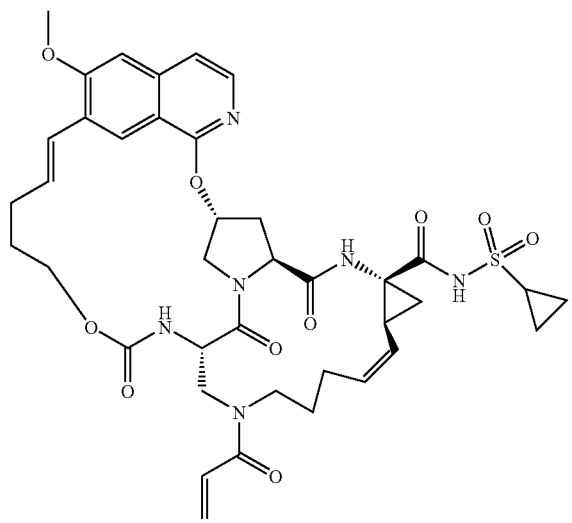
I-113
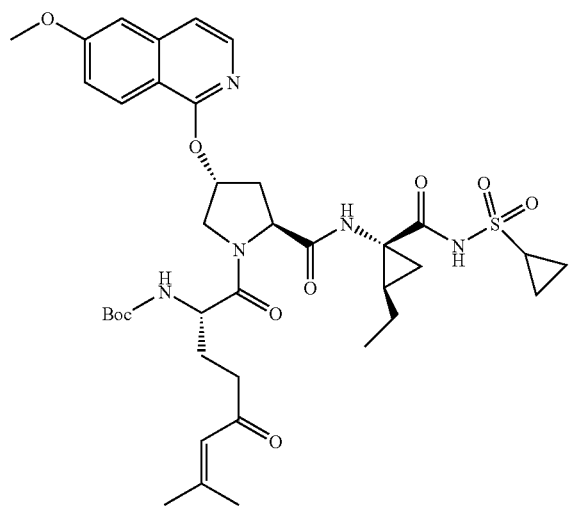
I-114

TABLE 3-continued
Exemplary Compounds of Formula I
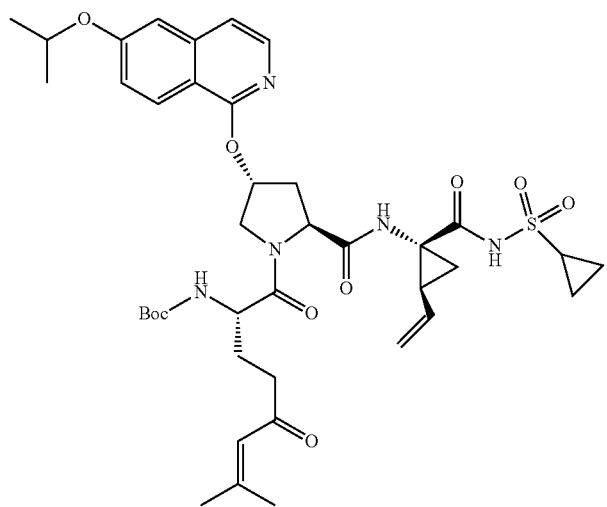
I-115
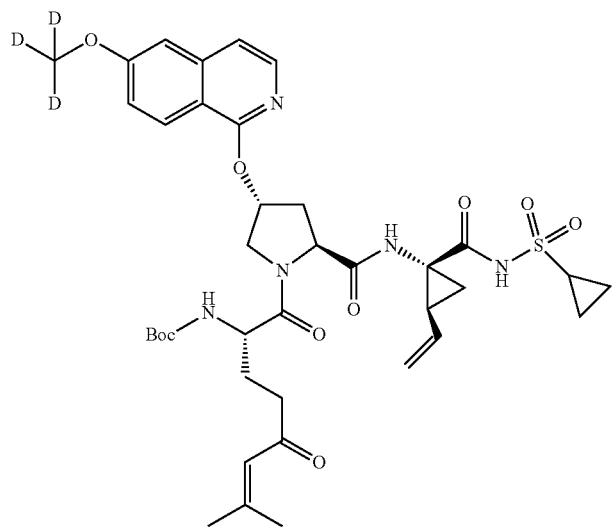
I-116

TABLE 3-continued
Exemplary Compounds of Formula I
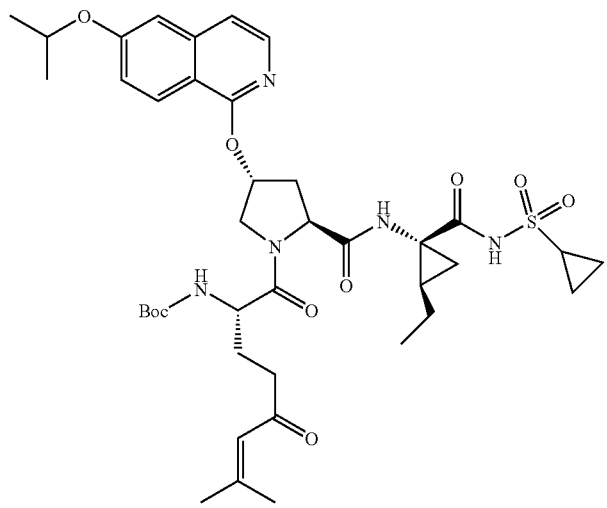
I-117
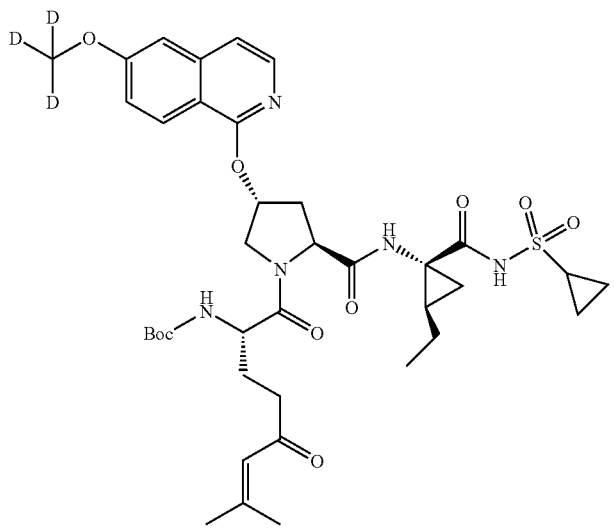
I-118

TABLE 3-continued
Exemplary Compounds of Formula I
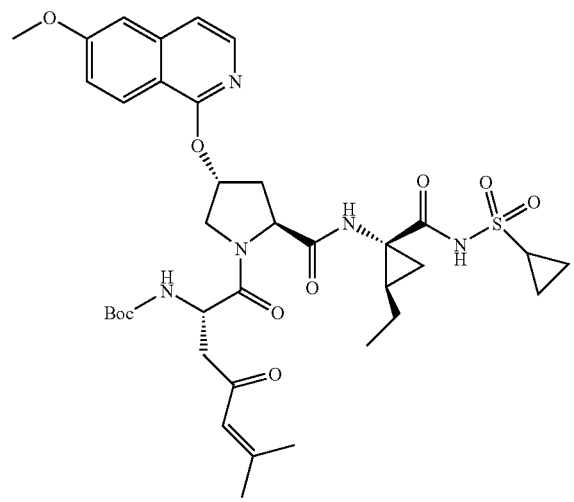
I-119
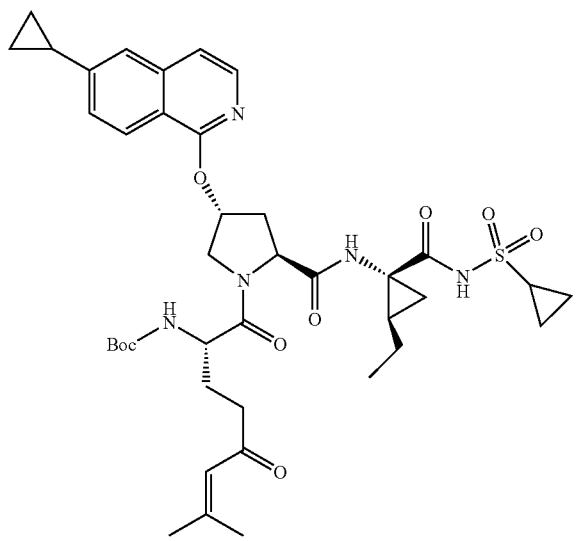
I-120

TABLE 3-continued
Exemplary Compounds of Formula I
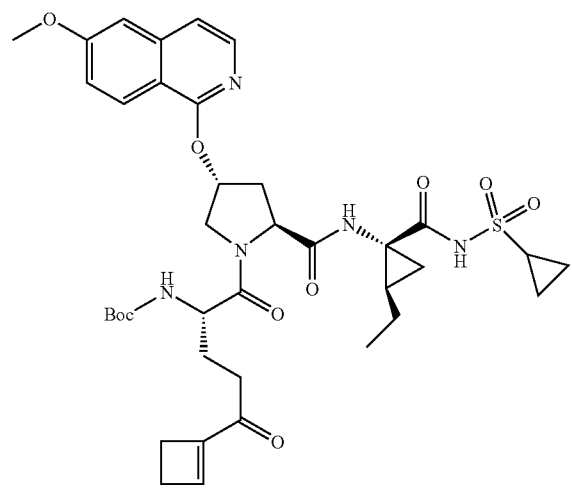
I-121
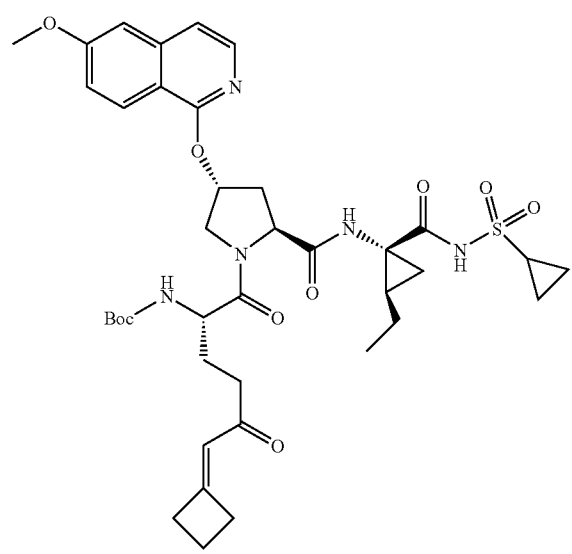
I-122

TABLE 3-continued
Exemplary Compounds of Formula I
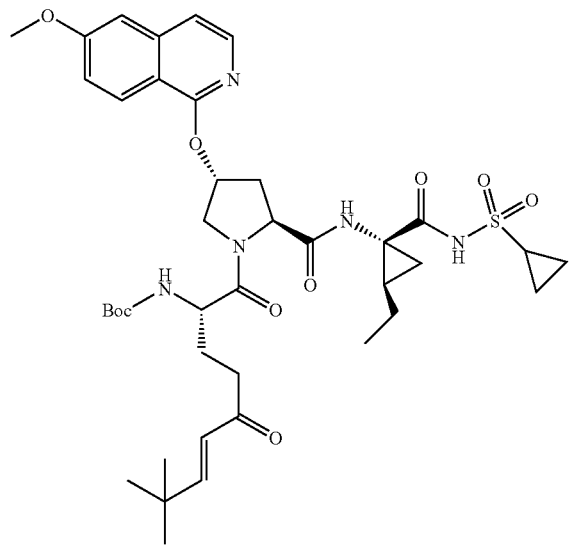
I-123
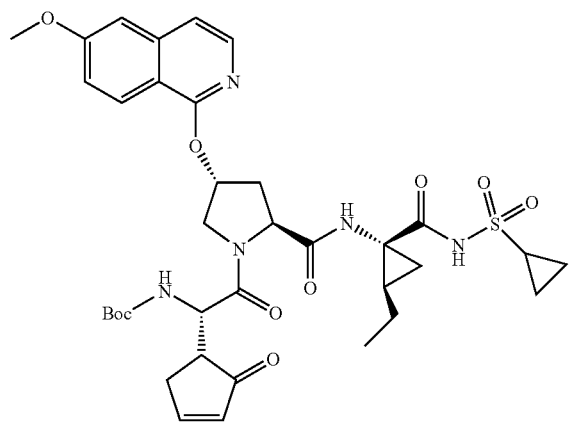
I-124
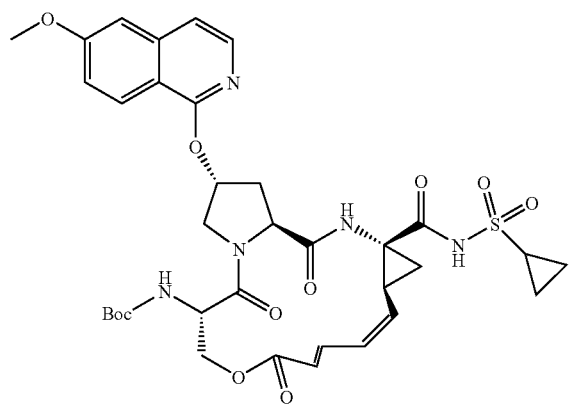
I-125

TABLE 3-continued
Exemplary Compounds of Formula I
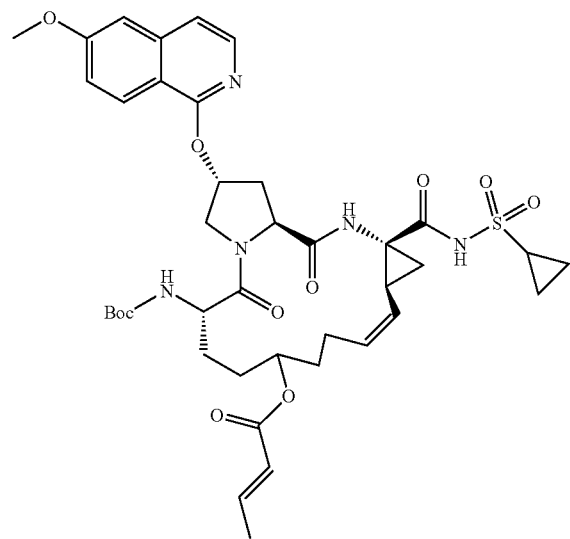
I-126
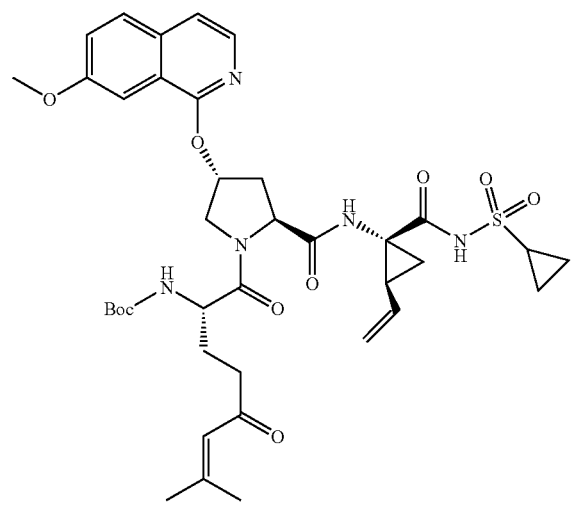
I-127

TABLE 3-continued
Exemplary Compounds of Formula I
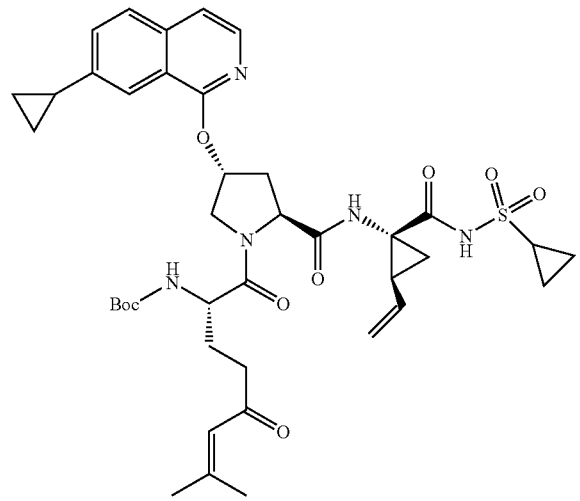
I-128
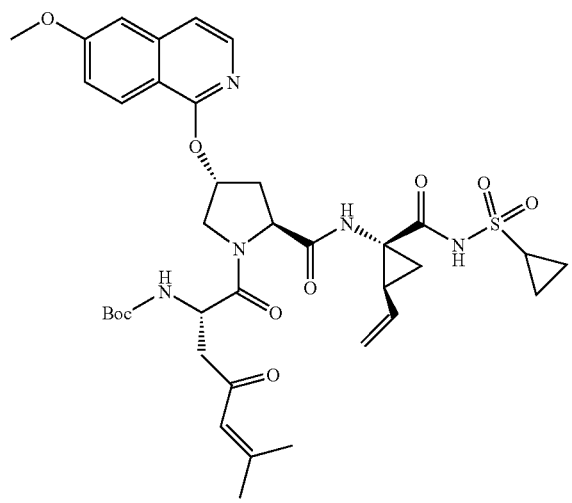
I-129
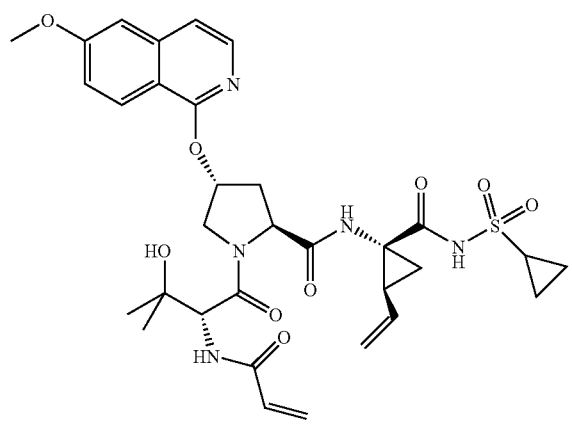
I-130

TABLE 3-continued
Exemplary Compounds of Formula I
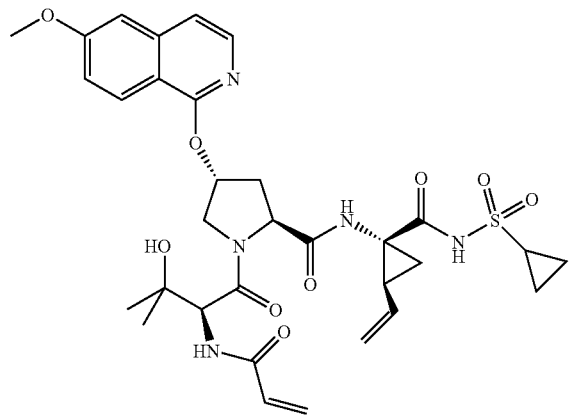
I-131
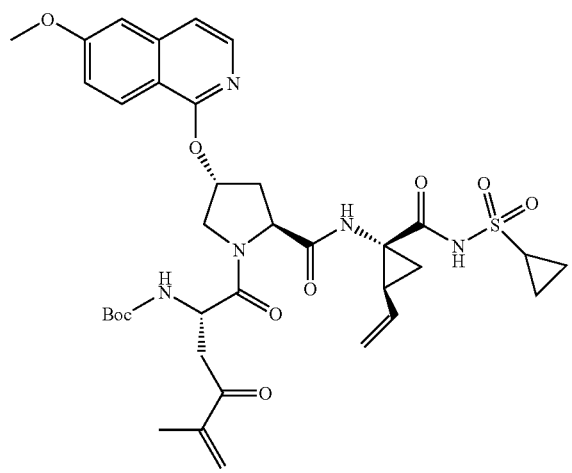
I-132
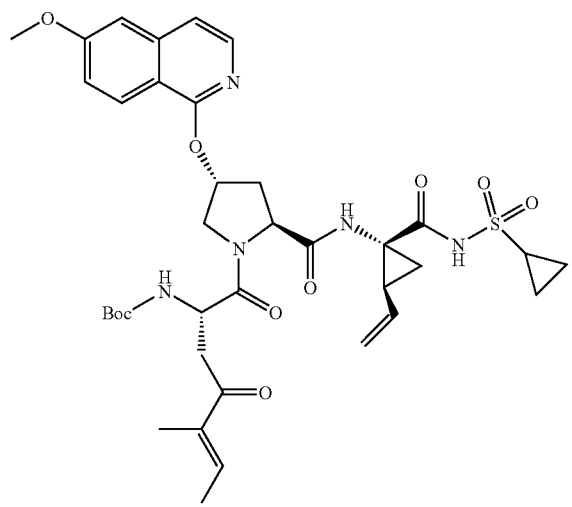
I-133

TABLE 3-continued
Exemplary Compounds of Formula I
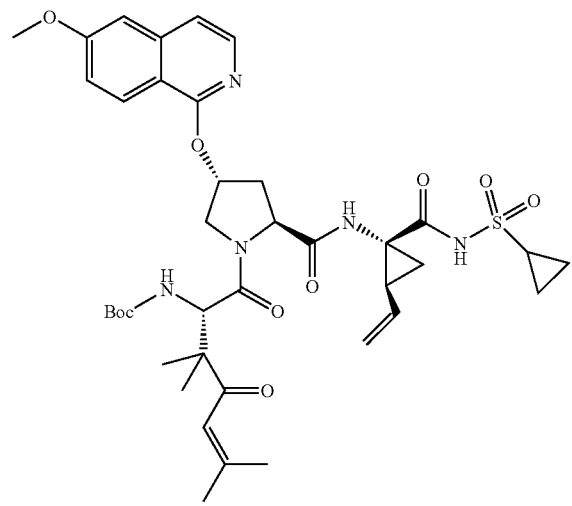
I-134
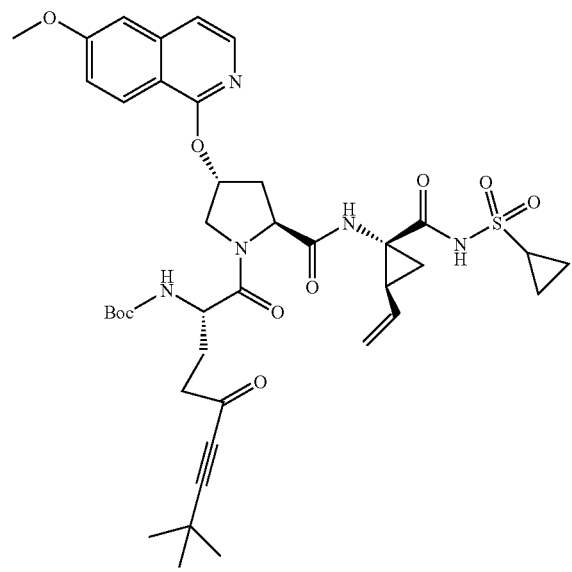
I-135

TABLE 3-continued
Exemplary Compounds of Formula I
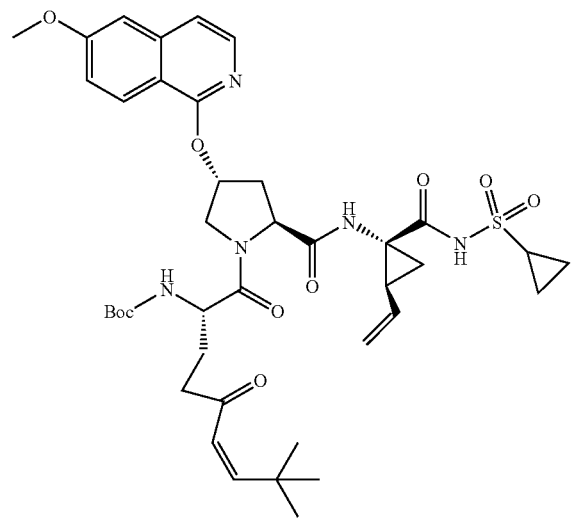
I-136
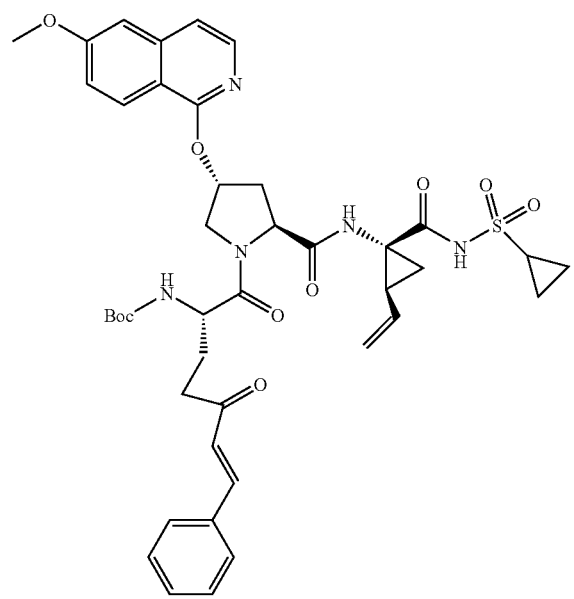
I-137

TABLE 3-continued
Exemplary Compounds of Formula I
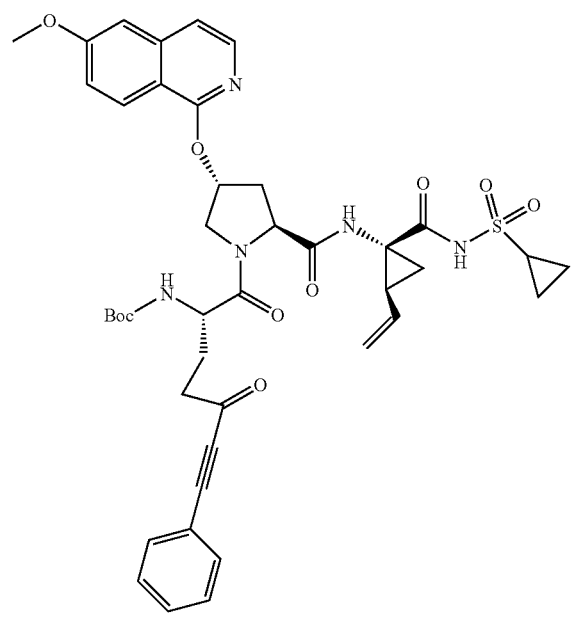
I-138
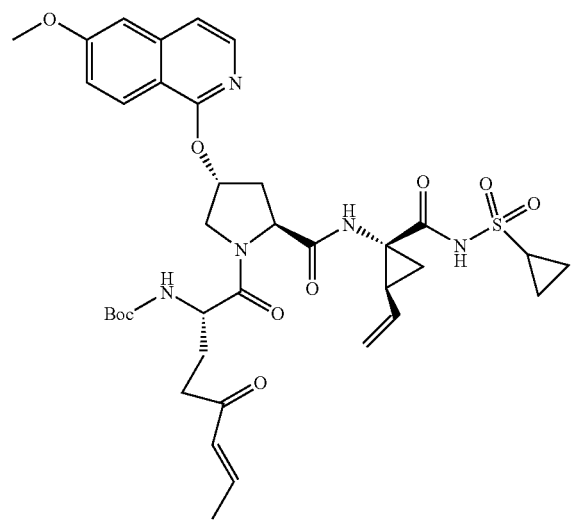
I-139

TABLE 3-continued
Exemplary Compounds of Formula I
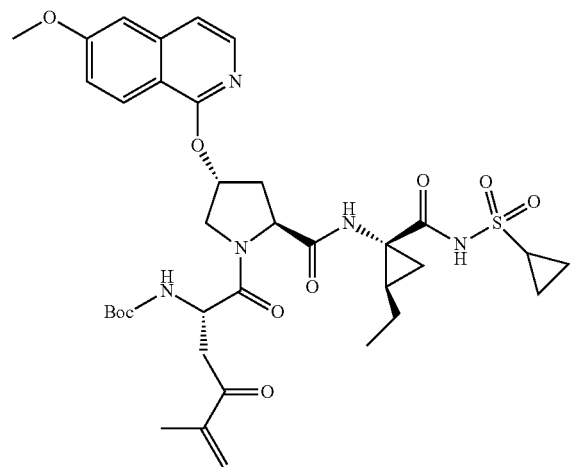
I-140
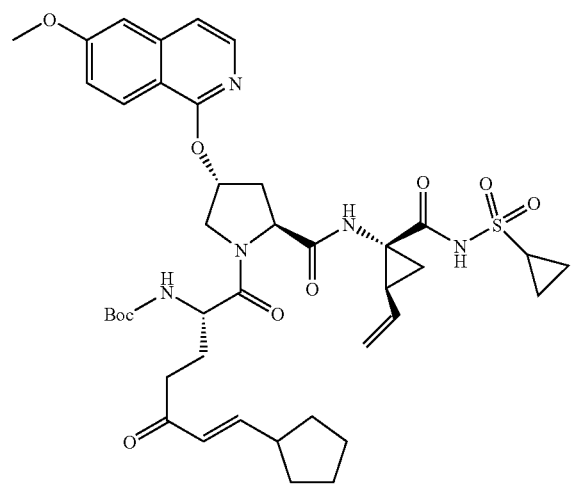
I-141

TABLE 3-continued
Exemplary Compounds of Formula I
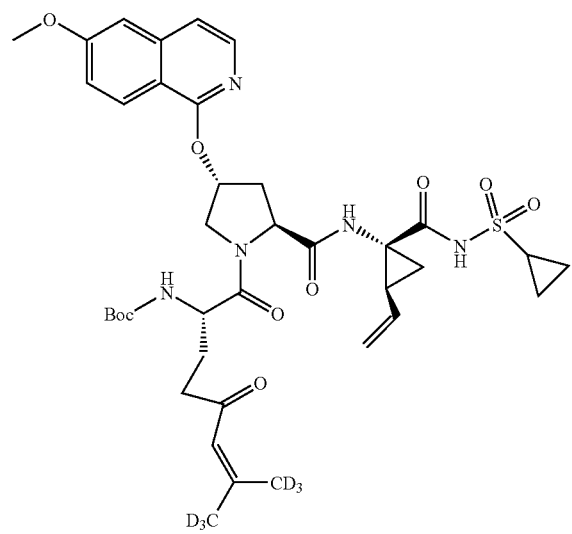
I-142
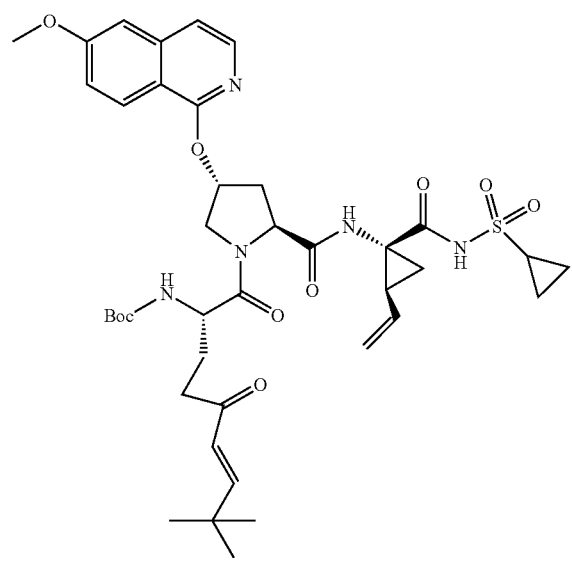
I-143

TABLE 3-continued
Exemplary Compounds of Formula I
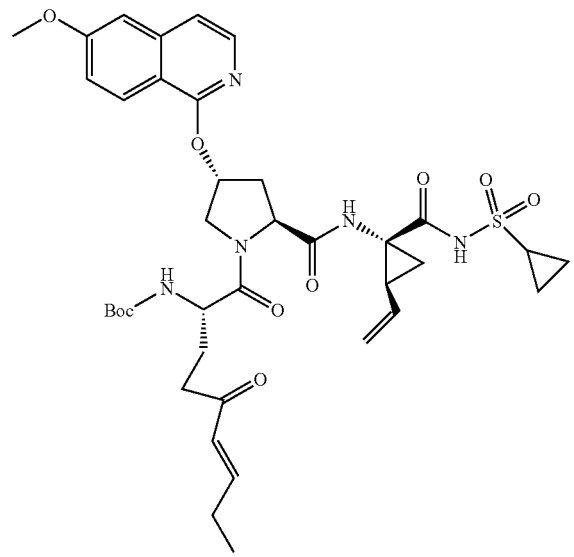
I-144
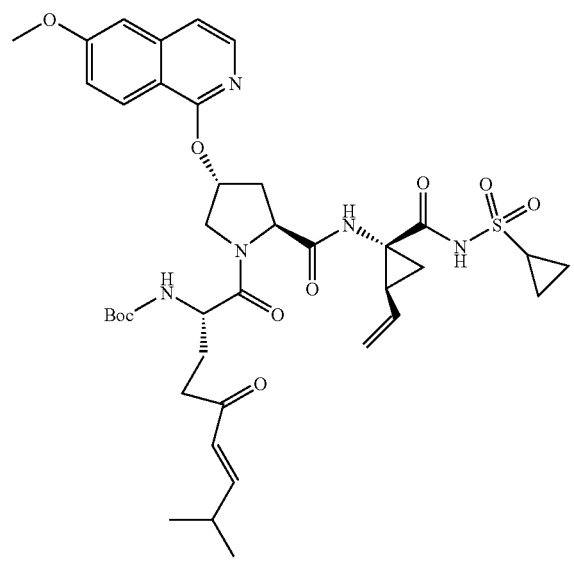
I-145

TABLE 3-continued

Exemplary Compounds of Formula I

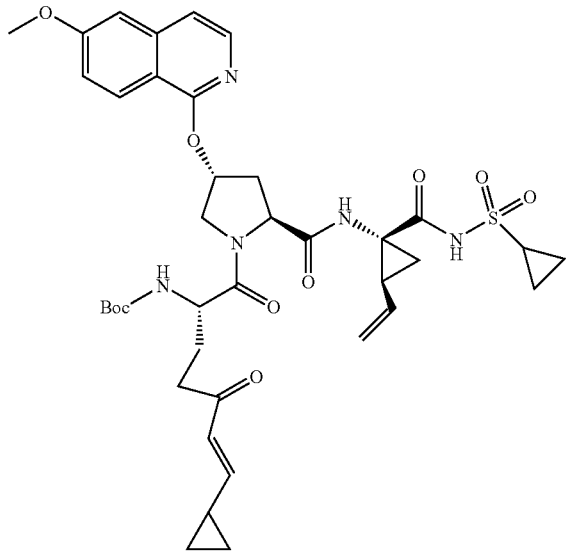

I-146

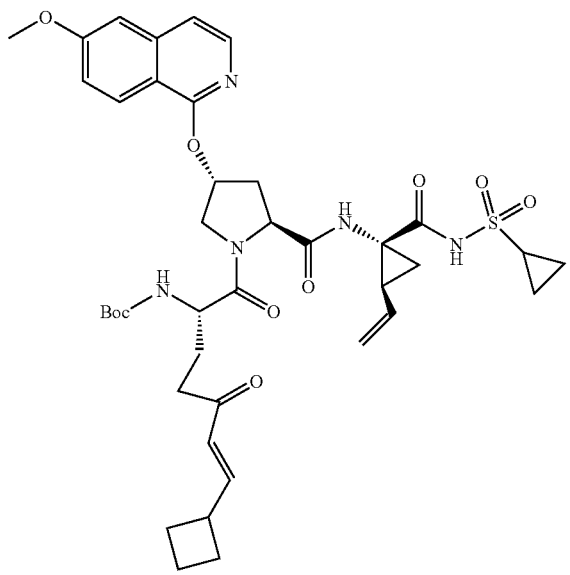

I-147

In certain embodiments, the present invention provides any compound depicted in Table 3, above, or a pharmaceutically acceptable salt thereof.

As defined generally above, $R^3$ is a warhead group. Without wishing to be bound by any particular theory, it is believed that such $R^3$ groups, i.e. warhead groups, are particularly suitable for covalently binding to a key cysteine residue in the binding domain of HCV protease. One of ordinary skill in the art will appreciate that HCV protease, and mutants thereof, have a cysteine residue in the binding domain. In certain embodiments, compounds of the present invention have a warhead group characterized in that inventive compounds may target the C159 cysteine residue of HCV protease. In certain embodiments, compounds of the present invention have a warhead group characterized in that inventive compounds target the C16 cysteine residue of HCV protease.

Thus, in some embodiments, $R^3$ is characterized in that the -L-Y moiety is capable of covalently binding to a cysteine residue thereby irreversibly inhibiting the enzyme. In certain embodiments, the cysteine residue is Cys159 of HCV protease, or a mutant thereof, where the provided residue numbering is in accordance with Uniprot (code Q91RS4).

One of ordinary skill in the art will recognize that a variety of warhead groups, as defined herein, are suitable for such covalent bonding. Such R³ groups include, but are not limited to, those described herein and depicted in Table 3, supra. This phenomenon was determined by performing mass spectroscopic experiments using the protocol described in detail in Examples 25-28, infra. The results of this experiment are depicted in FIGS. 1 through 14 where it is shown that provided compounds covalently modify Cys159 of HCV protease. Indeed, these experiments show that provided compounds do not covalently modify the HCV C159S variant thereby demonstrating that the Cys159 is the residue that is covalently modified.

According to another aspect, the present invention provides a conjugate comprising HCV protease, or a mutant thereof, covalently bonded to an inhibitor at Cys159. In some embodiments, the inhibitor is covalently bonded via a linker moiety.

In certain embodiments, the present invention provides a conjugate of the formula Cys159-linker-inhibitor moiety. One of ordinary skill in the art will recognize that the "linker" group corresponds to an -L-Y warhead group as described herein. Accordingly, in certain embodiments, the linker group is as defined for -L-Y was defined above and described in classes and subclasses herein. It will be appreciated, however, that the linker group is bivalent and, therefore, the corresponding -L-Y group is also intended to be bivalent resulting from the reaction of the warhead with the Cys159 of HCV protease, or a mutant thereof.

As used herein, the term "inhibitor moiety" refers to a backbone group that binds in the active site of HCV protease. Such backbone groups are well known in the art and include those described, for example, in US 2006258868, U.S. Pat. No. 6,642,204, U.S. Pat. No. 7,091,184, U.S. Pat. No. 6,642,204, U.S. Pat. No. 7,091,184, US 2006205638, U.S. Pat. No. 7,189,844, US 2005267151, U.S. Pat. No. 7,148,347, WO 2007009227, US 2007243166, US 20070224167, US 2006287248, US 2006046956, U.S. Pat. No. 7,253,160, WO 2006122188, US 2005143316, U.S. Pat. No. 7,135,462, U.S. Pat. No. 7,132,504, U.S. Pat. No. 6,878,722, U.S. Pat. No. 7,041,698, U.S. Pat. No. 6,869,964, U.S. Pat. No. 6,995,174, U.S. Pat. No. 6,872,805, US 2007099825, U.S. Pat. No. 6,867,185, US 2007010455, US 2006199773, U.S. Pat. No. 7,208,600, U.S. Pat. No. 7,273,885, U.S. Pat. No. 7,273,851, US 2007072809, US 2006122123, and US 20050267018.

In certain embodiments, the inhibitor moiety is a compound of formula A:

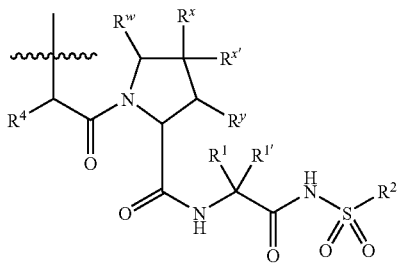

A wherein each of the R¹, R¹', R², R⁴, Rˣ, Rˣ', R⁴, and Rʸ groups of formula A is as defined for formula I above and described in classes and subclasses herein. Thus, in certain embodiments, the present invention provides a conjugate of the formula:

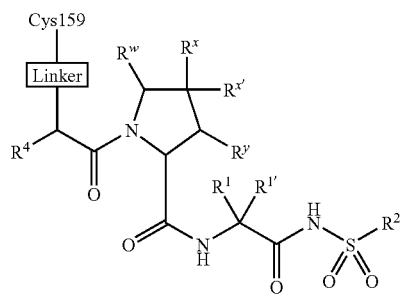

wherein each of the R¹, R¹', R², R⁴, Rʷ, Rˣ, Rˣ', R⁴, and Rʸ groups of the conjugate is as defined for formula I above and described in classes and subclasses herein.

In some embodiments, R³ is characterized in that the -L-Y moiety is capable of covalently binding to a cysteine residue thereby irreversibly inhibiting the enzyme. In certain embodiments, the cysteine residue is Cys16 of HCV protease, or a mutant thereof, where the provided residue numbering is in accordance with Uniprot (code Q91RS4).

According to another aspect, the present invention provides a conjugate comprising HCV protease, or a mutant thereof, covalently bonded to an inhibitor at Cys16. In some embodiments, the inhibitor is covalently bonded via a linker moiety.

In certain embodiments, the present invention provides a conjugate of the formula Cys16-linker-inhibitor moiety. One of ordinary skill in the art will recognize that the "linker" group corresponds to an -L-Y warhead group as described herein. Accordingly, in certain embodiments, the linker group is as defined for -L-Y was defined above and described in classes and subclasses herein. It will be appreciated, however, that the linker group is bivalent and, therefore, the corresponding -L-Y group is also intended to be bivalent resulting from the reaction of the warhead with the Cys16 of HCV protease, or a mutant thereof.

In certain embodiments, the inhibitor moiety is a compound of formula A-1:

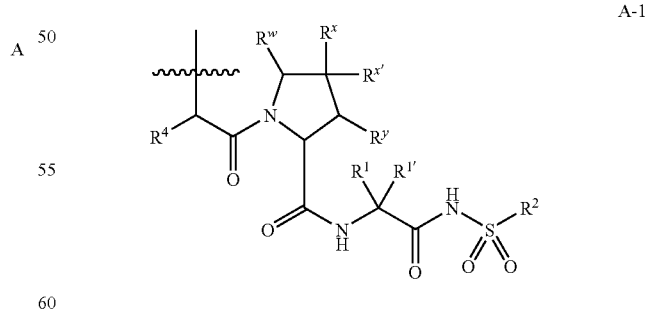

A-1 wherein each of the R¹, R¹', R², R⁴, Rˣ, Rˣ', R⁴, and Rʸ groups of formula A-1 is as defined for formula I above and described in classes and subclasses herein. Thus, in certain embodiments, the present invention provides a conjugate of the formula:

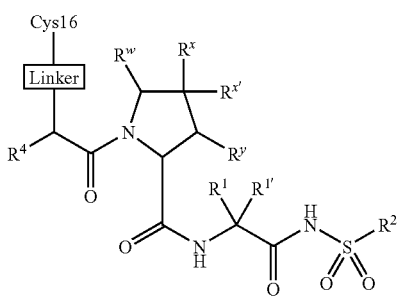

wherein each of the $R^1$, $R^{1'}$, $R^2$, $R^4$, $R^w$, $R^x$, $R^{x'}$, $R^4$, and $R^y$ groups of the conjugate is as defined for formula I above and described in classes and subclasses herein.

One of ordinary skill in the art will recognize that certain compounds of the present invention are reversible inhibitors. In certain embodiments, such compounds are useful as assay comparator compounds. In some embodiments, such reversible compounds are useful as inhibitors of HCV protease, or a mutant thereof, and therefore useful for treating one or more disorders as described herein. In some embodiments, provided compounds are reversible counterparts of provided irreversible inhibitors. For example, compound $I^R$-3 (infra) is a reversible reference analog of compound I-3.

General Methods of Providing the Present Compounds

In certain embodiments, the present compounds are generally prepared according to Scheme 1 set forth below:

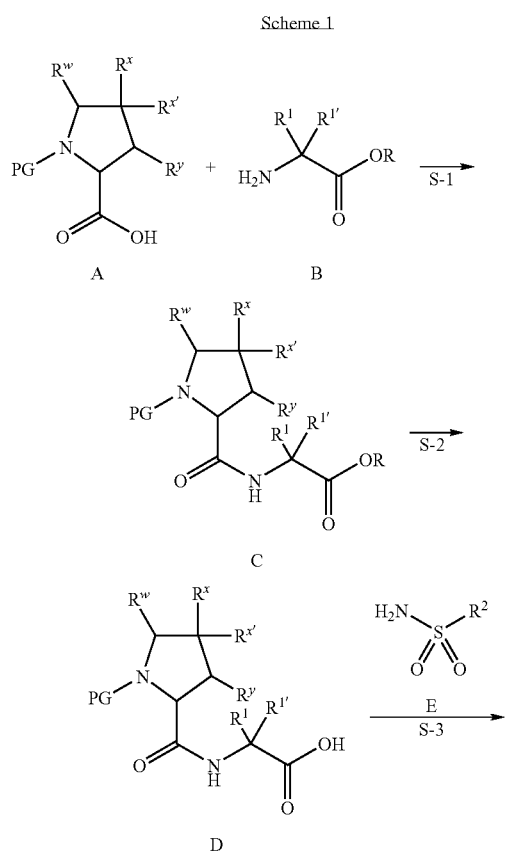

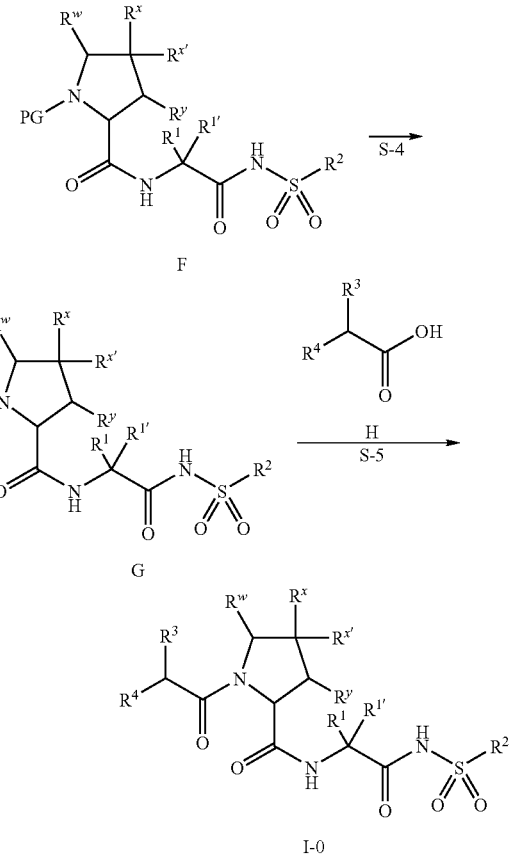

In one aspect, the present invention provides methods for preparing compounds of formula I, according to the steps depicted in Scheme 1 above wherein each variable is as defined and described herein and each PG is a suitable protecting group. At step S-1, an N-protected (e.g. Boc) proline derivative of formula A is condensed with an alpha-aminoester of formula B using peptide coupling conditions to give a dipeptide of formula C. Suitable peptide coupling conditions are well known in the art and include those described in detail in PCT publication number WO2002094822 (U.S. Pat. No. 6,825,347), the entirety of which is hereby incorporated by reference. Unless otherwise indicated, said conditions are referenced as suitable peptide coupling conditions throughout this application.

At step S-2, the ester group is hydrolyzed with a suitable base and subsequently neutralized to give a dipeptide of formula D. Suitable bases include, but are not limited to, alkaline metals, alkaline earth metal hydroxides, and combinations thereof. In some embodiments, the base is lithium hydroxide.

At step S-3, a dipeptide of formula D is coupled with a sulfonamide of formula E using suitable peptide coupling conditions to give an acylsulfonamide of formula F.

At step S-4, cleavage of the protective group (e.g. Boc removal) from a dipeptide of formula F gives an amine of formula G. In certain embodiments, cleavage of the Boc group is achieved by contacting a compound of formula F with a mineral or organic acid in a halogenated hydrocarbon solvent. In some embodiments, In some embodiments, the acid is trifluoroacetic acid and the solvent is dichloromethane.

At step S-5, an amine of formula G is coupled with a carboxylic acid of formula H using suitable peptide coupling conditions to give an intermediate compound of formula I-0.

Intermediate compound of formula I-0 is converted to compounds of formula I in steps which are described as examples herein.

As defined generally above, the PG group of formulae A, C, D, and F is a suitable amino protecting group. Suitable amino protecting groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like.

In other embodiments, the present compounds are generally prepared according to Scheme 2 set forth below.

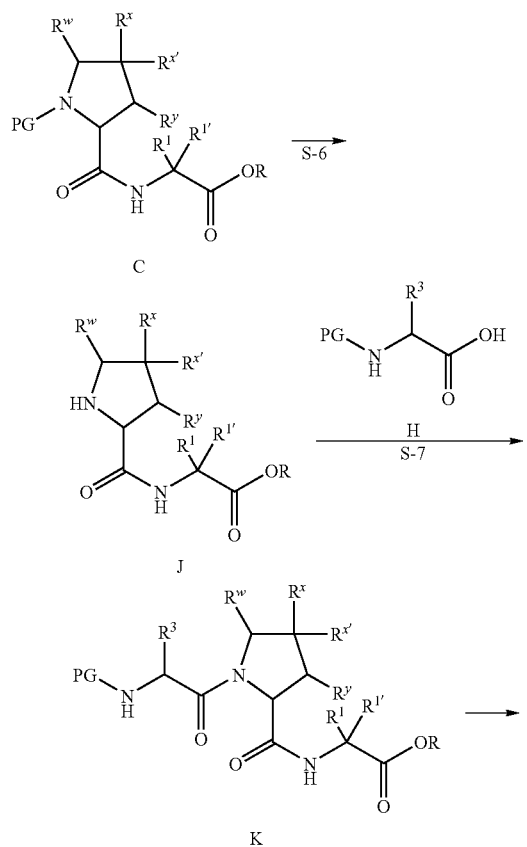

Scheme 2

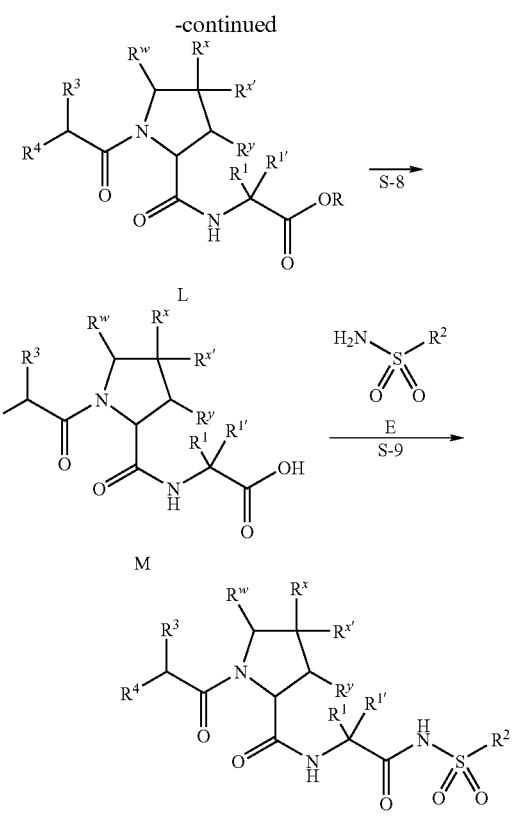

In one aspect, the present invention provides methods for preparing compounds of formula I, according to the steps depicted in Scheme 1 above. At step S-6, removal of the Boc group from a dipeptide of formula C is achieved under acid-catalyzed conditions to give a dipeptide ester of formula J.

At step S-7, a dipeptide ester of formula J is condensed with a functionalized amino acid of formula H using suitable peptide coupling conditions to give a tripeptide ester of formula K which is further converted to a tripeptide ester of formula L in steps which are described as examples herein.

At step S-8, the ester group on a compound of formula L is hydrolyzed with a suitable base and subsequently neutralized to give a tripeptide of formula M. Suitable bases include, but are not limited to, alkaline metals, alkaline earth metal hydroxides, and combinations thereof. In some embodiments, the base is lithium hydroxide.

At step S-9, a tripeptide of formula M is condensed with a sulfonamide of formula E using suitable peptide coupling conditions to give compounds of formula I.

The PG group of formulae C, H, and K is a suitable amino protecting group as described above.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit HCV protease, or a mutant thereof, in a biological sample or in a patient. In certain embodiments, the amount of compound in compositions of this invention is such that is effective to measurably inhibit HCV protease, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of HCV protease, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of HCV protease activity and/or the activity of a mutant thereof. Thus, provided compounds are useful for treating non-A, non-B hepatitis, including hepatitis C.

HCV is an extremely variable virus that forms polymorphic swarms of variants within the host. Worldwide, six different genotypes have now been defined (Simmonds et al., Hepatology, Vol. 42, No. 4, 2005). These genotypes have been further classified into more closely related, genetically distinct subtypes. Comparative sequence portions, known as consensus sequences, are set forth in Table 3a, below. HCV genotypes and subtypes are distributed differently in different parts of the world, and certain genotypes predominate in certain areas. Genotypes 1-3 are widely distributed throughout the world. Subtype 1a is prevalent in North and South America, Europe, and Australia. Subtype 1b is common in North America and Europe, and is also found in parts of Asia. Genotype 2 is present in most developed countries, but is less common than genotype 1 (http://www.hcvadvocate.org/hepatitis/factsheets_pdf/genotype_FS.pdf). Other genotypes are prevalent in ex-US patient populations and are therefore important targets.

Notably, a cysteine located at amino acid position 159 in genotype 1b is conserved in all genotypes and subtypes of HCV NS3 sequenced to date, although the amino acid position may be different in other genotypes and subtypes. Targeting this cysteine residue with irreversible inhibitors should enable the development of agents which are effective against multiple HCV genotypes.

As described herein, the present invention provides irreversible inhibitors of one or more HCV protease genotypes, and variants thereof. Such compounds, comprising a warhead group designated as $R^3$, include those of formulae I, I-a, I-b, I-c-1, I-c-2, I-c-3, I-c-4, I-c-5, I-c-6, I-d, I-e, I-f, I-g, I-h, II-a, II-b, III-a, III-b, IV-a, IV-b, IV-c, IV-d, V-a, V-b, V-c, V-d, VI-a, VI-b, VII-a, VII-b, VIII-a, and VIII-b, as described herein. In some embodiments, $R^3$ is characterized in that the -L-Y moiety is capable of covalently binding to a cysteine residue thereby irreversibly inhibiting the enzyme. Without wishing to be bound by any particular theory, it is believed that such $R^3$ groups, i.e. warhead groups, are particularly suitable for covalently binding to a key cysteine residue in the binding domain of one or more HCV protease genotypes or variants thereof. In some embodiments, one or more genotypes inhibited by compounds of the present invention include 1a, 1b, 2a, and 3a. In certain embodiments, one or more such variants include A156T, A156S, D168V, D168A, and R155K.

One of ordinary skill in the art will appreciate that HCV protease genotypes and variants thereof have one or more cysteine residues near the binding domain. Without wishing to be bound by any particular theory, it is believed that proximity of a warhead group to the cysteine of interest facilitates covalent modification of that cysteine by the warhead group. In some embodiments, the cysteine residue of interest is Cys159 of HCV protease subtype 1b, or a variant thereof, where the provided residue numbering is in accordance with Uniprot (code Q91RS4). Cysteine residues of other HCV protease genotypes and subtypes suitable for covalent modification by irreversible inhibitors of the present invention include those summarized in Table 3a, below, where the bold and underlined "C" refers to a cysteine residue conserved at an equivalent position to Cys159 of HCV protease subtype 1b.

TABLE 3a

| HCV genotype/subtype | Representative Sequence Portion[a] | Patient ID | Sequence Identifier |
|---|---|---|---|
| 1a | GHAVGLFRAAVCTRGVAKAV | _.H77.NC_004102 | SEQ ID NO: 1 |
| 1a | GHAVGIFRAAVCTRGVAKAV | CH.BID-V271.EU482858 | SEQ ID NO: 2 |
| 1a | GHAVGIFRAAVCTRGVAKAV | DE.BID-V25.EU482831 | SEQ ID NO: 3 |
| 1a | GHAVGLFRAAVCTRGVAKAV | US.H77-H21.AF011753 | SEQ ID NO: 4 |
| 1b | GHAVGIFRAAVCTRGVAKAV | AU.HCV-A.AJ000009 | SEQ ID NO: 5 |
| 1b | GHVVGIFRAAVCTRGVAKAV | CH.BID-V272.EU482859 | SEQ ID NO: 6 |
| 1b | GHAVGIFRAAVCTRGVAKAV | JP.HCV-BK.M58335 | SEQ ID NO: 7 |
| 1c | GHAVGIFRAAVCTRGVAKAV | ID.HC-G9.D14853 | SEQ ID NO: 8 |
| 1c | GHVAGIFRAAVCTRGVAKAV | IN.AY051292.AY051292 | SEQ ID NO: 9 |
| 2a | GHAVGIFRAAVCSRGVAKSI | JP.AY746460.AY746460 | SEQ ID NO: 10 |
| 2a | GHAVGIFRAAVCSRGVAKSI | JP.JCH-6.AB047645 | SEQ ID NO: 11 |
| 2a | GHAVGIFRAAVCSRGVAKSI | _.G2AK1.AF169003 | SEQ ID NO: 12 |
| 2b | GHAVGLFRAAVCARGVAKSI | JP.HC-J8.D10988 | SEQ ID NO: 13 |
| 2b | GHAVGLFRAAVCARGVAKSI | JP.MD2b1-2.AY232731 | SEQ ID NO: 14 |

TABLE 3a-continued

| HCV genotype/ subtype | Representative Sequence Portion[a] | Patient ID | Sequence Identifier |
|---|---|---|---|
| 2c | GHAVGIFRAAV*C*SRGVAKSI | _.BEBE1.D50409 | SEQ ID NO: 15 |
| 2i | AHAVGIFRAAV*C*SRGVAKSI | VN.D54.DQ155561 | SEQ ID NO: 16 |
| 2k | GHAVGIFRAAI*C*TRGAAKSI | MD.VAT96.AB031663 | SEQ ID NO: 17 |
| 3a | GHVAGIFRAAV*C*TRGVAKAL | CH.452.DQ437509 | SEQ ID NO: 18 |
| 3a | GHVAGIFRAAV*C*TRGVAKAL | DE.HCVCENS1.X76918 | SEQ ID NO: 19 |
| 3a | GHVAGIFRAAV*C*TRGVAKAL | ID.ps23.EU315121 | SEQ ID NO: 20 |
| 3b | GHVMGIFIAVV*C*TRGVAKAL | IN.RG416.DQ284965 | SEQ ID NO: 21 |
| 3b | GHVVGIFRAAV*C*TRGVAKAL | JP.HCV-Tr.D49374 | SEQ ID NO: 22 |
| 3k | GHVAGIFRAAV*C*TRGVAKAL | ID.JK049.D63821 | SEQ ID NO: 23 |
| 4a | GHAAGIFRAAV*C*TRGVAKAV | EG.Eg9.DQ988077 | SEQ ID NO: 24 |
| 4a | GHAAGLFRAAV*C*TRGVAKAV | _.01-09.DQ418782 | SEQ ID NO: 25 |
| 4a | GHAAGLFRAAV*C*TRGVAKAV | _.F753.DQ418787 | SEQ ID NO: 26 |
| 4d | GHAAGIFRAAV*C*TRGVAKAV | _.03-18.DQ418786 | SEQ ID NO: 27 |
| 4d | GHAAGIFRAAV*C*TRGVAKTV | _.24.DQ516083 | SEQ ID NO: 28 |
| 4f | GHAVGIFRAAV*C*TRGVAKAV | FR.IFBT84.EF589160 | SEQ ID NO: 29 |
| 4f | GHAVGIFRAAV*C*TRGVAKAV | FR.IFBT88.EF589161 | SEQ ID NO: 30 |
| 5a | GHVVGVFRAAV*C*TRGVAKAL | GB.EUH1480.Y13184 | SEQ ID NO: 31 |
| 5a | GHVVGVFRAAV*C*TRGVAKAL | ZA.SA13.AF064490 | SEQ ID NO: 32 |
| 6a | GHVVGLFRAAV*C*TRGVAKSL | HK.6a74.DQ480524 | SEQ ID NO: 33 |
| 6a | GHVVGLFRAAV*C*TRGVAKSL | HK.6a77.DQ480512 | SEQ ID NO: 34 |
| 6a | GHVVGLFRAAV*C*TRGVAKSL | HK.EUHK2.Y12083 | SEQ ID NO: 35 |
| 6b | GHVVGLFRAAV*C*TRGVAKAL | _.Th580.NC_009827 | SEQ ID NO: 36 |
| 6c | GHVVGLFRAAV*C*TRGVAKAL | TH.Th846.EF424629 | SEQ ID NO: 37 |
| 6d | DHVVGLFRAAV*C*TRGVAKAL | VN.VN235.D84263 | SEQ ID NO: 38 |
| 6e | GHVVGLFRAAV*C*TRGVAKAI | CN.GX004.DQ314805 | SEQ ID NO: 39 |
| 6f | GHAVGIFRAAV*C*TRGVAKAI | TH.C-0044.DQ835760 | SEQ ID NO: 40 |
| 6f | GHAVGIFRAAV*C*TRGVAKAI | TH.C-0046.DQ835764 | SEQ ID NO: 41 |
| 6g | GHVVGLFRAAV*C*TRGVAKAL | HK.HK6554.DQ314806 | SEQ ID NO: 42 |
| 6g | GHVVGLFRAAV*C*TRGVAKAL | ID.JK046.D63822 | SEQ ID NO: 43 |
| 6h | GHVAGIFRAAV*C*TRGVAKSL | VN.VN004.D84265 | SEQ ID NO: 44 |
| 6i | GHVAGIFRAAV*C*TRGVAKSL | TH.C-0159.DQ835762 | SEQ ID NO: 45 |
| 6j | GHVAGIFRAAV*C*TRGVAKSL | TH.C-0667.DQ835761 | SEQ ID NO: 46 |
| 6j | GHVAGIFRAAV*C*TRGVAKSL | TH.Th553.DQ835769 | SEQ ID NO: 47 |
| 6k | GHVAGIFRAAV*C*TRGVAKSL | CN.KM41.DQ278893 | SEQ ID NO: 48 |
| 6k | GHVAGIFRAAV*C*TRGVAKSL | CN.KM45.DQ278891 | SEQ ID NO: 49 |
| 6k | GHVAGIFRAAV*C*TRGVAKSL | VN.VN405.D84264 | SEQ ID NO: 50 |
| 6l | GHVAGIFRAAV*C*TRGVAKSL | US.537796.EF424628 | SEQ ID NO: 51 |
| 6m | GHAVGVFRAAV*C*TRGVAKSL | TH.C-0185.DQ835765 | SEQ ID NO: 52 |

TABLE 3a-continued

| HCV genotype/ subtype | Representative Sequence Portion[a] | Patient ID | Sequence Identifier |
|---|---|---|---|
| 6m | GHAVGVFRAAVCTRGVAKSL | TH.C-0208.DQ835763 | SEQ ID NO: 53 |
| 6n | GHVVGIFRAAVCTRGVAKSL | CN.KM42.DQ278894 | SEQ ID NO: 54 |
| 6n | GHVVGIFRAAVCTRGVAKSL | TH.D86/93.DQ835768 | SEQ ID NO: 55 |
| 6o | GHAVGLFRAAVCTRGVAKAI | CA.QC227.EF424627 | SEQ ID NO: 56 |
| 6p | GHVVGLFRAAVCTRGVAKAI | CA.QC216.EF424626 | SEQ ID NO: 57 |
| 6q | GHAVGLFRAAVCTRGVAKAI | CA.QC99.EF424625 | SEQ ID NO: 58 |
| 6t | GHVVGLFRAAVCTRGVAKAI | VN.TV241.EF632069 | SEQ ID NO: 59 |
| 6t | GHVVGLFRAAVCTRGVAKAI | VN.TV249.EF632070 | SEQ ID NO: 60 |
| 6t | GHVVGLFRAAVCTRGVAKAI | VN.VT21.EF632071 | SEQ ID NO: 61 |
| 7a | SHCVGIFRAAVCTRGVAKAV | CA.QC69.EF108306 | SEQ ID NO: 62 |

[a] It will be appreciated by one of ordinary skill in the art that every virus is prone to mutation and subject to polymorphisms, and any genotype consensus sequences described herein are representative of a given genotype or subtype. Such representative consensus sequences are available at http://hcv.lanl.gov/content/sequence/NEWALIGN/align.html.

Drug resistance is emerging as a significant challenge for targeted therapies. For example, drug resistance has been reported for HCV protease inhibitors in development. Such compounds include BILN 2061 and VX-950, developed by Boehringer Ingelheim and Vertex Pharmaceuticals, respectively. The structures of BILN 2061 and VX-950 are depicted below.

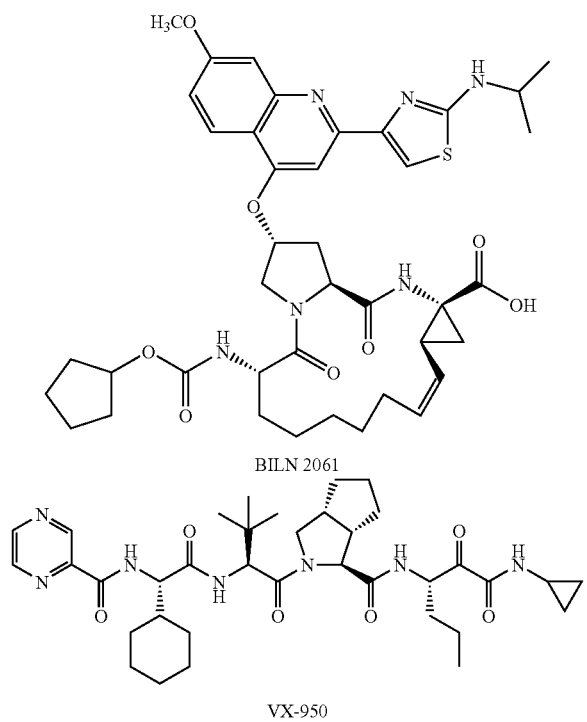

BILN 2061

VX-950

In fact, a recent article published by Vertex Pharmaceuticals, entitled, "In Vitro Resistance Studies of Hepatitis C Virus Serine Protease," squarely addresses the problem of mutant resistance observed with VX-950 and BILN 2061. See Lin et al., The Journal of Biological Chemistry, Vol. 279, No. 17, Issue of April 23, pp. 17508-17514, 2004. This article concludes that "future hepatitis C therapy involving small molecule inhibitors of HCV enzymes might require multi-drug combination, as in the case of the current HIV treatments." See page 17513, last paragraph.

Resistance to specific antiviral drugs is a major factor limiting the efficacy of therapies against many retroviruses or RNA viruses. The error-prone nature of these viruses allows for the development of mutations that afford resistance to currently available drugs or drugs undergoing clinical testing. The resistance problem is a critical hurdle faced in drug development of new HCV-specific inhibitors to treat HCV patients.

A recent in vitro resistance study using two HCV NS3·4A protease inhibitors, VX-950 and BILN 2061, found that resistance mutations selected against either inhibitor resulted in a significant reduction in susceptibility to the inhibitor itself. However, the primary resistance mutations against BILN 2061 were fully susceptible to VX-950, and the major resistance mutation against VX-950 remained sensitive to BILN 2061 (Lin et al., Jour. Biol. Chem. 279(17): 17508-14, 2004).

It has been surprisingly found that provided compounds inhibit at least five HCV protease mutants, including A156T, A156S, D168V, and D168A and R155K. This stands in contrast to other known HCV protease inhibitors (e.g., VX-950 and BILN 2061) which inhibit only two mutants each. In fact, no drug described in the prior art has been shown to be an effective inhibitor of all known HCV protease mutants. For example, and as set forth in Tables 4a and 4b below, where the BILN 2061 and VX-950 data are as reported by Lin et al. and elsewhere in the HCV literature, and the data for compound I-3 was obtained according to methods set forth in the Examples, infra. Without wishing to be bound by any particular theory, it is believed that compounds of the present invention may be effective inhibitors of drug resistant forms of HCV protease. While Table 4b shows compound I-3 activity against four reference HCV variants (A156T, A156S, D168V, and D168A), the ensuing examples will describe other provided compounds of the invention that are active against these variants as well as a fifth (R155K) variant.

TABLE 4a

Comparative $K_i$ Values (nM)[a]

| | BILN 2061 | VX-950 |
|---|---|---|
| WT | 19 | 100 |
| A156T | >1200 | 9900 |
| A156S | 112 | 2900 |
| D168V | >1200 | 43 |
| D168A | >1200 | 150 |

[a]Wild-type data were obtained from cell-based assays, and mutant data were obtained from biochemical assays. See Lin et al. and protocols described herein.

TABLE 4b

Comparative $IC_{50}$ Values (nM)[a]

| | BILN 2061 | VX-950 | Compound I-3 |
|---|---|---|---|
| WT | 4 | 402 | 20 |
| A156T | — | — | 18 |
| A156S | 7 | 4650 | 1 |
| D168V | 5090 | 163 | 77 |
| D168A | 1860 | 193 | 45 |

[a]Wild-type data were obtained from cell-based assays, and mutant data were obtained from biochemical assays. See Lin et al. and protocols described herein.

Without wishing to be bound by any particular theory, it is believed that a compound of formula I is more effective at inhibiting HCV protease, or a mutant thereof, as compared to a corresponding compound of formula I wherein the $R^3$ moiety of formula I is instead a non-warhead group, such as straight alkyl (e.g., unsubstituted alkyl), branched alkyl, cycloalkyl, or alkenyl. For example, a compound of formula I can be more effective at inhibition of HCV protease, or a mutant thereof, as compared to a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl.

A compound of formula I, as disclosed above, can be more potent with respect to an IC50 against HCV protease, or a mutant such as A156T, A156S, D168V, D168A, or other mutants such as those disclosed herein, than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl. Such comparative potency of a compound of formula I as compared to a corresponding compound of formula I wherein the $R^3$ moiety of formula I is instead a non-warhead moiety, can be determined by standard time-dependent assay methods, such as those described in detail in the Examples section, infra. In certain embodiments, a compound of formula I is measurably more potent than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl. In some embodiments, a compound of formula I is measurably more potent, wherein such potency is observed after about 1 minute, about 2 minutes, about 5 minutes, about 10 minutes, about 20 minutes, about 30 minutes, about 1 hour, about 2 hours, about 3 hours, about 4 hours, about 8 hours, about 12 hours, about 16 hours, about 24 hours, or about 48 hours, than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl. In some embodiments, a compound of formula I is any of about 1.5 times, about 2 times, about 5 times, about 10 times, about 20 times, about 25 times, about 50 times, about 100 times, or even about 1000 times more potent than a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl.

As used herein, the term "clinical drug resistance" refers to the loss of susceptibility of a drug target to drug treatment as a consequence of mutations in the drug target As used herein, the term "resistance" refers to changes in the wild-type nucleic acid sequence coding a target protein, and/or the protein sequence of the target, which changes decrease or abolish the inhibitory effect of the inhibitor on the target protein.

Examples of proteases that are inhibited by the compounds and compositions described herein and against which the methods described herein are useful include NS3, NS3·4A, or a mutant thereof.

The activity of a compound utilized in this invention as an inhibitor of NS3, NS3·4A, or a mutant thereof, may be assayed in vitro, in vivo or in a cell line. In vitro assays include assays that determine inhibition of either the serine protease activity and/or the subsequent functional consequences, or ATPase activity of activated NS3, NS3·4A, or a mutant thereof. Alternate in vitro assays quantitate the ability of the inhibitor to bind to NS3 or NS3·4A. Inhibitor binding may be measured by radiolabelling the inhibitor prior to binding, isolating the inhibitor/NS3 or inhibitor/NS3·4A complex and determining the amount of radiolabel bound. Alternatively, inhibitor binding may be determined by running a competition experiment where new inhibitors are incubated with NS3 or NS3·4A bound to known radioligands. Detailed conditions for assaying a compound utilized in this invention as an inhibitor of NS3 or NS3·4A, or a mutant thereof, are set forth in the Examples below.

Serine proteases are a large family of proteolytic enzymes that cleave peptide bonds in proteins. The serine protease family includes the digestive enzymes chymotrypsin, trypsin, and elastase, and proteases involved in blood clotting. Serine proteases possess a characteristic "catalytic triad" comprising serine, aspartic acid, and histidine, that together function to activate serine to form a covalent bond with the enzyme substrate, thereby hydrolyzing a peptide bond. In addition to those stated above, serine proteases participate in a variety of functions including immunity and inflammation.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a provided composition is administered to a patient in need thereof once daily. Without wishing to be bound by any particular theory, it is believed that prolonged duration of action of an irreversible inhibitor of HCV NS3 protease is particularly advantageous for once daily administration to a patient in need thereof for the treatment of a disorder associated with HCV NS3 protease. In certain embodiments, a provided composition is administered to a patient in need thereof at least once daily. In other embodiments, a provided composition is administered to a patient in need thereof twice daily, three times daily, or four times daily.

Compounds of formula I, for example, generally provide prolonged duration of action when administered to a patient as compared to a corresponding compound of formula I wherein the $R^3$ moiety of formula I is instead a non-warhead moiety such as straight alkyl (e.g., unsubstituted alkyl), branched alkyl, cycloalkyl, or alkenyl. For example, a compound of formula I can provide prolonged duration of action when administered to a patient as compared to a corresponding compound of formula I wherein the $R^3$ moiety of formula I is instead a non-warhead moiety such as methyl, ethyl, propyl, butyl (e.g., t-butyl), unsubstituted straight or branched alkenyl (e.g. $C_{1-8}$ alkenyl), cyclohexyl, or cyclopentyl.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting serine protease activity in a biological sample comprising the step of contacting said biological sample with a compound of this invention, or a composition comprising said compound.

According to another embodiment, the invention relates to a method of inhibiting HCV protease, or a mutant thereof, activity in a biological sample comprising the step of contacting said biological sample with a compound of this invention, or a composition comprising said compound. In certain embodiments, the invention relates to a method of irreversibly inhibiting HCV protease, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of HCV protease, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting HCV protease, or a mutant thereof, activity in a patient comprising the step of administering to said patient a compound of the present invention, or a composition comprising said compound.

According to another embodiment, the invention relates to a method of inhibiting HCV protease, or a mutant thereof, activity in a patient comprising the step of administering to said patient a compound of the present invention, or a composition comprising said compound. According to certain embodiments, the invention relates to a method of irreversibly inhibiting HCV protease, or a mutant thereof, activity in a patient comprising the step of administering to said patient a compound of the present invention, or a composition comprising said compound. In other embodiments, the present invention provides a method for treating a disorder mediated by HCV protease, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of HCV protease, or a variant thereof. In some embodiments, a provided compound, or composition thereof, is administered in combination with another antiviral agent. Such antiviral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors, e.g. BILN 2061 and VX-950); inhibitors of other targets in the HCV life cycle, including helicase and polymerase inhibitors; inhibitors of internal ribosome entry; broad-spectrum viral inhibitors, such as IMPDH inhibitors (e.g., mycophenolic acid and derivatives thereof); or combinations of any of the above.

In certain embodiments, a combination of 2 or more antiviral agents may be administered. In certain embodiments, a combination of 3 or more antiviral agents may be administered. In some embodiments, the antiviral agents are selected from ribavirin or interferon. In other embodiments, the antiviral agent is α-interferon.

Other examples of agents the inhibitors of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples, below, correspond to compound numbers set forth in Table 3, supra.

General Method A of Preparing Compounds wherein $R^3$ Contains a Secondary Amide Group

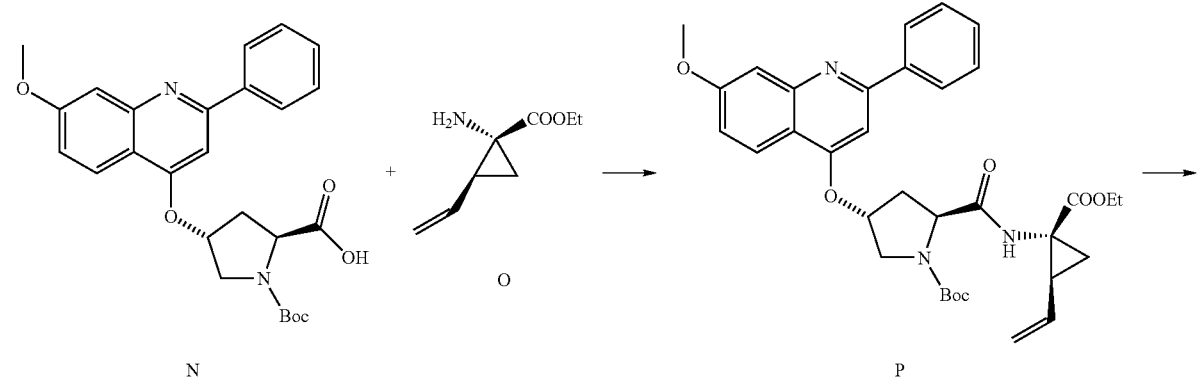

Scheme 3

N                                                                 P

-continued
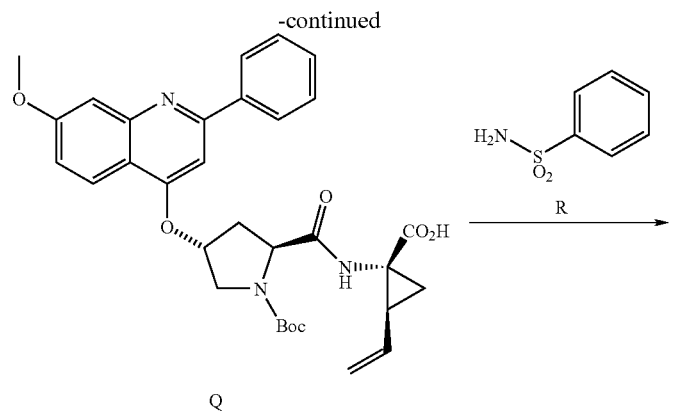
Q
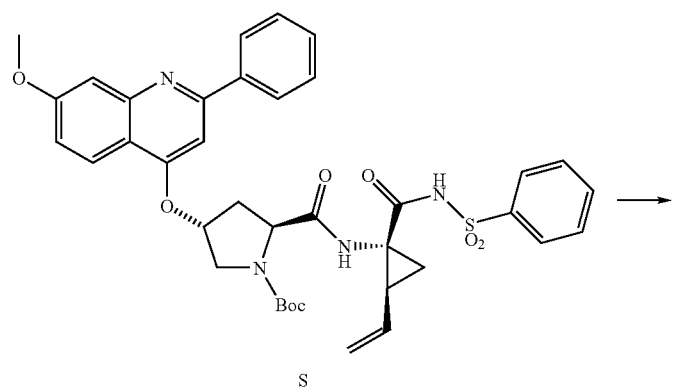
S
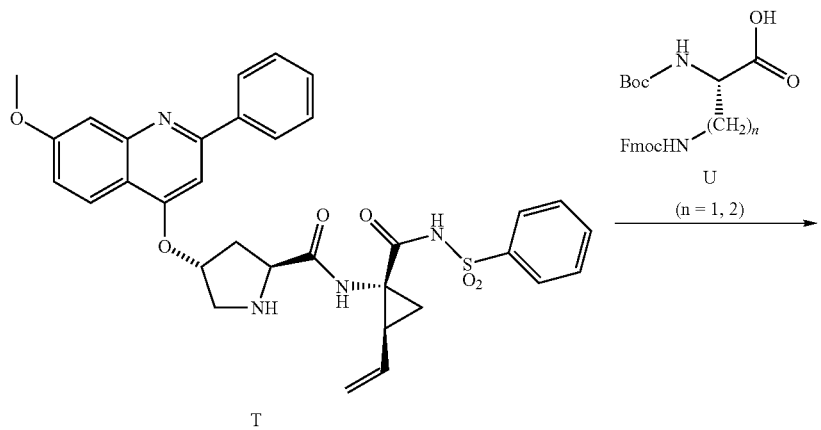
T
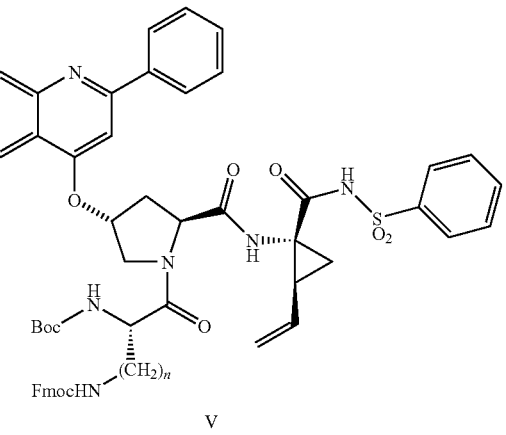
V

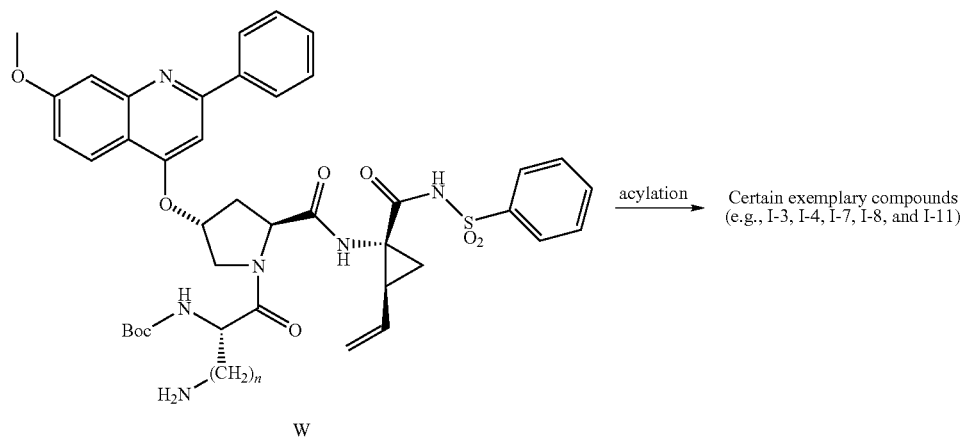

As depicted in Scheme 3 above, Boc-proline derivative N was condensed with alpha-amino acid derivative O using suitable peptide coupling conditions to give dipeptide ester P. Hydrolysis of ester P with aqueous lithium hydroxide followed by acidification gave acid Q. Condensation of Q with sulfonamide R gave the acyl sulfonamide S. Acid-catalyzed removal of Boc from S gave intermediate T. Condensation of T with a Boc/Fmoc-protected amino acid U using suitable peptide coupling conditions gave intermediate V. Selective removal of the Fmoc protective group from V using piperidine gave an amine W, which was acylated with an acid chloride to give the compounds I-3, I-4, I-7, I-8, and I-11 (and others provided in additional Examples herein). While this method generally describes the synthesis of these compounds, one of ordinary skill in the art will recognize that this method can be used to synthesize other compounds of formula I.

General Method B of Preparing Compounds wherein $R^3$ Contains a Tertiary Amide Group

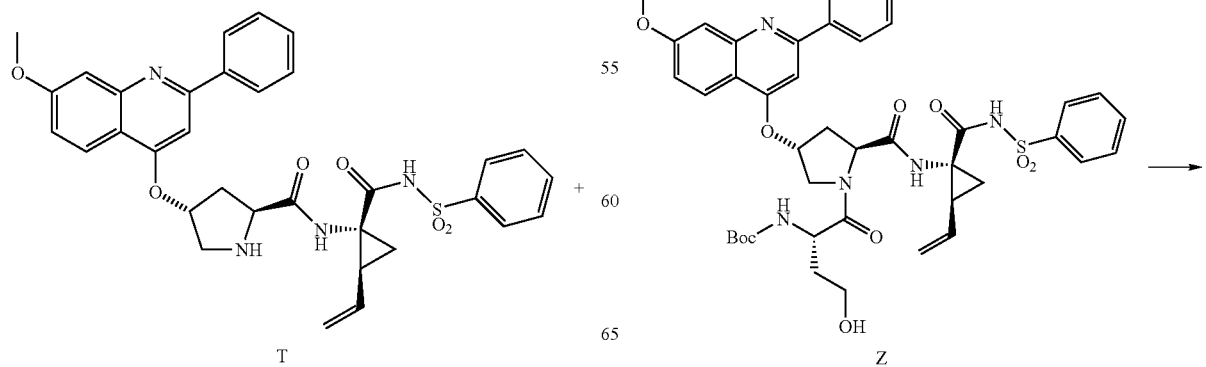

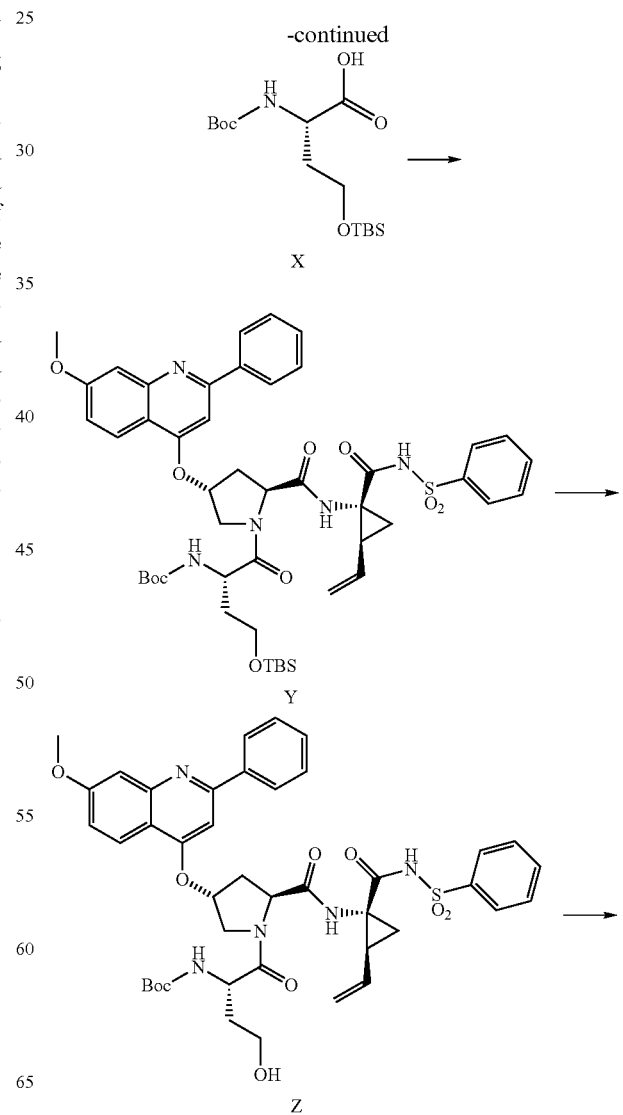

-continued

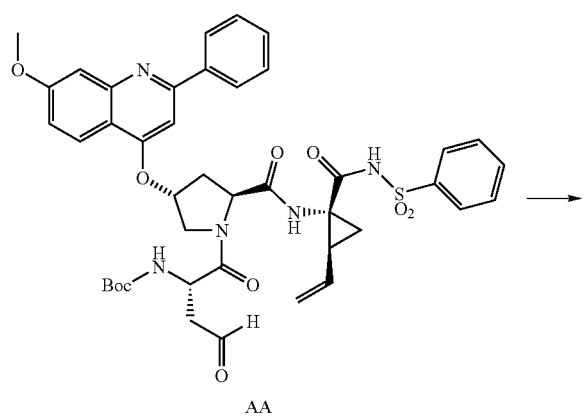

AA

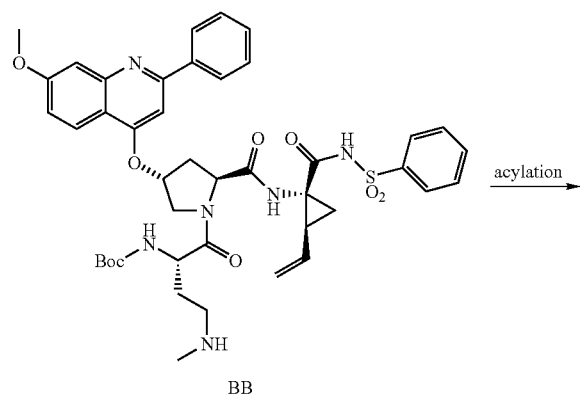

BB

Certain exemplary compounds
(e.g., I-9, I-12)

As depicted in Scheme 4 above, the intermediate T from general method A was condensed with N-Boc-O-TBS-homoserine X using suitable peptide coupling conditions to give tripeptide Y. Fluoride-catalyzed desilylation of Y gave the alcohol Z, which was oxidized with Dess-Martin periodinane to give aldehyde AA, Reductive amination of AA with triacetoxyborohydride and methyl amine gave methylamine BB. Acylation of BB gave the compounds I-9 and I-12 (and others provided in additional Examples herein). While this method generally describes the synthesis of these compounds, one of ordinary skill in the art will recognize that this method can be used to synthesize other compounds of formula I.

General Method C of Preparing Compounds Wherein $R^3$ Contains an Epoxide

Scheme 5

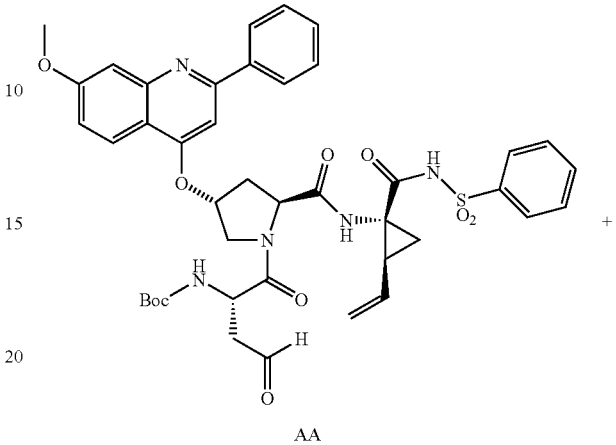

AA

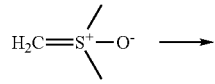

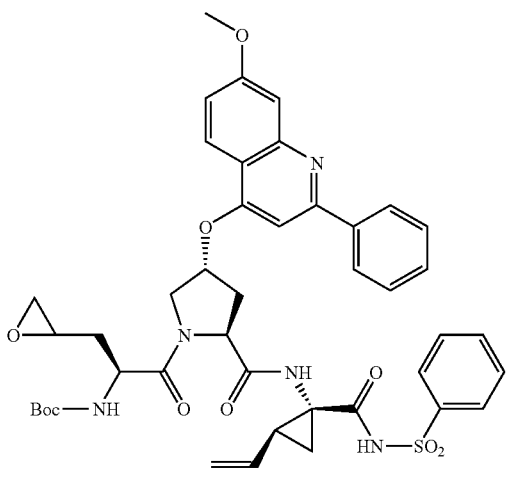

I-6

As depicted in Scheme 5 above, the aldehyde intermediate AA of general method B was reacted with dimethyl sulfoxonium methylide to give the epoxide I-6. While this method generally describes the synthesis of this compound, one of ordinary skill in the art will recognize that this method can be used to synthesize other compounds of formula I.

General Method D of Preparing Compounds Wherein R³ Contains a 2-enamide
Scheme 6
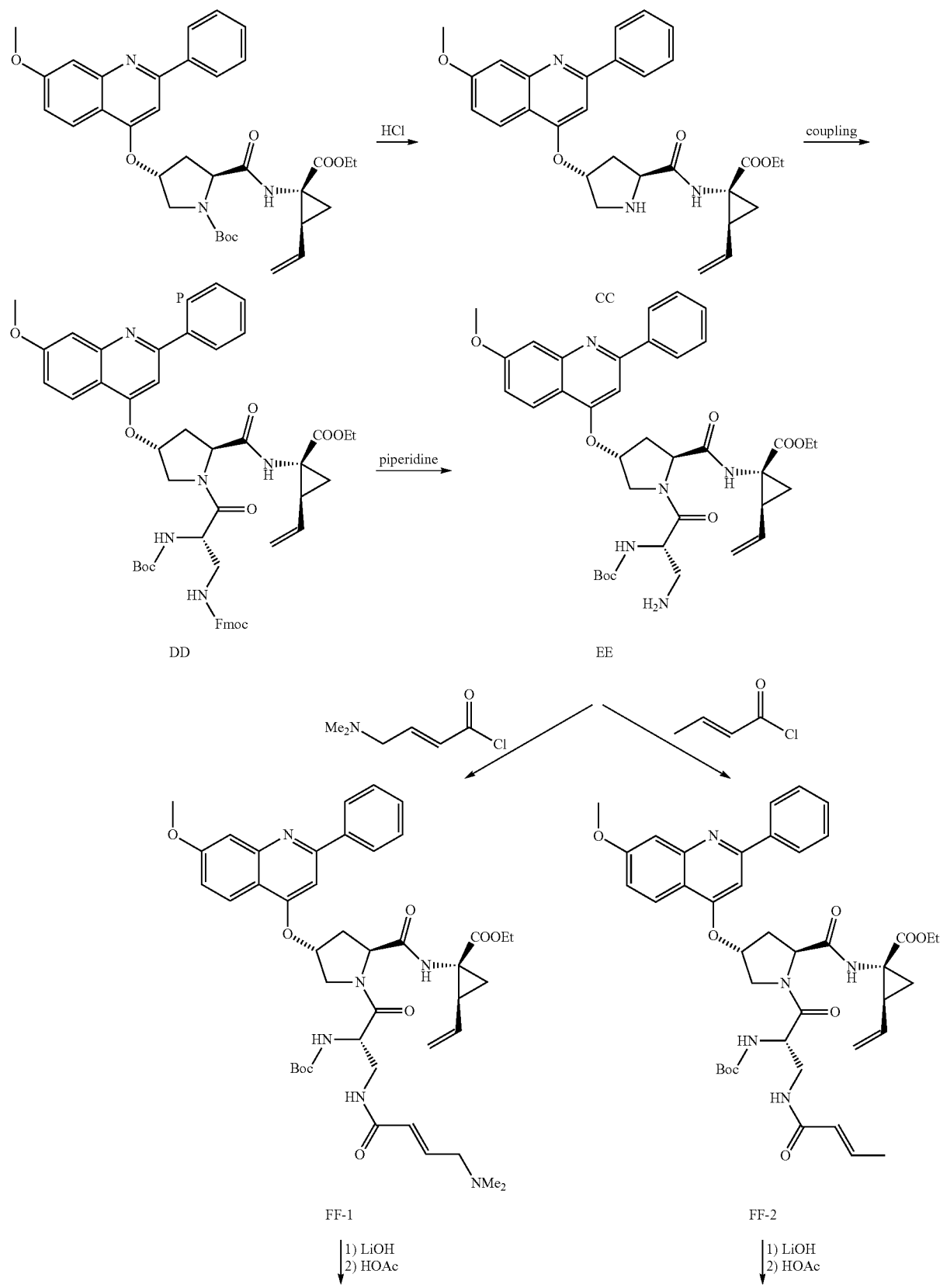

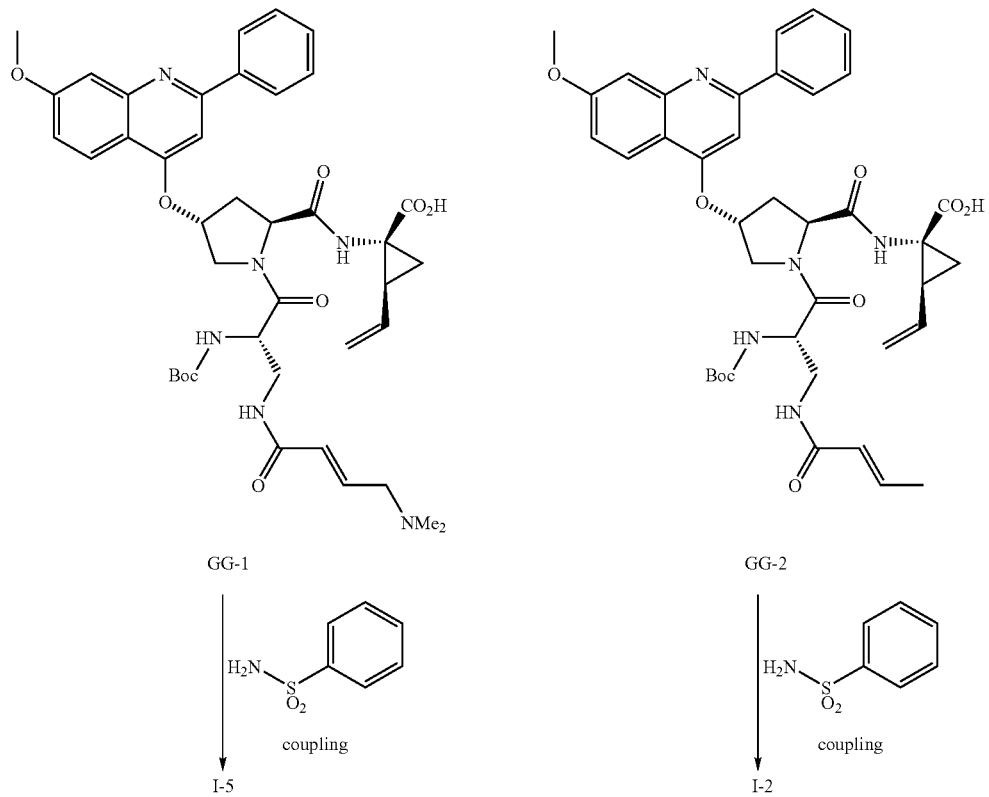

GG-1 → I-5 (coupling with H₂N-SO₂-Ph)

GG-2 → I-2 (coupling with H₂N-SO₂-Ph)

As depicted in Scheme 6 above, the Boc group of intermediate P of general method A was removed with hydrochloric acid to give amine CC. Intermediate CC was condensed with N-Boc-3-(Fmoc)amino-L-alanine using suitable peptide coupling conditions to give the tripeptide intermediate DD. Selective removal of the Fmoc protective group from DD with piperidine gave the amine EE. Acylation of EE with an acid chloride gave amide FF-1 or FF-2. Hydroylsis of FF-1 or FF-2 with lithium hydroxide followed by acidification gave acid GG-1 or GG-2. Coupling of acid GG-1 or GG-2 with benzene sulfonamide using suitable peptide coupling conditions gave I-2 and I-5. While this method generally describes the synthesis of these compounds, one of ordinary skill in the art will recognize that this method can be used to synthesize other compounds of formula I. It will be appreciated that the steps of acylation and sulfonamide coupling may be reversed so as to append an $R^3$ group after appending an $R^2$ group.

Although particular protecting groups are depicted in the Schemes above, e.g. Boc and TBS, one of ordinary skill in the art will recognize that other amine and hydroxyl protecting groups are amendable for use in preparing compounds of the present invention. Accordingly, a variety of amine hydroxyl protecting groups is contemplated. Such protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

Example 1

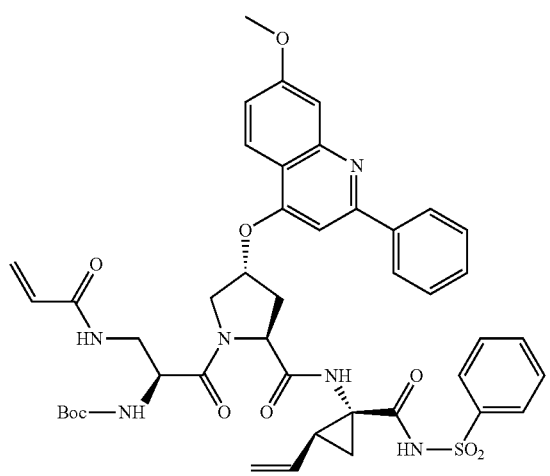

N-[(1,1-dimethylethoxy)carbonyl]-3-[(2-propenoyl) amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-3): The title compound was prepared according to the steps and intermediates as described below.

Intermediate 1

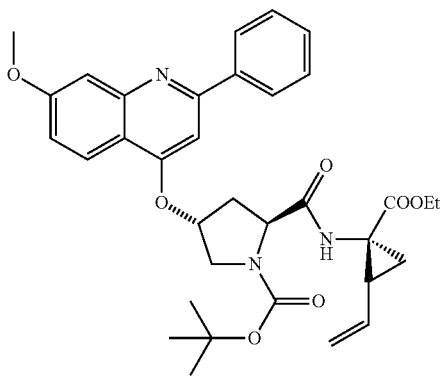

Ethyl-1-[[[(2S,4R)-1-[(1,1-dimethylethoxy)carbonyl]-4-[(7-methoxy-2-phenyl-4-quinolinyl)oxy]-2-pyrrolidinyl]carbonyl]amino]-2-ethenyl-(1R,2S)-cyclopropanecarboxylate: To a solution of (1R,2S)-1-amino-2-vinylcyclopropane carboxylic acid ethyl ester toluenesulfonic acid (2.29 g, 7.0 mmol) and N-Boc(2S,4R)-(2-phenyl-7-methoxy quinoline-4-oxo)proline (3.4 g, 7.3 mmol) in 100 ml of DCM was added HATU (3.44 g, 9.05 mmol) and then DIEA (3.81 ml, 21.9 mmol) under stirring. The mixture was stirred at r.t. for two hours. After the complete consumption of starting materials, the reaction mixture was washed with brine twice and dried over MgSO$_4$. After removal of solvent, the crude product was subject to chromatography on silica gel (hexane:EtOAc=2:1). 3.45 g of the title compound was obtained: R$_f$ 0.3 (EtOAc:hexane=2:1); MS m/z: 602.36 (M+H$^+$).

Intermediate 2

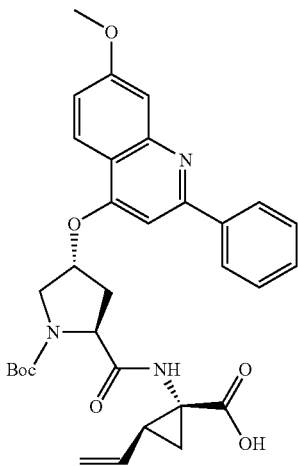

1-[[[(2S,4R)-1-[(1,1-dimethylethoxy)carbonyl]-4-[(7-methoxy-2-phenyl-4-quinolinyl)oxy]-2-pyrrolidinyl]carbonyl]amino]-2-ethenyl-(1R,2S)-cyclopropanecarboxylic acid: To a solution of the product of Intermediate 1 (1.70 g, 2.83 mmol) in 140 ml of THF/H$_2$O/MeOH (9:5:1.5) was added lithium hydroxide monohydrate (0.95 g, 22.6 mmol). After stirring at r.t. for 24 hours, the reaction mixture was neutralized with 1.0 N HCl. The organic solvents were evaporated under vacuum, and the remaining aqueous phase was acidified to pH~3 using 1.0 N HCl and was extracted with EtOAc. The organic layer was washed with brine, and was dried over anhydrous magnesium sulfate. After removal of solvent, 1.6 g of the title compound was obtained: R$_f$ 0.2 (EtOAc:MeOH=10:1); MS m/z: 574.36 (M+H$^+$).

Intermediate 3

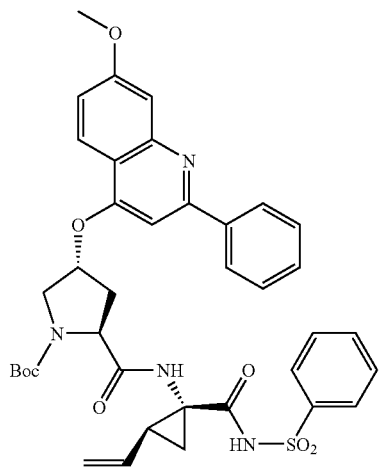

N-(1,1-dimethylethoxy)carbonyl)-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product of Intermediate 2 (1.24 g, 2.16 mmol) in 20 ml of DMF was added HATU (0.98 g, 2.58 mmol) and DIEA (1.43 ml, 8.24 mmol), the mixture was stirred for one hour before adding a solution of benzenesulfonamide (1.30 g, 8.24 mmol), DMAP (1.0 g, 8.24 mmol) and DBU (1.29 g, 8.4 mmol) in 15 ml of DMF. Stirring continued for additional four hours. The reaction mixture was diluted with EtOAc and was washed with aqueous NaOAc buffer (pH~5, 2×10 ml), NaHCO$_3$ solution and brine. After drying over MgSO$_4$ and removal of solvent a pure product precipitated by adding one portion of DCM. The filtrate was concentrated and the residue was subjected to chromatography on silica gel using hexane/EtOAc (1:1~1:2). A total of 0.76 g of the title compound was obtained: R$_f$ 0.3 (EtOAc:hexane=3:1), MS m/z: 713.45 (M+H$^+$), 735.36 (M+Na$^+$).

Intermediate 4

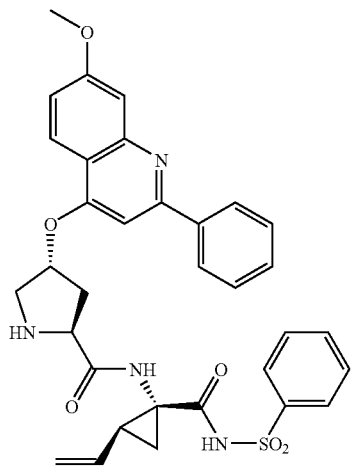

(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product from Intermediate 3 in 30 ml of DCM was added dropwise 15 ml of TFA. The mixture was stirred at r.t. for two hrs. After removal of solvents, a 20-ml portion of DCM was poured in followed by evaporation to dryness. This process of DCM addition followed by evaporation was repeated four times. Toluene (20 ml) was added and then removed by evaporation to dryness. Two repeats of this cycle gave a residue that solidified into 0.9 g white powder as TFA salt of the title compound. A small sample of the TFA salt was neutralized with NaHCO$_3$ to obtain the title compound: R$_f$ 0.4 (DCM:MeOH=10:1); MS m/z: 613.65 (M+H$^+$).

Intermediate 5

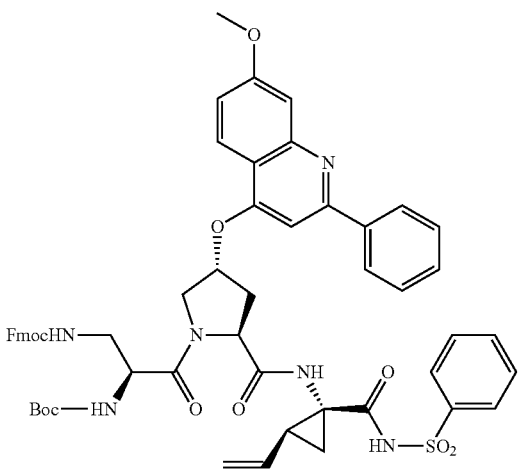

N-[(1,1-dimethylethoxy)carbonyl]-3-[[(9H-fluoren-9-yl-methoxy)carbonyl]amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product of Intermediate 4 (0.15 g, 0.178 mmol) and N-Boc-3-(Fmoc)amino-L-alanine (0.107 g, 0.25 mmol) in 3.0 ml of DMF was added HATU (85.1 mg, 0.224 mmol) and NMM (90.5 mg, 0.895 mmol) at r.t. under stirring. TLC analysis indicated completion of the coupling reaction had occurred after one hour. A 20-ml portion of EtOAc was poured in and the mixture was washed with a buffer (pH~4, AcONa/AcOH), NaHCO$_3$ and brine, and was dried over MgSO$_4$. After removal of solvent, the crude oil product was subject to chromatography on silica gel (eluents: EtOAc/hexane). A total of 0.12 g of the title compound was obtained: R$_f$ 0.4 (EtOAc:hexane=1:1); MS m/z: 1021.56 (M+H$^+$).

Intermediate 6

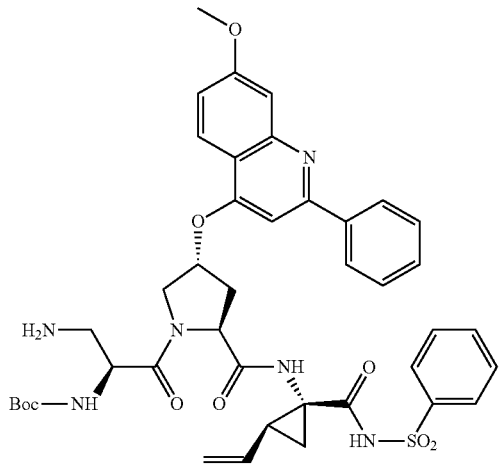

N-[(1,1-dimethylethoxy)carbonyl]-3-amino-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: A solution of 110 mg of the product of Intermediate 5 (0.108 mmol) in 1 ml of DMF with 12% piperidine was stirred for 1.5 hours at r.t. and then was evaporated to dryness under high vacuum. The residue was triturated with hexane/ether (4:1) to yield 70 mg of the title compound: R$_f$ 0.25 (EtOAc:MeOH=10:1); MS m/z: 798.9 (M+H$^+$).

Compound (I-3)

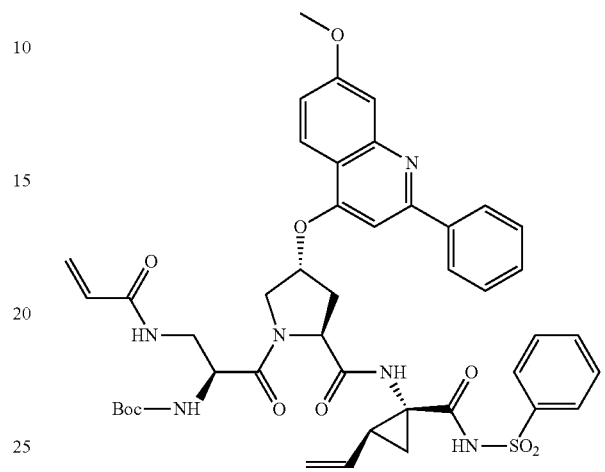

N-[(1,1-dimethylethoxy)carbonyl]-3-[(2-propenoyl)amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: Acryloyl chloride (11 uL, 0.132 mmol) was added dropwise at 0° C. to a stirred solution of 69 mg of the product from Intermediate 6 in 3 ml of DCM containing 3 eq. of triethylamine. The reaction mixture was stirred at r.t. for 1.5 hrs and then was diluted with 10 ml of DCM. The resulting solution was washed twice with brine and was dried over magnesium sulfate. Removal of solvent afforded the crude product, which was purified by chromatography on silica gel eluting first with hexane/EtOAc (1:3~1:5) and then with DCM-methanol (50:1~25:1)). A total of 36 mg of the title compound was obtained: R$_f$ 0.25 (DCM:MeOH=25:1); MS m/z: 892.55 (M+H$^-$).

In similar fashion using the product of Intermediate 6 the following compounds were prepared:

2-chlorosulfenylbenzoyl chloride afforded N-[(1,1-dimethylethoxy)carbonyl]-3-(benzoisothiazolin-3-one-2-yl)-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-10): R$_f$ 0.3 (EtOAc:Hexane=5:1); MS m/z: 933.55 (M+H$^+$), 955.55 (M+Na$^+$).

1-cyanocyclopropylcarbonylchloride afforded N-[(1,1-dimethylethoxy)carbonyl]-3-[(1-cyano-cyclopropylcarboxyl)amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-11): 0.15 (EtOAc:hexane=5:1); MS m/z: 892.55 (M+H$^+$).

propionyl chloride afforded N-[(1,1-dimethylethoxy)carbonyl]-3-[(propionyl)amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I$^R$-3): R$_f$ 0.35 (EtOAc:Hexane=5:1); MS m/z: 855.45 (M+H$^+$), 877.36 (M+Na$^+$).

chloroacetyl chloride afforded N-[(1,1-dimethylethoxy)carbonyl]-3-[(chloroacetyl)amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-7): R$_f$ 0.3 (EtOAc:hexane=3:1); MS m/z: 875.45 (M+H$^+$).

R-chloropropionyl chloride afforded N-[(1,1-dimethylethoxy)carbonyl]-3-[R-(chloropropionyl)amino]-L-alanyl- (4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-13): R$_f$ 0.5 (EtOAc/hexane=2/1), M/Z 889.55 (M+H+).

(S)-2-chloropropanoyl chloride afforded tert-butyl(S)-3-((S)-2-chloropropanamido)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-ylcarbamate (I-21): M/Z 889.45 (M+H+).

(R)-2-bromopropanoyl chloride afforded tert-butyl(S)-3-(2-bromopropanamido)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-ylcarbamate (I-22): M/Z 934.70 (M+H+).

2-chloro-2-phenylacetyl chloride afforded tert-butyl(S)-3-(2-chloro-2-phenylacetamido)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-ylcarbamate (I-23): M/Z 952.3 (M+H+).

tert-butyl-(S)-3-acrylamido-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxopropan-2-ylcarbamate (I-35) was made following the procedures described in Example 1 except replacing benzenesulfonamide with cyclopropylsulfonamide in the Intermediate 3 step. M/Z 817.30 (M+H+).

(1R,2S)-1-((2S,4R)-1-((S)-3-acrylamido-2-(tert-butoxycarbonylamino)propanoyl)-4-(7-methoxy-2-phenylquinolin-4-yloxy)pyrrolidine-2-carboxamido)-2-vinylcyclopropanecarboxylic acid (I-41) was made following the procedures described in Example 1 by using the ester in stead of sulfonamide followed by a LiOH hydrolysis of the ester to the carboxylic acid at the last step. M/Z 714.30 (M+H+).

t-butyl-(S)-3-acrylamido-1-((2S,4R)-2-((1R,2S)-1-(4-ethynylphenylsulfonylcarbamoyl)-2-vinylcyclopropylcarbamoyl)-4-(7-methoxy-2-phenylquinolin-4-yloxy)pyrrolidin-1-yl)-1-oxopropan-2-ylcarbamate (I-61) was made following the procedures described in Example 1 by using 4-ethynylbenzenesulfonamide in the synthesis of intermediate 3: R$_f$ 0.58 (EtOAc/MeOH 10:1); MS m/z: 877.3 (M+H$^+$).

Example 2

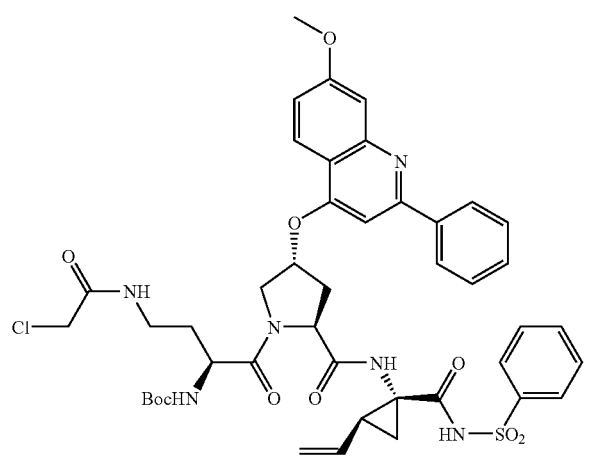

(2S)-2-[[(1,1-dimethylethoxy)carbonyl]amino]-4-(chloroacetyl)amino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-4): The title compound was prepared According to the steps and intermediates as described below:

Intermediate 7

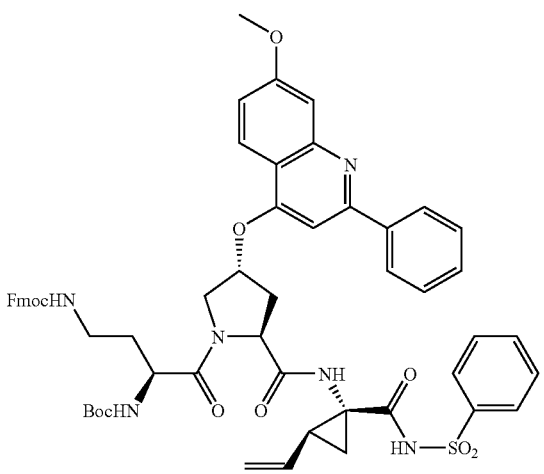

(2S)-2-[[(1,1-dimethylethoxy)carbonyl]amino]-4-[[(9H-fluoren-9-ylmethoxy)carbonyl]amino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product of Intermediate 4 (0.15 g, 0.178 mmol) and (2S)-2-Boc-amino]-4-Fmoc-aminobutanoic acid (0.107 g, 0.25 mmol) in 3.0 ml of DMF was added HATU (85.1 mg, 0.224 mmol) and NMM (90.5 mg, 0.895 mmol) at r.t. under stirring. One hour later, TLC analysis showed the completion of reaction. A 20-ml portion of EtOAc was poured in and the mixture was washed with a buffer (pH~4, AcONa/AcOH), NaHCO$_3$ solution and brine, and was dried over MgSO$_4$. After removal of solvent, the crude product was subjected to chromatography on silica gel (eluent: EtOAc/hexane) to give 0.12 g of the title compound: R$_f$ 0.35 (EtOAc:hexane=2:1); MS m/z: 1035.45 (M+H$^+$).

Intermediate 8

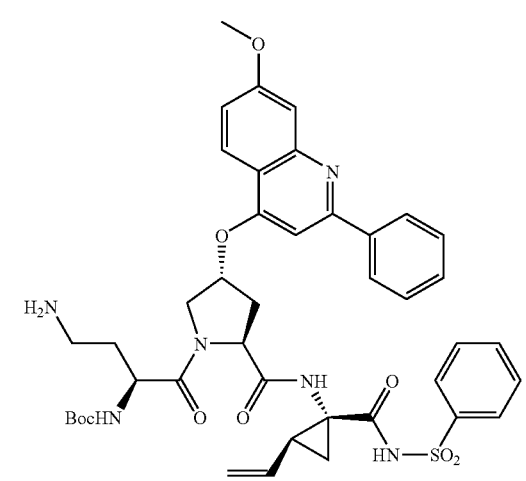

(2S)-2-[[(1,1-dimethylethoxy)carbonyl]amino]-4-aminobutanoyl-(4R)-4-[7-methoxy-2-phenyl-4-quinolinyl)oxy]-L-prolyl-1-amino-2-ethenyl-N-(phenylsulfonyl)-(1R,2S)-cyclopropanecarboxamide: A solution of 110 mg of the product of Intermediate 7 was dissolved in a solution of 1 ml of DMF with 12% piperidine. The mixture was stirred for 1.5 hours at r.t. and then was evaporated to dryness under high vacuum. The residue was triturated with hexane/ether (4:1) to yield 70 mg of the title compound: $R_f$ 0.55 (DCM/MeOH=25:1); MS m/z: 813.66 (M+H$^+$).

Compound (I-4)

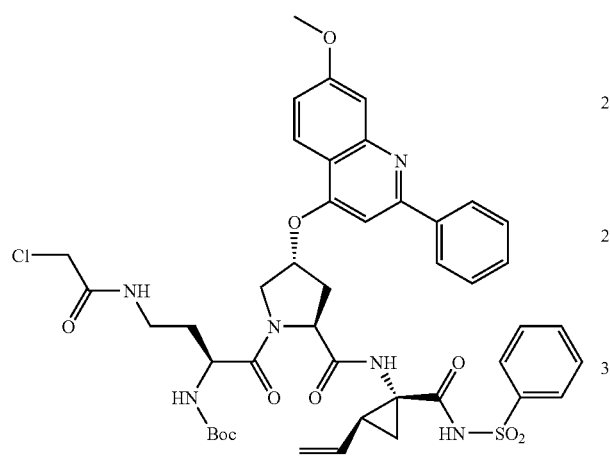

(2S)-2-[[(1,1-dimethylethoxy)carbonyl]amino]-4-(chloroacetyl)amino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product from Intermediate 8 (60 mg, 0.074 mmol) in 3 ml of methylene chloride in the presence of triethylamine (70 ul, 0.5 mmol) at 0° C. was added dropwise chloroacetyl chloride (15 uL, 0.18 mmol, 3.0 eq) under stirring. The reaction mixture was stirred at r.t. for 1.5 hrs. The reaction mixture was diluted with 10 ml of DCM, was washed with brine twice and was dried over magnesium sulfate. Removal of solvent afforded the crude product, which was purified by chromatography on silica gel (eluents: hexane/EtOAc (1:3~1:5) and DCM/MeOH (50:1~25:1)). 27 mg of the title compound: $R_f$ 0.45 (DCM/MeOH=50:1), MS m/z: 889.55 (M+H$^+$).

In similar fashion condensing the product from Intermediate 8 with acryoyl chloride afforded (2S)-2-[[(1,1-dimethylethoxy)carbonyl]amino]-4-(2-propenoyl)amino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-8): $R_f$ 0.65 (EtOAc:MeOH=10:1); MS m/z: 867.55 (M+H$^+$), 889.45 (M+Na$^+$).

rac-2-chloropropionyl chloride afforded (2S)-2-[[(1,1-dimethylethoxy)carbonyl]amino]-4-(R,S-chloropropionyl)amino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-1): $R_f$ 0.6 (EtOAc/MeOH=10/1), M/Z 903.64 (M+H+); 925.55 (M+Na+).

2-bromopropanoyl chloride afforded I-20: M/Z 949.36 (M+H+).

Example 3

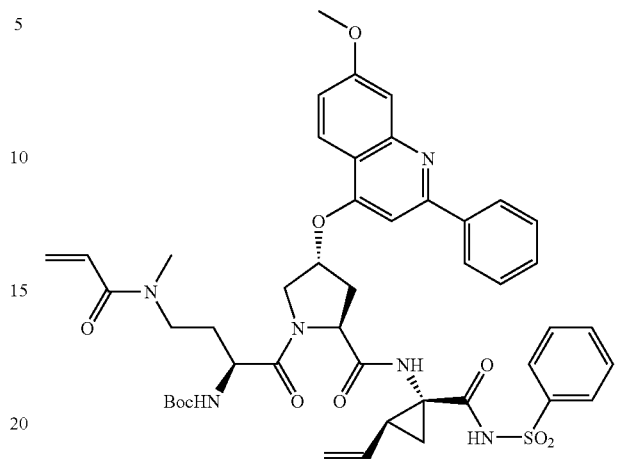

(2S)-2-[[(1,1-dimethylethoxy)carbonyl]amino]-4-(2-propenoyl)methylamino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-12): The title compound was prepared According to the steps and intermediates as described below:

Intermediate 9

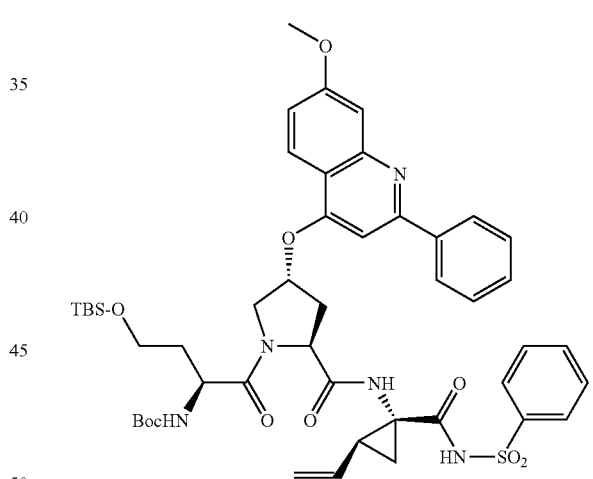

N-[(1,1-dimethylethoxy)carbonyl]-O-[(1,1-dimethylethyl)dimethylsilyl]-L-homoserinyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product of Intermediate 4 (0.20 g, 0.326 mmol) and N-[(1,1-dimethylethoxy)carbonyl]-O-[(1,1-dimethylethyl)dimethylsilyl]-L-homoserine (0.152 g, 0.457 mmol) in 10 ml of DMF was added HATU (0.155 g, 0.408 mmol) and then NMM (0.175 ml, 1.63 mmol) dropwise under stirring. The mixture was stirred at room temperature for 1 hour. The reaction solution was neutralized with saturated NaHCO$_3$, extracted with EtOAc. The organic phase was washed with brine three times, dried over anhydrous magnesium sulfate, filtered and evaporated to get a residue which was purified by flash chromatography with EtOAc/hexane=1:2 to give 0.21 g of the title compound: $R_f$ 0.30 (EtOAc/hexane=1:1); MS m/z: 928.64 (M+H$^+$), 950.55 (M+Na$^+$).

Intermediate 10

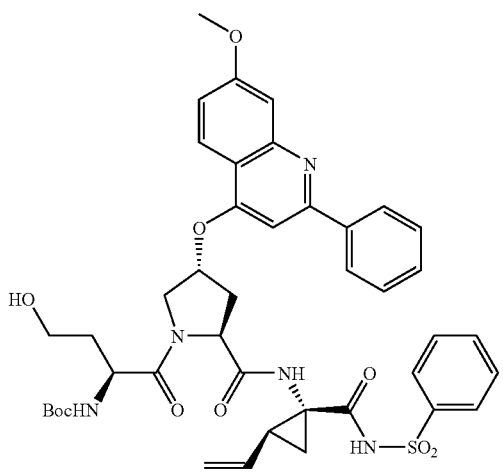

N-[(1,1-dimethylethoxy)carbonyl]-L-homoserinyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: A solution of the product from Intermediate 9 (189 mg, 0.2 mmol) in TBAF (0.4 ml of 1.0 M of TBAF in THF) and 4 ml of THF was stirred at room temperature for 3 hours. The reaction solution was evaporated in vacuo to remove THF. The residue was dissolved in EtOAc. This solution was washed with water and brine, was dried over anhydrous magnesium sulfate, was filtered and was evaporated to get a residue that was purified by flash chromatography (EtOAc/hexane=5:1) giving 150 mg of the title compound: $R_f$ 0.30 (EtOAc/hexane=5:1); MS m/z: 814.36 (M+H$^+$), 836.27 (M+Na$^-$).

Intermediate 11

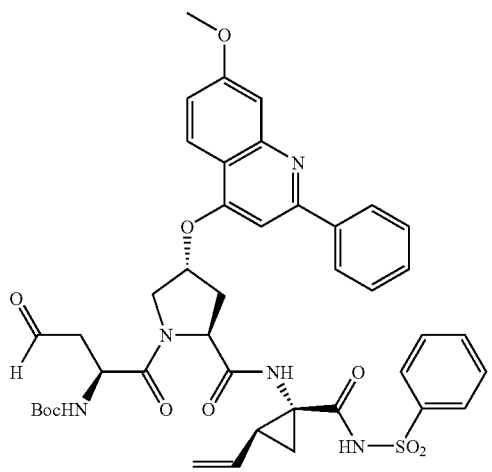

(2S)—N-[(1,1-dimethylethoxy)carbonyl]-4-oxobutanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of the product from Intermediate 10 (100 mg, 0.123 mmol) in 8 ml of DCM was added Dess-Martin periodinane (62.8 mg, 0.148 mmol) at ice-water bath. The mixture was stirred at 0° C. for 1 hour and then at room temperature for 30 minutes. The reaction mixture was treated with diethyl ether, and evaporated. The residue was directly introduced onto a chromatographic column for purification with EtOAc/Hexane=2:1 to give 66.7 mg of the title compound: $R_f$ 0.30 (EtOAc/hexane=2:1); MS m/z: 812.45 (M+H$^+$).

Intermediate 12

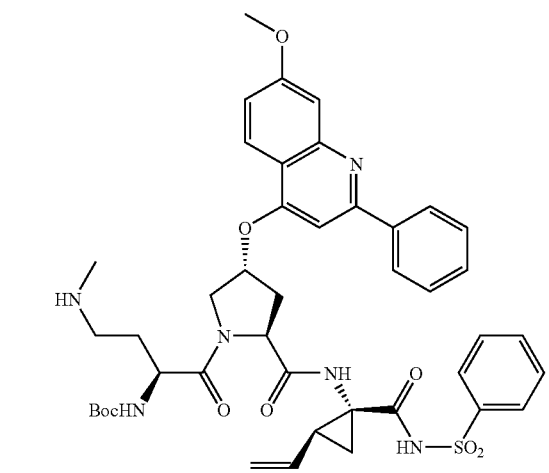

(2S)-2-[[(1,1-dimethylethoxy)carbonyl]amino]-4-methylaminobutanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide: To a solution of methyl amine (87.6 µl, 1.01 mmol) in mixed solvents (6 ml of MeOH/3 ml of CHCl$_3$) was added the product of Intermediate 11 (82.3 mg, 0.101 mmol), followed by the addition of tetramethylammonium triacetoxyborohydride (66.4 mg, 0.253 mmol) with stirring. The mixture was stirred at room temperature for 1 hour. The resulting solution was evaporated to remove solvents and was extracted with EtOAc (3×20 ml). The extracts were combined, washed with brine twice, dried over anhydrous magnesium sulfate. After removal of the solvent, the residue was purified by flash chromatography with EtOAc/hexane=5:1 to give 59 mg of the title compound: $R_f$ 0.20 (EtOAc/hexane=5:1); MS m/z: 827.55 (M+H$^+$), 849.45 (M+Na$^+$).

Compound I-12

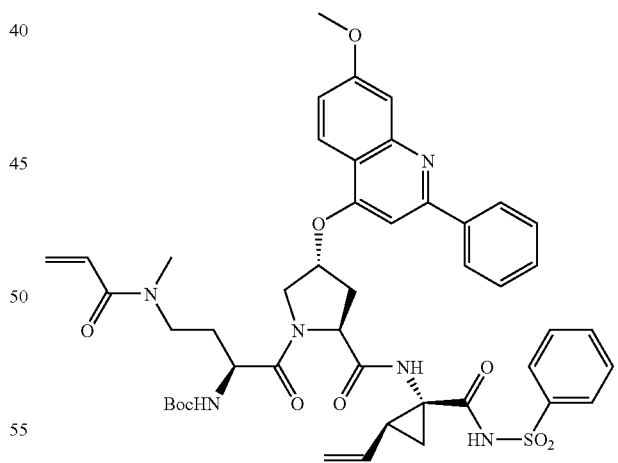

(2S)-2-[[(1,1-dimethylethoxy)carbonyl]amino]-4-(2-propenoyl)methylamino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-12): To a solution of the product from Intermediate 12 (67.8 mg, 0.082 mmol) and triethylamine (46 µl, 0.328 mmol) in 4 ml of dichloromethane was added acryloyl chloride (7.4 µl, 0.090 mmol) at 0° C. The mixture was stirred at room temperature overnight. The solution was washed with water twice and dried over magnesium sulfate, and evaporated. The residue was purified by flash chromatography with EtOAc/hexane=5:1 to give 15 mg of the title compound: $R_f$ 0.65 (EtOAc/MeOH=10:1); MS m/z: 881.55 (M+H$^+$), 903.55 (M+Na$^+$).

In similar fashion condensing the product of Intermediate 12 with chloroacetyl chloride gave: (2S)-2-[[(1,1-dimethylethoxy)carbonyl]amino]-4-(chloroacetyl)methylamino-butanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-9): $R_f$ 0.35 (EtOAc/Hexane=5:1); MS m/z: 903.55 (M+H$^+$).

Example 4

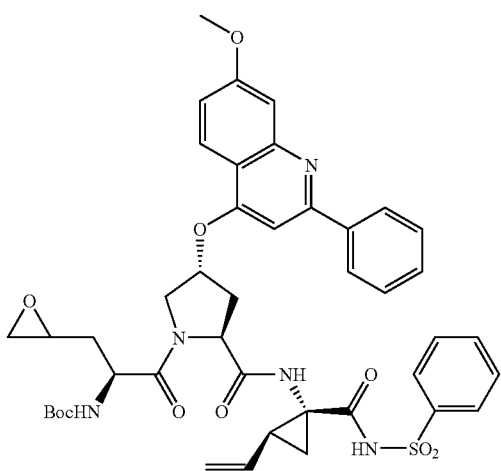

(2S)-2-[[(1,1-dimethylethoxy)carbonyl]amino]-3-oxiranepropanoyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-6): A solution of the product from Intermediate 11 (26.8 mg, 0.033 mmol) in DMSO was added all at once to a dry mixture of trimethyl sulfoxonium iodide (Me$_3$SOI, 21.8 mg, 0.099 mmol) and KOt-Bu (11.1 mg, 0.099 mmol) at room temperature under nitrogen. The resulting clear solution was stirred at room temperature for overnight. The reaction mixture was treated with water and extracted with EtOAc. The organic extracts were washed with brine, dried over anhydrous magnesium sulfate, filtered, and evaporated. The crude product was purified on TLC plates with EtOAc/Hexane=2:1, giving 4.5 mg of the title compound: $R_f$ 0.36 (EtOAc/Hexane=2:1); MS m/z: 808.45 (M+H$^+$—H$_2$O).

Example 5

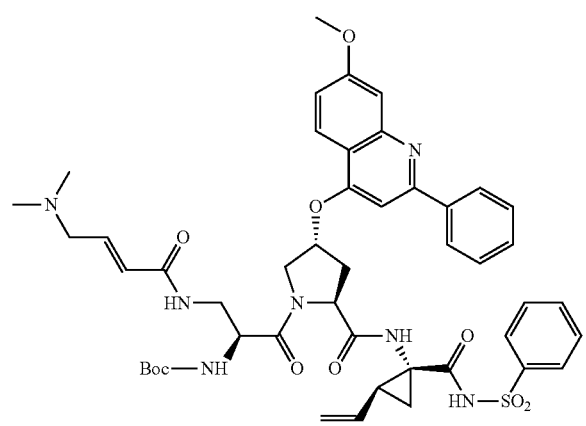

N-[(1,1-dimethylethoxy)carbonyl]-3-[(4-dimethylamino-2-butenoyl)amino]-L-alanyl-(4R)-4-[(7-methoxy-2-phenyl-4-quinolinyl)oxy]-L-prolyl-1-amino-2-ethenyl-N-(phenyl-sulfonyl)-(1R,2S)-cyclopropanecarboxamide (I-5): The title compound was prepared According to the steps and intermediates as described below:

Intermediate 13

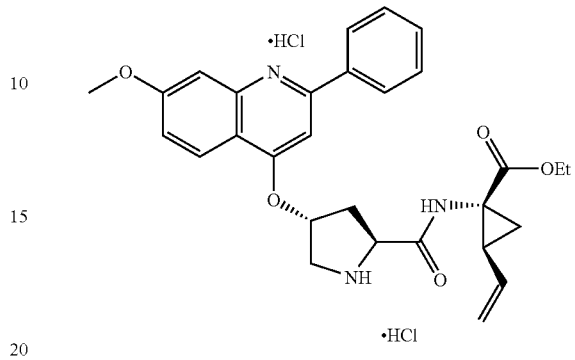

Ethyl-1-[[[(2S,4R)-4-[(7-methoxy-2-phenyl-4-quinolinyl)oxy]-2-pyrrolidinyl]carbonyl]amino]-2-ethenyl-(1R,2S)-cyclopropanecarboxylate dihydrochloride: 5.22 g of the product from Intermediate 1 (8.68 mmol) was dissolved in 190 ml of 4N HCl in dioxane. The mixture was stirred for 2.0 hrs at r.t. The reaction mixture was concentrated to afford a semi-solid product (5.0 g), which was solidified by addition of hexane giving 4.3 g of the title compound.

Intermediate 14

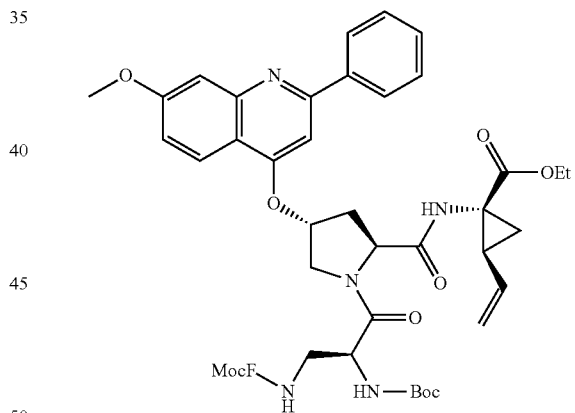

Ethyl-N-[(1,1-dimethylethoxy)carbonyl]-3-[[(9H-fluoren-9-ylmethoxy)carbonyl]amino]-L-alanyl-(4R)-4-[(7-methoxy-2-phenyl-4-quinolinyl)oxy]-L-prolyl-1-amino-2-ethenyl-(1R,2S)-cyclopropanecarboxylate: To a solution of the product from Intermediate 13 (0.1145 g, 0.2 mmol) and (2S)-2-Boc-amino]-4-Fmoc-aminobutanoic acid (0.119 g, 0.28 mmol) in 1.47 ml of DMF was added HATU (0.095 g, 0.25 mmol). NMM (0.1086 ml, 0.68 mmol) was added dropwise and stirring was continued at room temperature for 1 hour. The reaction mixture was diluted with 30 ml of EtOAc and was washed with 5% NaHCO$_3$ and brine, and was dried over MgSO$_4$. After removal of solvent, the crude product was purified by flash chromatography (hexane:EtOAc=2:1) to yield 0.143 g of the title compound $R_f$ 0.30 (EtOAc:hexane=1:1). MS m/z: 910.55 (M+H$^+$).

Intermediate 15

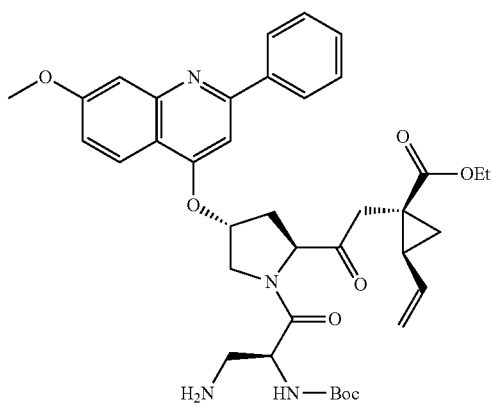

Ethyl N-[(1,1-dimethylethoxy)carbonyl]-3-amino-L-alanyl-(4R)-4-[(7-methoxy-2-phenyl-4-quinolinyl)oxy]-L-prolyl-1-amino-2-ethenyl-(1R,2S)-cyclopropanecarboxylate: To a solution of the the product from Intermediate 14 (0.429 g, 0.47 mmol) in 4.5 ml of DMF was added 0.5 ml of piperidine under stirring. Stirring continued at room temperature for 30 minutes. The reaction mixture was poured into 30 ml of water, was extracted with EtOAc (3×30 ml), and was dried over MgSO$_4$. After the solvent was evaporated, the residue was purified by flash chromatography (EtOAc:MeOH=10:1) to give 0.15 g of the title compound: R$_f$ 0.20 (EtOAc:MeOH=10:1); MS m/z: 688.45 (M+H$^+$), 710.45 (M+Na$^+$).

Intermediate 16

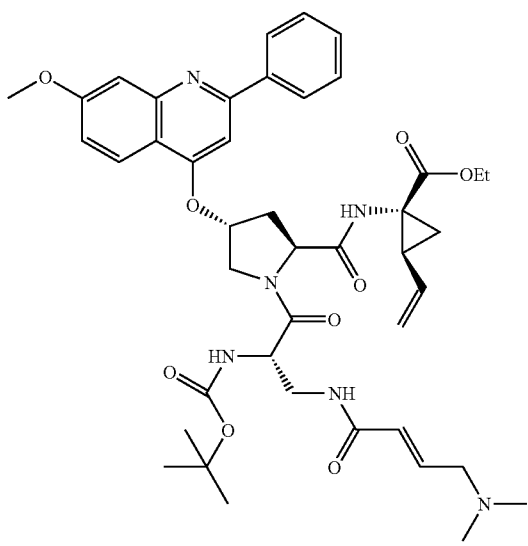

Ethyl N-[(1,1-dimethylethoxy)carbonyl]-3-(4-dimethylamino-2-butenoyl)amino-L-alanyl-(4R)-4-[(7-methoxy-2-phenyl-4-quinolinyl)oxy]-L-prolyl-1-amino-2-ethenyl-(1R,2S)-cyclopropanecarboxylate: To a solution of the product of Intermediate 15 (100 mg, 0.145 mmol) and 4-dimethylamino2-butenoic acid (24.1 mg, 0.145 mmol) in 5 ml of DCM was added HATU (68.6 mg, 0.18 mmol) and then DIEA (75.8 µl, 0.436 mmol). The mixture was stirred at room temperature overnight. The reaction mixture was washed with water twice and dried over MgSO$_4$, filtered and evaporated. The mixture was purified by flash chromatography with EtOAc:MeOH=1:1 to give 0.10 g of the title compound: R$_f$ 0.25 (EtOAc:MeOH=10:1) MS m/z: 799.45 (M+H$^+$).

Similarly prepared using crotonyl chloride was ethyl N-[(1,1-dimethylethoxy)carbonyl]-3-(2-butenoyl)amino-L-alanyl-(4R)-4-[(7-methoxy-2-phenyl-4-quinolinyl)oxy]-L-prolyl-1-amino-2-ethenyl-(1R,2S)-cyclopropanecarboxylate: R$_f$ 0.30 (EtOAc:Hexane=3:1). MS m/z: 756.45 (M+H$^+$).

Intermediate 17

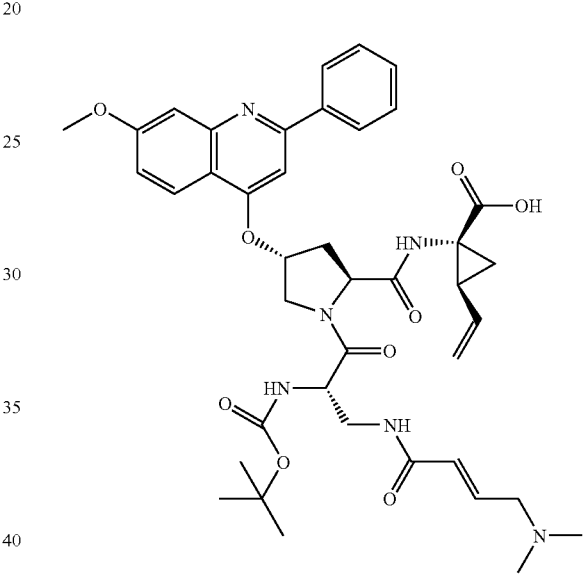

N-[(1,1-dimethylethoxy)carbonyl]-3-(4-dimethylamino-2-butenoyl)amino-L-alanyl-(4R)-4-[(7-methoxy-2-phenyl-4-quinolinyl)oxy]-L-prolyl-1-amino-2-ethenyl-(1R,2S)-cyclopropanecarboxylic acid: To a solution of the product of Intermediate 16 (100 mg, 0.125 mmol) in 10 ml of THF/H$_2$O/MeOH (9:5:1.5) was added LiOH.H$_2$O (42 mg, 1.0 mmol). The reaction mixture was stirred at room temperature for 24 hours and was neutralized with acetic acid. The organic solvents were evaporated under vacuum, and the remaining aqueous phase was extracted with EtOAc. The organic layer was washed with brine, dried over MgSO$_4$. After removal of solvent there was obtained 77.1 mg of the title compound: MS m/z: 771.45 (M+H$^+$), 793.45 (M+Na$^+$).

Similarly prepared starting with ethyl N-[(1,1-dimethylethoxy)carbonyl]-3-(2-butenoyl)amino-L-alanyl-(4R)-4-[(7-methoxy-2-phenyl-4-quinolinyl)oxy]-L-prolyl-1-amino-2-ethenyl-(1R,2S)-cyclopropanecarboxylate was N-[(1,1-dimethylethoxy)carbonyl]-3-(2-butenoyl)amino-L-alanyl-(4R)-4-[(7-methoxy-2-phenyl-4-quinolinyl)oxy]-L-prolyl-1-amino-2-ethenyl-(1R,2S)-cyclopropanecarboxylic acid: m/z: 728.2 (M+H$^+$), 750.2 (M+Na$^+$).

Compound I-5

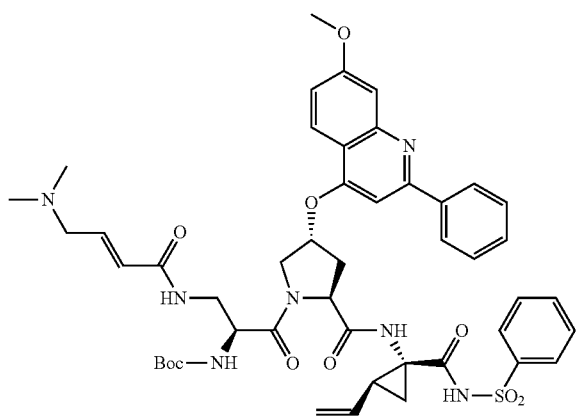

N-[(1,1-dimethylethoxy)carbonyl]-3-[(4-dimethylamino-2-butenoyl)amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-5): A solution of the product from Intermediate 17 (77.1 mg, 0.10 mmol), HATU (47.5 mg, 0.125 mmol), DIPEA (69.5 µl, 0.4 mmol) in 2 ml of dry DMF was stirred for 1 hour and 15 minutes. Then, to the above reaction solution was added a solution of benzenesulfonamide (62.9 mg, 0.4 mmol), DMAP (56.2 mg, 0.413 mmol) and DBU (61.6 µl, 0.413 mmol) in 2 ml of dry DMF. The reaction was stirred at room temperature overnight. The resulting reaction mixture was diluted with EtOAc (45 ml), and was washed successively with aqueous sodium acetate buffer (pH~4, 2×15 ml), 5% aqueous sodium bicarbonate (15 ml), and brine (20 ml). The organic layer was dried over MgSO$_4$, was filtered, and was evaporated. The crude residue was purified on preparative TLC plates (EtOAc:MeOH=1:1) to give 15 mg of the title compound: $R_f$ 0.40 (EtOAc:MeOH=1:1); MS m/z: 910.55 (M+H$^+$).

Similarly prepared from N-[(1,1-dimethylethoxy)carbonyl]-3-(2-butenoyl)amino-L-alanyl-(4R)-4-[(7-methoxy-2-phenyl-4-quinolinyl)oxy]-L-prolyl-1-amino-2-ethenyl-(1R,2S)-cyclopropanecarboxylic acid was N-[(1,1-dimethylethoxy)carbonyl]-3-[(2-butenoyl)amino]-L-alanyl-(4R)-4-[(7-methoxy-2-phenyl-4-quinolinyl)oxy]-L-prolyl-1-amino-2-ethenyl-N-(phenylsulfonyl)-(1R,2S)-cyclopropanecarboxamide (I-2): $R_f$ 0.35 (EtOAc:hexane=5:1); MS m/z: 867.55 (M+H$^+$).

Example 6

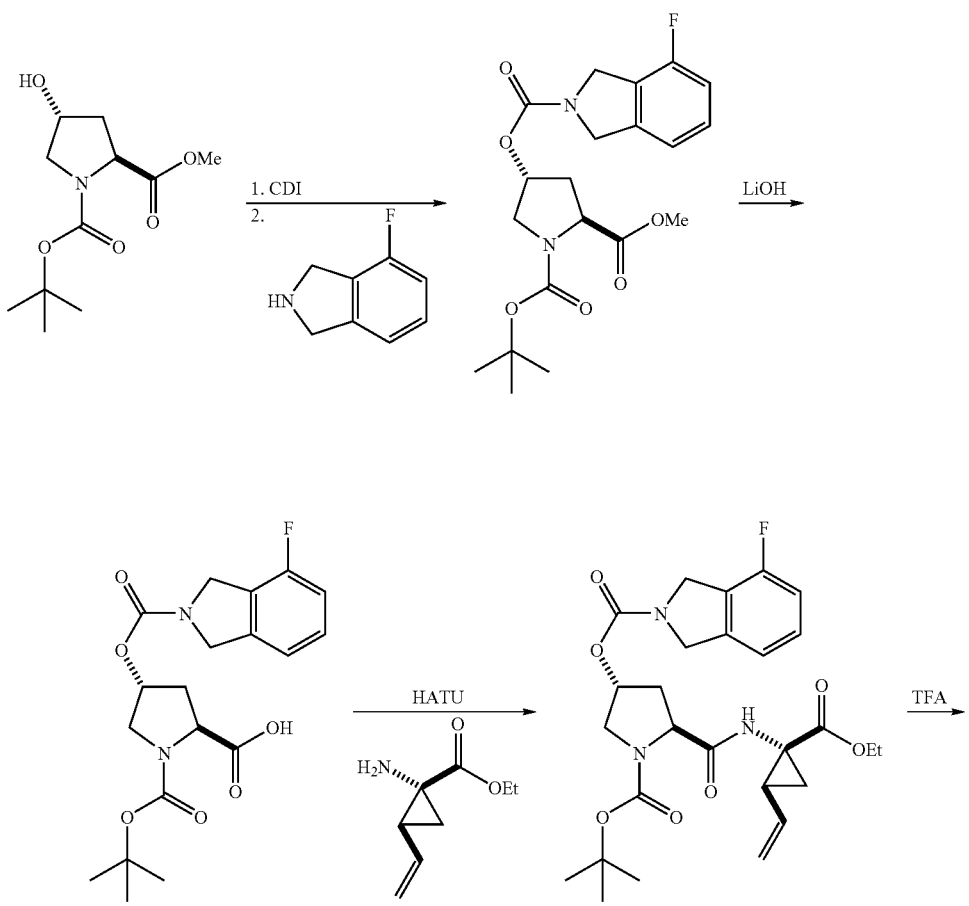

-continued
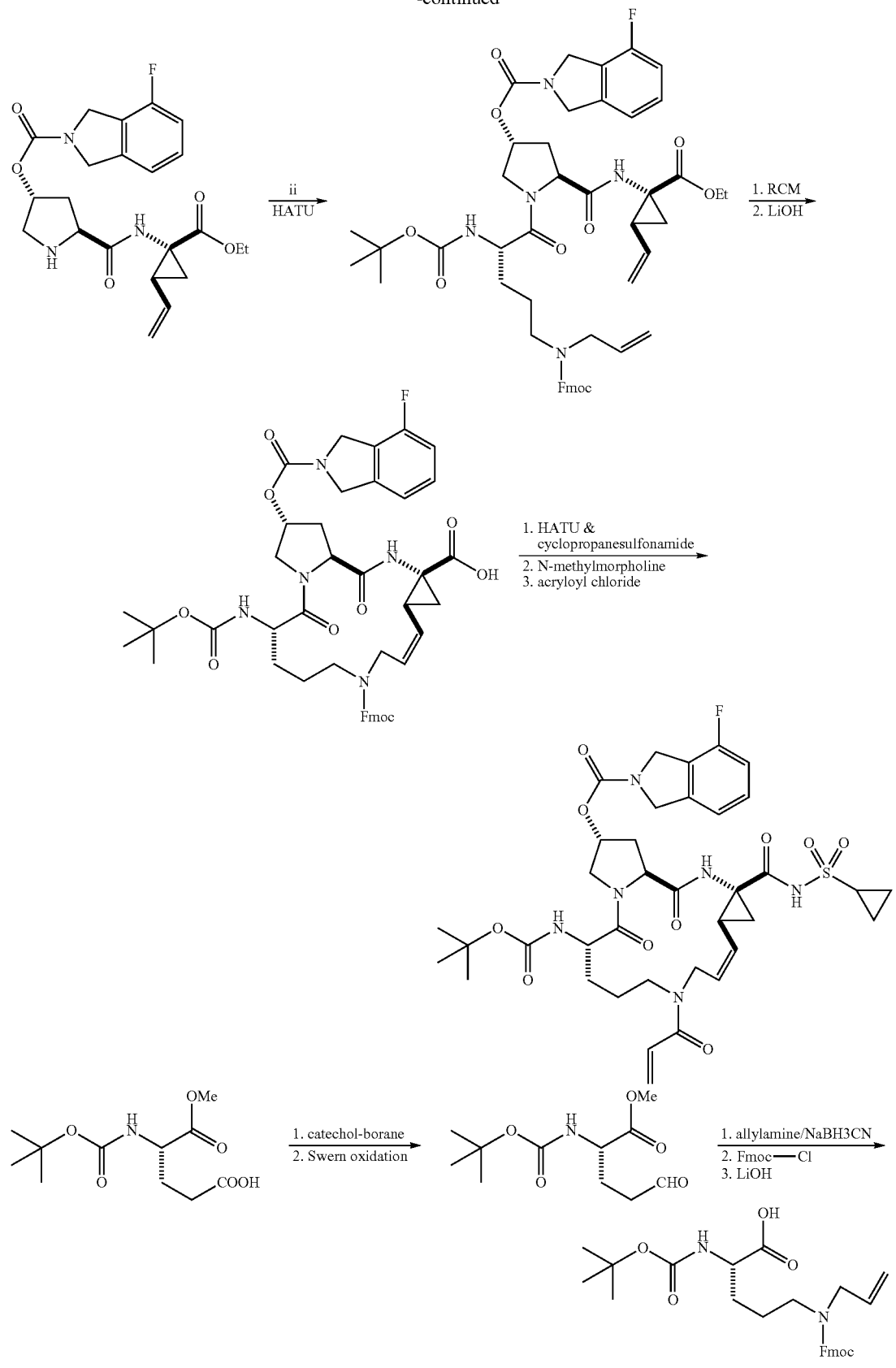

Boc-proline methyl ester is condensed with carbonyl diimidazole (CDI), to form an intermediate imidazole carbamate which will then exposed to 4-fluoroisoindoline. The methyl ester is hydrolyzed by lithium hydroxide and the resulting free carboxylate coupled to 2-vinyl-1-aminocyclopropanecarboxylic acid ethyl ester using HATU. The Boc protecting group on the resulting dipeptide is removed using trifluoroacetic acid (TFA) and the resulting amine acylated with protected allyl-ornithine. The macrocyclic is formed using ruthenium-catalyzed ring-closing metathesis (RCM) and the C-terminal ester hydrolyzed with lithium hydroxide (LiOH). This free acid is coupled to cyclopropanesulfonamide using HATU, the Fmoc protecting group on the ornithine sidechain removed using N-methylmorpholine and that free amine acylated with acryloyl chloride to yield the final product compound I-18. The aforementioned protected allyl-ornithine can be accessed by selective reduction of suitably protected glutamic acid using catechol-borane, oxidation of the resulting alcohol to an aldehyde, introduction of allylamine via reductive amination, protection of the sidechain amine using Fmoc-chloride, and finally hydrolysis of the ester using lithium hydroxide to give the required intermediate.

Using the procedures described in the preceeding scheme, the following compounds can be made:

Compound I-19

Compound I-16

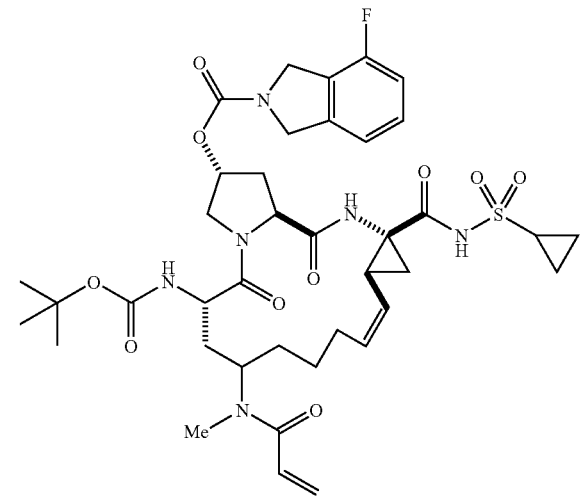

(1aR,3aS,5R,9S,16aS,Z)-9-(tert-butoxycarbonylamino)-1a-(cyclopropylsulfonylcarbamoyl)-11-(N-methylacrylamido)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-5-yl 4-fluoroisoindoline-2-carboxylate Example 7

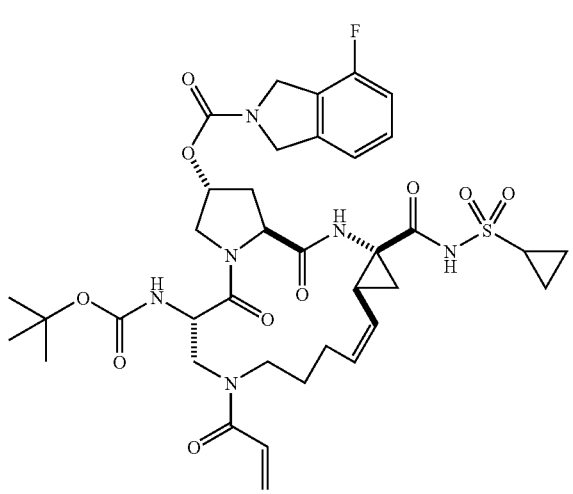

(1aR,3aS,5R,9S,16aS,Z)-11-acryloyl-9-(tert-butoxycarbonylamino)-1a-(cyclopropylsulfonylcarbamoyl)-3,8-dioxo-1,1a,2,3,3a,4,5,6,8,9,10,11,12,13,14,16a-hexadecahydrocyclopropa[n]pyrrolo[2,1-c][1,4,8]triazacyclopentadecin-5-yl-4-fluoroisoindoline-2-carboxylate

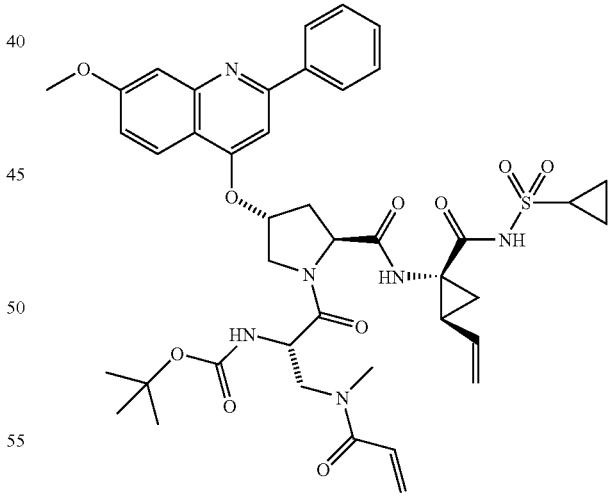

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3-(N-methylacrylamido)-1-oxopropan-2-ylcarbamate (I-52): The title compound was prepared according to the steps and intermediates as described below.

Intermediate 7-1

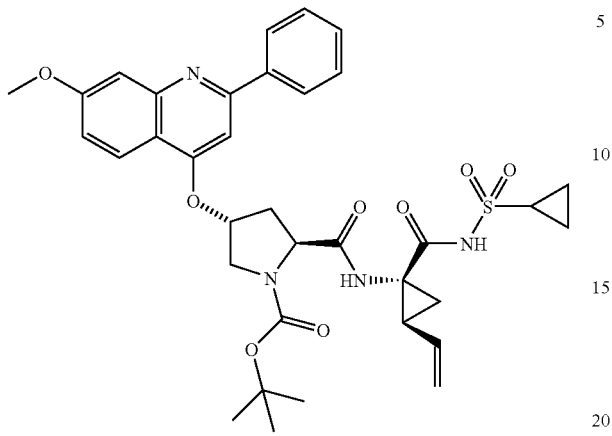

(2S,4R)-tert-butyl-2-((1R,2S)-1-(cyclopropylsulfonylcarbamoyl)-2-vinylcyclopropylcarbamoyl)-4-(7-methoxy-2-phenylquinolin-4-yloxy)pyrrolidine-1-carboxylate: Intermediate 7-1 was made from Intermediate 2 (Example 1) following the procedures described for Intermediate 3 by using cyclopropylsulfonamide in stead of benezensulfonamide. $R_f$ 0.3 (EtOAc:hexane=3:1), MS m/z: 677.2 (M+H$^+$).

Intermediate 7-2

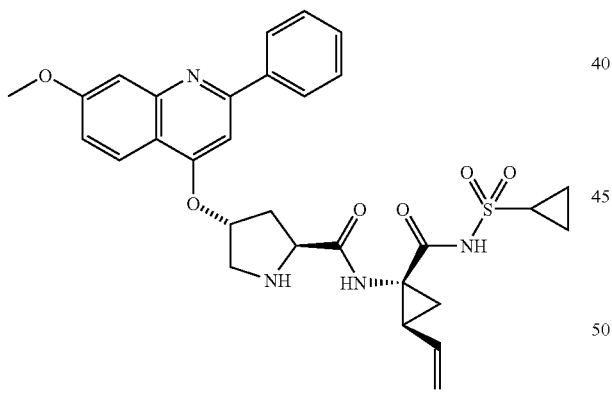

(2S,4R)—N-((1R,2S)-1-(cyclopropylsulfonylcarbamoyl)-2-vinylcyclopropyl)-4-(7-methoxy-2-phenylquinolin-4-yloxy)pyrrolidine-2-carboxamide: The product from Intermediate 7-1 (0.8 g, 1.18 mmol) was dissolved in 5 ml of 4N HCl in dixoxane and the reaction was stirred for 1 hour at RT. After removal of solvents, a 20-ml portion of DCM was poured in followed by evaporation to dryness. This process of DCM addition followed by evaporation was repeated three times to give compound 6 as its HCl salt. MS m/z: 577.2 (M+H$^+$).

Intermediate 7-3

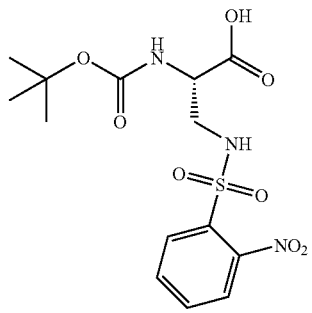

(S)-2-(tert-butoxycarbonylamino)-3-(2-nitrophenylsulfonamido)propanoic acid: To a solution of (S)-3-amino-2-(tert-butoxycarbonylamino)propanoic acid (2.04 g, 10 mmol), TEA (4.5 ml, 30 mmol) in 50 ml CH$_2$Cl$_2$ was added nitrobenzenesulfonyl chloride (2.9 g, 13.0 mmol) at RT. The mixture was stirred for 10 hours at RT. The solvent was removed under vacuum followed by the addition of 100 ml EtOAc. The organic layer was washed with 1N HCl (to pH 3), water and brine. The organic layer was dried over Na$_2$SO$_4$, filtered and the solvent was removed to afford the crude Intermediate 7-3 (4.0 g).

Intermediate 7-4

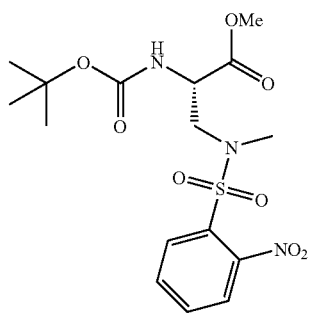

(S)-methyl-2-(tert-butoxycarbonylamino)-3-(N-methyl-2-nitrophenylsulfonamido)propanoate: The crude Intermediate 7-3 (2.0 g), K$_2$CO$_3$ (1.5 g, 4 equiv.) were dissolved in 10 ml DMF. MeI (0.8 ml, 4 equiv.) was added to the reaction at RT. The resulting mixture was stirred for 20 hours. The DMF was mostly removed under vacuum and 100 ml EtOAc was added and the mixture was washed with water and brine. The organic layer was dried over Na$_2$SO$_4$. After removal of solvent, the crude product was subject to a short silica gel column (eluents: EtOAc/hexane) to produce 1.62 g of the Intermediate 7-4. MS m/z: 439.9 (M+Na$^+$).

Intermediate 7-5

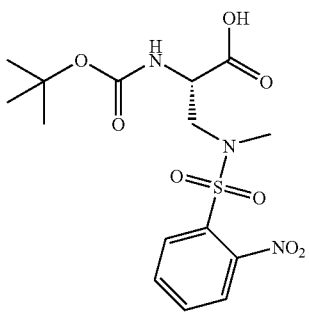

(S)-2-(tert-butoxycarbonylamino)-3-(N-methyl-2-nitrophenylsulfonamido)propanoic acid: To a solution of Intermediate 7-4 (1.6 g, 3.8 mmol) in 10 mL of THF/MeOH (1:1) was added 1N LiOH aqueous solution (5.8 mL, 5.8 mmol). After stirring at RT. for 10 hours, the reaction mixture was neutralized with 1.0 N HCl. The organic solvent was evaporated under vacuum, and the remaining aqueous phase was acidified to pH~3 using 1.0 N HCl and was extracted with EtOAc. The organic layer was washed with brine, and was dried over anhydrous sodium sulfate. After removal of solvent, 1.5 g of Intermediate 7-5 was obtained. MS m/z: 402.0 (M−1, negative mode).

Intermediate 7-6

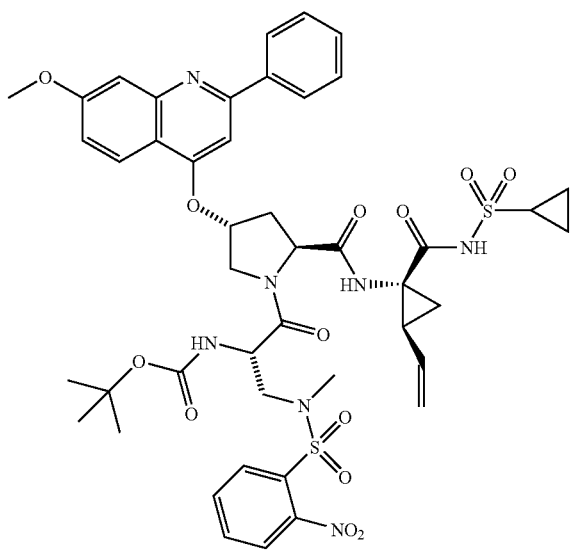

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3-(N-methyl-2-nitrophenylsulfonamido)-1-oxopropan-2-ylcarbamate: To a solution of Intermediate 7-2 (0.27 g, 0.44 mmol) and Intermediate 7-5 (0.24 g, 0.58 mmol) in 5.0 mL of anhydrous acetonitrile was added HATU (0.22 g, 0.58 mmol) and DIEA (0.23 mL, 1.3 mmol) at RT under stirring. TLC analysis and LC-MS indicated completion of the coupling reaction after one hour. A 20-ml portion of EtOAc was poured in and the mixture was washed with a buffer (pH~4, AcONa/AcOH), NaHCO₃ and brine. The organic layer was dried over Na₂SO₄. After removal of solvent, the crude product was subject to chromatography on silica gel (eluents: EtOAc/hexane). A total of 0.35 g of Intermediate 7-6 was obtained: R_f 0.4 (EtOAc:hexane=1:1); MS m/z: 962.2 (M+H$^+$).

Intermediate 7-7

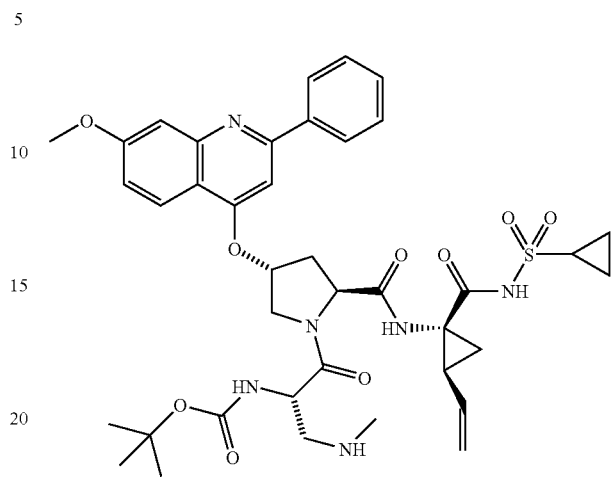

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3-(methylamino)-1-oxopropan-2-ylcarbamate: To a solution of Intermediate 7-6 (0.35 g, 0.36 mmol) in 5 mL DMF was added phenylthiol (80 mg, 0.72 mmol) and K₂CO₃ (0.20 g, 1.0 mmol). The resulting mixture was stirred for 10 hours at RT. 30 mL EtOAc was added and the mixture was washed with water and brine and water. The organic layer was dried over Na₂SO₄. After removal of solvent, the crude product was subject to chromatography on silica gel (eluents: EtOAc/hexane) to produce 0.2 g of Intermediate 7-7. MS m/z: 777.2 (M+H$^+$).

Compound (I-52)

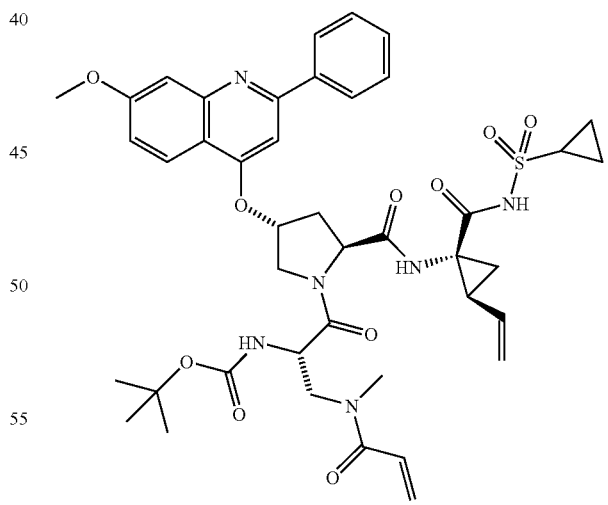

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3-(N-methylacrylamido)-1-oxopropan-2-ylcarbamate (I-52): Acryloyl chloride (18 uL, 0.207 mmol) was added dropwise at 0° C. to a stirred solution of 108 mg of the product from Intermediate 7-7 in 3 mL of DCM containing 3 equiv. of triethylamine. The reaction mixture was stirred at RT for 1.5 hrs and then was diluted with 10 mL of DCM. The resulting solution was washed twice with brine and was dried over magnesium sulfate. Removal of solvent afforded the crude product, which was purified by chromatography on silica gel eluting first with hexane/EtOAc (1:3~1:5) and then with DCM-methanol (50:1~25:1). A total of 100 mg of the title compound was obtained: $R_f$ 0.25 (DCM:MeOH=25:1); MS m/z: 831.3 (M+H$^+$).

t-butyl-(S)—N-ethyl-3-acrylamido-1-((2S,4R)-2-((1R,2S)-1-(cyclopropylsulfonylcarbamoyl)-2-vinylcyclopropyl-carbamoyl)-4-(7-methoxy-2-phenylquinolin-4-yloxy)pyrrolidin-1-yl)-1-oxopropan-2-ylcarbamate (I-78): In similar fashion, compound I-78 was made by using ethyl iodide in the step for Intermediate 7-4. MS m/z: 845.3 (M+H$^+$).

t-butyl-(S)—N-2-propenyl-3-acrylamido-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxopropan-2-ylcarbamate (I-79): Compound I-79 was made by using allyl bromide in the step for Intermediate 7-4. MS m/z: 857.3 (M+H$^-$).

t-butyl-(S)-3-(2-oxopyrrol-3-enyl)-1-((2S,4R)-2-((1R,2S)-1-(cyclopropylsulfonylcarbamoyl)-2-vinylcyclopropyl-carbamoyl)-4-(7-methoxy-2-phenylquinolin-4-yloxy)pyrrolidin-1-yl)-1-oxopropan-2-ylcarbamate (I-80): Compound I-80 was made from compound I-79 by using ruthenium-catalyzed ring closing metathesis. MS m/z: 829.3 (M+H$^+$).

t-butyl-(S)—N-methyl-4-acrylamido-1-((2S,4R)-2-((1R,2S)-1-(cyclopropylsulfonylcarbamoyl)-2-vinylcyclopropyl-carbamoyl)-4-(7-methoxy-2-phenylquinolin-4-yloxy)pyrrolidin-1-yl)-1-oxobutan-2-ylcarbamate (I-82): Compound I-82 was made by using (2S)-2-boc-amino-4-aminobutanoic acid in the step for Intermediate 7-3 in place of (S)-3-amino-2-boc-aminopropanoic acid. $R_f$ 0.35 (EtOAc/MeOH 10:1); MS m/z: 845.30 (M+H$^+$).

Example 8

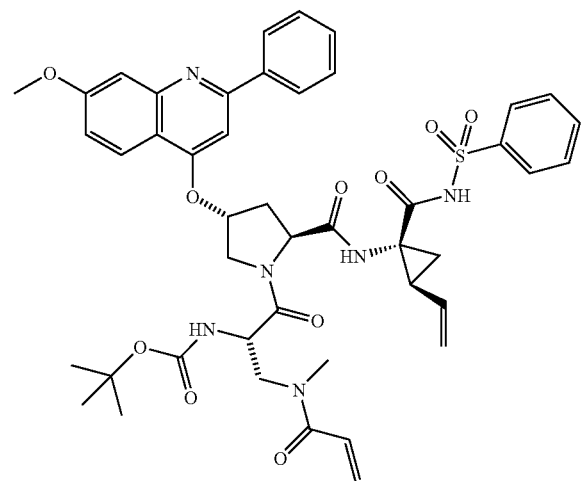

tert-butyl-(S)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-3-(N-methylacrylamido)-1-oxopropan-2-ylcarbamate (I-28): The title compound was prepared according to the steps and intermediates as described below.

Intermediate 8-1

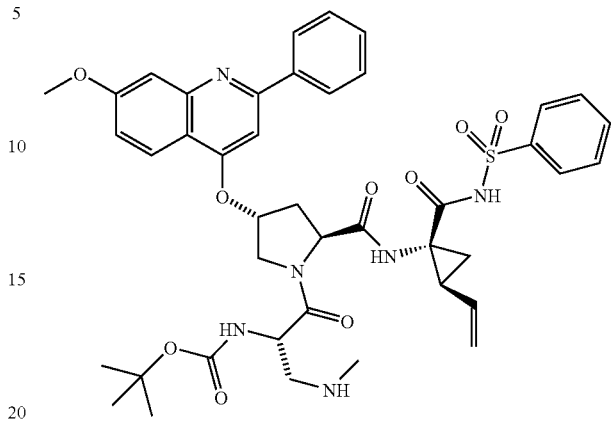

tert-butyl-(S)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-3-(methylamino)-1-oxopropan-2-ylcarbamate: Intermediate 8-1 was prepared according to the procedures for Intermediate 7-7 as described in Example 7 by using Intermediate 4 from Example 1 in place of Intermediate 7-2. MS m/z: 813.3 (M+H$^+$).

Compound I-28

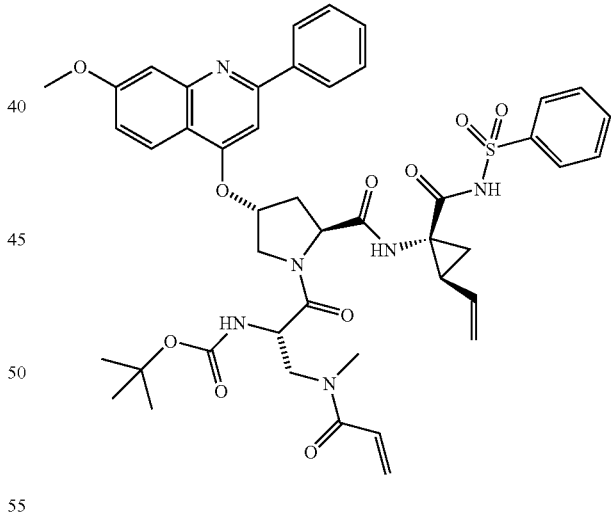

tert-butyl-(S)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-3-(N-methylacrylamido)-1-oxopropan-2-ylcarbamate (I-28): Acryloyl chloride (1.2 equiv.) was added dropwise at 0° C. to a stirred solution of 100 mg of the product from Intermediate 8-1 in 3 mL of DCM containing 3 equiv. of triethylamine. The reaction mixture was stirred at RT for 1.5 hrs and then was diluted with 10 mL of DCM. The resulting solution was washed twice with brine and was dried over magnesium sulfate. Removal of solvent afforded the crude product, which was purified by chromatography on silica gel eluting first with hexane/EtOAc (1:3~1:5) and then with DCM-methanol (50:1~25:1). A total of 80 mg of the title compound was obtained: R$_f$ 0.25 (DCM: MeOH=25:1); MS m/z: 867.2 (M+H$^+$).

In similar fashion using the product of Intermediate 8-1 the following compounds were prepared:

chloroacetyl chloride afforded tert-butyl-(S)-3-(2-chloro-N-methylacetamido)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-ylcarbamate (I-29): MS m/z: 890.30 (M+H$^+$);

(E)-4-(dimethylamino)but-2-enoyl chloride afforded tert-butyl-(S)-3-((E)-4-(dimethylamino)-N-methylbut-2-enamido)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-ylcarbamate (I-30): M/Z 924.3 (M+H+);

Methacryloyl chloride afforded tert-butyl-(S)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-3-(N-methylmethacrylamido)-1-oxopropan-2-ylcarbamate (I-32): MS m/z: 881.3 (M+H$^+$);

2-chloro-2-phenylacetyl chloride afforded tert-butyl-(2S)-3-(2-chloro-N-methyl-2-phenylacetamido)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-ylcarbamate (I-33): MS m/z: 965.20 (M+H$^+$);

but-2-ynoyl chloride afforded tert-butyl-(S)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-3-(N-methylbut-2-ynamido)-1-oxopropan-2-ylcarbamate (I-51): MS m/z: 879.30 (M+H$^+$);

2-(trifluoromethyl)acryloyl chloride afforded tert-butyl-(S)-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-3-(N-methyl-2-(trifluoromethyl)acrylamido)-1-oxopropan-2-ylcarbamate (I-53): MS m/z: 935.30 (M+H$^+$).

Example 9

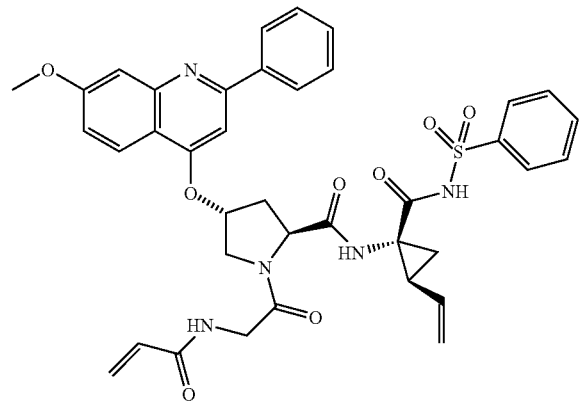

(2S,4R)-1-(2-acrylamidoacetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-27):

The title compound was prepared according to the steps and intermediates as described below.

Intermediate 9-1

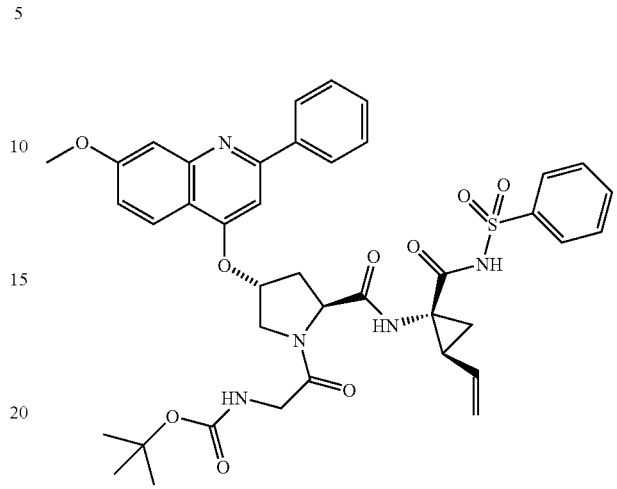

(2S,4R)-1-(2-t-butoxycarbonylaminoacetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide: To a solution of the product of Intermediate 4 from Example 1 (0.10 g, 0.15 mmol) and N-Boc-glycine (0.035 g, 0.20 mmol) in 3.0 mL of acetonitrile was added HATU (85.1 mg, 0.22 mmol) and DIEA (0.09 mL, 0.5 mmol) at RT under stirring. The reaction mixture was stirred for 2 h. LC-MS and TLC analysis indicated completion of the coupling reaction. A 20-mL of EtOAc was poured in and the mixture was washed with a buffer (pH~4, AcONa/AcOH), NaHCO$_3$ and brine, and was dried over Na$_2$SO$_4$. After removal of solvent, the crude product was subject to chromatography on silica gel (eluents: EtOAc/hexane). A total of 0.11 g of the title compound was obtained: R$_f$ 0.2 (EtOAc:hexane=2:1); MS m/z: 770.3 (M+H$^+$).

Intermediate 9-2

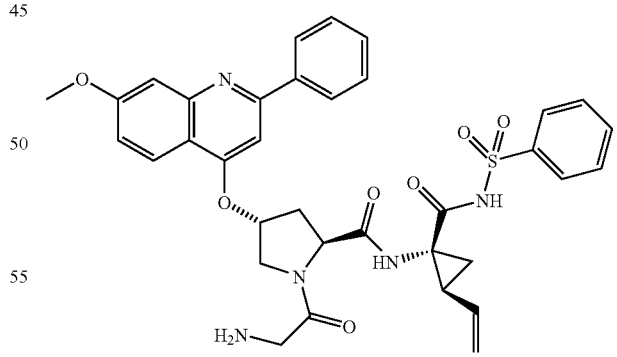

(2S,4R)-1-(2-aminoacetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide: The product from Intermediate 9-1 (0.11 g, 0.13 mmol) was dissolved in 2 mL of 4N HCl in dixoxane and the reaction was stirred for 1 hour at RT. After removal of solvents, a 3-mL portion of DCM was poured in followed by evaporation to dryness. This process of DCM addition followed by evapo- Compound I-27

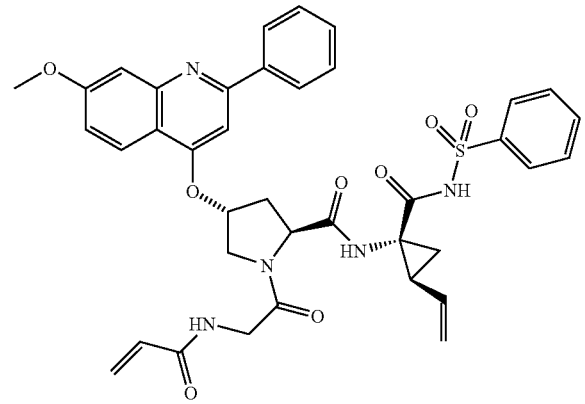

(2S,4R)-1-(2-acrylamidoacetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-27): The title compound was made by coupling Intermediate 9-2 and acrylic acid using HATU following the coupling reactions described for Intermediate 9-1. A total of 0.10 g of the title compound was obtained 87%: $R_f$ 0.5 (5% MeOH in DCM); MS m/z: 724.3 (M+H$^+$).

Following the procedures described in Example 9, the following compounds were made similarly:

Compound I-34

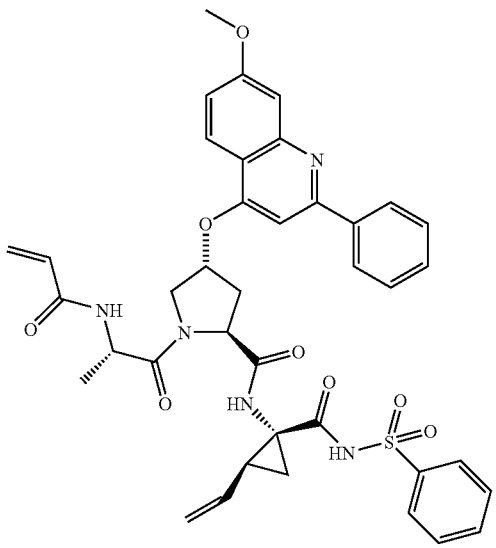

(2S,4R)-1-((S)-2-acrylamidopropanoyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-34): $R_f$ 0.4 (5% MeOH in DCM); MS m/z: 738.20 (M+H$^+$).

Compound I-43

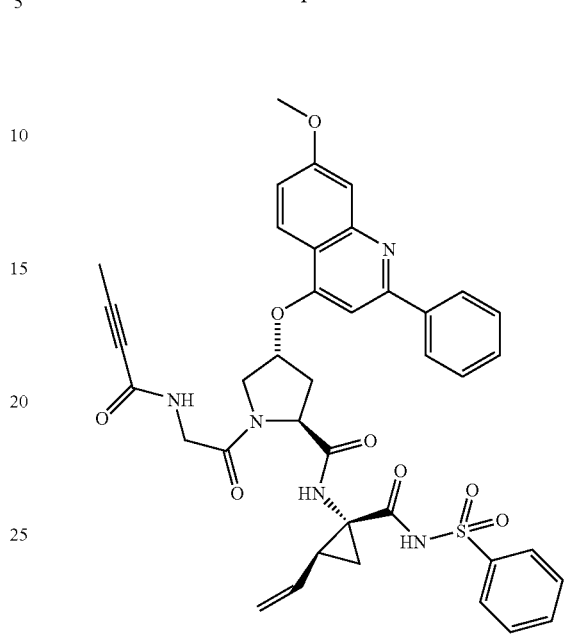

(2S,4R)-1-(2-but-2-ynamidoacetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-43): $R_f$ 0.4 (5% MeOH in DCM); MS m/z: 736.2 (M+H$^+$).

Compound I-44

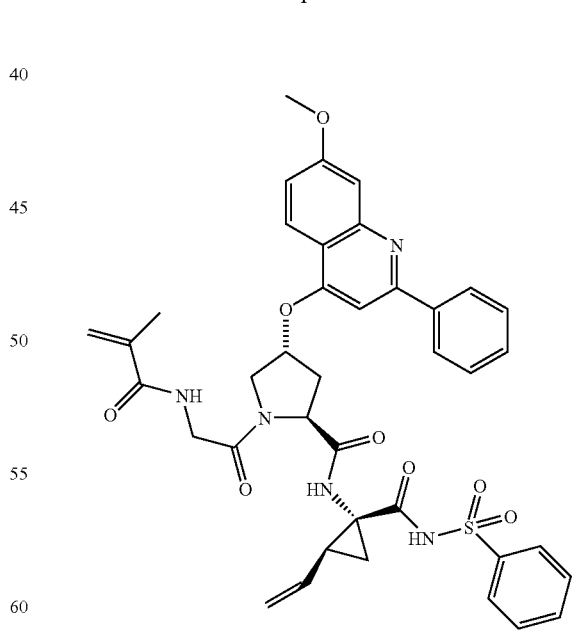

(2S,4R)-1-(2-methacrylamidoacetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-44): $R_f$ 0.45 (5% MeOH in DCM); MS m/z: 738.3 (M+H$^+$).

287

Compound I-45

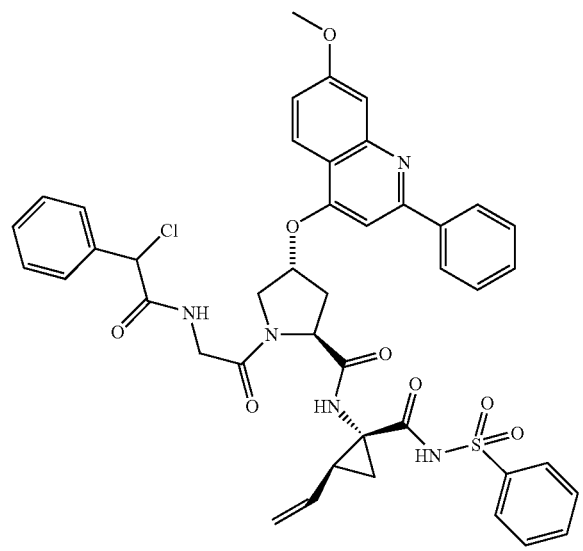

(2S,4R)-1-(2-((S,R)-2-chloro-2-phenylacetamido)-acetyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-45): $R_f$ 0.55 (5% MeOH in DCM); MS m/z: 822.3 (M+H$^+$).

Compound I-46

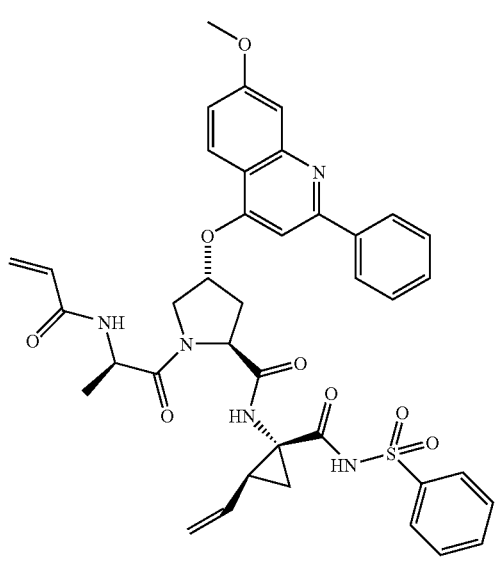

(2S,4R)-1-((R)-2-acrylamidopropanoyl)-4-(7-methoxy-2-phenylquinolin-4-yloxy)-N-((1R,2S)-1-(phenylsulfonyl-carbamoyl)-2-vinylcyclopropyl)pyrrolidine-2-carboxamide (I-46): $R_f$ 0.4 (5% MeOH in DCM); MS m/z: 738.2 (M+H$^+$).

288

Compound I-47

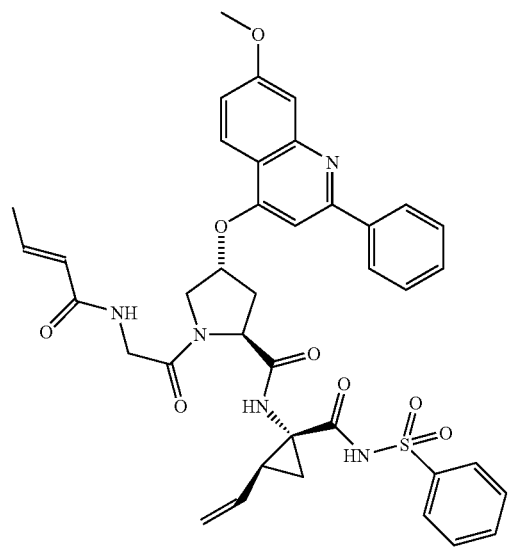

(2S,4R)-1-(2-(E)-but-2-enamidoacetyl)-4-(7-methoxy-2-phenylquinolin-4-yloxy)-N-((1R,2S)-1-(phenylsulfonylcar-bamoyl)-2-vinylcyclopropyl)pyrrolidine-2-carboxamide (I-47): $R_f$ 0.45 (5% MeOH in DCM); MS m/z: 738.3 (M+H$^+$).

Compound I-24

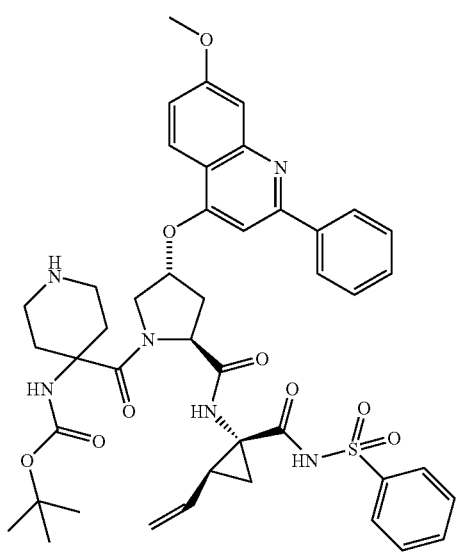

tert-butyl-4-((2S,4R)-4-(7-methoxy-2-phenylquinolin-4-yloxy)-2-((1R,2S)-1-(phenylsulfonylcarbamoyl)-2-vinylcy-clopropylcarbamoyl)pyrrolidine-1-carbonyl)piperidin-4-yl-carbamate (I-24): $R_f$ 0.20 (10% MeOH in DCM); MS m/z: 839.3 (M+H$^+$).

Compound I-25

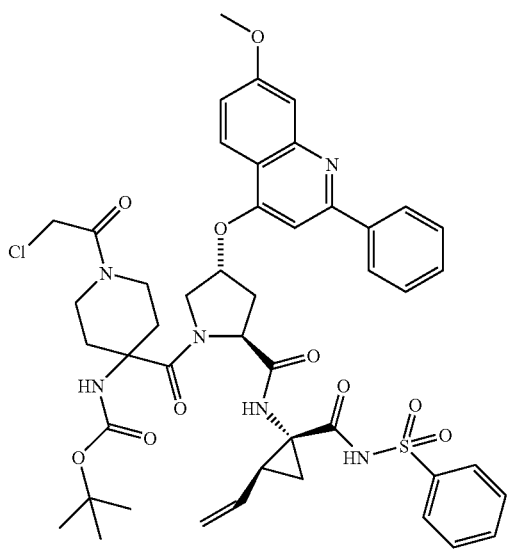

tert-butyl-1-(2-chloroacetyl)-4-((2S,4R)-4-(7-methoxy-2-phenylquinolin-4-yloxy)-2-(((1R,2S)-1-(phenylsulfonylcarbamoyl)-2-vinylcyclopropylcarbamoyl)pyrrolidine-1-carbonyl)piperidin-4-ylcarbamate (I-25): R$_f$ 0.50 (10% MeOH in EtOAc); MS m/z: 915.3 (M+H$^+$).

Compound I-26

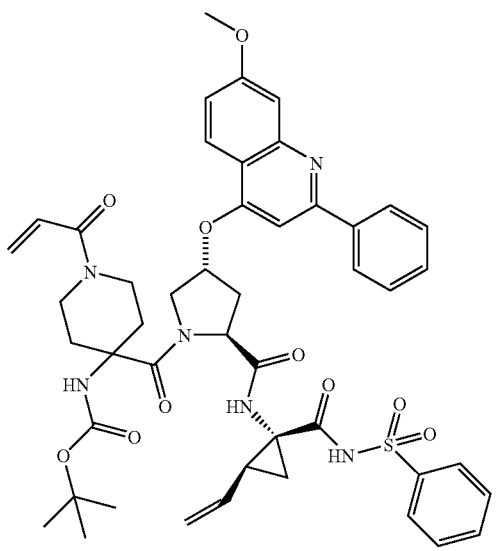

tert-butyl-1-acryloyl-4-((2S,4R)-4-(7-methoxy-2-phenylquinolin-4-yloxy)-2-(((1R,2S)-1-(phenylsulfonylcarbamoyl)-2-vinylcyclopropylcarbamoyl)pyrrolidine-1-carbonyl)piperidin-4-ylcarbamate (I-26): R$_f$ 0.40 (5% MeOH in DCM); MS m/z: 893.4 (M+H$^+$).

Compound I-59

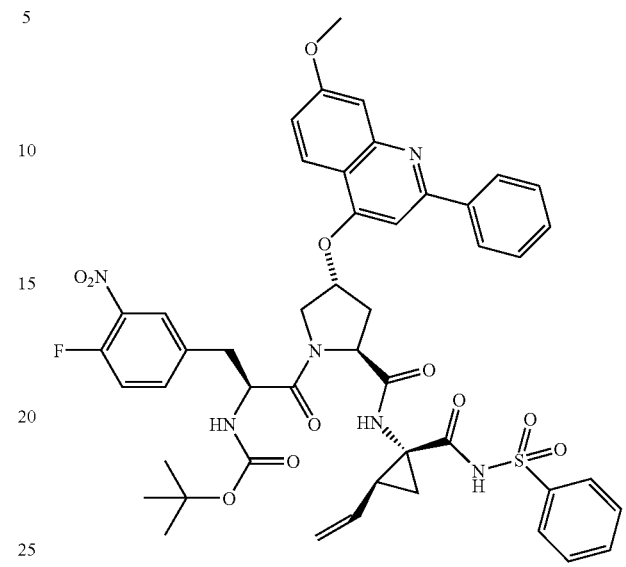

tert-butyl-(S)-1-((2S,4R)-4-(7-methoxy-2-phenylquinolin-4-yloxy)-2-(((1R,2S)-1-(phenylsulfonylcarbamoyl)-2-vinylcyclopropylcarbamoyl)pyrrolidin-1-yl)-3-(4-fluoro-3-nitrophenyl)-1-oxopropan-2-ylcarbamate (I-59): R$_f$ 0.40 (5% MeOH in DCM); MS m/z: 923.3 (M+H$^+$).

Compound I-63

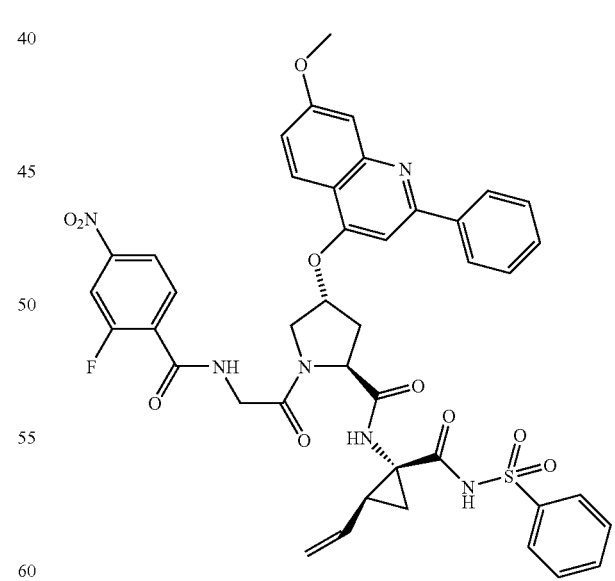

(2S,4R)-1-(2-fluoro-4-nitrobenzamidoacetyl)-N-((1R,2S)-1-(phenylsulfonylcarbamoyl)-2-vinylcyclopropyl)-4-(7-methoxy-2-phenylquinolin-4-yloxy)pyrrolidine-2-carboxamide (I-63): R$_f$ 0.61 (EtOAc/MeOH 10:1); MS m/z: 837.3 (M+H$^+$).

Compound I$^R$-27

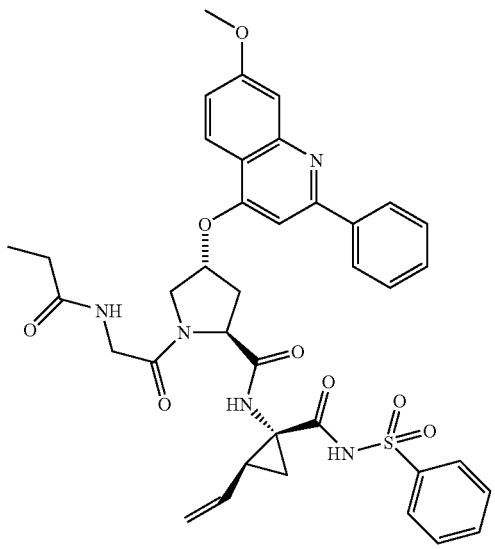

By reacting with vinyl sulfonyl chloride, the following structure can be made: (2S,4R)-4-(7-methoxy-2-phenylquinolin-4-yloxy)-N-((1R,2S)-1-(phenylsulfonylcarbamoyl)-2-vinylcyclopropyl)-1-(2-propionamidoacetyl)pyrrolidine-2-carboxamide (I$^R$-27): MS m/z: 726.30 (M+H$^+$).

Example 10

Compound I-39

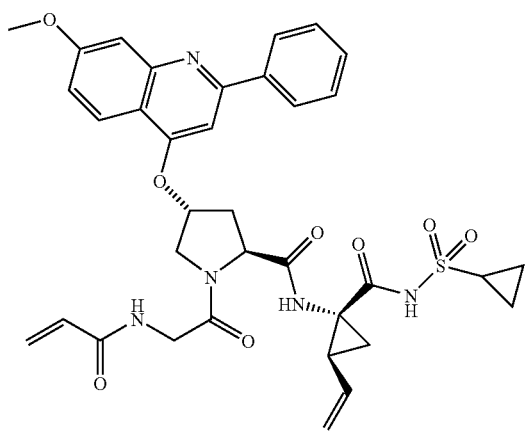

(2S,4R)-1-(2-acrylamidoacetyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-39): The title compound was prepared according to the steps and intermediates as described in Example 9 by using Intermediate 7-2 in place of Intermediate 4 in the first step.

MS m/z: 687.8 (M+H$^+$).

I-R

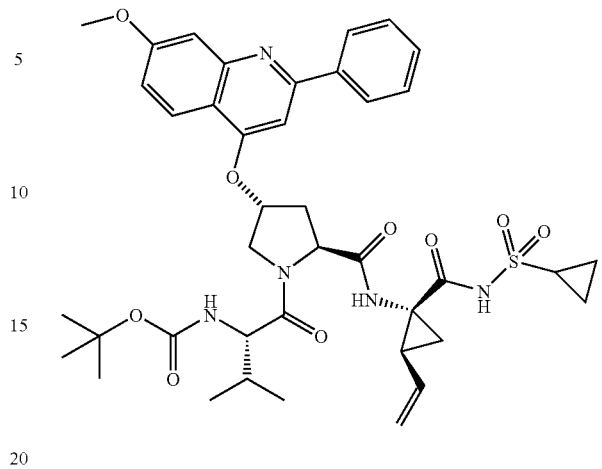

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3-methyl-1-oxobutan-2-ylcarbamate (I-R): The title compound was prepared according to the steps and intermediates as described in Example 9 by using Intermediate 7-2 in place of Intermediate 4 and using Boc-L-valine instead of Boc-Glycine in the first step.

MS m/z: 776.3 (M+H$^+$).

Following the procedures described in Example 10, the following compounds were made similarly:

Compound I-37

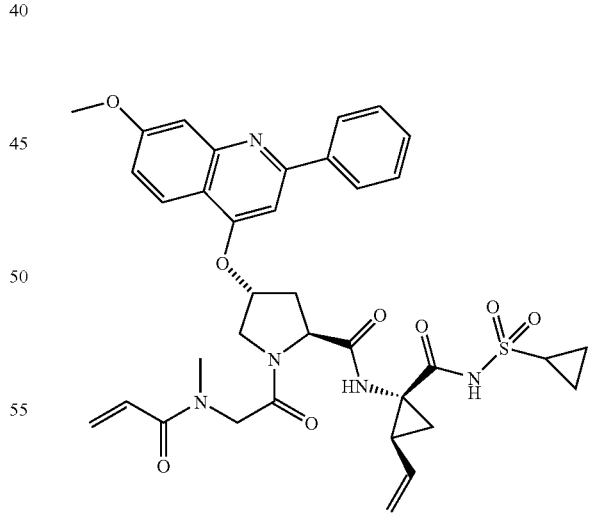

(2S,4R)—N-((1R,2S)-1-(cyclopropylsulfonylcarbamoyl)-2-vinylcyclopropyl)-4-(7-methoxy-2-phenylquinolin-4-yloxy)-1-(2-(N-methylacrylamido)acetyl)pyrrolidine-2-carboxamide (I-37): MS m/z: 702.0 (M+H$^+$).

Compound I-38

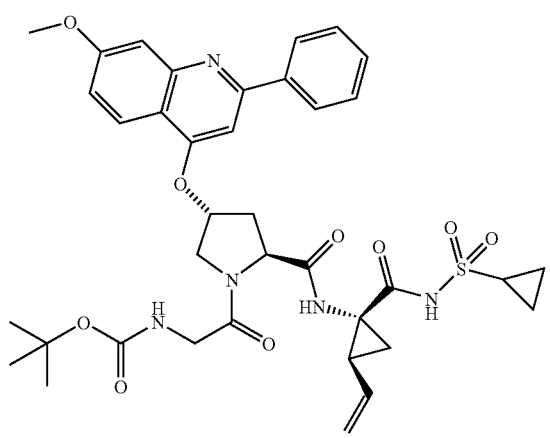

tert-butyl-2-((2S,4R)-2-((1R,2S)-1-(cyclopropylsulfonyl-carbamoyl)-2-vinylcyclopropylcarbamoyl)-4-(7-methoxy-2-phenylquinolin-4-yloxy)pyrrolidin-1-yl)-2-oxoethylcarbamate (I-38): MS m/z: 733.9 (M+H⁺).

Compound I-48

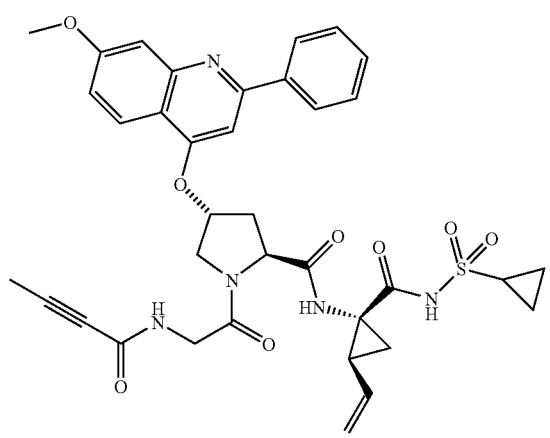

(2S,4R)-1-(2-but-2-ynamidoacetyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-48): R$_f$ 0.4 (5% MeOH in DCM); MS m/z: 700.20 (M+H⁺).

Compound I-49

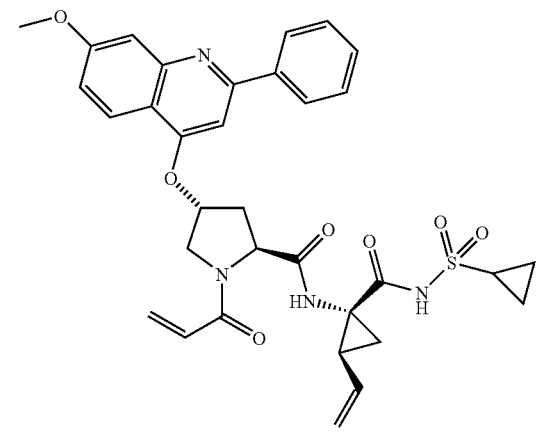

(2S,4R)-1-acryloyl-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide (I-49): MS m/z: 631.0 (M+H⁺).

Compound I-54

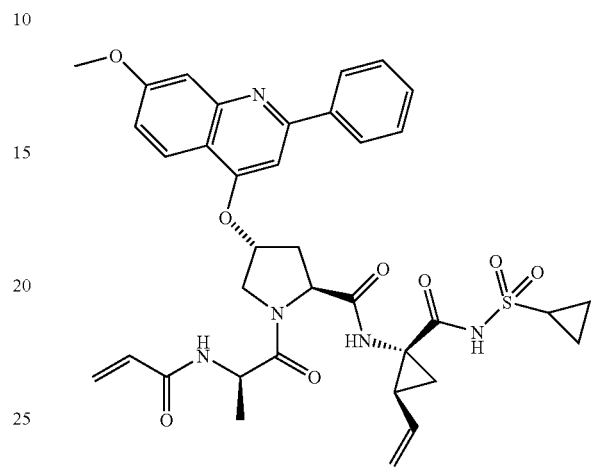

(2S,4R)-1-((R)-2-acrylamidopropanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-54): R$_f$ 0.66 (10% MeOH in DCM); MS m/z: 702.30 (M+H⁺).

Compound I-56

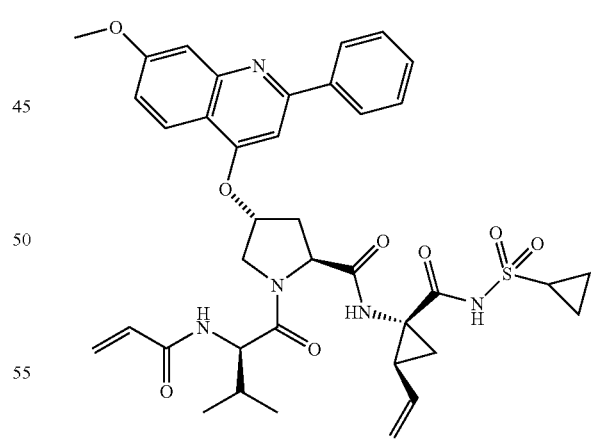

(2S,4R)-1-((R)-2-acrylamido-3-methylbutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-56): R$_f$ 0.61 (10% MeOH in DCM); MS m/z: 730.30 (M+H⁺).

Compound I-57

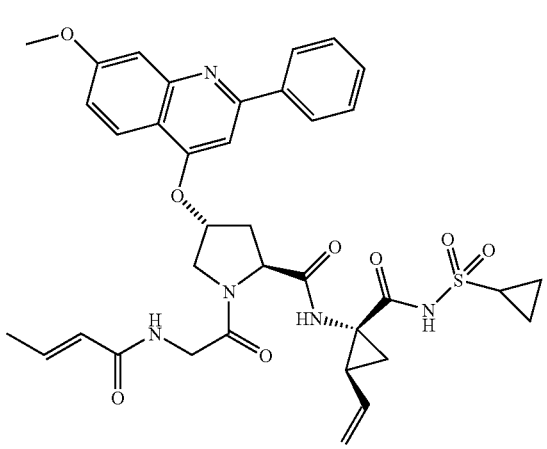

(2S,4R)-1-(2-(E)-but-2-enamidoacetyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-57): $R_f$ 0.6 (10% MeOH in DCM); MS m/z: 702.2 (M+H$^+$).

Compound I-60

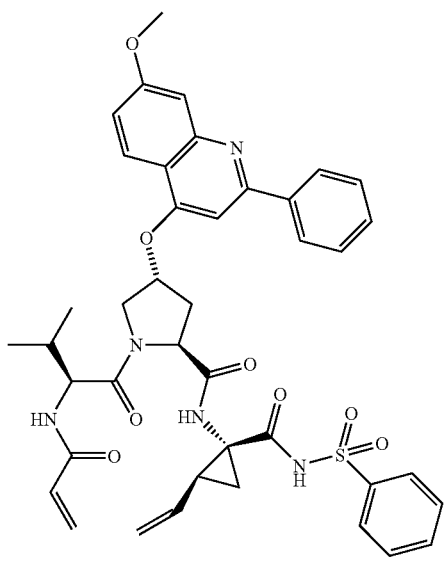

(2S,4R)-1-((S)-2-acrylamido-3-methylbutanoyl)-N-((1R,2S)-1-(phenylylsulfonylcarbamoyl)-2-vinylcyclopropyl)-4-(7-methoxy-2-phenylquinolin-4-yloxy)pyrrolidine-2-carboxamide (I-60): $R_f$ 0.45 (5% MeOH in DCM); MS m/z: 766.3 (M+H$^+$).

Compound I-65

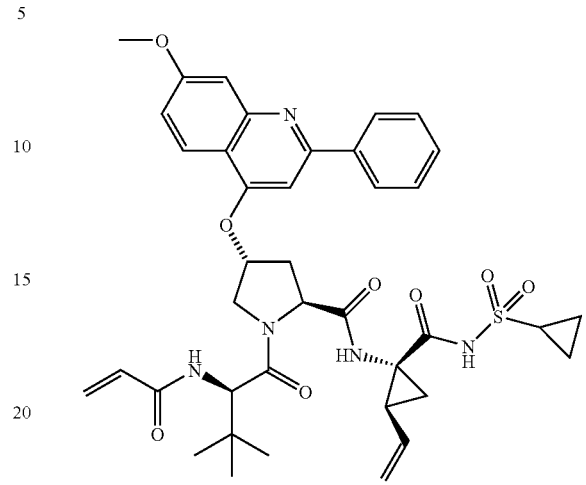

(2S,4R)-1-((R)-2-acrylamido-3,3-dimethylbutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-65): MS m/z: 744.30 (M+H$^+$).

Compound I-66

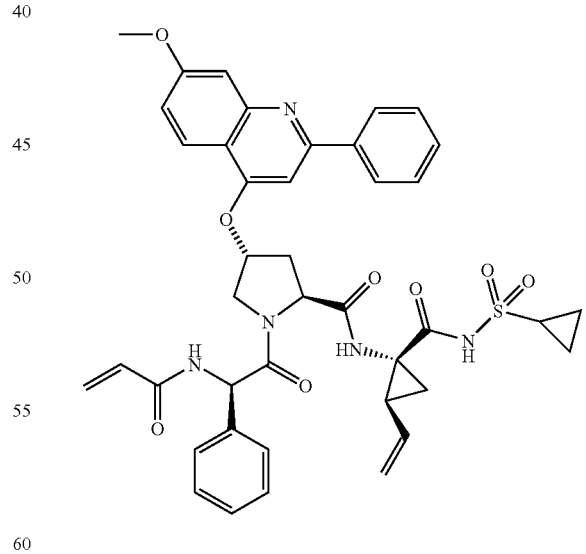

(2S,4R)-1-((R)-2-acrylamido-phenylacetyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (I-66): MS m/z: 764.30 (M+H$^+$).

Compound I-67

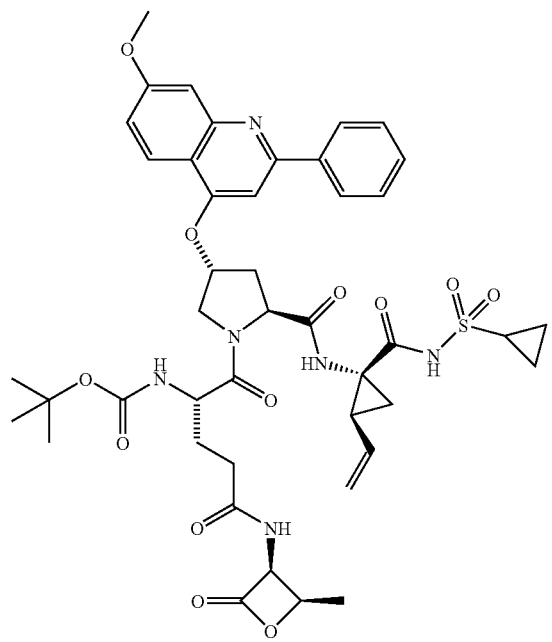

t-butyl-(2S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-5-((2R,3S)-2-methyl-4-oxooxetan-3-ylamino)-1,5-dioxopentan-2-ylcarbamate (I-67): MS m/z: 889.2 (M+H$^+$).

Compound I-69

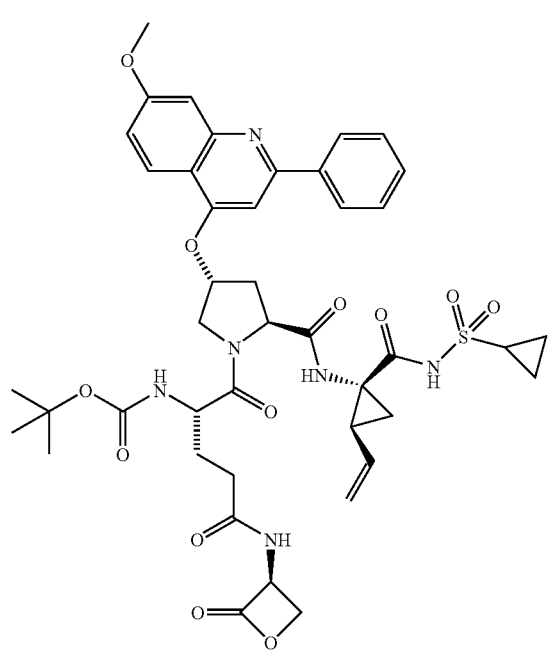

t-butyl-(2S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-5-((3S)-2-oxooxetan-3-ylamino)-1,5-dioxopentan-2-ylcarbamate (I-69): MS m/z: 875.3 (M+H$^+$).

Compound I-70

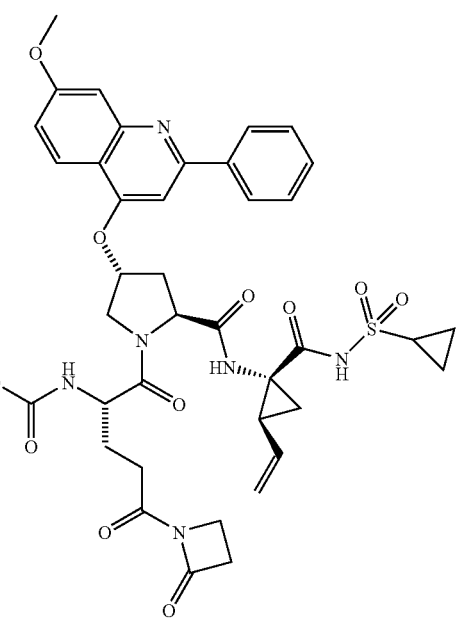

t-butyl-(2S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-5-(2-oxoazetidinyl)-1,5-dioxopentan-2-ylcarbamate (I-70): MS m/z: 859.2 (M+H$^+$).

Example 11

Compound I-31

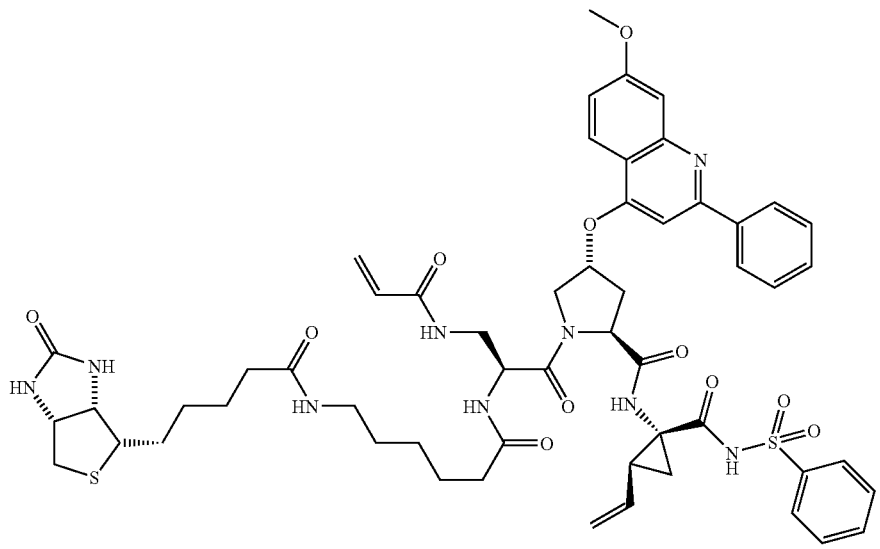

(2S,4R)-1-((S)-3-acrylamido-2-(6-(5-((3aS,4S,6aR)-2-oxohexahydro-1H-thieno[3,4-d]imidazol-4-yl)pentanamido)hexanamido)propanoyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-31) The title compound was prepared According to the steps and intermediates as described below:

Intermediate 11-1

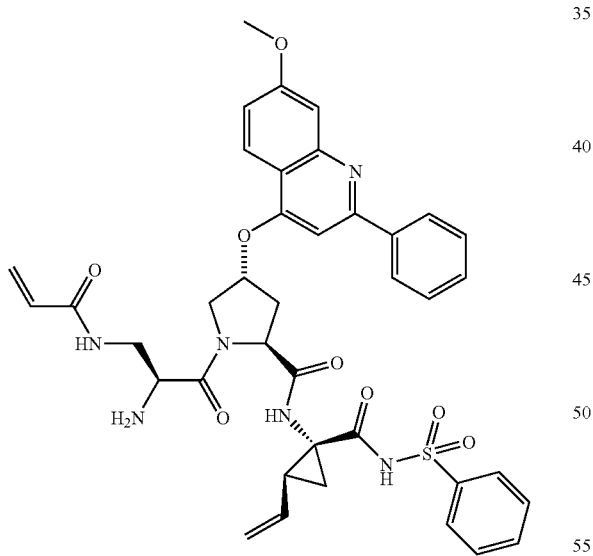

(2S,4R)-1-((S)-3-acrylamido-2-aminopropanoyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide: To a solution of the product of Example 1 (I-3) (30 mg, 0.04 mmol) in 3 mL of DCM was added dropwise 0.5 mL of TFA. The mixture was stirred at RT for two hrs. After removal of solvents, a 5-mL portion of DCM was poured in followed by evaporation to dryness. This process of DCM addition followed by evaporation was repeated four times. Toluene (4 mL) was added and then removed by evaporation to dryness to obtain the title compound: MS m/z: 753.2 (M+H$^+$)

Compound I-31

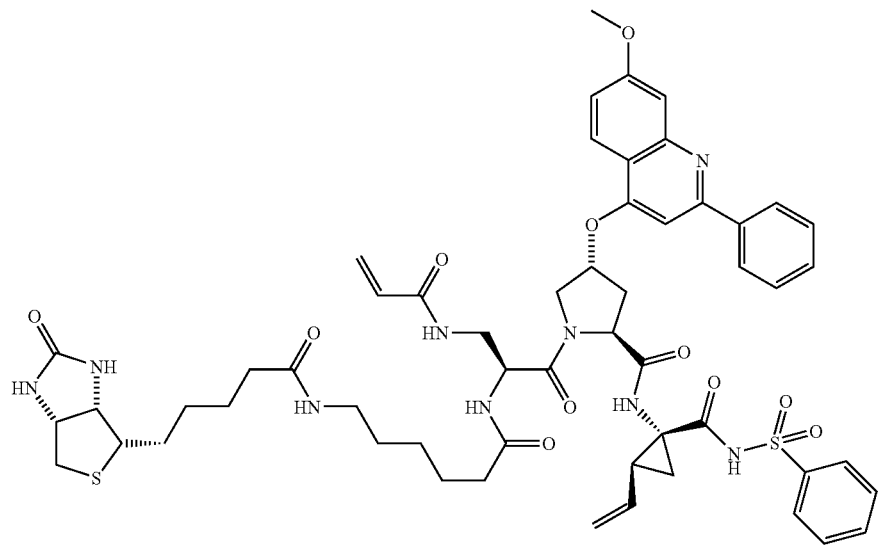

(2S,4R)-1-((S)-3-acrylamido-2-(6-(5-((3aS,4S,6aR)-2-oxohexahydro-1H-thieno[3,4-d]imidazol-4-yl)pentanamido)hexanamido)propanoyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide (I-31): The title compound was prepared by coupling Intermediate 11-1 with the biotinylated carboxylic acid

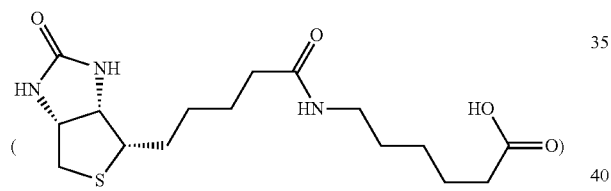

according to the steps described for Intermediate 9-1 in Example 9. MS m/z: 1092.4 (M+H$^+$).

In similar fashion using the product of Intermediate 11-1 the following compounds were prepared:

Compound I-42

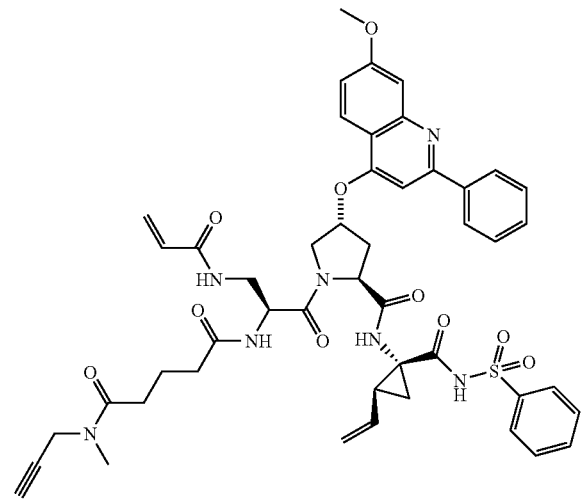

N1-((S)-3-acrylamido-1-((2S,4R)-4-(7-methoxy-2-phenylquinolin-4-yloxy)-2-((1R,2S)-1-(phenylsulfonylcarbamoyl)-2-vinylcyclopropylcarbamoyl)pyrrolidin-1-yl)-1-oxopropan-2-yl)-N1,N5-dimethyl-N5-(prop-2-ynyl) glutaramide (I-42): R$_f$ 0.45 (5% MeOH in DCM); MS m/z: 918.3 (M+H$^+$).

By starting with compound I-35 (Example 1), following the TFA-boc removal procedure described above, and using chlorocyclopentyl formate to acylate the resulting amine, compound I-55 was provided:

Compound I-55

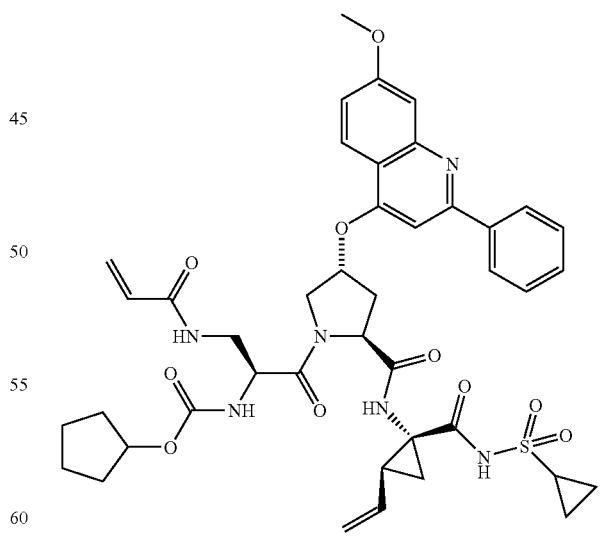

Cyclopentyl-(S)-3-acrylamido-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxopropan-2-ylcarbamate (I-55): R$_f$ 0.59 (10% MeOH in EtOAc); MS m/z: 829.30 (M+H$^+$).

By starting with compound I-52 (Example 7), following the TFA-boc removal procedure described above, and using chlorocyclopentyl formate to acylate the resulting amine, compound I-72 was provided:

Compound I-72

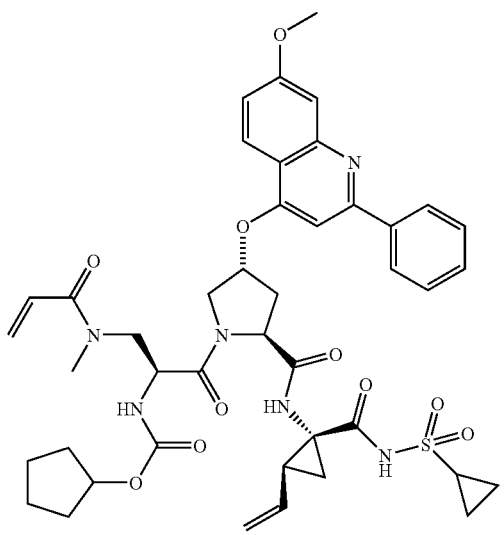

Cyclopentyl-(S)—N-methyl-3-acrylamido-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxopropan-2-ylcarbamate (I-72): $R_f$ 0.40 (5% MeOH in DCM); MS m/z: 843.3 (M+H$^+$).

By starting with compound I-52 (Example 7), following the TFA-boc removal procedure described above, and using pyrazine-2-carboxylic acid and HATU to acylate the resulting amine, compound I-58 was provided:

Compound I-58

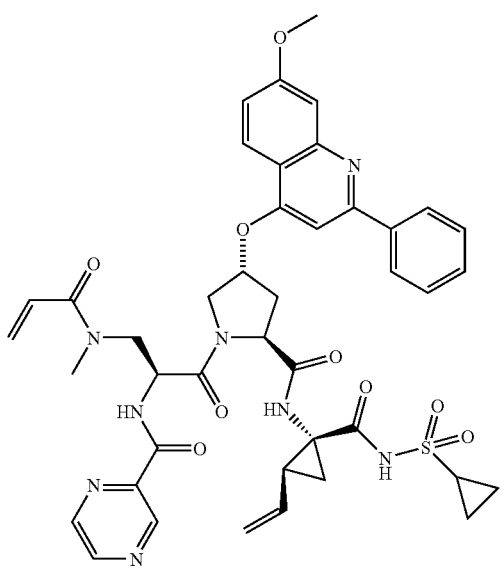

(S)—N-3-(N-methyl)acrylamido-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxo-2-propylpyrazinecarboxamide (I-58): $R_f$ 0.35 (5% MeOH in DCM); MS m/z: 837.3 (M+H$^+$).

By starting with compound I-52 (Example 7), following the TFA-boc removal procedure described above, and using chloropropargyl formate to acylate the resulting amine, compound I-81 was provided:

Compound I-81

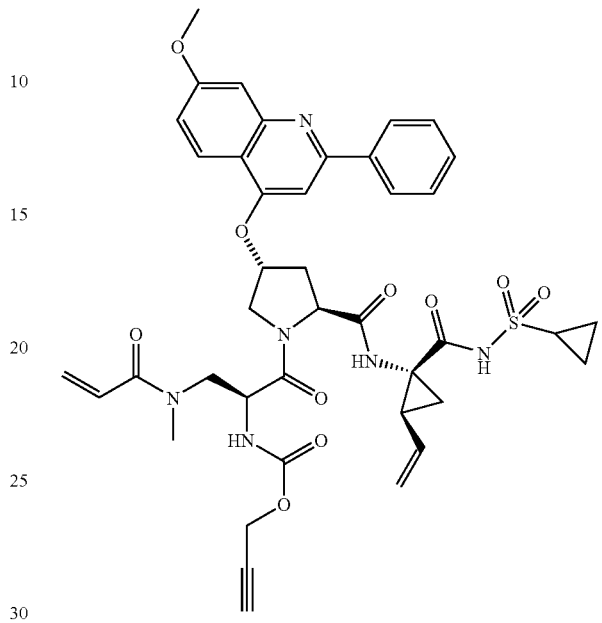

Prop-2-ynyl-(S)—N-methyl-3-acrylamido-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxopropan-2-ylcarbamate (I-81): MS m/z: 813.3 (M+H$^+$).

By starting with compound I-82 (Example 7), following the TFA-boc removal procedure described above, and using chlorocyclopentyl formate to acylate the resulting amine, compound I-85 was provided:

Compound I-85

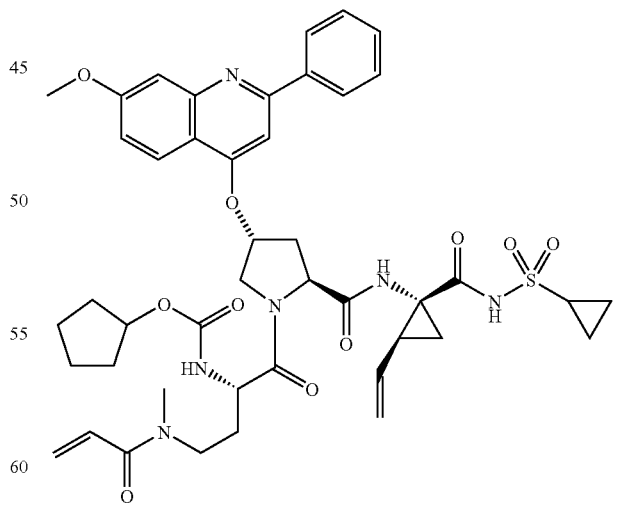

Cyclopentyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-4-(N-methylacrylamido)-1-oxobutan-2-ylcarbamate (I-85): MS m/z: 857.5 (M+1).

Example 12

Compound I-50

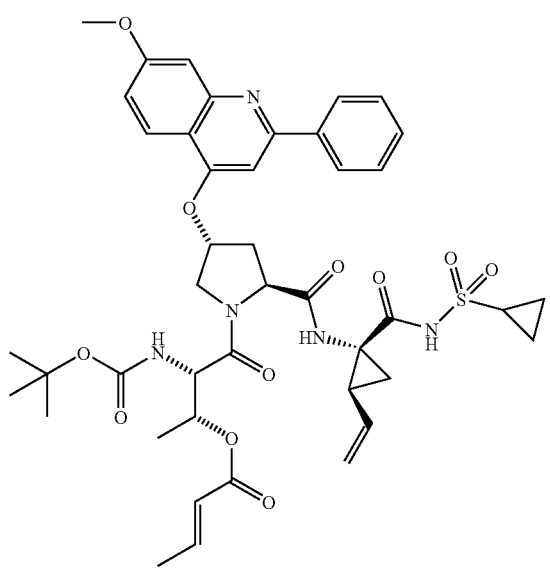

(E)-((2R,3S)-3-(tert-butoxycarbonylamino)-4-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-4-oxobutan-2-yl)but-2-enoate (I-50): The title compound was prepared according to the steps and intermediates as described below:

Intermediate 12-1

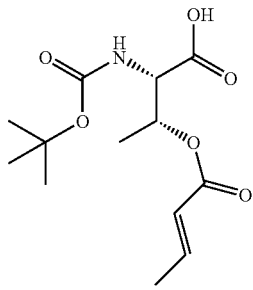

(2S,3R)-3-((E)-but-2-enoyloxy)-2-(tert-butoxycarbonylamino)butanoic acid: To a solution of Boc-L-Threonine (0.44 g 2.0 mmol) in 10.0 ml of DCM was added crotyl chloride (0.32 g, 3.0 mmol) at RT followed by the addition of catalytic amount of DMAP and TEA (1.0 ml, 6 mmol). The reaction mixture was stirred for 10 h at RT. Aqueous NaHCO3 solution (10 mL) was added to quench the reaction. After 2 hours, 1N HCl aqueous solution was added slowly to PH~3. The DCM layer was collected and the aqueous was extracted by DCM (2×10 mL). The organic layer was dried over Na2SO4, filtered and the solvent was removed to provide the crude product.

Compound I-50

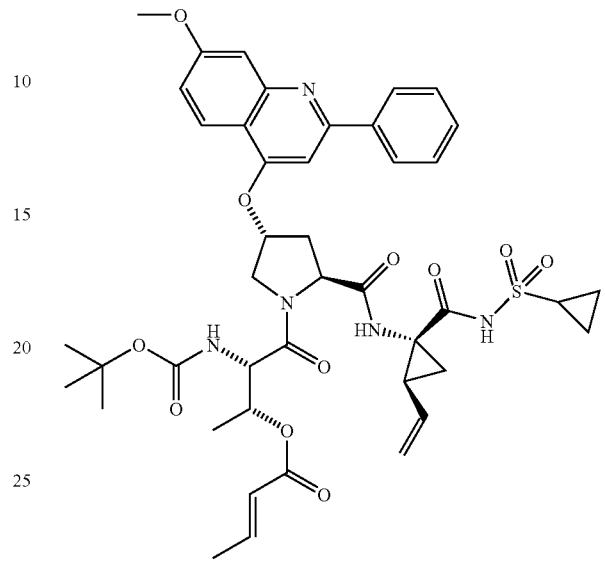

(E)-((2R,3S)-3-(tert-butoxycarbonylamino)-4-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-4-oxobutan-2-yl)but-2-enoate (I-50): The title compound was made by coupling Intermediate 7-2 from Example 7 and Intermediate 12-1 using HATU following the coupling reactions described for Intermediate 5 in Example 1. A total of 58 mg of the title compound was obtained in ~40% yield. $R_f$ 0.5 (EtOAc); MS m/z: 846.0 (M+H$^+$).

Similarly, compound I-64 was made from Intermediate 7-2 (Example 7):

Compound I-64

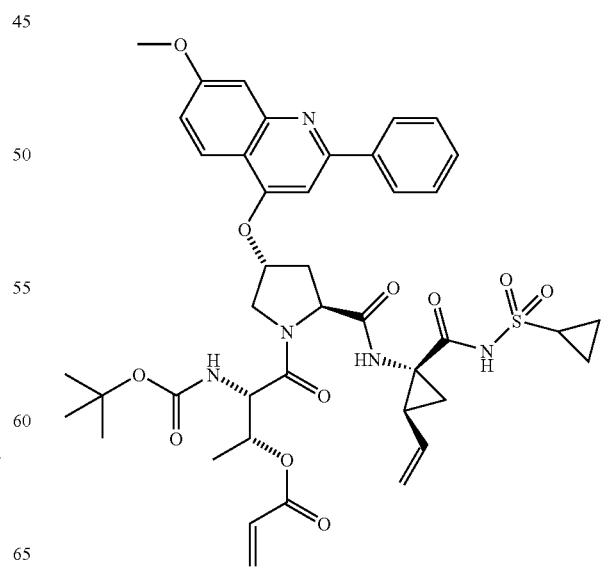

t-butyl-(2S,3R)-3-acryloxy-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-1-oxobutan-2-ylcarbamate (I-64): MS m/z: 832.2 (M+H⁺).

Example 13

Compound I-68

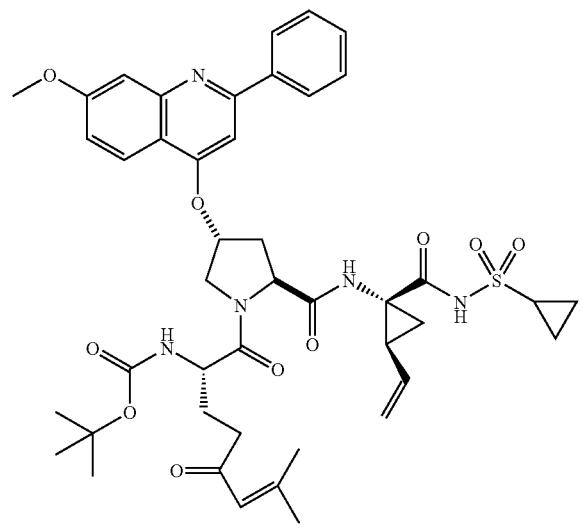

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-7-methyl-1,5-dioxooct-6-en-2-ylcarbamate: (I-68): The title compound was prepared according to the steps and intermediates as described below:

Intermediate 13-1

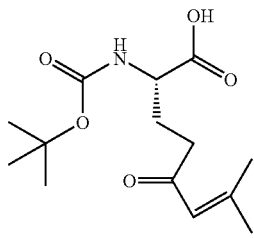

(S)-2-(tert-butoxycarbonylamino)-7-methyl-5-oxooct-6-enoic acid: To a solution of N-Boc-pyroglutamic acid (0.23 g 1.0 mmol) in 10.0 ml of anhydrous THF was added 2-methylprop-1-enyl)magnesium bromide (0.5 M in THF, 5 mL, 2.5 mmol) at −78° C. slowly. The reaction mixture was stirred for 1 h at −78° C. 1 N HCl (2.5 ml) aqueous solution was added and the mixture was slowly warmed up to RT. The pH was adjusted to ~3 by 1 N HCl. The THF was then removed under vacuum and the remaining aqueous was extracted by DCM (3×20 mL). The organic layer was dried over Na₂SO₄, filtered and the solvent was removed to provide the crude product.

Compound I-68

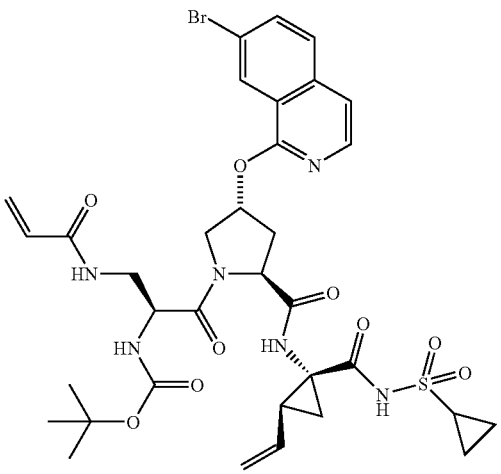

tert-butyl-(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-7-methyl-1,5-dioxooct-6-en-2-ylcarbamate (I-68): The title compound was made by coupling Intermediate 7-2 from Example 7 and Intermediate 13-1 using HATU following the coupling reactions described for Intermediate 5 in Example 1. A total of 70 mg of the title compound was obtained 65%: R$_f$ 0.5 (EtOAc); MS m/z: 844.2 (M+H⁺).

Example 14

Compound I-73 tert-butyl-(S)-3-acrylamido-1-((2S,4R)-4-(7-bromoisoquinolin-1-yloxy)-2-((1R,2S)-1-(cyclopropylsulfonylcarbamoyl)-2-vinylcyclopropylcarbamoyl)pyrrolidin-1-yl)-1- oxopropan-2-ylcarbamate (I-73): The title compound was prepared according to the steps and intermediates as described below:

Intermediate 14-1

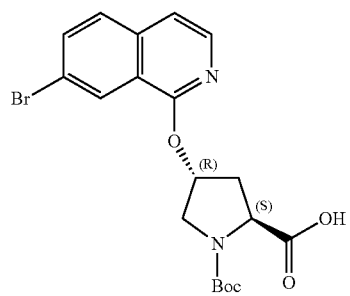

(2S,4R)-4-(7-bromoisoquinolin-1-yloxy)-1-(3,3-dimethylbutanoyl)pyrrolidine-2-carboxylic acid: To a solution of trans 4-hydroxy L-BOC-proline (5 g, 21.6 mmol) in DMSO (60 mL) at RT was added potassium t-butoxide (7.3 g, 65 mmol) in a single portion. The mixture was stirred at RT for 30 min, cooled with an ice-water bath (~17° C.) and 7-bromo-1-chloroisoquinoline (5.24 g, 21.6 mol) added in 2 portions. The reaction was allowed to warm to RT, stirred for 1 h (LC-MS showed completion of reaction, extended reaction time may be needed if larger scale is carried out). The reaction mixture was poured into 400 mL of ice-water containing 45 mmol of HCl. The reaction mixture was extracted with EtOAc, washed with brine, and dried over anhydrous $Na_2SO_4$. The solvent was evaporated to give Intermediate 14-1 (~8 g). $^1$HNMR (DMSO-$d_6$, 400 MHz) δ 8.32 (t, 1H, J=0.8 Hz), 8.06 (d, 1H, J=5.2 Hz), 7.92 (dd, 2H, J=8.0, 1.6 Hz), 7.46 (d, 1H, J=6.0 Hz), 5.67 (br s, 1H), 4.40 (t, 1H, J=8.0 Hz), 3.77 (m, 1H), 3.65 (br d, 1H, J=12 Hz), 3.33 (s, 3H, OMe), 2.65 (m, 1H), 2.35 (m, 1H), 1.36 (s, 9H). LC/Ms: m/z 435 (M−1, ES−).

Intermediate 14-2

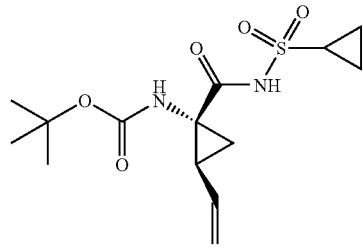

tert-butyl-(1R,2S)-1-(cyclopropylsulfonylcarbamoyl)-2-vinylcyclopropylcarbamate: To a stirring solution of 500 mg (1R,2S)-1-BOC-amino-2-vinylcyclopropane carboxylic acid (2.2 mmol) in 4 mL of DMA (N,N-dimethylacetamide), was added 370 mg of carbonyl diimidazole (CDI, 2.3 mmol). The reaction mixture was stirred at RT for 1 hr, followed by addition of 280 mg of cyclopropylsulfonamide (2.3 mmol), 1 mL of diisopropylethylamine and 350 uL of DBU. The resulting mixture was stirred at 60° C. overnight. The solvent was removed, and normal workup was applied with 100 mL of EtOAc, washed with 10 mL of 1.0 N aqueous HCl, dried over anhydrous $Na_2SO_4$. After concentration, the residue was purified by flash column chromatography giving 580 mg of white solid. $^1$HNMR (CDCl$_3$, 400 MHz) δ 9.7 (br s, 1H), 5.61 (m, 1H), 5.33 (br dd, 2H, J=9.6, 1.2 Hz), 5.18 (dd, J=9.6, 1.2 Hz), 2.92 (m, 1H) 2.14 (q, 1H, J=8.0 Hz), 1.91 dd, 1H, J=8.4, 2.4 Hz), 1.55 (br s, 2H), 1.47 (s, 9H), 1.40 (m, 2H), 1.30 (m, 2H), 0.95-1.15 (m, 2H). LC/MS: m/z 329.1, (M−1, ES−).

Intermediate 14-3

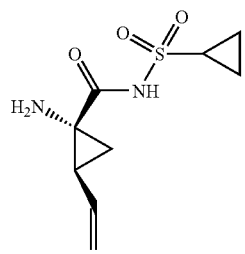

(1R,2S)-1-amino-N-(cyclopropylsulfonyl)-2-vinylcyclopropanecarboxamide: To the 580 mg of Intermediate 14-2 obtained above in 2 mL of anhydrous dichloromethane, was added 9 mL of 4.0 M HCl in dioxane. The mixture was stirred at RT for 30 min, then concentrated under reduced pressure, and dried in vacuum, giving about 532 mg of the salt of Intermediate 14-3.

Intermediate 14-4

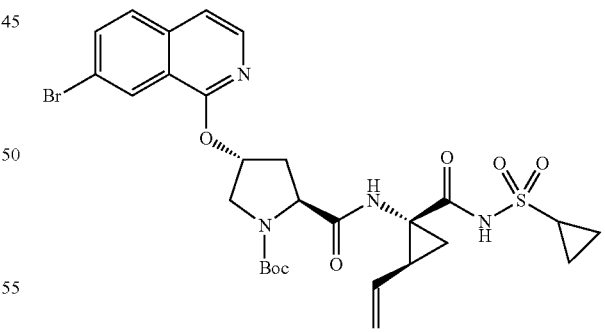

(2S,4R)-tert-butyl-4-(7-bromoisoquinolin-1-yloxy)-2-((1R,2S)-1-(cyclopropylsulfonylcarbamoyl)-2-vinylcyclopropylcarbamoyl)pyrrolidine-1-carboxylate: The title compound was made by coupling Intermediate 14-1 and Intermediate 14-3 using HATU following the coupling reactions described for Intermediate 5 in Example 1. A total of 435 mg Intermediate 14-4 was produced (~67%). LC/MS: m/z 649.6 (ES+), m/z=647.6 (ES−).

Compound I-73

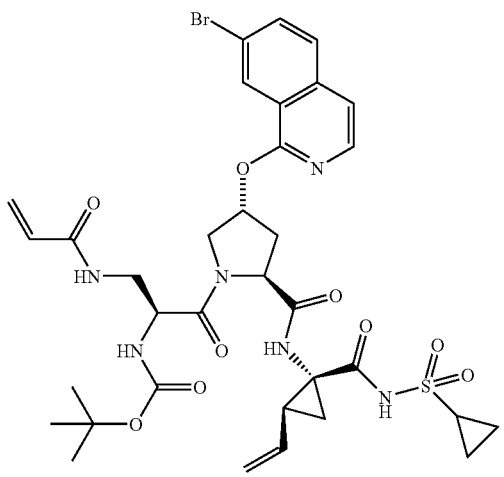

tert-butyl-(S)-3-acrylamido-1-((2S,4R)-4-(7-bromoisoquinolin-1-yloxy)-2-((1R,2S)-1-(cyclopropylsulfonylcarbamoyl)-2-vinylcyclopropylcarbamoyl)pyrrolidin-1-yl)-1-oxopropan-2-ylcarbamate (I-73) was made from Intermediate 14-4 following the procedures described for the synthesis of compound I-3 in Example 1. The compound was purified by flash column chromatography with EtOAc as eluting, giving 93 mg of the title compound. ¹HNMR (CD₃OD, 400 MHz) δ 8.30 (s, 1H), 8.01 (d, 1, J=5.6 Hz), 7.80 (dd, 1H, J=8.8, 2.0 Hz), 7.75 (d, 1H, J=8.8 Hz), 7.33 (d, 1H, J=5.6 Hz), 6.24 (br d, 2H, J=8.0 Hz), 5.92 (br s, 1H), 5.70-5.80 (m, 1H), 5.65 (dd, 1H, J=8.8, 3.2 Hz), 5.34 (d, 1H, J=18.4 Hz), 5.13 (d, 1H, J=12.0 Hz), 4.55-4.63 (m, 1H), 4.35 (m, 1H), 3.58 (dd, 1H, J=13.2, 5.2 Hz), 3.47 (m, 1H), 3.35 (m, 1H), 2.97 (m, 1H, 2.60 (dd, 1H, J=13.2, 6.8 Hz), 2.36 (m, 1H), 2.30 (q, 1H, J=8.4 Hz), 1.89 (dd, 1H, J=7.6, 5.2 Hz), 1.43 (dd, 1H, J=4.8, 8.4 Hz), 1.10-1.30 (m, 13 H). LC/MS: m/z 787.2 (ES-).

In similar fashion using the product of Intermediate 14-4 the following compound was prepared following the procedures described in Example 9:

Compound I-74

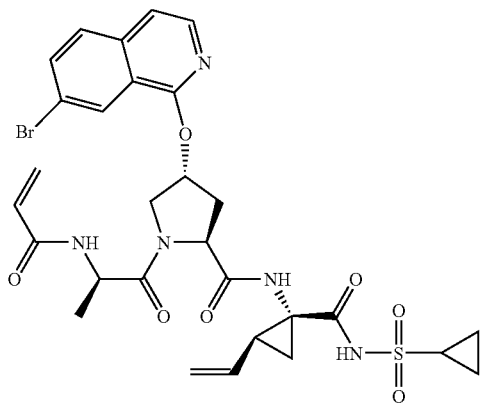

(2S,4R)-1-((R)-2-acrylamidopropanoyl)-4-(7-bromoisoquinolin-1-yloxy)-N-((1R,2S)-1-(cyclopropylsulfonylcarbamoyl)-2-vinylcyclopropyl)pyrrolidine-2-carboxamide: MS m/z: 674.0 (M+H⁺).

Using the product of Intermediate 14-4 and Intermediate 13-1, following the procedure described in Example 13, the following compound was prepared:

Compound I-75

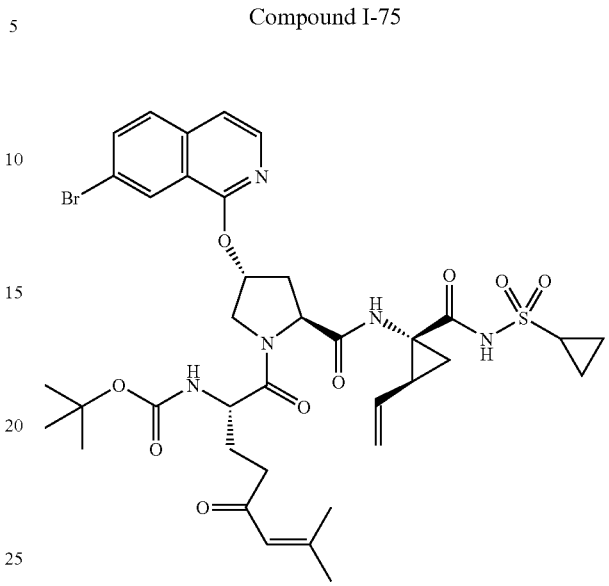

tert-butyl-(S)-1-((2S,4R)-4-(7-bromoisoquinolin-1-yloxy)-2-((1R,2S)-1-(cyclopropylsulfonylcarbamoyl)-2-vinylcyclopropylcarbamoyl)pyrrolidin-1-yl)-7-methyl-1,5-dioxooct-6-en-2-ylcarbamate: ¹HNMR (CD₃OD, 400 MHz) δ 9.38 (s, 1H), 8.31 (d, 1H, J=0.8 Hz), 8.03 (d, 1, J=6.0 Hz), 7.80-7.75 (m, 2H), 7.33 (d, 1H, J=6.0 Hz), 6.20 (t, 1H, J=1.2 Hz), 5.92 (br s, 1H), 5.70-5.80 (m, 1H), 5.34 (dd, 1H, J=17.2, 1.6 Hz), 5.13 (d, 1H, J=11.6 Hz), 4.63 (m, 1H), 4.47 (d, 1H, J=11.6 Hz), 4.33 (t, 1H, J=6.8 Hz), 4.08-4.18 (m, 2H), 2.96 (m, 1H), 2.52-2.60 (m, 2H), 2.24-2.35 (m, 2H), 2.12 (s, 3H, Me), 2.00 (m, 1H), 1.90 (s+m, 4H, Me+1H),1.80 (m, 1H), 1.40-1.43 (m, 1H), 1.25 (m, 1H), 1.17 (s, 9H), 1.05-1.15 (m, 2 H). LC/MS: m/z 814.2 (ES-).

Using the product of Intermediate 14-4 and Intermediate 7-5, following the procedure described in Example 7, the following compound was prepared:

Compound I-84

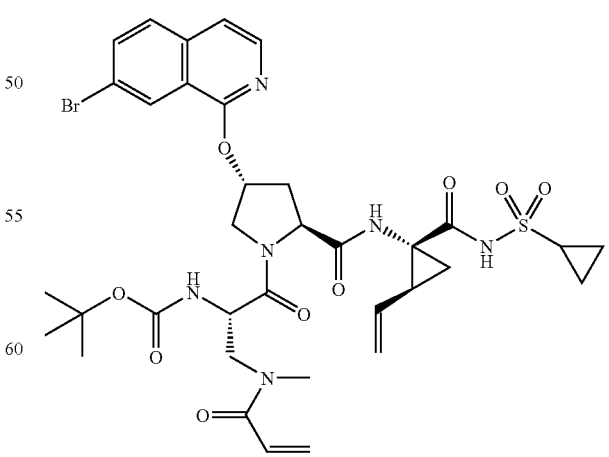

tert-butyl-(S)-1-((2S,4R)-4-(7-bromoisoquinolin-1-yloxy)-2-((1R,2S)-1-(cyclopropylsulfonylcarbamoyl)-2-vinylcyclopropylcarbamoyl)pyrrolidin-1-yl)-3-(N-methylacrylamido)-1-oxopropan-2-ylcarbamate (I-84): LC/MS: m/z: 801.1, 803.2 (ES−).

By starting with 1-chloroisoquinoline in place of 7-bromo-1-chloroisoquinoline in the synthesis of intermediate 14-1, and following the coupling step in Example 14, compound I-97 was made:

Compound I-97

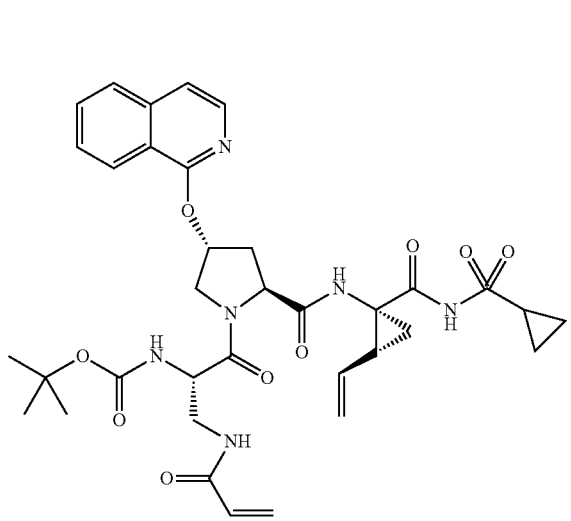

{1-(Acryloylamino-methyl)-2-[2-(1-cyclopropanesulfonylaminocarbonyl-2-vinyl-cyclopropylcarbamoyl)-4-(isoquinolin-1-yloxy)-pyrrolidin-1-yl]-2-oxo-ethyl}-carbamic acid tert-butyl ester (I-97) LC-MS: m/z=711.2 (ES+), 709.2 (ES−).

By starting with 1-chloroisoquinoline in place of 7-bromo-1-chloroisoquinoline in the synthesis of intermediate 14-1, and following the coupling step in Example 7, compound I-98 was made:

Compound I-98

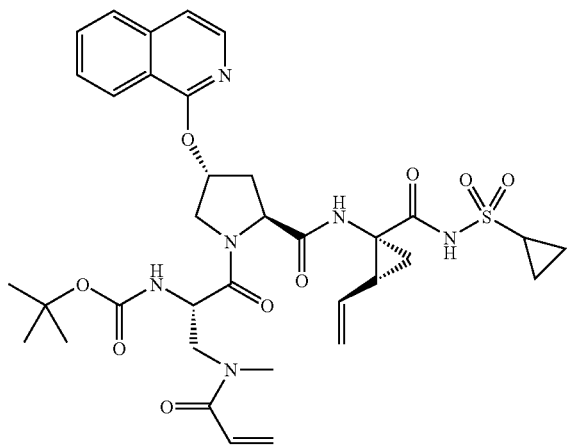

{1-[(Acryloyl-methyl-amino)-methyl]-2-[2-(1-cyclopropanesulfonylaminocarbonyl-2-vinyl-cyclopropylcarbamoyl)-4-(isoquinolin-1-yloxy)-pyrrolidin-1-yl]-2-oxo-ethyl}-carbamic acid tert-butyl ester (I-98) LC-MS: m/z=723.2 (ES−).

By starting with 1-chloroisoquinoline in place of 7-bromo-1-chloroisoquinoline in the synthesis of Intermediate 14-1, and following the coupling step in Example 13, compound I-86 was made:

Compound I-86

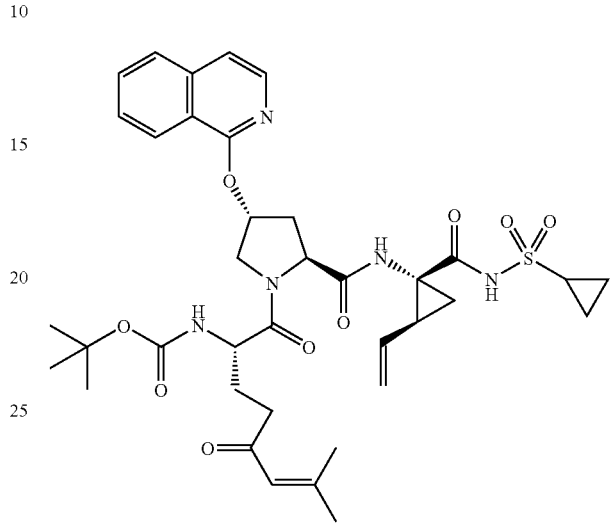

tert-butyl-(S)-1-((2S,4R)-2-((1R,2S)-1-(cyclopropylsulfonylcarbamoyl)-2-vinylcyclopropylcarbamoyl)-4-(isoquinolin-1-yloxy)pyrrolidin-1-yl)-7-methyl-1,5-dioxooct-6-en-2-ylcarbamate (I-86): LC/MS: m/z: 736.3 (ES−).

By coupling Intermediate 14-4 and the appropriate acid prepared similarly as Intermediate 13-1, following the procedure described in Example 13, the following compound can be prepared:

Compound I-90

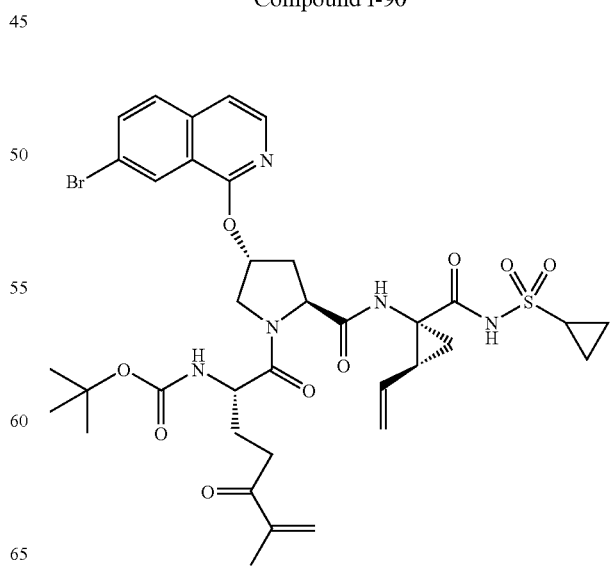

By coupling Intermediate 14-4 and the appropriate acid prepared similarly as Intermediate 13-1, following the procedure described in Example 13, the following compound was prepared:

Compound I-91

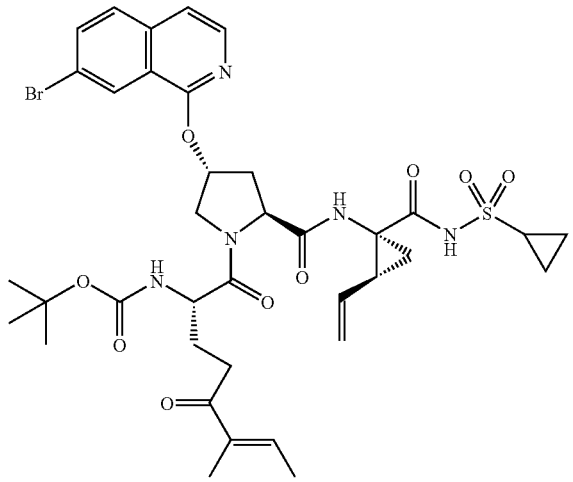

{1-[4-(7-Bromo-isoquinolin-1-yloxy)-2-(1-cyclopropanesulfonylaminocarbonyl-2-vinyl-cyclopropylcarbamoyl)-pyrrolidine-1-carbonyl]-5-methyl-4-oxo-hept-5-enyl}-carbamic acid tert-butyl ester (I-91), LC-MS: m/z 838.0 (ES+, M+Na), 814.2 (ES−).

By starting from the 1-chloro-6-methoxyisoquinoline in the step for the synthesis of Intermediate 14-1 and following the procedures described above, the following compounds can be prepared:

Compound I-93

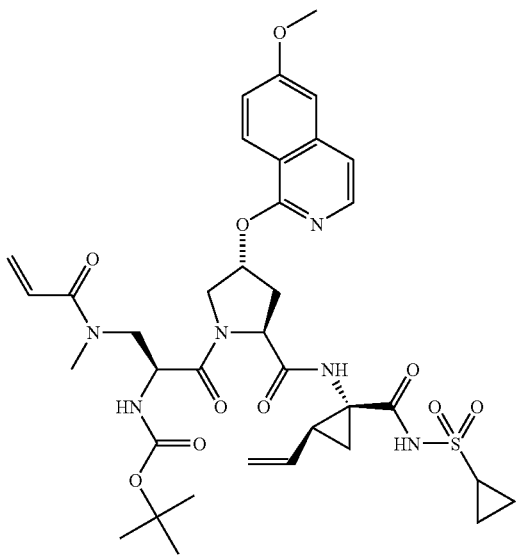

Compound I-94

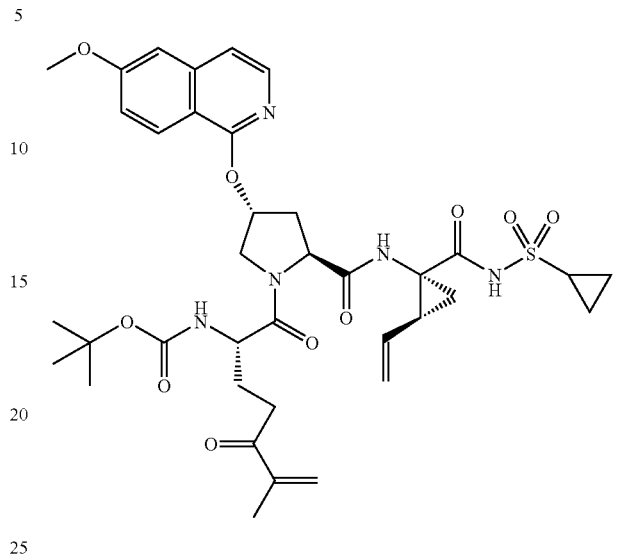

By starting from the 1-chloro-6-methoxyisoquinoline in the step for the synthesis of Intermediate 14-1 and following the procedures described above, the following compounds were prepared:

Compound I-92

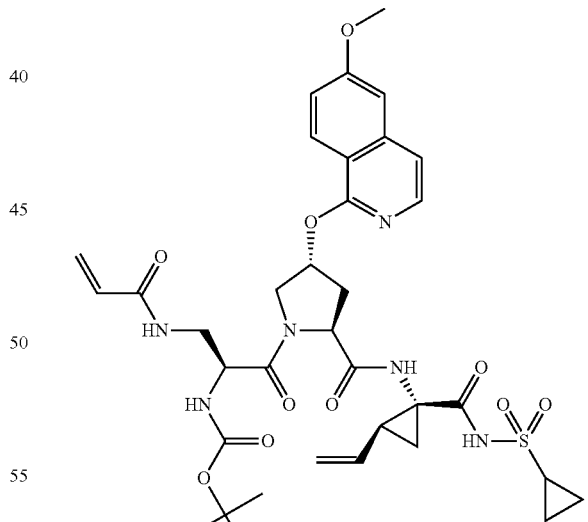

{1-(Acryloylamino-methyl)-2-[2-(1-cyclopropanesulfonylaminocarbonyl-2-vinyl-cyclopropylcarbamoyl)-4-(6-methoxy-isoquinolin-1-yloxy)-pyrrolidin-1-yl]-2-oxo-ethyl}-carbamic acid tert-butyl ester (I-92), LC-MS: m/z=741.2 (ES+).

Compound I-95

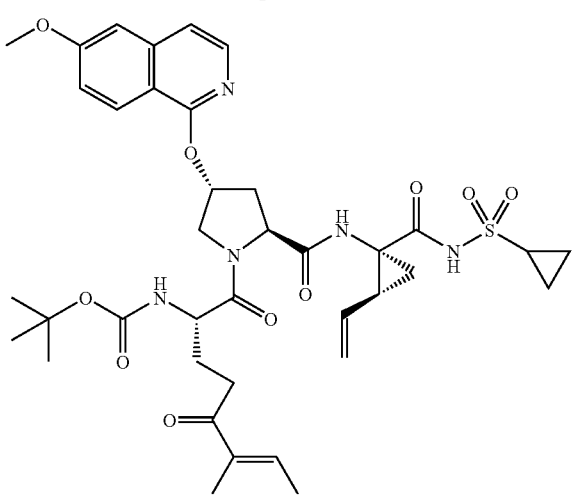

{1-[2-(1-Cyclopropanesulfonylaminocarbonyl-2-vinyl-cyclopropylcarbamoyl)-4-(6-methoxy-isoquinolin-1-yloxy)-pyrrolidine-1-carbonyl]-5-methyl-4-oxo-hept-5-enyl}-carbamic acid tert-butyl ester (I-95), LC-MS: m/z=768.2 (ES+)

Compound I-96

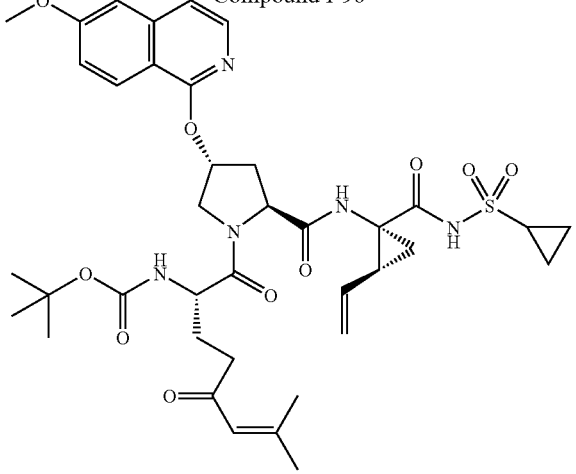

{1-[2-(1-Cyclopropanesulfonylaminocarbonyl-2-vinyl-cyclopropylcarbamoyl)-4-(6-methoxy-isoquinolin-1-yloxy)-pyrrolidine-1-carbonyl]-6-methyl-4-oxo-hept-5-enyl}-carbamic acid tert-butyl ester (I-96), LC-MS: m/z=768.2 (ES+).

Compound I-99

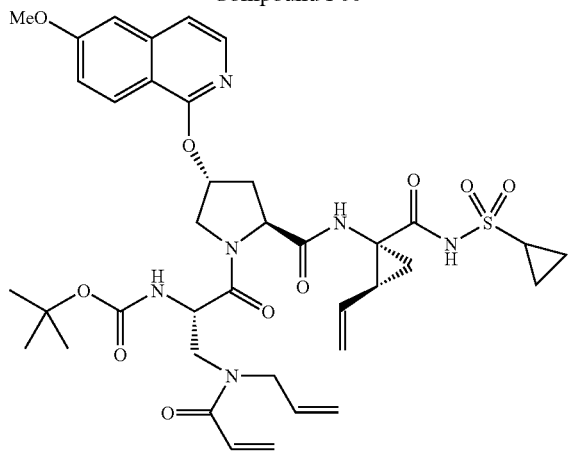

{1-[2-(1-Cyclopropanesulfonylaminocarbonyl-2-vinyl-cyclopropylcarbamoyl)-4-(6-methoxy-isoquinolin-1-

{1-[(Acryloyl-allyl-amino)-methyl]-2-[2-(1-cyclopropanesulfonylaminocarbonyl-2-vinyl-cyclopropylcarbamoyl)-4-(6-methoxy-isoquinolin-1-yloxy)-pyrrolidin-1-yl]-2-oxo-ethyl}-carbamic acid tert-butyl ester (I-99), LC-MS: m/z=779.3 (ES−)

Compound I-100

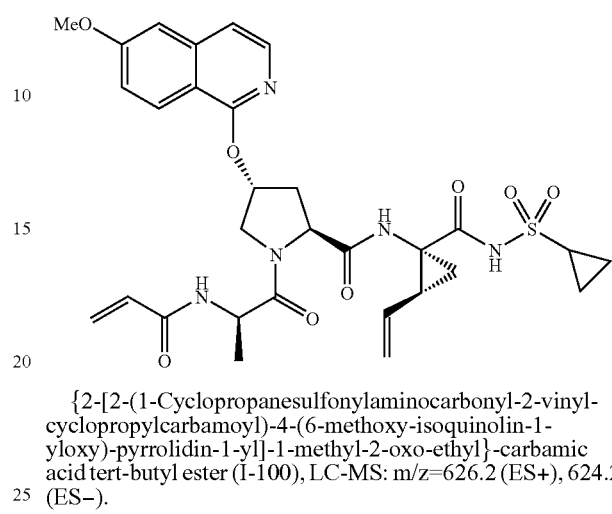

{2-[2-(1-Cyclopropanesulfonylaminocarbonyl-2-vinyl-cyclopropylcarbamoyl)-4-(6-methoxy-isoquinolin-1-yloxy)-pyrrolidin-1-yl]-1-methyl-2-oxo-ethyl}-carbamic acid tert-butyl ester (I-100), LC-MS: m/z=626.2 (ES+), 624.2 (ES−).

Compound I$^R$-100

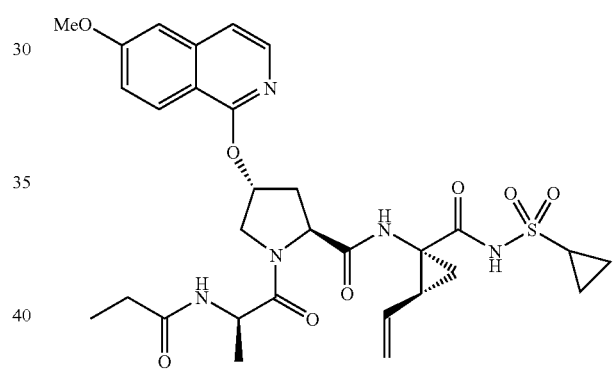

(2S,4R)—N-((1R,2S)-1-(cyclopropylsulfonylcarbamoyl)-2-vinylcyclopropyl)-4-(6-methoxyisoquinolin-1-yloxy)-1-((R)-2-propionamidopropanoyl)pyrrolidine-2-carboxamide (I$^R$-100), LC-MS: m/z=628.2 (ES+), 626.2 (ES−).

Compound I-101

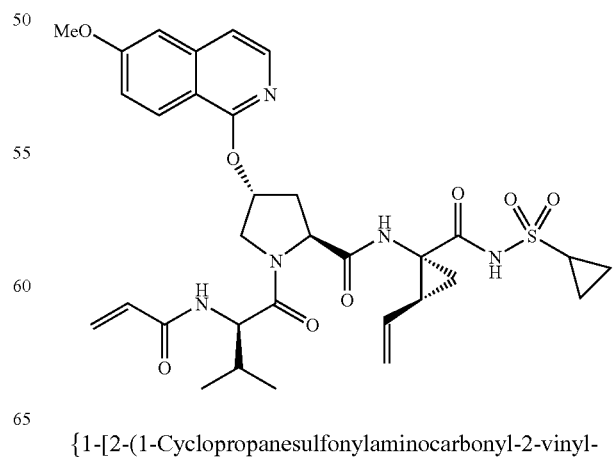

{1-[2-(1-Cyclopropanesulfonylaminocarbonyl-2-vinyl-cyclopropylcarbamoyl)-4-(6-methoxy-isoquinolin-1- yloxy)-pyrrolidine-1-carbonyl]-2-methyl-propyl}-carbamic acid tert-butyl ester (I-101), LC-MS: m/z=654.2 (ES+), 652.2 (ES−).

I-105

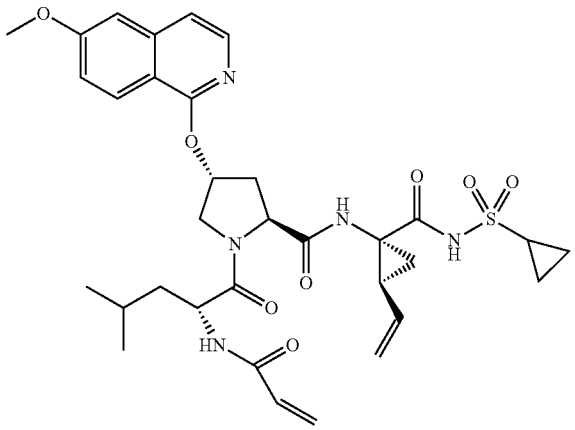

(2S,4R)-1-((R)-2-acrylamido-4-methylpentanoyl)-N-((1R,2S)-1-(cyclopropylsulfonylcarbamoyl)-2-vinylcyclopropyl)-4-(6-methoxyisoquinolin-1-yloxy)pyrrolidine-2-carboxamide, MS m/z: 668.2 (M+H$^+$).

I-106

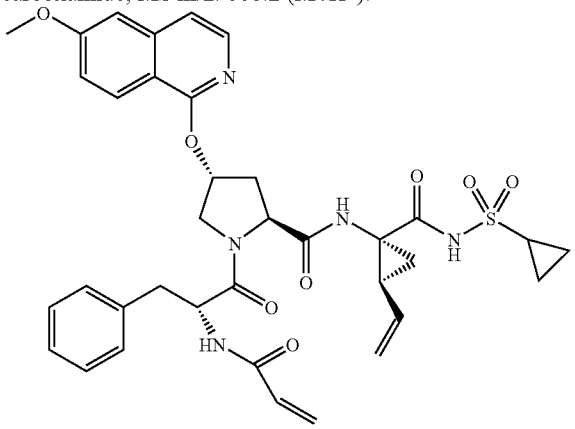

(2S,4R)-1-((R)-2-acrylamido-3-phenylpropanoyl)-N-((1R,2S)-1-(cyclopropylsulfonylcarbamoyl)-2-vinylcyclopropyl)-4-(6-methoxyisoquinolin-1-yloxy)pyrrolidine-2-carboxamide, MS m/z: 702.2 (M+H$^+$).

I-130

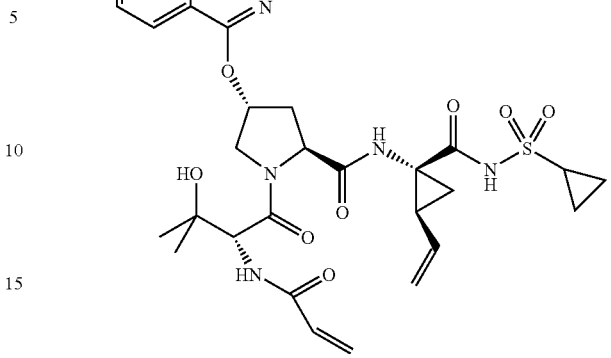

(2S,4R)-1-((R)-2-acrylamido-3-hydroxy-3-methylbutanoyl)-N-((1R,2S)-1-(cyclopropylsulfonylcarbamoyl)-2-vinylcyclopropyl)-4-(6-methoxyisoquinolin-1-yloxy)pyrrolidine-2-carboxamide, MS m/z: 670.2 (M+H$^+$).

I-131

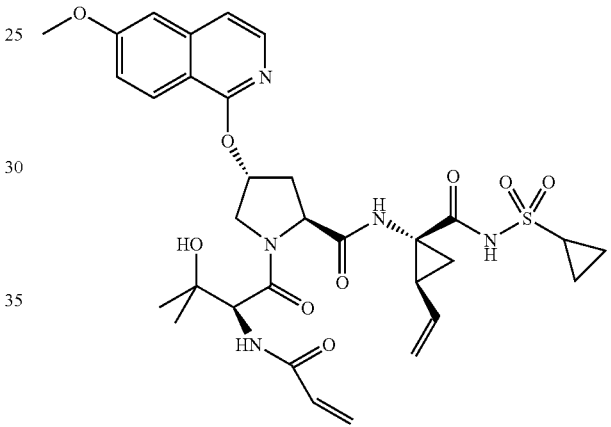

(2S,4R)-1-((S)-2-acrylamido-3-hydroxy-3-methylbutanoyl)-N-((1R,2S)-1-(cyclopropylsulfonylcarbamoyl)-2-vinylcyclopropyl)-4-(6-methoxyisoquinolin-1-yloxy)pyrrolidine-2-carboxamide, MS m/z: 670.2 (M+H$^+$).

I-129

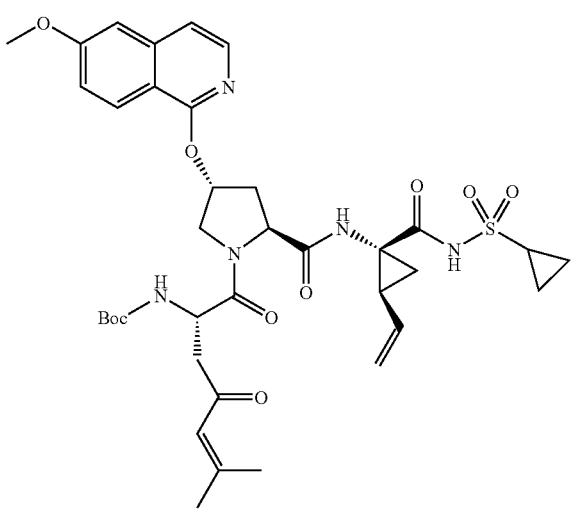

MS: m/e=754.2 (M+1)

I-132

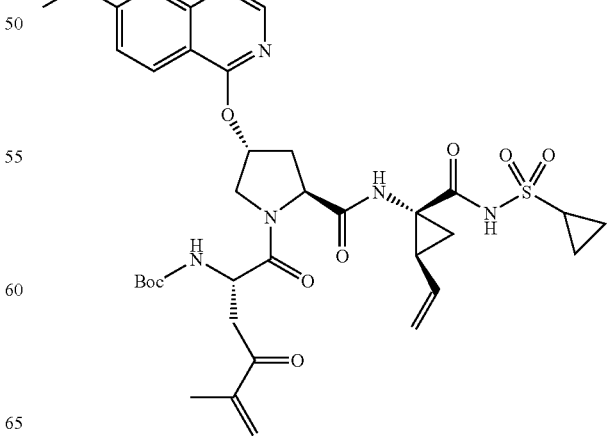

tert-butyl(S)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-5-methyl-1,4-dioxohex-5-en-2-ylcarbamate, MS m/z: 740.3 (M+H⁺).

I-133

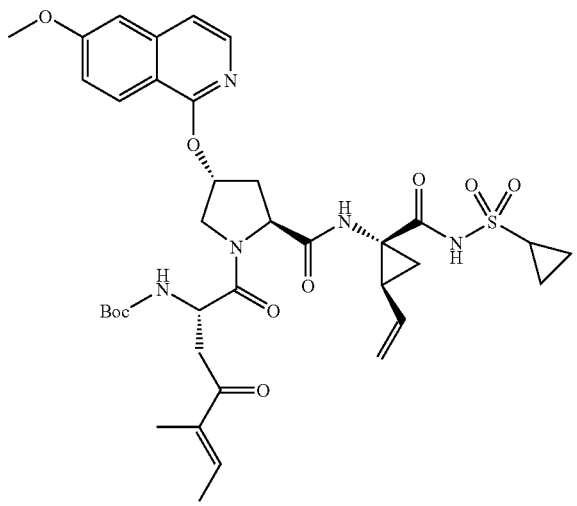

tert-butyl(S,E)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-5-methyl-1,4-dioxohept-5-en-2-ylcarbamate, MS m/z: 754.2 (M+H⁺).

I-134

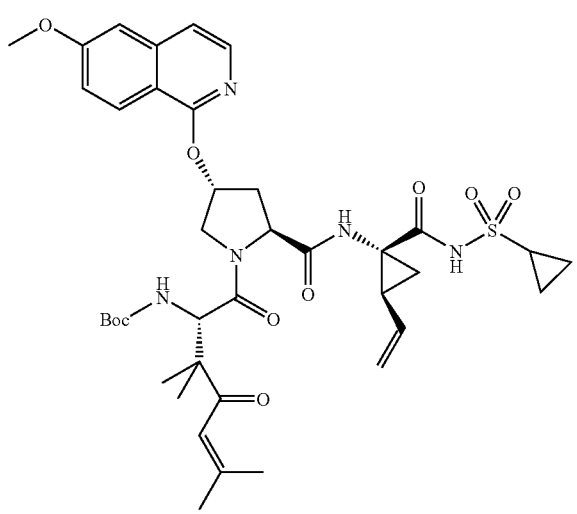

tert-butyl(S)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-3,3,6-trimethyl-1,4-dioxohept-5-en-2-ylcarbamate, MS m/z: 782.3 (M+H⁺).

I-135

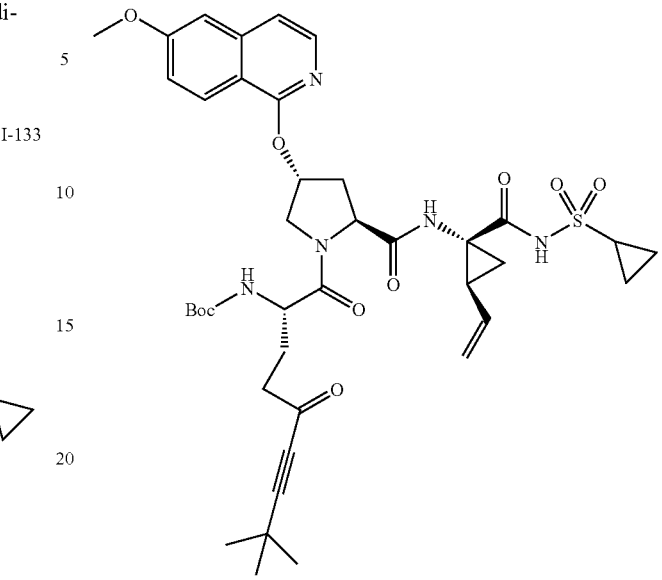

tert-butyl(S)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-8,8-dimethyl-1,5-dioxonon-6-yn-2-ylcarbamate, MS m/z: 794.3 (M+H⁺).

I-136

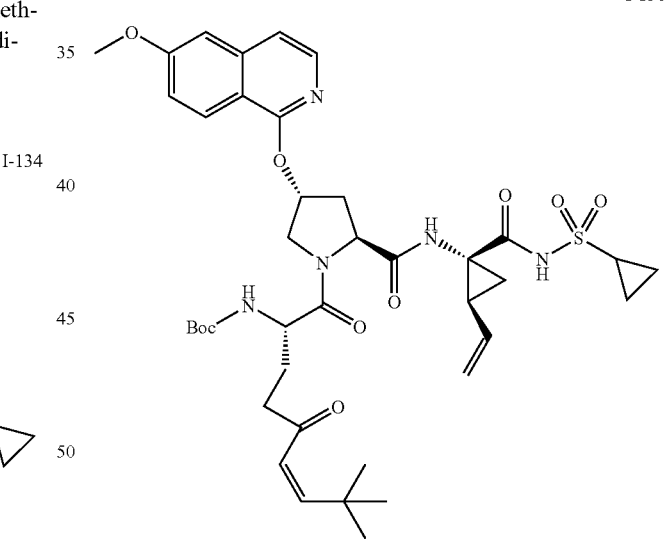

tert-butyl(S,Z)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-8,8-dimethyl-1,5-dioxonon-6-en-2-ylcarbamate ¹HNMR (CD₃OD, 400 MHz) δ 8.09 (d, 1H, J=8.8 Hz), 7.87 (d, 1H, J=6.0 Hz), 7.23 (d, 1H, J=6.0 Hz), 7.16 (d, 1H, J=1.8 Hz), 7.10 (d, 1H, J=9.2 Hz), 6.02 (d, 1H, J=13.2 Hz), 5.84 (br, 2H), 5.74 (m, 1H), 5.30 (d, 1H, J=17.0 Hz), 5.11 (d, 1H, J=11.5 Hz), 4.55 (m, 1H), 4.39 (br, 2H), 4.08 (m, 1H), 3.90 (s, 3H), 2.95 (m, 1H), 2.60 (m, 2H), 2.25 (m, 2H), 2.04-1.90 (m, 2H), 1.41 (m, 2H), 1.26 (s, 9H), 1.12 (s, 9H), 1.08 (m, 2H). MS m/z: 796.2 (M+H⁺).

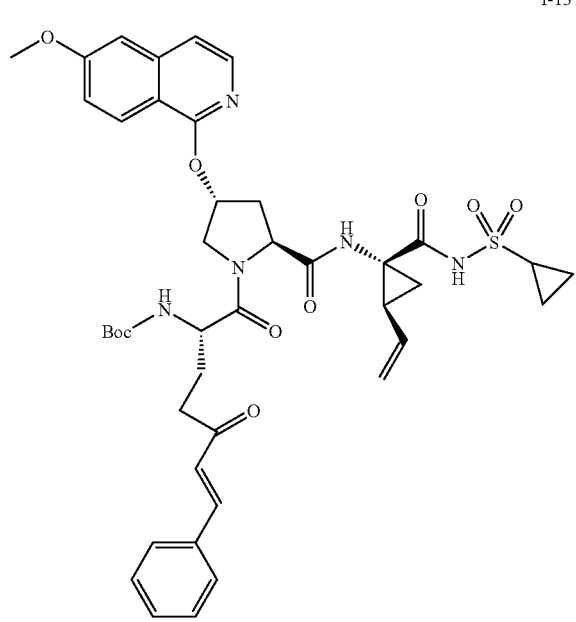

I-137 tert-butyl(S,E)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-7-phenylhept-6-en-2-ylcarbamate, MS m/z: 816.3 (M+H⁻).

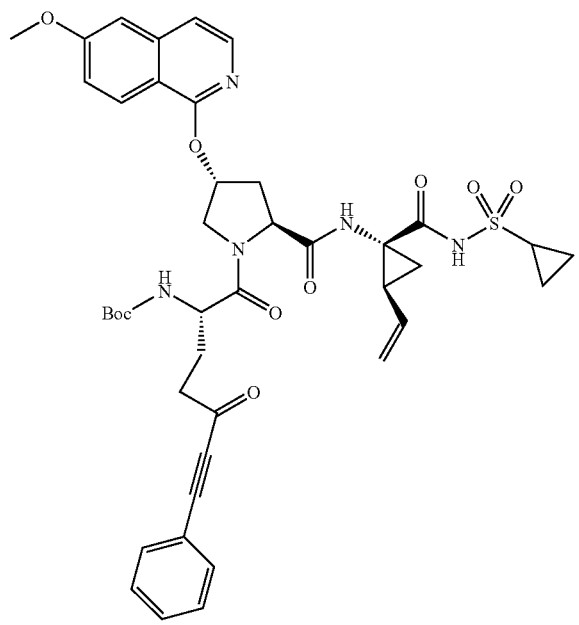

I-138 tert-butyl(S)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxo-7-phenylhept-6-yn-2-ylcarbamate, MS m/z: 814.2 (M+H⁺).

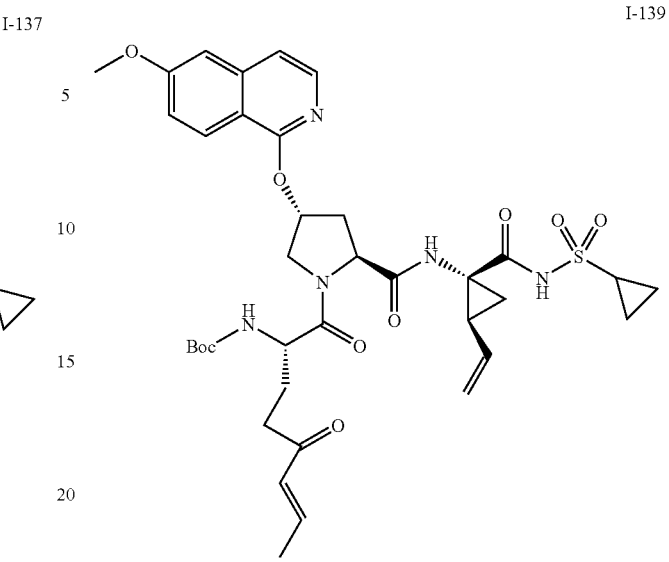

I-139 tert-butyl(S,E)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxooct-6-en-2-ylcarbamate, MS m/z: 752.2 (ES−).

In similar manner, the biotinylated compounds were made starting from I-92 followed by de-Boc, and coupling reactions as for I-31.

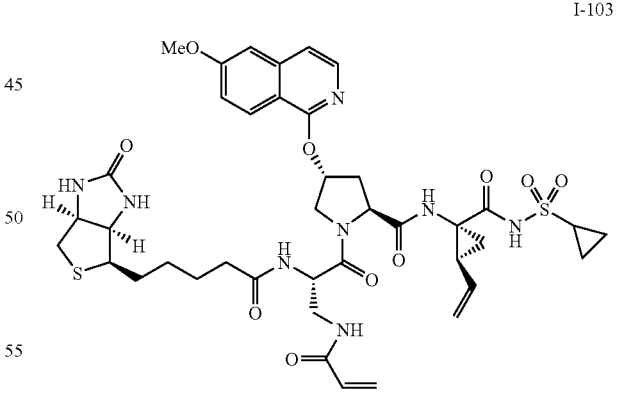

I-103

1-{3-Acryloylamino-2-[5-(2-oxo-hexahydro-thieno[3,4-d]imidazol-6-yl)-pentanoylamino]-propionyl}-4-(6-methoxy-isoquinolin-1-yloxy)-pyrrolidine-2-carboxylic acid (1-cyclopropanesulfonylaminocarbonyl-2-vinyl-cyclopropyl)-amide I-103, LC-MS: m/z=867.3 (ES+), 865.2 (ES−).

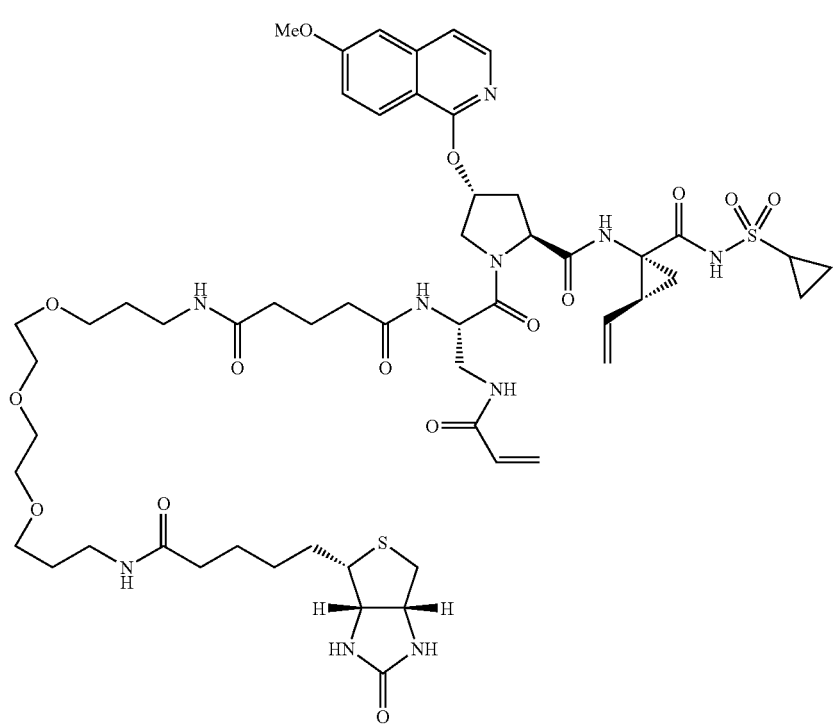

I-104, LC-MS: m/z=1183.4 (ES+), 1181.4 (ES−).

Starting from the (2S,4R)-1-(tert-butoxycarbonyl)-4-(5-(4-methoxyphenyl)-2H-tetrazol-2-yl)pyrrolidine-2-carboxylic acid, following the procedures described in Example 14, the following compound was made:

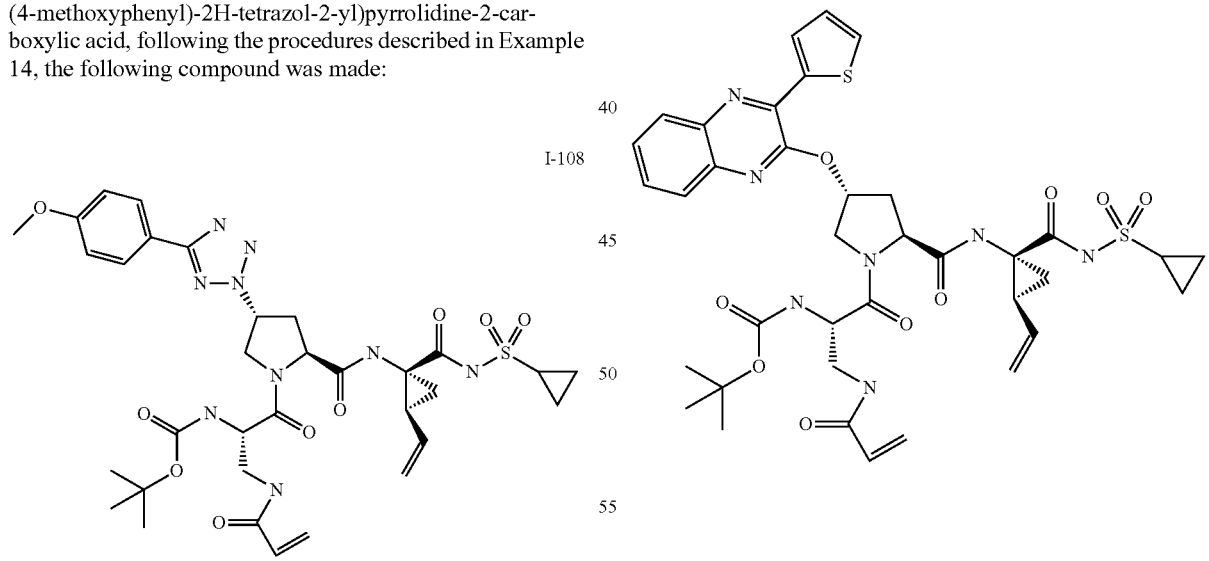

tert-butyl-(S)-3-acrylamido-1-((2S,4R)-2-((1R,2S)-1-(cyclopropylsulfonylcarbamoyl)-2-vinylcyclopropylcarbamoyl)-4-(5-(4-methoxyphenyl)-2H-tetrazol-2-yl)pyrrolidin-1-yl)-1-oxopropan-2-ylcarbamate, MS m/z: 742.1 (M+H$^+$).

Starting from the (2S,4R)-1-(tert-butoxycarbonyl)-4-(3-(thiophen-2-yl)quinoxalin-2-yloxy)pyrrolidine-2-carboxylic acid, following the procedures described in Example 14, the following compound was made:

tert-butyl-(S)-3-acrylamido-1-((2S,4R)-2-((1R,2S)-1-(cyclopropylsulfonylcarbamoyl)-2-vinylcyclopropylcarbamoyl)-4-(3-(thiophen-2-yl)quinoxalin-2-yloxy)pyrrolidin-1-yl)-1-oxopropan-2-ylcarbamate, MS m/z: 794.2 (M+H$^+$).

Starting from the (2S,4R)-1-(tert-butoxycarbonyl)-4-(5-(4-methoxyphenyl)-2H-tetrazol-2-yl)pyrrolidine-2-carboxylic acid, following the procedures described in Example 14 and Example 13, the following compound was made:

I-107

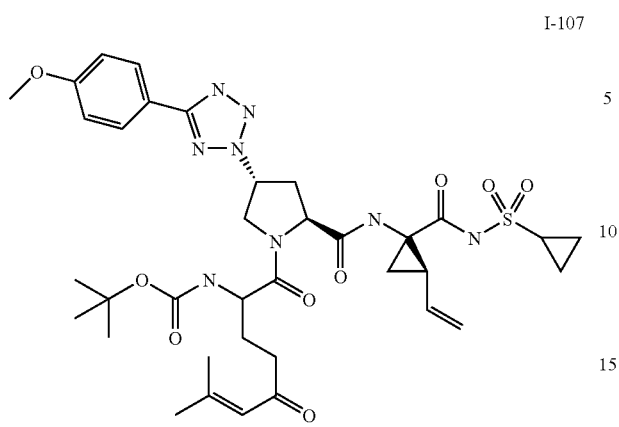

tert-butyl-(S)-1-((2S,4R)-2-((1R,2S)-1-(cyclopropylsulfonylcarbamoyl)-2-vinylcyclopropylcarbamoyl)-4-(5-(4-methoxyphenyl)-2H-tetrazol-2-yl)pyrrolidin-1-yl)-7-methyl-1,5-dioxooct-6-en-2-ylcarbamate, MS m/z: 769.1 (M+H$^+$).

Starting from the (2S,4R)-1-(tert-butoxycarbonyl)-4-(3-(thiophen-2-yl)quinoxalin-2-yloxy)pyrrolidine-2-carboxylic acid, following the procedures described in Example 14 and Example 13, the following compound was made:

I-110

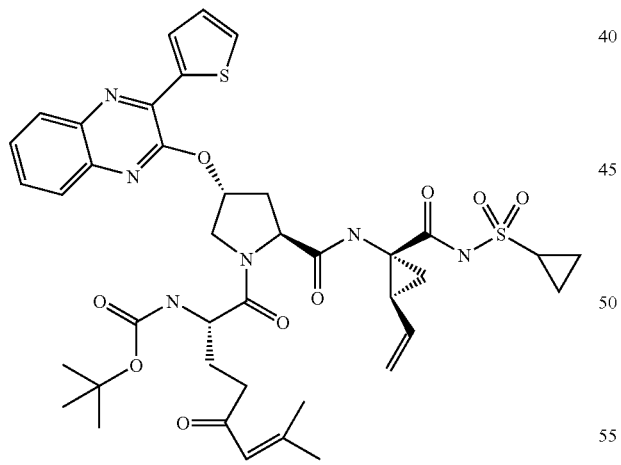

tert-butyl-(S)-1-((2S,4R)-2-((1R,2S)-1-(cyclopropylsulfonylcarbamoyl)-2-vinylcyclopropylcarbamoyl)-4-(3-(thiophen-2-yl)quinoxalin-2-yloxy)pyrrolidin-1-yl)-7-methyl-1,5-dioxooct-6-en-2-ylcarbamate, MS m/z: 821.2 (M+H$^+$).

I-114

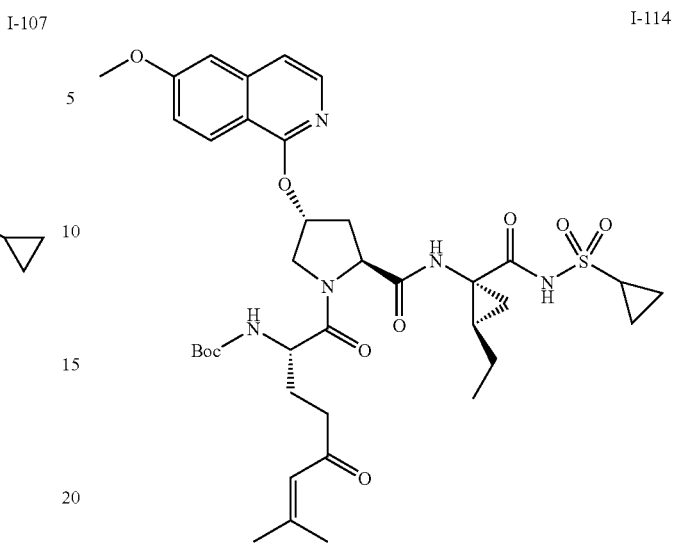

tert-butyl-(S)-1-((2S,4R)-2-((1R,2R)-1-(cyclopropylsulfonylcarbamoyl)-2-ethylcyclopropylcarbamoyl)-4-(6-methoxyisoquinolin-1-yloxy)pyrrolidin-1-yl)-7-methyl-1,5-dioxooct-6-en-2-ylcarbamate, MS m/z: 770.3 M+H$^+$). In similar fashion, the title compound was prepared following the procedures used for compound I-96 in Example 14 by starting with the saturated intermediate 14-2. Saturated Intermediate 14-2 was prepared via a palladium catalyzed hydrogenation reaction of Intermediate 14-2.

In similar manner, the following compound was prepared:

I-140

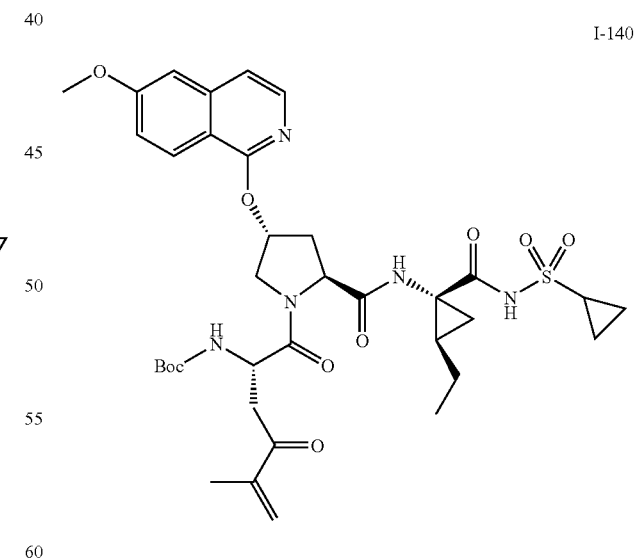

tert-butyl (S)-1-((2S,4R)-2-((1R,2R)-1-(cyclopropylsulfonylcarbamoyl)-2-ethylcyclopropylcarbamoyl)-4-(6-methoxyisoquinolin-1-yloxy)pyrrolidin-1-yl)-5-methyl-1,4-dioxohex-5-en-2-ylcarbamate, MS m/z: 742.2 M+H$^+$).

Example 15

Compound I-76

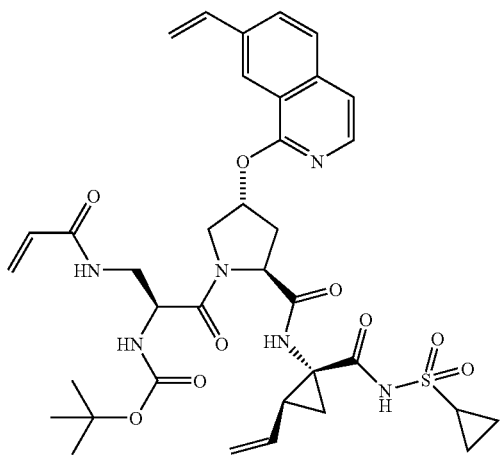

(S)-tert-butyl-3-(acrylamidomethyl)-4-((2S,4R)-2-((1R, 2S)-1-(cyclopropylsulfonylcarbamoyl)-2-vinylcyclopropylcarbamoyl)-4-(7-vinylisoquinolin-1-yloxy)pyrrolidin-1-yl)-4-oxobutanoate (I-76): The title compound was prepared according to the steps and intermediates as described below:

Intermediate 15-1

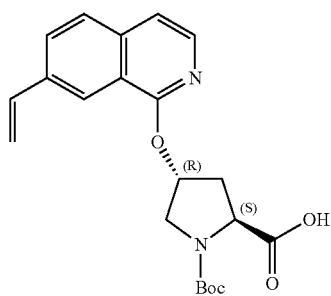

(2S,4R)-1-(tert-butoxycarbonyl)-4-(7-vinylisoquinolin-1-yloxy)pyrrolidine-2-carboxylic acid: Intermediate 15-1 was prepared by treating Intermediate 14-1 with vinyl boronic acid under a Suzuki reaction condition.

Compound I-76

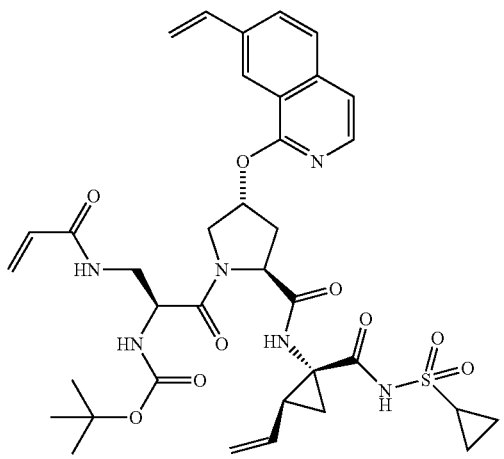

(S)-tert-butyl-3-(acrylamidomethyl)-4-((2S,4R)-2-((1R, 2S)-1-(cyclopropylsulfonylcarbamoyl)-2-vinylcyclopropylcarbamoyl)-4-(7-vinylisoquinolin-1-yloxy)pyrrolidin-1-yl)-4-oxobutanoate (I-76): The title compound was prepared from Intermediate 15-1 according to the procedures described in Example 14. LC/MS: m/z 762.2 (M-1, ES−).

The following compounds were made similarly by following Example 15, using 2-thiophene boronic acid in place of the vinyl boronic acid:

Compound I-87

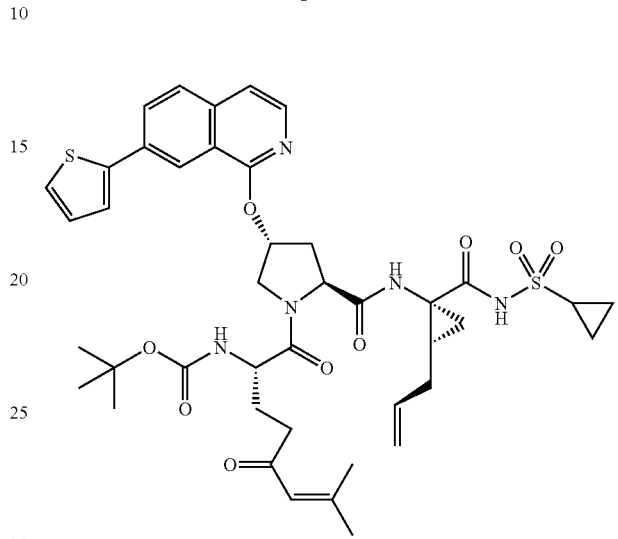

tert-butyl-(S)-1-((2S,4R)-2-((1R,2S)-1-(cyclopropylsulfonylcarbamoyl)-2-vinylcyclopropylcarbamoyl)-4-(7-(thiophen-2-yl)isoquinolin-1-yloxy)pyrrolidin-1-yl)-7-methyl-1,5-dioxooct-6-en-2-ylcarbamate. LC/MS: m/z 818.2 (ES−).

Compound I-88

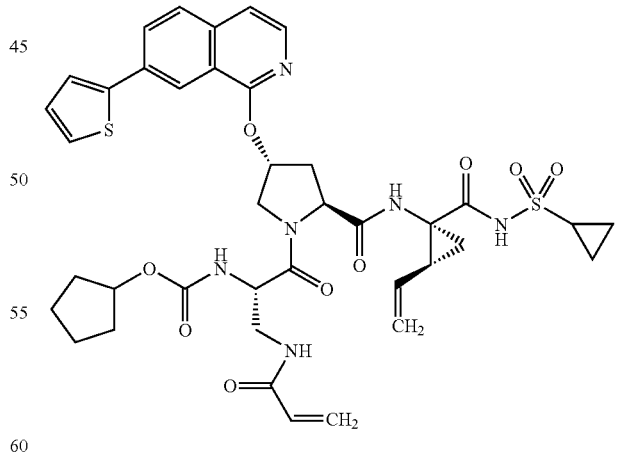

Cyclopentyl-(S)-3-acrylamido-1-((2S,4R)-2-((1R,2S)-1-(cyclopropylsulfonylcarbamoyl)-2-vinylcyclopropylcarbamoyl)-4-(7-(thiophen-2-yl)isoquinolin-1-yloxy)pyrrolidin-1-yl)-1-oxopropan-2-ylcarbamate. LC/MS: m/z 805.2 (ES+).

Example 16

Compound I-77

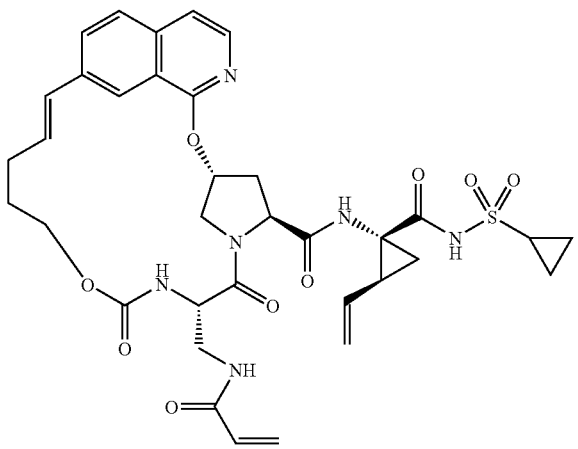

(1R,2S)-N-1-cyclopropylsulfonylcarboxamido-2-vinyl-cyclopropyl (2R,4S,7S,14E)-7-acrylamidomethyl-2H-16,18-etheno-2,5-methano-11H-pyrido[2,3-k][1,10,3,6]dioxadiazacyclononadecine-4-ylcarboxamide (I-77): The title compound was prepared according to the steps and intermediates as described below:

Intermediate 16-1

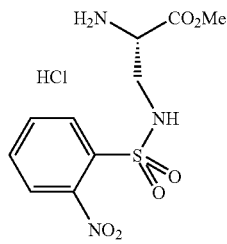

Methyl (S)-2-amino-3-(2-nitrophenylsulfonamido)propanoate hydrochloride: To 1.2 g of Intermediate 7-3 (Example 7, 3.08 mmol) in 30 mL of MeOH at RT, was bubbled in hydrochloride gas until it was saturated in MeOH. The resulting mixture was stirred overnight, and concentrated to dryness under reduced pressure, giving the Me-ester HCl salt of Intermediate 16-1 in quantitive yield. $^1$HNMR (CD$_3$OD, 400 MHz) δ 8.13 (m, 1H), 7.89 (m, 1H), 7.76 (m, 2H), 4.23 (t, 1H, J=4.4 Hz), 3.85 (s, 3H, OMe), 3.56 (t, 2H, J=5.6 Hz).

Intermediate 16-2

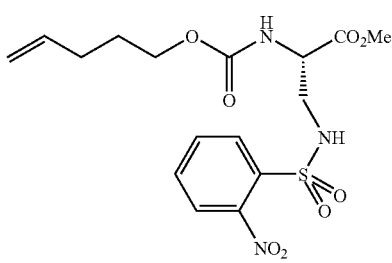

Methyl-(S)-2-(4-pentenyloxycarbonylamino)-3-(2-nitrophenylsulfonamido)propanoate: To the Intermediate 16-1 (obtained above) suspension between 20 mL of saturated NaHCO$_3$ aqueous solution and 20 mL of THF, was added 6.4 mL of 0.5 M pent-4-enyl carbonochloridate toluene solution. The resulting mixture was stirred at RT for 3 hr, then acidified to pH~3, extracted with EtOAc (40 mL×2). The combined organic layer was dried over anhydrous sodium sulfate. After concentration, the residue was subject to flash column chromatography on silica gel, giving yellowish oil 890 mg. $^1$HNMR (CDCl$_3$, 400 MHz) δ 8.13 (m, 1H), 7.89 (m, 1H), 7.76 (m, 2H), 5.81 (m, 1H), 5.76 (t, 1H, J=6.4 Hz), 5.49 (br d, 1H), 5.05 (dq, 1H, J=2.0, 16.8 Hz), 5.00 (dq, 1H, J=1.5, 10.4 Hz), 4.43 (br q, 1H), 4.07 (t, 2H, J=7.2 Hz), 3.80 (s, 3H), 3.55 (t, 2H, J=4.8 Hz), 2.13 (q, 2H, J=7.2 Hz), 1.72 (m, 2H).

Intermediate 16-3

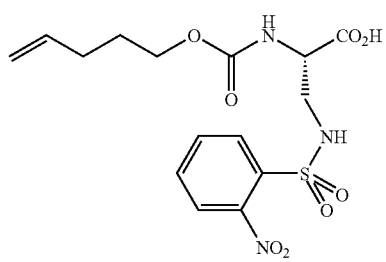

(S)-2-(4-pentenyloxycarbonylamino)-3-(2-nitrophenylsulfonamido)propanoic acid: To a mixture of 890 mg of Intermediate 16-2 in a mixed solvent (THF/MeOH 10 mL/10 mL), was added 900 mg of lithium hydroxide monohydrate and 10 mL of water. The reaction mixture was stirred at rt for 2 hr, then acidified to pH ~5. The reaction mixture was extracted with EtOAc (60 mL×2), dried over anhydrous sodium sulfate. After concentration, 860 mg of slightly yellow solid was obtained. $^1$HNMR (CDCl$_3$, 400 MHz) δ 8.13 (m, 1H), 7.88 (m, 1H), 7.76 (m, 2H), 5.93 (br s, 1H), 5.81 (m, 1H), 5.67 (br d, 1H, J=6.0 Hz), 5.05 (dq, 1H, J=2.0, 18.4 Hz), 5.00 (dq, 1H, J=1.6, 10.0 Hz), 4.43 (br q, 1H), 4.11 (m, 2H), 3.58 (t, 2H, J=5.2 Hz), 2.11 (q, 2H, J=7.2 Hz), 1.75 (m, 2H).

Intermediate 16-4

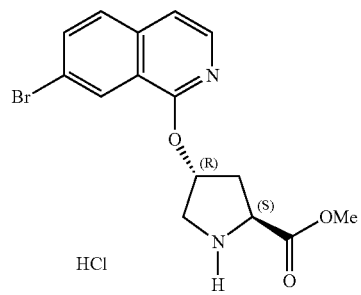

(2S,4R)-methyl-4-(7-bromoisoquinolin-1-yloxy)pyrrolidine-2-carboxylate hydrochloride: The Intermediate 15-1 from Example 15 (~15 mmol) was dissolved in methanol and 20 mL of 4.0 M HCl in dioxane, the stirring was continued overnight (LC-MS showed ~70% conversion). Additional 20 mL of 4.0 M HCl in dioxane was added, and the reaction was continued for another 18 hr. The reaction mixture was concentrated; 4.0 g pale white solid was obtained after filtration (~70%). $^1$HNMR (CD$_3$OD, 400 MHz) δ 8.51 (s, 1H), 8.03 (d, 1H, J=5.6 Hz), 7.86 (dd, 1H, J=8.0, 1.6 Hz), 7.80 (d, 1H, J=8.0 Hz), 7.41 (d, 1H, J=6.0 Hz), 5.96 (t, 1H, J=4.4 Hz), 4.86 (dd, 1H, J=8.4, 10.4 Hz), 3.88 (s, 3H), 3.86 (dd, 1H, J=13.2, 4.8 Hz), 3.78 (d, 1H, J=13.2 Hz), 2.91 (qt, 1H, J=8.0, 1.2 Hz), 2.64 (dq, 1H, J=4.8, 14.8 Hz).

LC/MS: m/z 351.0, 353.0 (ES+)

Intermediate 16-5

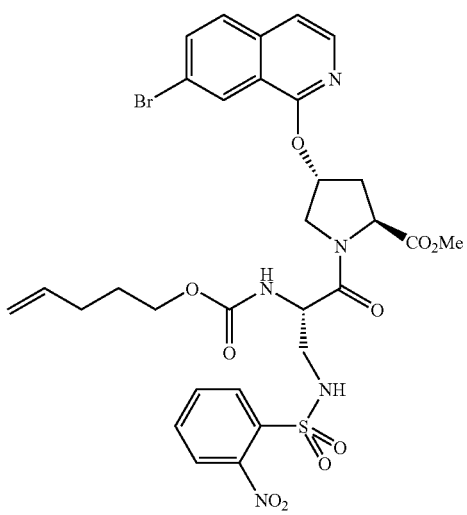

(2S,4R)-methyl-4-(7-bromoisoquinolin-1-yloxy)-1-((S)-3-(2-nitrophenylsulfonamido)-2-((pent-4-enyloxy)carbonylamino)propanoyl)pyrrolidine-2-carboxylate: To a mixture of 812 mg of Intermediate 16-4 (2.1 mmol) and 860 mg of Intermediate 16-3 (2.14 mmol) in 30 mL of acetonitrile, was added 2 mL of N,N-diisopropylethyl amine followed by 1.0 g of HATU (2.5 mmol). The reaction mixture was stirred at rt for 2 hr, then subject to normal workup procedure and the product was purified by flash column chromatography with eluent (heptane/EtOAc v/v 1:2), giving 1.18 g Intermediate 16-5 (77%). LC/MS: m/z 733.9, 735.0 (ES+); 732.0, 734.0 (ES−)

Intermediate 16-6

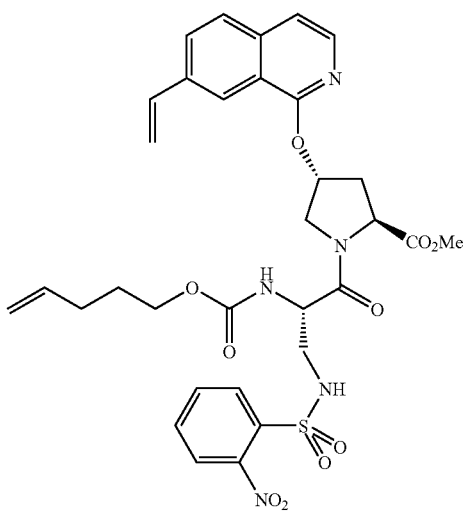

(2S,4R)-methyl-1-((S)-3-(2-nitrophenylsulfonamido)-2-((pent-4-enyloxy)carbonylamino)propanoyl)-4-(7-vinylisoquinolin-1-yloxy)pyrrolidine-2-carboxylate: The toluene solution of 1.10 g Intermediate 16-5 (1.5 mmol) was purged with nitrogen stream for 30 min before 660 μL of vinyl tributyltin (2.25 mmol) and 200 mg of palladium tetrakis (triphenylphosphene) were added in. The resulting mixture was heated at 100° C. for 48 hr, then cooled down to RT. The reaction mixture was filtered through a celite short column, and washed with 50 mL of EtOAc. The combined organic layer was concentrated, and the residue was subject to flash column chromatography on silica gel with eluent (heptane/ EtOAc v/v 1:2 to 1:3) giving desired product about 520 mg. LC/MS: m/z 682.2 (ES+); 680.0 (ES−).

Intermediate 16-7

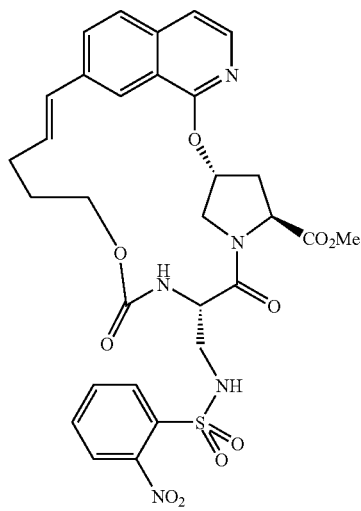

Methyl-(2R,4S,7S,14E)-7-(2-nitrobenzenesulfonyl)aminomethyl-2H-16,18-etheno-2,5-methano-11H-pyrido [2,3-k][1,10,3,6]dioxadiazacyclononadecine-4-ylcarboxylate:
The solution of 350 mg of Intermediate 16-6 in 75 mL of anhydrous dichloroethane was purged with nitrogen stream for 30 min before 75 mg of Grubbs catalyst was added. The resulting mixture was heated at 55° C. overnight, and additional 50 mg of Grubbs reagent was added. The reaction was continued for additional 24 hr, then cooled down. The reaction mixture was concentrated under reduced pressure, and the residue was subject to flash column chromatography on silica gel with eluent (heptane/EtOAc v/v 1:1 to 1:3), giving 310 mg of brown solid.

Intermediate 16-8

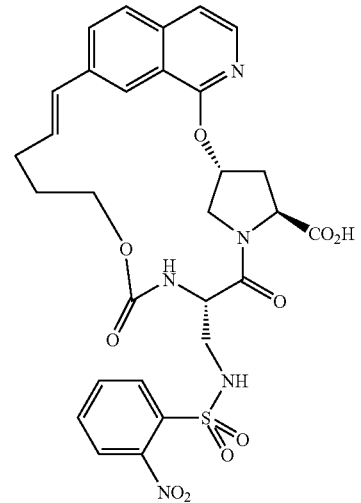

(2R,4S,7S,14E)-7-(2-nitrobenzenesulfonyl)aminomethyl-2H-16,18-etheno-2,5-methano-11H-pyrido [2,3-k][1,10,3,6]

dioxadiazacyclononadecine-4-ylcarboxylic acid: Intermediate 16-8 was made from Intermediate 16-7 following the procedures described for Intermediate 16-3. LC/MS: m/z 640.2 (ES+); 638.0 (ES−).

Intermediate 16-9

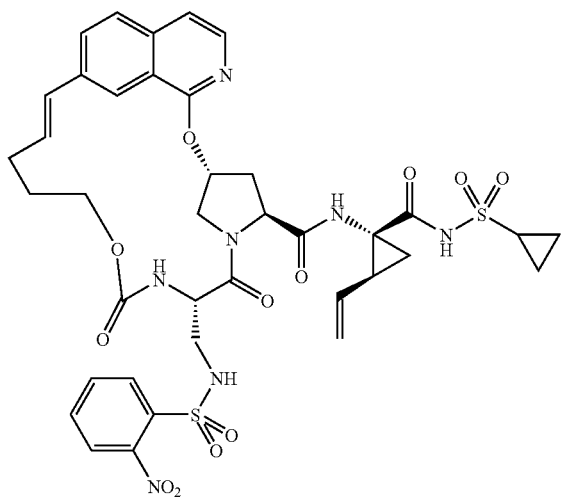

(1R,2S)-N-1-cyclopropylsulfonylcarboxamido-2-vinyl-cyclopropyl (2R,4S,7S,14E)-7-(2-nitrobenzenesulfonyl)aminomethyl-2H-16,18-etheno-2,5-methano-11H-pyrido[2,3-k][1,10,3,6]dioxadiazacyclononadecine-4-ylcarboxamide: Intermediate 16-9 was made by coupling Intermediate 16-8 and Intermediate 14-3 following the procedures described for Intermediate 16-5. (yield=123 mg) LC/MS: m/z 852.1 (ES+); 850.2 (ES−).

Compound I-77

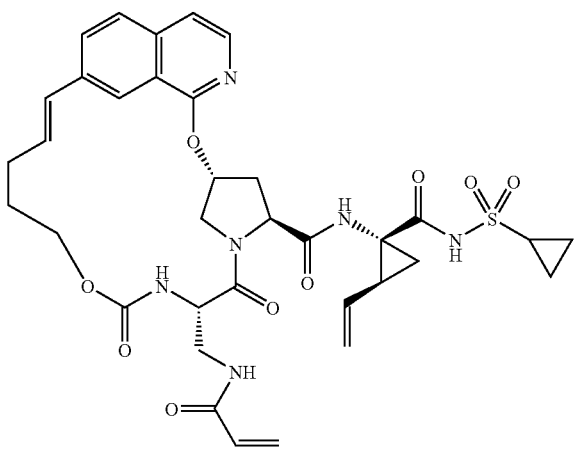

(1R,2S)-N-1-cyclopropylsulfonylcarboxamido-2-vinyl-cyclopropyl (2R,4S,7S,14E)-7-acrylamidomethyl-2H-16,18-etheno-2,5-methano-11H-pyrido [2,3-k][1,10,3,6]dioxadiazacyclononadecine-4-ylcarboxamide (1-77): To a solution of 12 mg of Intermediate 16-9 in 1 mL of DMF, was added 40 uL of thiophenol and 50 mg of potassium carbonate. The mixture was stirred at RT overnight, then diluted with 10 mL of EtOAc. The precipitate was filtered out, the filtrate was concentrated and dried in vacuum.

To the residue was added 3 mL of acetonitrile, 20 mg of acrylic acid and 300 uL of N,N-diisopropylethyl amine followed by 100 mg of HATU. The reaction mixture was stirred at RT for 2 hr, then subject to normal workup and finally purified by flash column chromatography on silica gel (eluent—5% methanol in EtOAc), giving 9.5 mg of compound I-77. $^1$HNMR (CD$_3$OD, 400 MHz) δ 9.14 (s, 1H), 8.44 (s, 1H), 7.87 (d, 2H, J=6.0 Hz), 7.72 (d, 1H, J=8.4 Hz), 7.55 (dd, 1H, J=8.8, 1.2 Hz), 7.27 (d, 1 h, 6.0 Hz), 6.56 (d, 1H, J=15.6 Hz), 6.44 (m, 1H), 6.29 (d, 1H, J=10.8 Hz), 6.26 (d, 1H, J=4.4 Hz), 5.65-5.75 (m, 3H), 5.28 (dd, 1H, J=1.2, 16.8 Hz), 5.09 (dd, 1H, J=2.0, 10.4 Hz), 4.80 (m, 1H), 4.40-4.48 (m, 2H), 4.00 (m, 2H)3.50-3.70 (m, 2H), 2.95-3.01 (m, 1H), 2.19-2.35 (m, 4H), 1.80-1.90 (m, 2H), 1.20-1.50 (m, 5H), 1.10 (m, 2H).

LC/MS: m/z 721.2 (ES+); 719.2 (ES−).

In similar fashion, combining procedures with Example 7, the following compound was prepared:

I-83

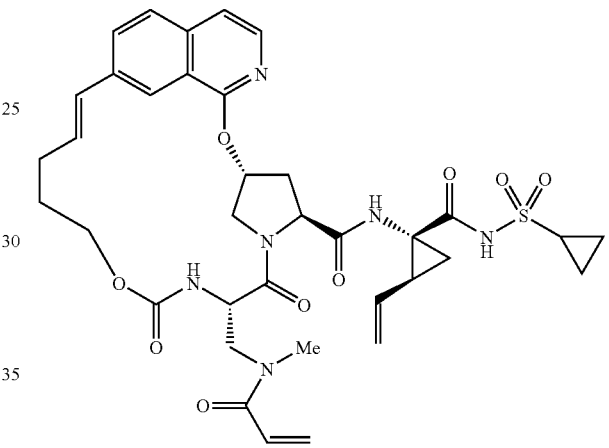

(1R,2S)-N-1-cyclopropylsulfonylcarboxamido-2-vinyl-cyclopropyl (2R,4S,7S,14E)-7-(N-methylacrylamidomethyl-2H-16,18-etheno-2,5-methano-11H-pyrido [2,3-k][1,10,3,6]dioxadiazacyclononadecine-4-ylcarboxamide (I-83): LC/MS: m/z 735.2 (ES+).

In similar fashion, the following compounds can be prepared:

I-15

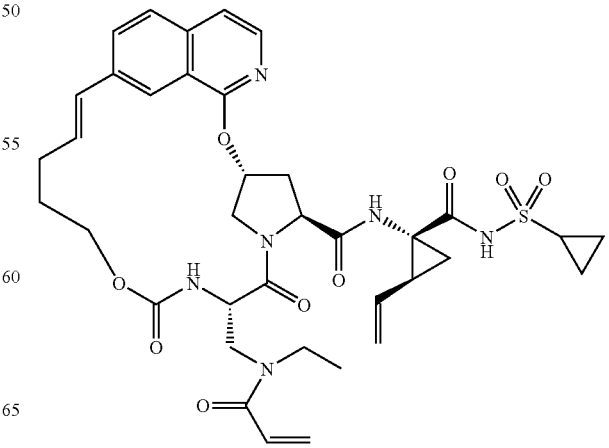

I-89

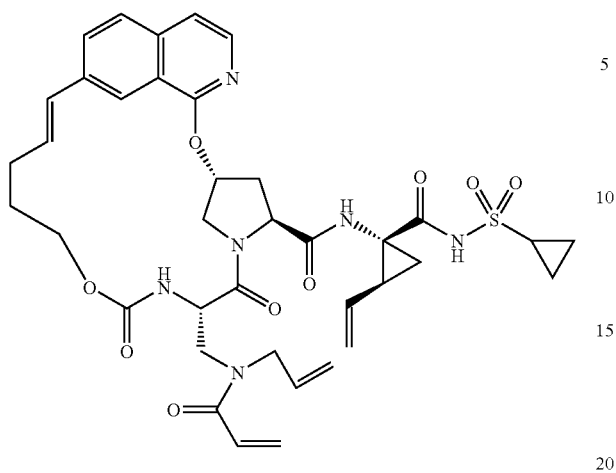

Example 17

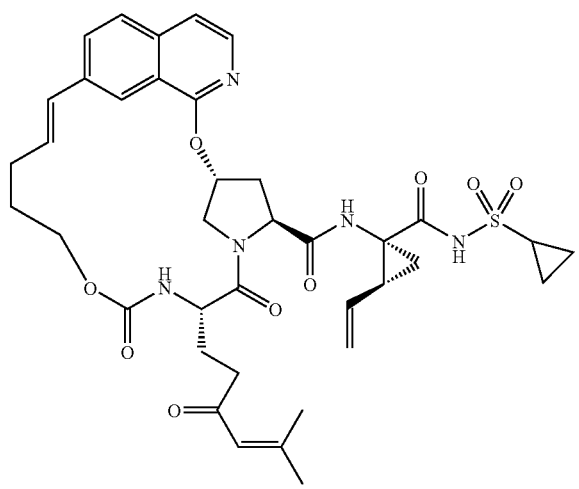

I-102

(I-102), The title compound was prepared according to the steps and intermediates as described below:

Intermediate 17-1

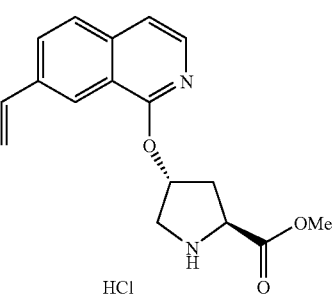

4-(7-Vinyl-isoquinolin-1-yloxy)-pyrrolidine-2-carboxylic acid methyl ester hydrochloride. Intermediate 17-1 was prepared by stirring intermediate 15-1 in HCl saturated methanol overnight. LC-MS: m/z=299.2 (ES+).

Intermediate 17-2

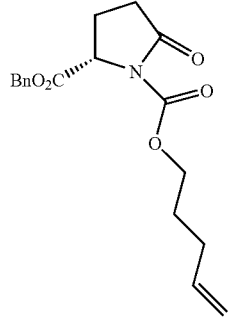

5-Oxo-pyrrolidine-1,2-dicarboxylic acid 2-benzyl ester 1-pent-4-enyl ester (intermediate 17-2). At 0° C., to a stirring solution of 5.5 g of 5-Oxo-pyrrolidine-2-carboxylic acid benzyl ester (25 mmol), 4 mL of triethylamine, 3.3 g of N,N-dimethylaminopyridine (27 mmol) in 40 mL of dichloromethane, was added 4.1 g of 4-pentenyl-1-yl chloroformate (27.6 mmol). The reaction mixture was then warmed to rt, and stirred over weekend. After concentration, the resulting residue was dissolved in ethyl ether 120 mL, washed with 30 mL of 1.0 N aq. HCl, brine subsequently, dried over anhydrous sodium sulfate. The organic solvent was evaporated under reduced pressure, and the residue was purified by flash chromatography on silica gel using heptane/EtOAc (v/v 1/1), giving 7.3 g of colorless oil as intermediate 17-2 (88%). LC-MS: m/z=331.2 (ES+).

Intermediate 17-3

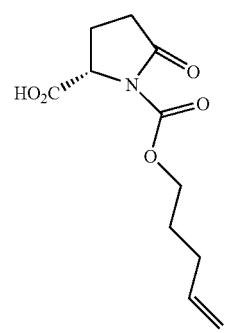

5-Oxo-pyrrolidine-1,2-dicarboxylic acid 1-pent-4-enyl ester (intermediate 17-3). Under nitrogen, to a stirring solution of 240 mg of palladium acetate (1.1 mmol) in 20 mL of de-gassed dichloromethane, was added 460 uL of triethylamine (3.3 mmol), and 5.33 mL of triethylsilane (33 mmol). After stirring at rt for 15 min, 7.3 g of intermediate 17-2 in 25 mL of de-gassed dichloromethane was added in. The resulting solution was stirred at rt overnight. The reaction mixture was passed through a celite pad, and the filtrate was concentrated and purified by flash column chromatography using DCM/MeOH (v/v 9/1) as eluent, giving colorless oil 4.55 g (85%). LC-MS: m/z=240.1 (ES−).

Intermediate 17-4

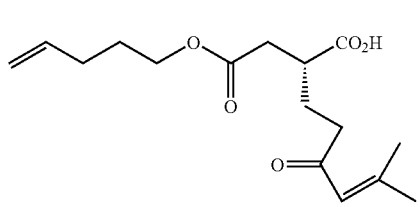

2-(5-Methyl-3-oxo-hex-4-enyl)-succinic acid 4-pent-4-enyl ester (intermediate 17-4). Under nitrogen, to a stirring solution of 1.0 g of intermediate 17-3 (4.0 mmol) in 30 mL of anhydrous THF at −78° C., was added 24 mL of 0.5 M 2-methyl-1-propenyl magnesium bromide THF solution. The reaction mixture was stirred at −78° C. for 1 hr before 12 mL of 1.0 N aqueous HCl was added. After warming up to rt, the reaction mixture was extracted with 50 mL of EtOAc, washed with brine, and dried over sodium sulfate. The organic layer was concentrated, 1.02 g intermediate 17-4 was obtained which can be used directly without further purification (86% yield). LC-MS: m/z=298.1 (ES+), 296.2 (ES−).

Intermediate 17-5

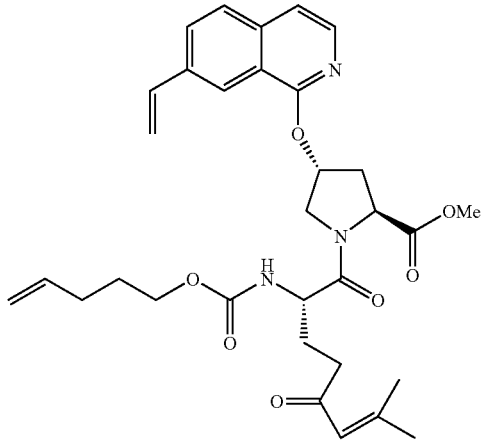

1-(7-Methyl-5-oxo-2-pent-4-enyloxycarbonylamino-oct-6-enoyl)-4-(7-vinyl-isoquinolin-1-yloxy)-pyrrolidine-2-carboxylic acid methyl ester. Intermediate 17-5 was prepared via coupling reaction of intermediate 17-1 and intermediate 17-4, as similarity described in Example 15. LC-MS: m/z=578.2 (ES+).

Intermediate 17-6

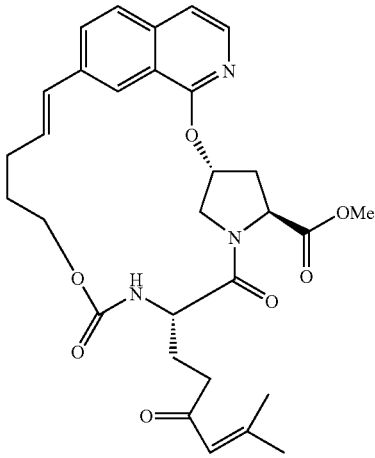

Intermediate 17-6 was prepared via olefin metathesis as described for Intermediate 16-7. LC-MS: 572.2 (M+Na+, ES+).

Intermediate 17-7

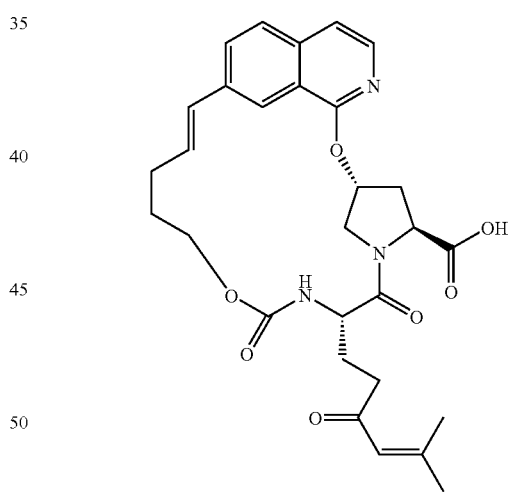

Intermediate 17-7. To a stirring mixture of 420 mg of intermediate 17-6 (0.76 mmol) in 6 mL of t-BuOH and 3 mL of THF, was added 8 mL of 1.0 N LiOH solution. After stirring at rt for 1 hr, the solution was acidified to pH=5 with 1.0 N HCl solution. The reaction mixture was extracted with 60 mL of dichloromethane, washed with brine and dried over anhydrous MgSO4. After filtration and concentration, the resulting mixture can be used directly for the next step. (330 mg gummy solid, 980%). LC-MS: m/z=534.2 (ES−).

I-102

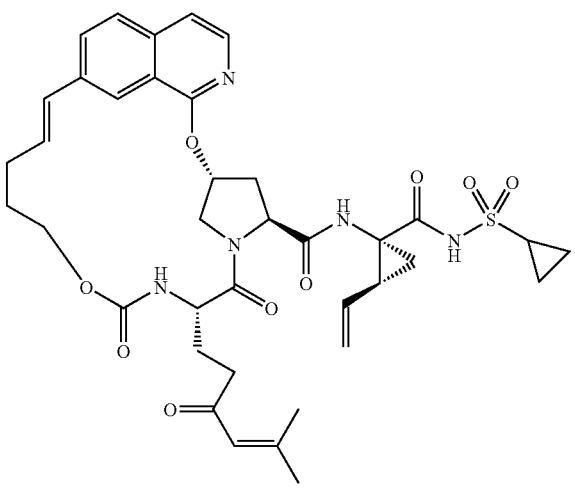

(I-102). The title compound was made by coupling Intermediate 17-7 and Intermediate 14-3 following the procedures described for Intermediate 16-5, giving pink white solid 223 mg (53%). LC/MS: m/z 748.3 (ES+); 746.2 (ES−).

Example 18

Compound I-141

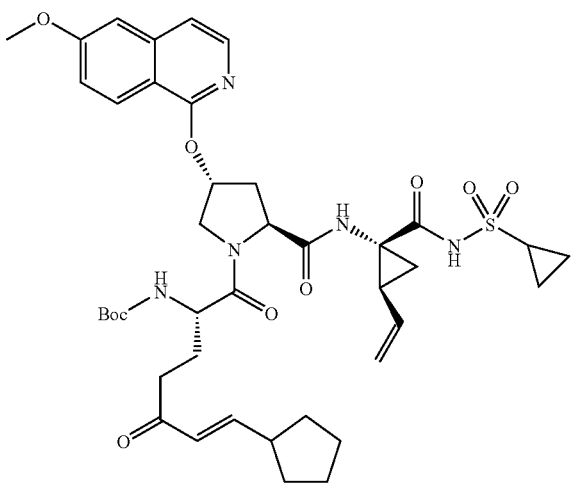

tert-butyl-(S,E)-7-cyclopentyl-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxohept-6-en-2-ylcarbamate: The title compound was prepared according to the steps and intermediates as described below:

Intermediate 18-1

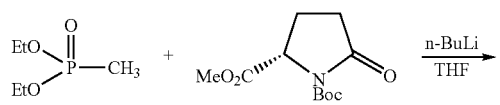

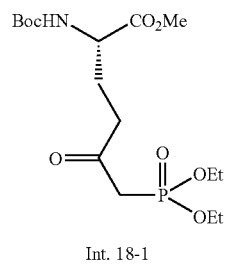

Int. 18-1

To a stirring solution of 1 mmol diethyl methylphosphonate in 2 mL of anhydrous THF under Ar at −78° C., was added dropwise 650 uL of 1.6 M n-butyllithium solution in hexane. The resulting mixture was stirred 30 min at −78° C. before N-Boc methyl pyroglutamate (1 mmol) in 1 mL of THF was added. The reaction mixture was then warmed slowly to room temperature, and stirred at rt overnight. Aqueous NH$_4$Cl solution (5 mL) was added in, and the reaction mixture was extracted with ethyl acetate (30 mL). The organic layer was then dried over sodium sulfate, filtrated, and concentrated. The residue was purified by flash column chromatography on silica gel with heptan/EtOAc 1/3 (v/v) as eluting solvent, giving color less oil 220 mg (55%).

Intermediate 18-2

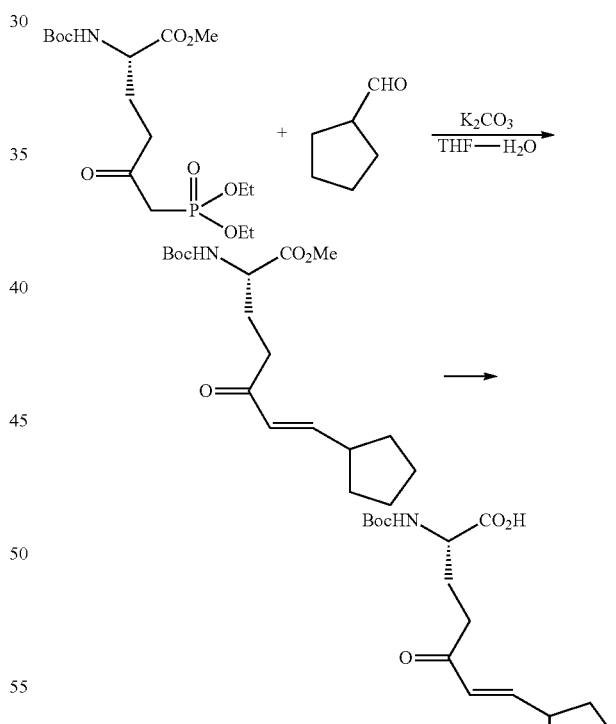

Int. 18-2

A solution of 105 mg of phosphonate from above (0.265 mmol), 52 mg of cyclopentanyl carboxaldehyde (2 equiv), 110 mg of potassium carbonate in 2 mL of THF and 2 mL of water was stirred vigorously overnight. Ethyl acetate 30 mL was then added in, and the organic layer was dried over sodium sulfate. After concentration, the residue was purified by flash column chromatography on silica gel with heptane/EtOAc 1/3 (v/v) as eluting solvent, giving 52 mg (58%) of a colorless oil as desired ester.

The ester obtained was then subjected to basic hydrolysis in 1 mL of THF and 1 mL of t-butanol with 0.5 mL of 1 M aqueous LiOH solution. After 30 min, 0.6 mL of 1 M HCl was added, and the resulting mixture was extracted with 30 mL of ethyl acetate. After drying over anhydrous sodium sulfate, the organic layer was filtrated, concentrated to give the desired acid and was used directly for the next coupling step.

Intermediate 18-3

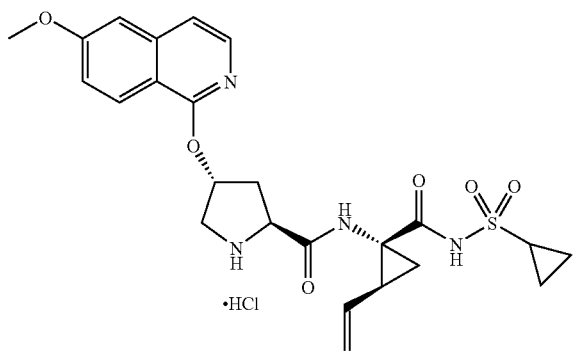

(2S,4R)-N-((1R,2S)-1-(cyclopropylsulfonylcarbamoyl)-2-vinylcyclopropyl)-4-(6-methoxyisoquinolin-1-yloxy)pyrrolidine-2-carboxamide. The title compound was prepared according to Example 14 by starting from the 1-chloro-6-methoxyisoquinoline in the step for the synthesis of Intermediate 14-1.

Compound I-141

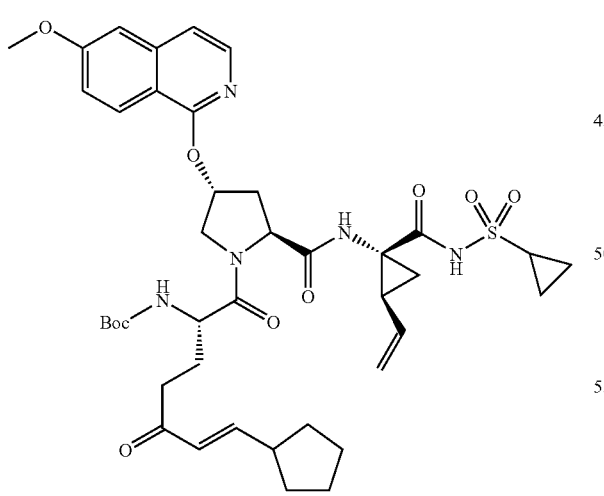

tert-butyl-(S,E)-7-cyclopentyl-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-1,5-dioxohept-6-en-2-ylcarbamate: The title compound was made by coupling Intermediate 18-3 and Intermediate 18-2 using HATU following the coupling reactions described in Example 13.

$^1$HNMR (CD$_3$OD, 400 MHz) δ 9.25 (s, 1H), 8.06 (d, 1H, J=8.8 Hz), 7.81 (d, 1H, J=6.0 Hz), 7.20 (d, 1H, J=6.0 Hz), 7.12 (d, 1H, J=2.4 Hz), 7.07 (dd, 1H, J=2.4, 7.2 Hz), 6.88 (dd, 1H, J=8.4, 16.0 Hz), 6.03 (d, 1H, J=16.0 Hz), 5.78 (br s, 1H), 5.68 (m, 1H), 5.26 (d, 1H, J=16.8 Hz), 4.84 (d, 1H, J=8.4 Hz), 4.32 (m, 1H), 3.85 (s, 3H), 2.86 (m, 1H), 2.53-2.64 (m, 4H), 2.18 (m, 2H), 1.96 (m, 1H), 1.81.50-1.65 (m, 2H), 1.35 (m, 2H), 1.20 (s, 9H), 1.00 (m, 2H). MS m/z: 808.3 M+H$^+$).

In a similar manner, by using an appropriate aldehyde in the step for the synthesis of Intermediate 18-2, the following compounds were prepared:

I-142

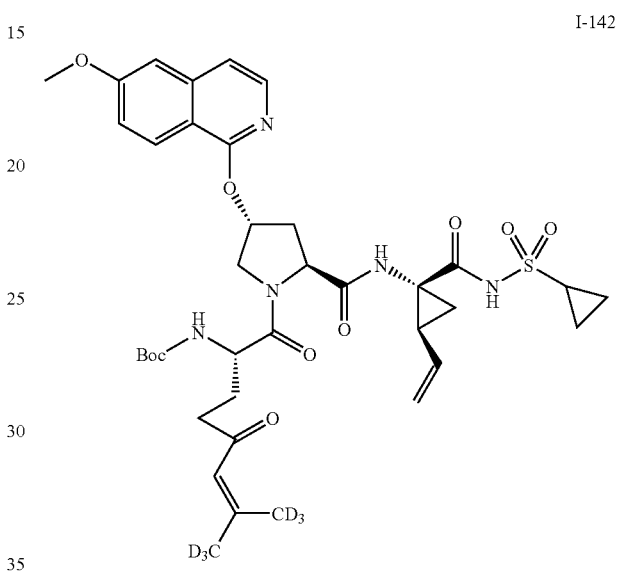

MS m/z: 774.2 M+H$^+$).

I-143

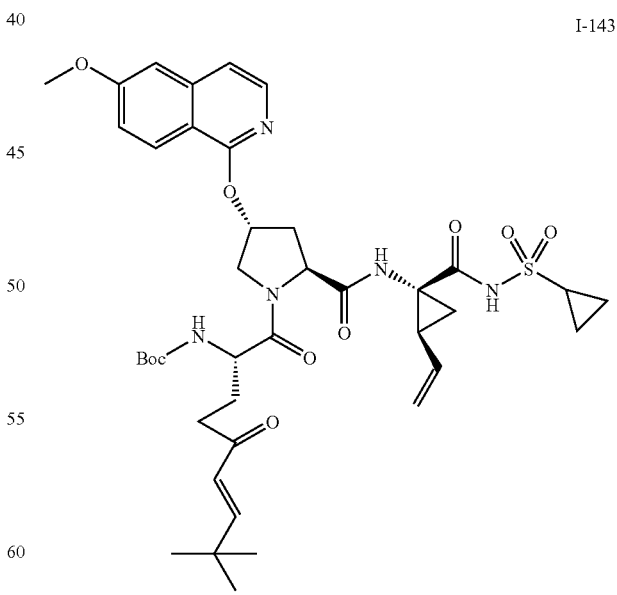

tert-butyl (S,E)-1-((2S,4R)-2-((1R,2S)-1-(cyclopropylsulfonylcarbamoyl)-2-vinylcyclopropylcarbamoyl)-4-(6-methoxyisoquinolin-1-yloxy)pyrrolidin-1-yl)-8,8-dimethyl-1,5-dioxonon-6-en-2-ylcarbamate, MS m/z: 796.2 M+H$^-$).

In similar manner, by using an appropriate aldehyde in the step for the synthesis of Intermediate 18-2, the following compounds can be prepared:

I-144

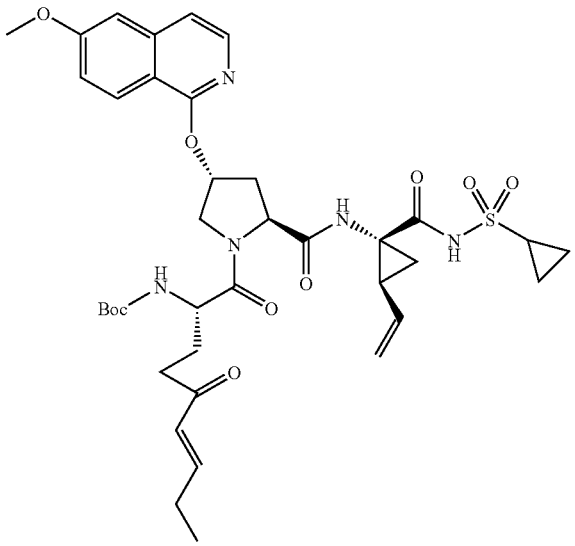

tert-butyl-(S,E)-1-((2S,4R)-2-((1R,2S)-1-(cyclopropyl-sulfonylcarbamoyl)-2-vinylcyclopropylcarbamoyl)-4-(6-methoxyisoquinolin-1-yloxy)pyrrolidin-1-yl)-1,5-dioxonon-6-en-2-ylcarbamate

I-145

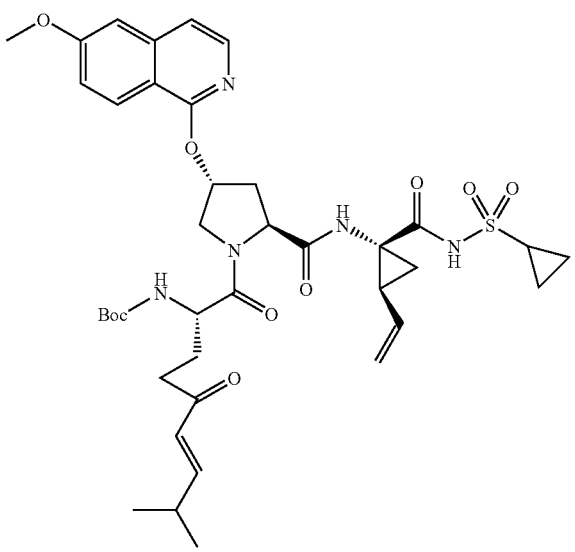

tert-butyl-(S,E)-1-((2S,4R)-2-((1R,2S)-1-(cyclopropyl-sulfonylcarbamoyl)-2-vinylcyclopropylcarbamoyl)-4-(6-methoxyisoquinolin-1-yloxy)pyrrolidin-1-yl)-8-methyl-1,5-dioxonon-6-en-2-ylcarbamate

I-146

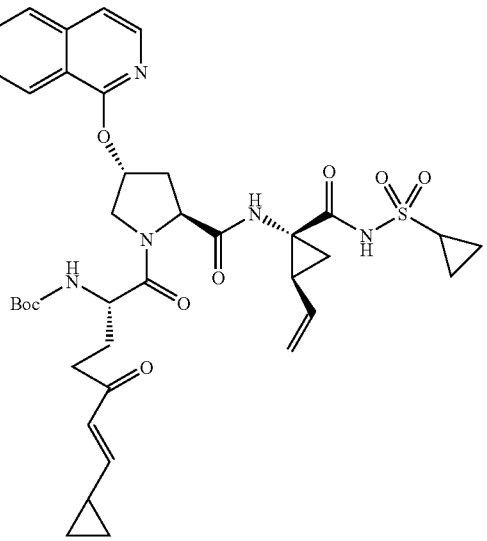

tert-butyl-(S,E)-7-cyclopropyl-1-((2S,4R)-2-((1R,2S)-1-(cyclopropylsulfonylcarbamoyl)-2-vinylcyclopropylcar-bamoyl)-4-(6-methoxyisoquinolin-1-yloxy)pyrrolidin-1-yl)-1,5-dioxohept-6-en-2-ylcarbamate

I-147

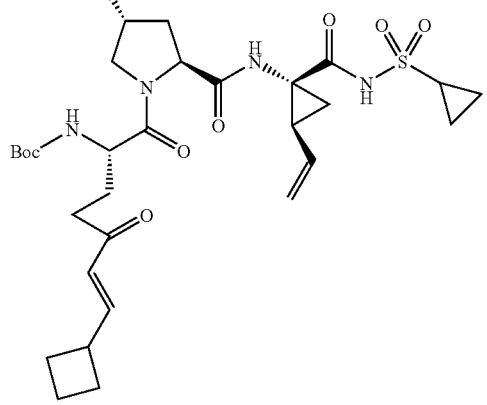

tert-butyl-(S,E)-7-cyclobutyl-1-((2S,4R)-2-((1R,2S)-1-(cyclopropylsulfonylcarbamoyl)-2-vinylcyclopropylcar-bamoyl)-4-(6-methoxyisoquinolin-1-yloxy)pyrrolidin-1-yl)-1,5-dioxohept-6-en-2-ylcarbamate Example 19

Single Chain HCV Protease (WT) Peptide Expression and Purification

The single-chain proteolytic domain (NS4A$_{21-32}$-GSGS-NS$_{33-631}$) was cloned into pET-14b (Novagen, Madison, Wis.) and transformed into DH10B cells (Invitrogen). The resulting plasmid was transferred into *Escherichia coli* BL21

(Novagen) for protein expression and purification as described previously (1, 2). Briefly, the cultures were grown at 37° C. in LB medium containing 100 µg/ml of ampicillin until the optical density at 600 nm (OD600) reached 1.0 and were induced by addition of isopropyl-β-D-thiogalactopyranoside (IPTG) to 1 mM. After an additional incubation at 18° C. for 20 h, bacteria were harvested by centrifugation at 6,000×g for 10 min and resuspended in a lysis buffer containing 50 mM $Na_3PO_4$, pH 8.0, 300 mM NaCl, 5 mM 2-mercaptoethanol, 10% glycerol, 0.5% Igepal CA630, and a protease inhibitor cocktail consisting of 1 mM phenylmethylsulfonyl fluoride, 0.5 µg/ml leupeptin, pepstatin A, and 2 mM benzamidine. Cells were lysed by freezing and thawing, followed by sonication. Cell debris was removed by centrifugation at 12,000×g for 30 min. The supernatant was further clarified by passing through a 0.45-µm filter (Corning) and then loaded onto a HiTrap chelating column charged with $NiSO_4$ (Amersham Pharmacia Biotech). The bound protein was eluted with an imidazole solution in a 100-to-500 mM linear gradient. Selected fractions were run through $Ni^{2-}$ column chromatography and were analyzed on a 10% sodium dodecyl sulfate (SDS)-polyacrylamide gel. The purified protein was resolved by electrophoresis in a 12% SDS-PAGE gel and then transferred onto a nitrocellulose membrane. The protein was analyzed by Western blot analysis using monoclonal antibodies against NS3. Proteins were visualized by using a chemiluminescence kit (Roche) with horseradish peroxidase-conjugated goat anti-mouse antibodies (Pierce) as secondary antibodies. The protein was aliquoted and stored at −80° C.

Example 20

Cloning and Expression of HCV Protease A156S, A156T, D168A, D168V Drug-Resistance Mutants and C159S Variant The mutant DNA fragments of NS4A/NS3 were generated by PCR and cloned into pET expression vector. After transformation into BL21 competent cells, the expression was induced with IPTG for 2 hours. The His-tagged fusion proteins were purified using affinity column followed by size exclusion chromatography.

Example 21

Assay buffer: 2% CHAPS, 50 mM Tris pH 7.5, 50% glycerol, 2 uM M-2235 (Bachem) substrate. In a 50 ul reaction, add 49 ul assay buffer, 1 ul (1U) HCV serine protease (Bioenza). Incubate 20 minutes at room temperature. The plate was read at either 350/460 nm (excitation/emission) on a fluorescent micro-plate reader or monitored at one-minute intervals to achieve the kinetic curve.

The enzyme tolerated 1% DMSO and 2% methanol. In the experiments of testing compounds, the compounds in pure DMSO were diluted 10 times with 20% methanol (10% DMSO and 20% methanol). This compound solution was added to the reaction (not exceeding 10% of the final reaction volume). The final concentration of the organic solvents was: 1% DMSO and 2% methanol.

Example 22

Additional Assay Protocols
Method A:
The compounds were assayed to evaluate the antiviral activity and cytotoxicity of compounds in vitro using HCV RNA replicons. This assay used the cell line ET (luc-ubi-neo/ ET), which is a human Huh7 hepatoma cell line that contains an HCV RNA replicon with a stable luciferase (Luc) reporter and three cell culture-adaptive mutations. The HCV RNA levels were directly measured by viral specific TaqMan RT-PCR:

```
Forward primer:
                                         (SEQ ID NO: 63)
ACGCAGAAAGCGTCTAGCCAT Reverse primer:
                                         (SEQ ID NO: 64)
TACTCACCGGTTCCGCAGA Probe:
                                         (SEQ ID NO: 65)
[6-FAM]-CCTGGAGGCTGCACGACACTCAT-[TAMRA]
```

The ET cell line was grown in Dulbecco's modified essential media (DMEM), 10% fetal bovine serum (FBS), 1% penicillin-streptomycin (pen-strep), 1% glutamine, 250 µg/ml G418 in a 5% $CO_2$ incubator at 37° C. All cell culture reagents were obtained from Mediatech (Manassas, Va.). Cells were trypsinized (1% trypsin:EDTA) and plated out at $5\times10^3$ cells/well in white 96-well assay plates (Costar) dedicated to cell number (cytotoxicity) or antiviral activity assessments. Drugs were added at six 3-fold concentrations each and the assay was run in DMEM, 5% FBS, 1% pen-strep, 1% glutamine. Human interferon alpha-2b (PBL Biolabs, New Brunswick, N.J.) was included in each run as a positive control compound. Cells were processed 72 hr post drug addition when the cells are still subconfluent. Antiviral activity was measured by analyzing replicon-derived luciferase activity using the Steady-Glo Luciferase Assay System (Promega, Madison, Wis.) according to manufacturer's instruction. The number of cells in each well was determined by CytoTox-1 reagent (Promega). Compound profile was derived by calculating applicable $EC_{50}$ (effective concentration inhibiting virus replication by 50%), $EC_{90}$ (effective concentration inhibiting virus replication by 90%), $IC_{50}$ (concentration decreasing cell viability by 50%) and $SI_{50}$ (selective index: $EC_{50}/IC_{50}$) values. $IC_{50}$ values for selected compounds are set forth in Table 5, below.

Method B: HCV Protease Assay using FRET Methodology

A quantitative, fluorescence resonance energy transfer (FRET)-based methodology was employed to identify HCV NS3/4A protease inhibitors. The assay employed a synthetic FRET peptide, derived from the HCV NS5A/5B cleavage site, with the HCV protease to evaluate the activity of compounds against the protease by monitoring the cleavage activity of the complex. A synthetic peptide which encompasses the NS5A-5B junction (NH2-EDVVCCSMSYK-COOH) was labeled with Dabcyl and Edans at N- and C-termini, respectively (Invitrogen, Carlsbad, Calif.). Fluorescence measurement was used to estimate the $IC_{50}$ value of the test compound. The two fluorophores form a quenching pair and exhibit FRET within the intact peptide. Upon cleavage of the FRET peptide by HCV NS3/4A proteinase complex (100 ng/mL), the fluorescence is recovered and can be continuously monitored at excitation/emission=340/490 nm.

Example 23

HCV Protease FRET Assay for Wild Type and Mutated NS3/ 4A 1b Enzymes ($IC_{50}$)

The protocol is a modified FRET-based assay (v_02) from *In Vitro Resistance Studies of HCV Serine Protease Inhibitors*, 2004, JBC, vol. 279, No. 17, pp 17508-17514. Inherent potency of compounds was assessed against A156S, A156T, D168A, and D168V mutants of the HCV NS3/4A 1b protease enzyme as follows:

10× stocks of NS3/4A protease enzyme from Bioenza (Mountain View, Calif.) and 1.13× 5-FAM/QXL™ 520 FRET peptide substrate from Anaspec (San Jose, Calif.) were prepared in 50 mM HEPES, pH 7.8, 100 mM NaCl, 5 mM DTT and 20% glycerol. 5 μL of each enzyme were pre-incubated in a Corning (#3573) 384-well, black, non-treated microtiter plate (Corning, N.Y.) for 30 min at 25° C. with a 0.5 μL volume of 50% DMSO and serially diluted compounds prepared in 50% DMSO. Protease reactions were started with the addition of 45 μL of the FRET substrate and monitored for 120 minutes at $\lambda_{ex}487/\lambda_{em}514$ through Quad$^4$ monochromoters in a Synergy$^4$ plate reader from BioTek (Winooski, Vt.). At the conclusion of each assay, progress curves from each well were examined for linear reaction kinetics and fit statistics ($R^2$, absolute sum of squares). Initial velocity (0 minutes to 30+ minutes) from each reaction was determined from the slope of a plot of relative fluorescence units vs time (minutes) and then plotted against inhibitor concentration to estimate $IC_{50}$ from log[Inhibitor] vs Response, Variable Slope model in GraphPad Prism from GraphPad Software (San Diego, Calif.).

Table 5 shows the activity of selected compounds of this invention in the FRET Assay. The compound numbers correspond to the compound numbers in Table 3. Compounds having an activity designated as "A" provided an $IC_{50} \leq 10$ nM; compounds having an activity designated as "B" provided an $IC_{50} > 10$ nM and $\leq 100$ nM; compounds having an activity designated as "C" provided an $IC_{50} > 100$ nM and $\leq 1000$ nM; compounds having an activity designated as "D" provided an $IC_{50} > 1000$ nM and $<10,000$ nM; and compounds having an activity designated as "E" provided an $IC_{50} \geq 10,000$ nM.

TABLE 5

Enzymatic Data for Exemplary Compounds

| Compound tested | Enzyme/Assay | Inhibition |
|---|---|---|
| (I-1) | WT | A |
|  | HCV D168A | D |
| (I-2) | Biochemical | C |
|  | Replicon[1] | C |
|  | Cytotoxicity | E |
|  | WT | A |
|  | HCV A156S | B |
|  | HCV A156T | B |
|  | HCV D168A | D |
|  | HCV D168V | C |
| (I-3) | Biochemical | B |
|  | Replicon[1] | B |
|  | Cytotoxicity | E |
|  | WT | A |
|  | HCV A156S | A |
|  | HCV A156T | B |
|  | HCV D168A | B |
|  | HCV D168V | B |
| (I$^R$-3) | Biochemical | B |
|  | Replicon[1] | D |
|  | Cytotoxicity | E |
|  | WT | A |
|  | HCV A156S | A |
|  | HCV A156T | B |
|  | HCV D168A | C |
|  | HCV D168V | C |
| (I-4) | Replicon[1] | B |
|  | Cytotoxicity | D |
|  | WT | A |
|  | HCV A156S | A |
|  | HCV A156T | B |
|  | HCV D168A | B |
|  | HCV D168V | B |
| (I-5) | Replicon[1] | D |
|  | Cytotoxicity | E |
|  | WT | A |
|  | HCV A156S | B |
|  | HCV A156T | D |
|  | HCV D168A | D |
|  | HCV D168V | D |
| (I-6) | WT | A |
|  | HCV D168A | C |
| (I-7) | Biochemical | B |
|  | Replicon[1] | B |
|  | Cytotoxicity | E |
|  | WT | A |
|  | HCV A156S | A |
|  | HCV A156T | B |
|  | HCV D168A | B |
|  | HCV D168V | B |
| (I-8) | Replicon[1] | C |
|  | Cytotoxicity | D |
|  | WT | A |
|  | HCV A156S | A |
|  | HCV A156T | B |
|  | HCV D168A | B |
|  | HCV D168V | B |
| (I-9) | Replicon[1] | B |
|  | Cytotoxicity | C |
|  | WT | A |
|  | HCV A156S | A |
|  | HCV A156T | A |
|  | HCV D168A | A |
|  | HCV D168V | A |
| (I-10) | Replicon[1] | C |
|  | Cytotoxicity | D |
|  | WT | A |
|  | HCV A156S | A |
|  | HCV A156T | B |
|  | HCV D168A | B |
|  | HCV D168V | B |
| (I-11) | WT | A |
|  | D168A | C |
| (I-12) | Replicon[1] | B |
|  | Cytotoxicity | D |
|  | WT | A |
|  | HCV A156S | A |
|  | HCV A156T | B |
|  | HCV D168A | B |
|  | HCV D168V | B |
| (I-13) | WT | A |
|  | HCV D168A | C |
| (I-20) | Replicon[1] | C |
|  | Cytotoxicity | D |
|  | WT | A |
|  | HCV A156S | A |
|  | HCV A156T | C |
|  | HCV D168A | C |
|  | HCV D168V | C |
| (I-21) | WT | A |
|  | HCV D168A | C |
| (I-22) | Replicon[1] | C |
|  | Cytotoxicity | D |
|  | WT | A |
|  | HCV A156S | A |
|  | HCV A156T | B |
|  | HCV D168A | B |
|  | HCV D168V | C |
| (I-23) | Replicon[1] | C |
|  | Cytotoxicity | D |
|  | WT | A |
|  | HCV A156S | A |
|  | HCV A156T | D |
|  | HCV D168A | C |
|  | HCV D168V | D |
| (I-24) | WT | C |
|  | HCV D168A | D |

TABLE 5-continued

Enzymatic Data for Exemplary Compounds

| Compound tested | Enzyme/Assay | Inhibition |
|---|---|---|
| (I-25) | Replicon[1] | E |
| | Cytotoxicity | C |
| | WT | A |
| | HCV D168A | B |
| (I-26) | Replicon[1] | E |
| | Cytotoxicity | E |
| | WT | A |
| | HCV D168A | C |
| (I-27) | Replicon[1] | B |
| | Cytotoxicity | D |
| | WT | A |
| | HCV A156S | A |
| | HCV A156T | B |
| | HCV D168A | B |
| | HCV D168V | B |
| (I[R]-27) | WT | C |
| | HCV D168A | D |
| (I-28) | Replicon[1] | A |
| | Cytotoxicity | D |
| | WT | A |
| | HCV A156S | A |
| | HCV A156T | B |
| | HCV D168A | C |
| | HCV D168V | C |
| (I-29) | Replicon[1] | B |
| | Cytotoxicity | C |
| | WT | A |
| | HCV A156S | A |
| | HCV A156T | A |
| | HCV D168A | A |
| | HCV D168V | A |
| (I-30) | Replicon[1] | B |
| | Cytotoxicity | E |
| | WT | A |
| | HCV D168A | C |
| (I-31) | WT | A |
| | HCV D168A | B |
| (I-32) | Replicon[1] | C |
| | Cytotoxicity | E |
| | WT | A |
| | HCV D168A | D |
| (I-33) | Replicon[1] | A |
| | Cytotoxicity | E |
| | WT | A |
| | HCV A156T | C |
| | HCV D168A | C |
| | HCV D168V | D |
| (I-34) | WT | B |
| | HCV D168A | D |
| (I-35) | Replicon[1] | A |
| | Cytotoxicity | C |
| | WT | A |
| | HCV A156S | A |
| | HCV A156T | A |
| | HCV D168A | A |
| | HCV D168V | A |
| (I-37) | WT | B |
| | HCV D168A | D |
| (I-38) | WT | A |
| | HCV D168A | C |
| (I-39) | Replicon[1] | B |
| | Cytotoxicity | C |
| | WT | A |
| | HCV A156S | A |
| | HCV A156T | A |
| | HCV D168A | A |
| | HCV D168V | A |
| (I-40) | WT | B |
| | HCV D168A | A |
| (I-41) | Replicon[1] | E |
| | Cytotoxicity | E |
| | WT | B |
| | HCV D168A | D |
| (I-42) | Replicon[1] | E |
| | Cytotoxicity | E |
| | WT | A |
| | HCV A156S | A |
| | HCV A156T | C |
| | HCV D168A | B |
| | HCV D168V | C |
| (I-43) | WT | C |
| | HCV D168A | D |
| (I-44) | WT | B |
| | HCV D168A | D |
| (I-45) | WT | C |
| | HCV D168A | D |
| (I-46) | Replicon[1] | A |
| | Cytotoxicity | C |
| | WT | A |
| | HCV A156S | A |
| | HCV A156T | A |
| | HCV D168A | A |
| | HCV D168V | A |
| (I-47) | Replicon[1] | D |
| | Cytotoxicity | E |
| | WT | B |
| | HCV D168A | D |
| (I-48) | Replicon[1] | D |
| | Cytotoxicity | E |
| | WT | B |
| | HCV D168A | D |
| (I-49) | WT | B |
| | HCV D168A | C |
| (I-73) | HCV R155K | A |
| (I-74) | HCV R155K | A |
| (I-75) | HCV R155K | B |

[1]Data collected from assay described in Example 22.

Example 24

HCV Protease FRET Assay for WT and Mutated NS3/4A 1b Enzymes ($IC_{50\_APP}$).

The following protocol was used to generate "apparent" $IC_{50}$ ($IC_{50\_APP}$) values as depicted in Table 6, below. Without wishing to be bound by any particular theory, it is believed that $IC_{50\_APP}$, contrasted with $IC_{50}$ values, may provide a more useful indication of time-dependent inhibition, and are thus more representative of binding affinity. The protocol is a modified FRET-based assay (v_03) developed to evaluate compound potency, rank-order and resistance profiles against wild type and C159S, A156S, A156T, D168A, D168V, R155K mutants of the HCV NS3/4A 1b protease enzyme as follows: 10× stocks of NS3/4A protease enzyme from Bioenza (Mountain View, Calif.) and 1.13× 5-FAM/QXL™520 FRET peptide substrate from Anaspec (San Jose, Calif.) were prepared in 50 mM Tris-HCl, pH 7.5, 5 mM DTT, 2% CHAPS and 20% glycerol. 5 µL of each enzyme were added to Corning (#3575) 384-well, black, microtiter plates (Corning, N.Y.) after spotting a 0.5 µL volume of 50% DMSO and serially diluted compounds prepared in 50% DMSO. Protease reactions were immediately started after enzyme addition with the addition of 45 µL of the FRET substrate and monitored for 60-90 minutes at $\lambda_{ex}485/\lambda_{em}520$ in a Synergy[4] plate reader from BioTek (Winooski, Vt.). At the conclusion of each assay, progress curves from each well were examined for linear reaction kinetics and fit statistics ($R^2$, 95% confidence intervals, absolute sum of squares). Initial velocity (0 minutes to 15+ minutes) from each reaction was determined from the slope of a plot of relative fluorescence units vs time (minutes) and then plotted against inhibitor concentration as a percent of the no inhibitor and no enzyme controls to estimate apparent $IC_{50}$ from log[Inhibitor] vs Response, Variable Slope model in GraphPad Prism from GraphPad Software (San Diego, Calif.).

Table 6 shows the activity of selected compounds of this invention in the FRET Assay. The compound numbers correspond to the compound numbers in Table 3. Compounds having an activity designated as "A" provided an $IC_{50} \leq 10$ nM; compounds having an activity designated as "B" provided an $IC_{50} > 10$ nM and $\leq 100$ nM; compounds having an activity designated as "C" provided an $IC_{50} > 100$ nM and $\leq 1000$ nM; compounds having an activity designated as "D" provided an $IC_{50} > 1000$ nM and $< 10,000$ nM; and compounds having an activity designated as "E" provided an $IC_{50} \geq 10,000$ nM.

TABLE 6

Enzymatic Data for Exemplary Compounds

| Compound tested | Enzyme/Assay | |
|---|---|---|
| (I-3) | WT | A |
| | HCV A156S | B |
| | HCV A156T | D |
| | HCV D168A | D |
| | HCV D168V | D |
| | Replicon[4] | B |
| (I-4) | WT | A |
| | HCV A156S | A |
| | HCV A156T | C |
| | HCV D168A | C |
| | HCV D168V | D |
| | Replicon[4] | B |
| | Replicon[4] | C[1] |
| (I-7) | WT | A |
| | HCV A156S | A |
| | HCV A156T | C |
| | HCV D168A | C |
| | HCV D168V | D |
| | Replicon[4] | B |
| | Replicon[4] | C[1] |
| (I-9) | WT | A |
| | HCV A156S | A |
| | HCV A156T | B |
| | HCV D168A | C |
| | HCV D168V | C |
| | Replicon[4] | B |
| | Replicon[4] | E[1] |
| (I-12) | WT | A |
| | HCV A156S | A |
| | HCV A156T | D |
| | HCV D168A | D |
| | HCV D168V | D |
| | Replicon[4] | B |
| | Replicon[4] | C[1] |
| (I-22) | WT | A |
| | HCV A156S | B |
| | HCV A156T | D |
| | HCV D168A | D |
| | HCV D168V | D |
| | Replicon[4] | C |
| | Replicon[4] | E[1] |
| (I-27) | WT | A |
| | HCV A156S | A |
| | HCV A156T | C |
| | HCV D168A | C |
| | HCV D168V | D |
| | Replicon[4] | C |
| | Replicon[4] | C[1] |
| (I-28) | WT | A |
| | HCV A156S | B |
| | HCV A156T | D |
| | HCV D168A | D |
| | HCV D168V | D |
| | Replicon[4] | B |
| | Replicon[4] | C[1] |
| (I-30) | WT | B |
| | HCV A156S | B |
| | HCV A156T | D |
| | HCV D168A | D |
| | HCV D168V | D |
| (I-33) | Replicon[4] | B |
| | Replicon[4] | C[1] |
| | WT | A |
| | HCV A156S | B |
| | HCV A156T | D |
| | HCV D168A | D |
| | HCV D168V | D |
| | Replicon[4] | A |
| | Replicon[4] | B[1] |
| (I-35) | WT | A |
| | HCV A156S | A |
| | HCV A156T | C |
| | HCV D168A | C |
| | HCV D168V | D |
| | Replicon[4] | B |
| | Replicon[4] | C[1] |
| (I-39) | WT | A |
| | HCV A156S | A |
| | HCV A156T | B |
| | HCV D168A | C |
| | HCV D168V | C |
| | Replicon[4] | B |
| | Replicon[4] | C[1] |
| (I-42) | WT | B |
| | HCV A156S | A |
| | HCV A156T | B |
| | HCV D168A | C |
| | HCV D168V | C |
| | Replicon[4] | E |
| | Replicon[4] | E[1] |
| (I-46) | WT | A |
| | HCV A156S | A |
| | HCV A156T | B |
| | HCV D168A | C |
| | HCV D168V | C |
| | Replicon[4] | A |
| | Replicon[4] | A[1] |
| (I-50) | WT | A |
| | HCV A156S | A |
| | HCV A156T | C |
| | HCV D168A | C |
| | HCV D168V | D |
| | Replicon[4] | A |
| | Replicon[4] | A[1] |
| (I-51) | WT | B |
| | HCV D168A | D |
| (I-52) | WT | A |
| | HCV A156S | A |
| | HCV A156T | C |
| | HCV D168A | D |
| | HCV D168V | D |
| | Replicon[4] | A |
| | Replicon[4] | A[1] |
| (I-53) | WT | A |
| | HCV A156S | B |
| | HCV A156T | B |
| | HCV D168A | C |
| | HCV D168V | C |
| | Replicon[4] | C |
| | Replicon[4] | E[1] |
| (I-54) | WT | A |
| | HCV A156S | A |
| | HCV A156T | B |
| | HCV D168A | B |
| | HCV D168V | C |
| | Replicon[4] | A |
| | Replicon[4] | A[1] |
| (I-55) | WT | A |
| | HCV A156S | A |
| | HCV A156T | C |
| | HCV D168A | C |
| | HCV D168V | C |
| | Replicon[4] | A |
| | Replicon[4] | C[1] |
| (I-56) | WT | A |
| | HCV A156S | A |

TABLE 6-continued

Enzymatic Data for Exemplary Compounds

| Compound tested | Enzyme/Assay | |
|---|---|---|
| | HCV A156T | B |
| | HCV D168A | C |
| | HCV D168V | C |
| | Replicon[4] | A |
| | Replicon[4] | B[1] |
| (I-57) | WT | C |
| | HCV D168A | D |
| (I-58) | WT | B |
| | HCV A156S | B |
| | HCV A156T | D |
| | HCV D168A | D |
| | HCV D168V | D |
| | Replicon[4] | C |
| | Replicon[4] | D[1] |
| (I-59) | WT | A |
| | HCV A156S | B |
| | HCV A156T | D |
| | HCV D168A | D |
| | HCV D168V | D |
| | Replicon[4] | C |
| | Replicon[4] | D[1] |
| (I-60) | WT | B |
| | HCV A156S | B |
| | HCV A156T | C |
| | HCV D168A | D |
| | HCV D168V | D |
| | Replicon[4] | B |
| | Replicon[4] | C[1] |
| (I-61) | WT | B |
| | HCV A156S | B |
| | HCV A156T | D |
| | HCV D168A | D |
| | HCV D168V | D |
| | Replicon[4] | C |
| | Replicon[4] | D[1] |
| (I-62) | WT | A |
| | HCV A156S | A |
| | HCV A156T | C |
| | HCV D168A | D |
| | HCV D168V | D |
| | Replicon[4] | B |
| | Replicon[4] | C[1] |
| (I-63) | WT | C |
| | HCV A156S | C |
| | HCV A156T | D |
| | HCV D168A | D |
| | HCV D168V | D |
| (I-64) | WT | A |
| | HCV A156S | A |
| | HCV A156T | B |
| | HCV D168A | B |
| | HCV D168V | B |
| | Replicon[4] | C |
| | Replicon[4] | C[1] |
| (I-65) | WT | C |
| | HCV A156S | C |
| | HCV A156T | D |
| | HCV D168A | D |
| | HCV D168V | D |
| (I-66) | WT | A |
| | HCV A156S | A |
| | HCV A156T | C |
| | HCV D168A | C |
| | HCV D168V | C |
| | Replicon[4] | B |
| | Replicon[4] | C[1] |
| (I-67) | WT | A |
| | HCV A156S | A |
| | HCV A156T | A |
| | HCV D168A | A |
| | HCV D168V | A |
| | Replicon[4] | B |
| | Replicon[4] | C[1] |
| (I-68) | WT | A |
| | HCV A156S | A |
| | HCV A156T | C |
| | HCV D168A | C |
| | HCV D168V | C |
| | Replicon[4] | A |
| | Replicon[4] | B[1] |
| (I-69) | WT | A |
| | HCV A156S | A |
| | HCV A156T | C |
| | HCV D168A | C |
| | HCV D168V | C |
| (I-70) | WT | A |
| | HCV A156S | A |
| | HCV A156T | A |
| | HCV D168A | A |
| | HCV D168V | A |
| | Replicon[4] | C |
| | Replicon[4] | C[1] |
| (I-71) | WT | A |
| | HCV A156S | A |
| | HCV A156T | C |
| | HCV D168A | C |
| | HCV D168V | C |
| | Replicon[4] | C |
| | Replicon[4] | C[1] |
| (I-72) | WT | A |
| | HCV A156S | A |
| | HCV A156T | C |
| | HCV D168A | C |
| | HCV D168V | D |
| | Replicon[4] | A |
| | Replicon[4] | B[1] |
| (I-73) | WT | A |
| | HCV A156S | B |
| | HCV A156T | B |
| | HCV D168A | C |
| | HCV D168V | D |
| | HCV R155K | B |
| | Replicon[4] | B |
| | Replicon[4] | C[1] |
| (I-74) | WT | A |
| | HCV A156S | A |
| | HCV A156T | B |
| | HCV D168A | C |
| | HCV D168V | C |
| | HCV R155K | B |
| | Replicon[4] | B |
| | Replicon[4] | B[1] |
| (I-75) | WT | A |
| | HCV A156S | B |
| | HCV A156T | C |
| | HCV D168A | D |
| | HCV D168V | C |
| | HCV R155K | C |
| | Replicon[4] | A |
| | Replicon[4] | B[1] |
| (I-77) | WT | A |
| | HCV A156S | B |
| | HCV A156T | C |
| | HCV D168A | C |
| | HCV D168V | D |
| | HCV R155K | B |
| | Replicon[4] | A |
| | Replicon[4] | B[1] |
| (I-83) | WT | B |
| | HCV D168A | D |
| | HCV A156S | D |
| | HCV R155K | D |
| (I-84) | WT | A |
| | HCV A156S | C |
| | HCV A156T | C |
| | HCV D168A | C |
| | HCV D168V | D |
| | Replicon[4] | B |
| | Replicon[4] | C[1] |
| (I-85) | WT | A |
| | HCV A156S | A |
| | HCV A156T | B |

TABLE 6-continued

Enzymatic Data for Exemplary Compounds

| Compound tested | Enzyme/Assay | |
|---|---|---|
| | HCV D168A | B |
| | HCV D168V | C |
| | Replicon[4] | B |
| | Replicon[4] | B[1] |
| (I-86) | WT | A |
| | HCV A156S | B |
| | HCV A156T | C |
| | HCV D168A | C |
| | HCV D168V | C |
| | Replicon[4] | A |
| | Replicon[4] | B[1] |
| (I-87) | WT | A |
| | HCV A156S | A |
| | HCV A156T | B |
| | HCV D168A | C |
| | HCV D168V | D |
| | Replicon[4] | A |
| | Replicon[4] | B[1] |
| (I-88) | WT | A |
| | HCV A156S | B |
| | HCV R155K | D |
| | HCV D168A | C |
| | HCV R155K | D |
| | Replicon[4] | A |
| | Replicon[4] | B[1] |
| (I-91) | WT | A |
| | HCV A156S | B |
| | HCV D168A | D |
| | HCV R155K | C |
| | Replicon | B[2] |
| | Replicon | C[3] |
| (I-92) | WT | A |
| | HCV A156S | A |
| | HCV D168A | C |
| | HCV R155K | B |
| | Replicon | B[2] |
| | Replicon | C[3] |
| (I-95) | WT | A |
| | HCV A156S | A |
| | HCV D168A | C |
| | HCV R155K | B |
| | Replicon | B[2] |
| | Replicon | C[3] |
| (I-96) | WT | A |
| | HCV A156S | A |
| | HCV D168A | C |
| | HCV D168V | C |
| | HCV R155K | B |
| | HCV C159S | A |
| | HCV A156T | B |
| | Replicon | A[2] |
| | Replicon | B[3] |
| (I-97) | WT | A |
| | HCV A156S | B |
| | HCV D168A | C |
| | HCV R155K | C |
| | Replicon | C[2] |
| | Replicon | C[3] |
| (I-98) | WT | B |
| | HCV A156S | B |
| | HCV D168A | C |
| | HCV R155K | C |
| | Replicon | B[2] |
| | Replicon | C[3] |
| (I-99) | WT | A |
| | HCV A156S | B |
| | HCV D168A | D |
| | HCV R155K | C |
| | Replicon | B[2] |
| (I-100) | WT | A |
| | HCV A156S | A |
| | HCV D168A | B |
| | HCV R155K | A |
| | Replicon | B[2] |
| (I[R]-100) | WT | C |
| | HCV A156S | C |
| | HCV D168A | D |
| | HCV R155K | D |
| | Replicon | D[2] |
| (I-101) | WT | A |
| | HCV A156S | A |
| | HCV D168A | C |
| | HCV R155K | B |
| | Replicon | B[2] |
| (I-102) | WT | A |
| | HCV A156S | B |
| | HCV D168A | D |
| | HCV R155K | B |
| | Replicon | A[2] |
| | Replicon | B[3] |
| (I-103) | WT | B |
| | HCV A156S | B |
| | HCV D168A | B |
| | HCV R155K | C |
| (I-104) | WT | A |
| | HCV A156S | A |
| | HCV D168A | B |
| | HCV R155K | B |
| (I-105) | WT | A |
| | HCV A156S | A |
| | HCV D168A | C |
| | HCV R155K | B |
| | HCV C159S | C |
| | HCV D168V | C |
| | HCV A156T | A |
| | Replicon | B[2] |
| (I-106) | WT | A |
| | HCV A156S | A |
| | HCV D168A | C |
| | HCV R155K | B |
| | HCV C159S | C |
| | HCV D168V | C |
| | HCV A156T | A |
| | Replicon | B[2] |
| (I-107) | WT | A |
| | HCV A156S | B |
| | HCV D168A | D |
| | HCV R155K | D |
| | HCV C159S | B |
| | Replicon | C[2] |
| (I-108) | WT | A |
| | HCV A156S | B |
| | HCV D168A | D |
| | HCV R155K | D |
| | HCV C159S | C |
| | Replicon | C[2] |
| (I-109) | WT | A |
| | HCV A156S | C |
| | HCV D168A | D |
| | HCV R155K | C |
| | HCV C159S | C |
| | Replicon | C[2] |
| (I-110) | WT | A |
| | HCV A156S | C |
| | HCV D168A | D |
| | HCV R155K | C |
| | HCV C159S | B |
| | Replicon | B[2] |
| (I-114) | WT | A |
| | HCV A156S | B |
| | HCV D168V | D |
| | HCV R155K | C |
| | Replicon | B[2] |
| (I-129) | WT | A |
| | HCV A156S | A |
| | HCV D168A | C |
| | HCV R155K | B |
| | Replicon | A[2] |
| (I-130) | WT | B |
| | HCV A156S | A |
| | HCV D168A | C |

TABLE 6-continued

Enzymatic Data for Exemplary Compounds

| Compound tested | Enzyme/Assay | |
|---|---|---|
| | HCV R155K | B |
| | Replicon | C[2] |
| (I-131) | WT | A |
| | HCV A156S | A |
| | HCV D168A | B |
| | HCV R155K | B |
| | Replicon | C[2] |
| (I-132) | WT | A |
| | HCV A156S | A |
| | HCV D168A | A |
| | HCV R155K | A |
| | Replicon | C[2] |
| (I-133) | WT | A |
| | HCV A156S | A |
| | HCV D168A | C |
| | HCV R155K | B |
| (I-134) | WT | A |
| | HCV A156S | A |
| | HCV D168A | C |
| | HCV R155K | B |
| (I-135) | WT | A |
| | HCV A156S | A |
| | HCV D168A | A |
| | HCV R155K | A |
| | Replicon | B[2] |
| (I-136) | WT | A |
| | HCV A156S | A |
| | HCV D168A | C |
| | HCV R155K | C |
| | Replicon | A[2] |
| (I-137) | WT | B |
| | HCV A156S | C |
| | HCV D168A | D |
| | HCV R155K | D |
| (I-138) | WT | A |
| | HCV A156S | A |
| | HCV D168A | B |
| | HCV R155K | A |
| | Replicon | C[2] |
| (I-139) | WT | A |
| | HCV A156S | A |
| | HCV D168A | A |
| | HCV R155K | A |
| | Replicon | B[2] |
| (I-140) | WT | A |
| | HCV A156S | A |
| | HCV D168A | B |
| | HCV R155K | A |
| | Replicon | C[2] |
| (I-141) | WT | A |
| | HCV A156S | A |
| | HCV D168A | C |
| | HCV R155K | B |
| | Replicon | A[2] |
| (I-142) | WT | A |
| | HCV A156S | A |
| | HCV D168A | C |
| | HCV R155K | B |
| (I-143) | WT | A |
| | HCV A156S | A |
| | HCV D168A | D |
| | HCV R155K | C |

[1]Designates IC$_{90}$ value (nM).
[2]Designates EC$_{50}$ value (nM). Data collected from assay described in Example 35.
[3]Designates EC$_{90}$ value (nM). Data collected from assay described in Example 35.
[4]Data collected from assay described in Example 22.

Example 25

Mass spectrometric analysis of HCV wild type or HCV variant C159S in the presence of test compound was performed. 100 pmols of HCV wild type (Bioenza Calif.) was incubated with compound for 1 hr and 3 hrs at 10-fold access of (1-3) to protein. 1 ul aliquots of the samples (total volume of 4.24 ul) were diluted with 10 ul of 0.1% TFA prior to micro C4 ZipTipping directly onto the MALDI target using Sinapinic acid as the desorption matrix (10 mg/ml in 01% TFA: Acetonitrile 50:50). Analyses were performed on a Shimadzu Biotech Axima TOF$^2$ (Shimadzu Instruments) matrix-assisted-laser desorption/ionization Time-of-Flight (MALDI-TOF) mass spectrometer. The same procedure was carried out on 100 pmols of HCV C159S mutant of HCV protease for 3 hrs at 10-fold excess of (I-3) to protein.

Figure 1:
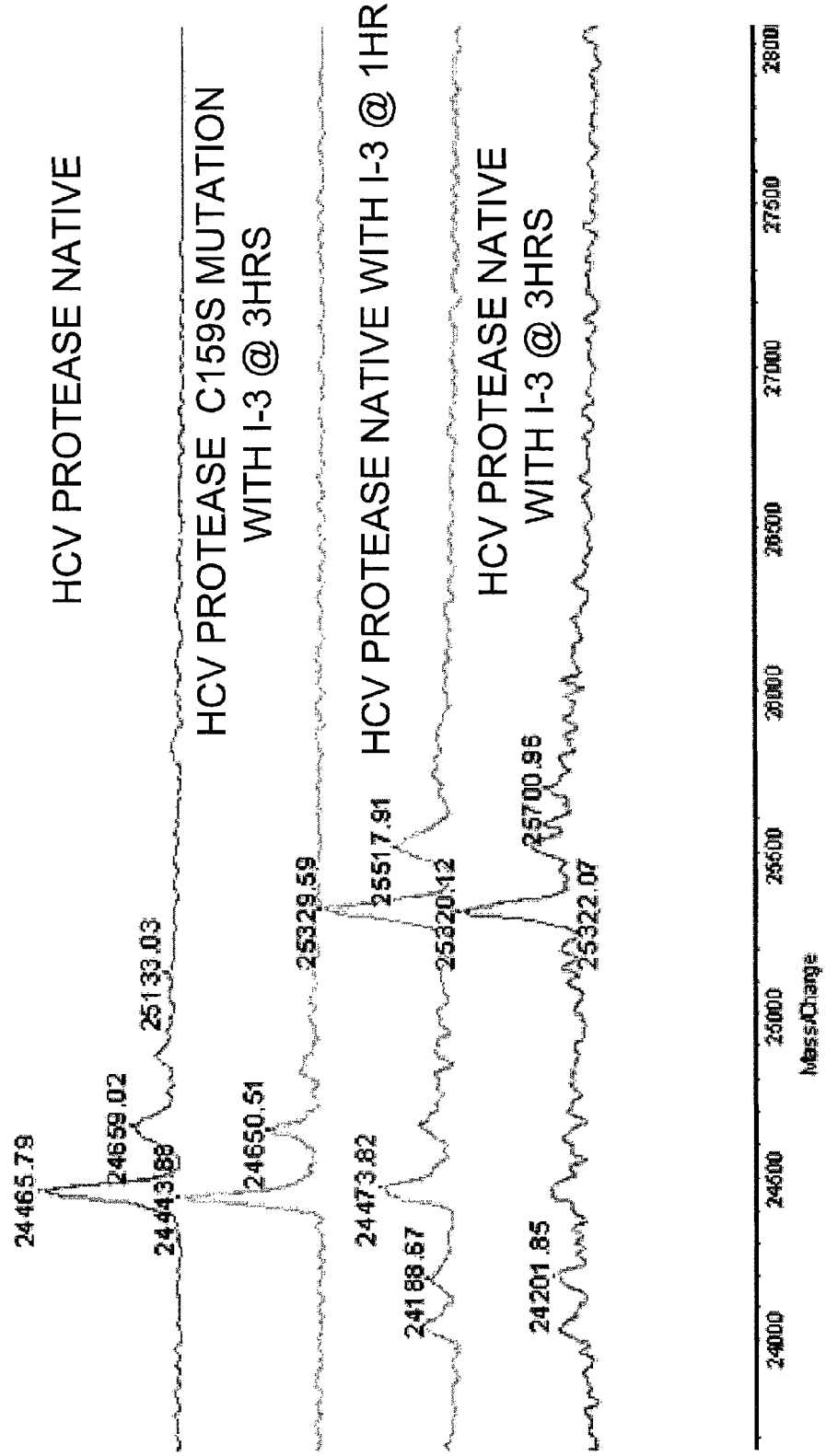
FIG. 1 depicts a mass spectroscopic analysis of HCV NS3/4A wild-type protease domain or HCV variant C159S in the presence of test compound (I-3).

Intact HCV protein occurred at MH+ of 24465 with corresponding sinapinic (matrix) adducts occurring about 200 Da higher. A stochiometric incorporation of the (I-3) compound (MW of 852 Da) occurred, producing a new mass peak which is approximately 850-860 Da higher (MH+ of 25320-25329). (FIG. 1) This is consistent with incorporation of a single molecule of (I-3). As depicted in FIG. 1, significant reaction occurred even after 1 hr at the 10× concentration of compound with nearly complete conversion after 3 hrs at the 10× concentration. The C159S variant form of the enzyme did not show any evidence of modification which confirms that the compound is modifying the Cys 159.

Figure 11:
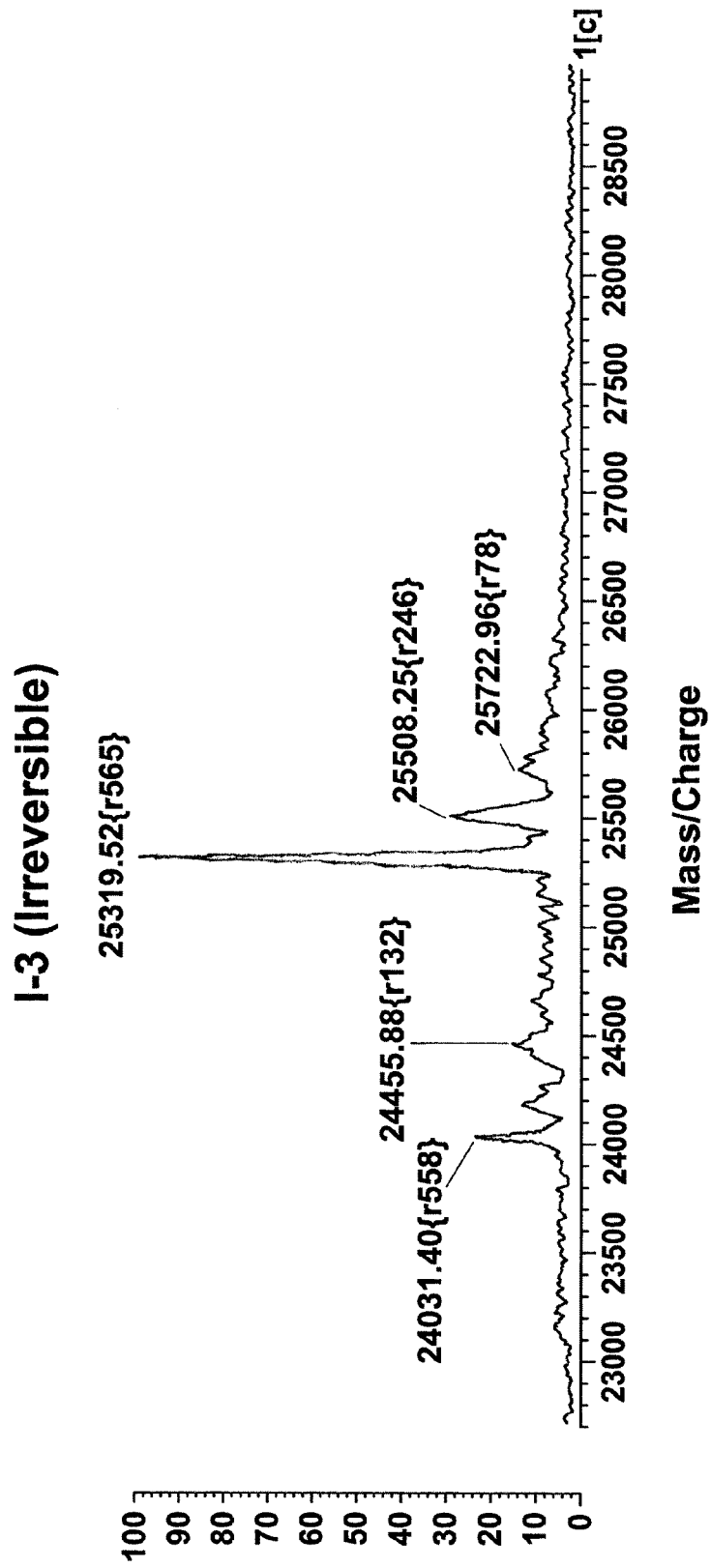

As depicted in FIGS. 11-11B, compound I-3 as compared to its reversible counterpart, compound I$^R$-3 and compared to no test compound with HCV wild type.

Example 26

As depicted in FIGS. 2, 3, 4, and 5, mass spectrometric analysis of HCV wild type or HCV mutants in the presence of test compound (I-3) was performed. HCV Mutants (A156S), (A156T), (D168A), and (D168V) were incubated for 1 hr and 3 hrs at a 10× fold access of (I-3) to protein. 1 ul aliquots of the samples were diluted with 10 ul of 0.1% TFA prior to micro C4 ZipTipping directly onto the MALDI target using Sinapinic acid as the desorption matrix (10 mg/ml in 0.1% TFA: Acetonitrile 50:50).

Figure 2:
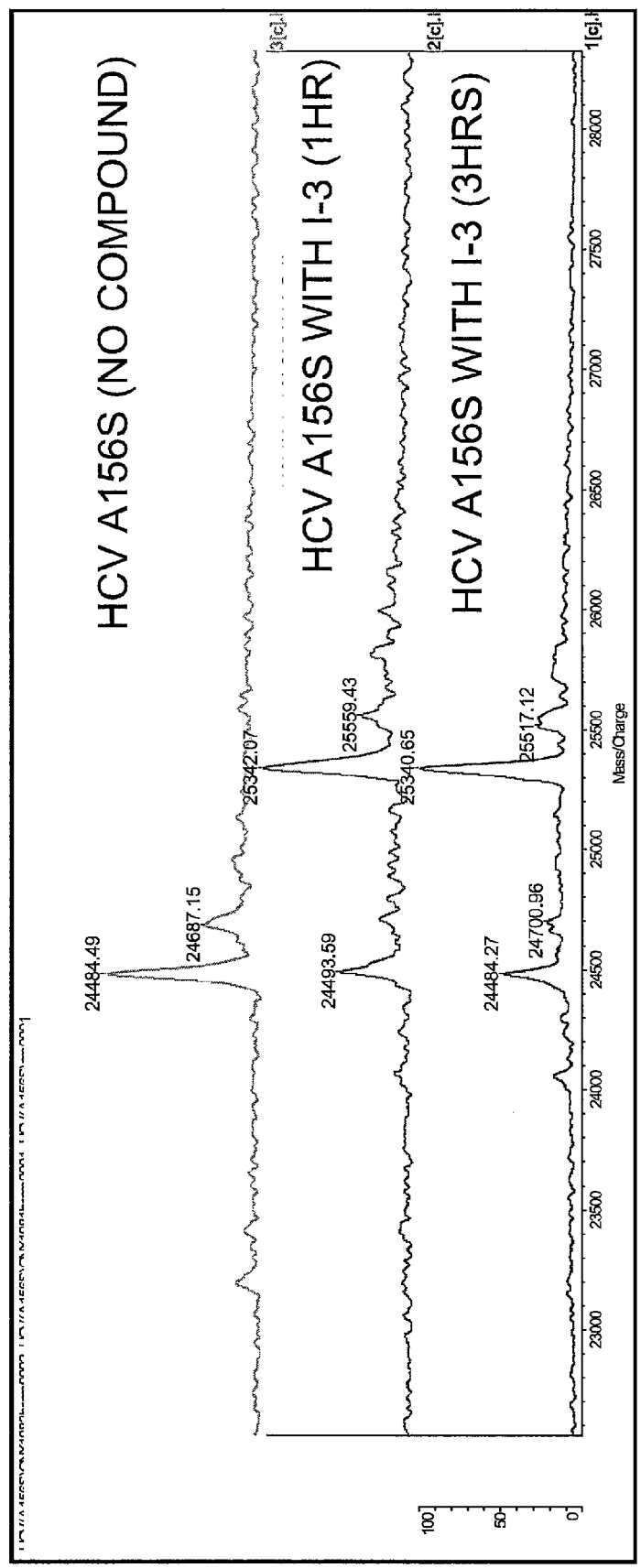
FIG. 2 depicts a mass spectroscopic analysis of HCV NS3/4A mutant A156S in the presence of test compound (I-3).

HCV(A156S): As can be seen in FIG. 2, compared to the protein with no compound, the protein incubated with (I-3) has reacted significantly to produce a new species at Mw 25,340 which is approximately 855 Da heavier in good agreement with the mass of compound (I-3) at 853 Da. There was very little change in conversion from a 1 hour reaction to the 3 hour reaction.

Figure 3:
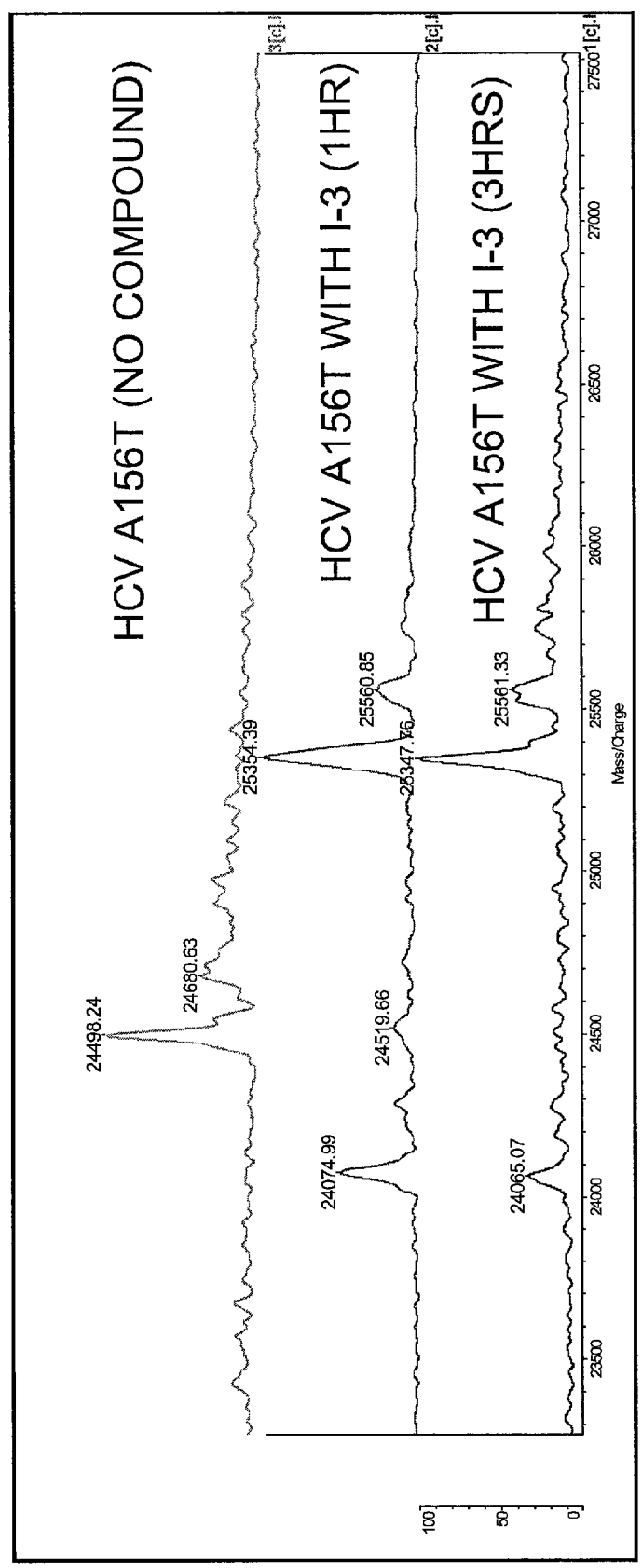
FIG. 3 depicts a mass spectroscopic analysis of HCV NS3/4A mutant A156T in the presence of test compound (I-3).

HCV(A156T): As depicted in FIG. 3, in the case of the HCV(A156T) mutant near complete reactivity was observed even at the 1 hour reaction time. Again there is good agreement in the mass difference between the new species at approximately 25,350 and the unreacted mutant at 24,498 which is 852 Da.

Figure 4:
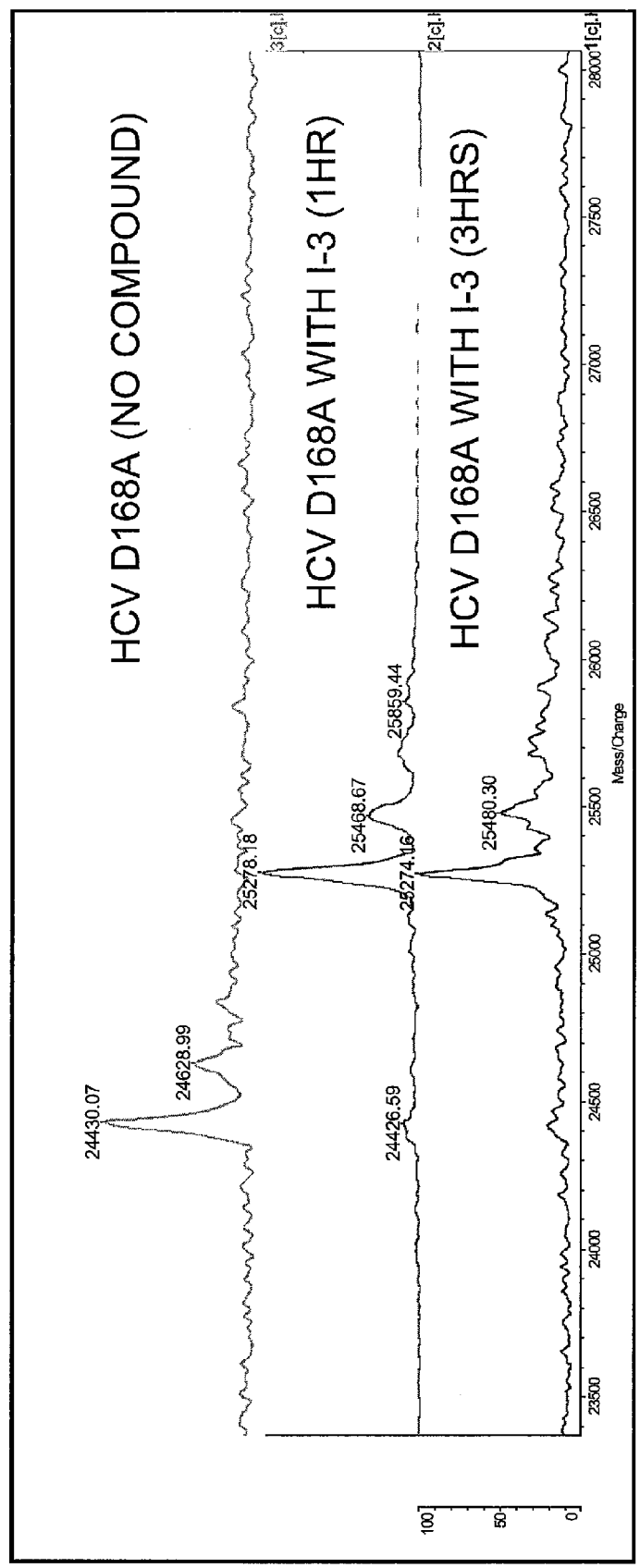
FIG. 4 depicts a mass spectroscopic analysis of HCV NS3/4A mutant D168A in the presence of test compound (I-3).

HCV(D168A): As depicted in FIG. 4, for the HCV (D168A) mutant there is nearly complete conversion even after 1 hour reaction time. In this case the mass difference between the new species at 25,278 and the unreacted at 24,430 is 848 Da again in good agreement with the mass of I-3.

Figure 5:
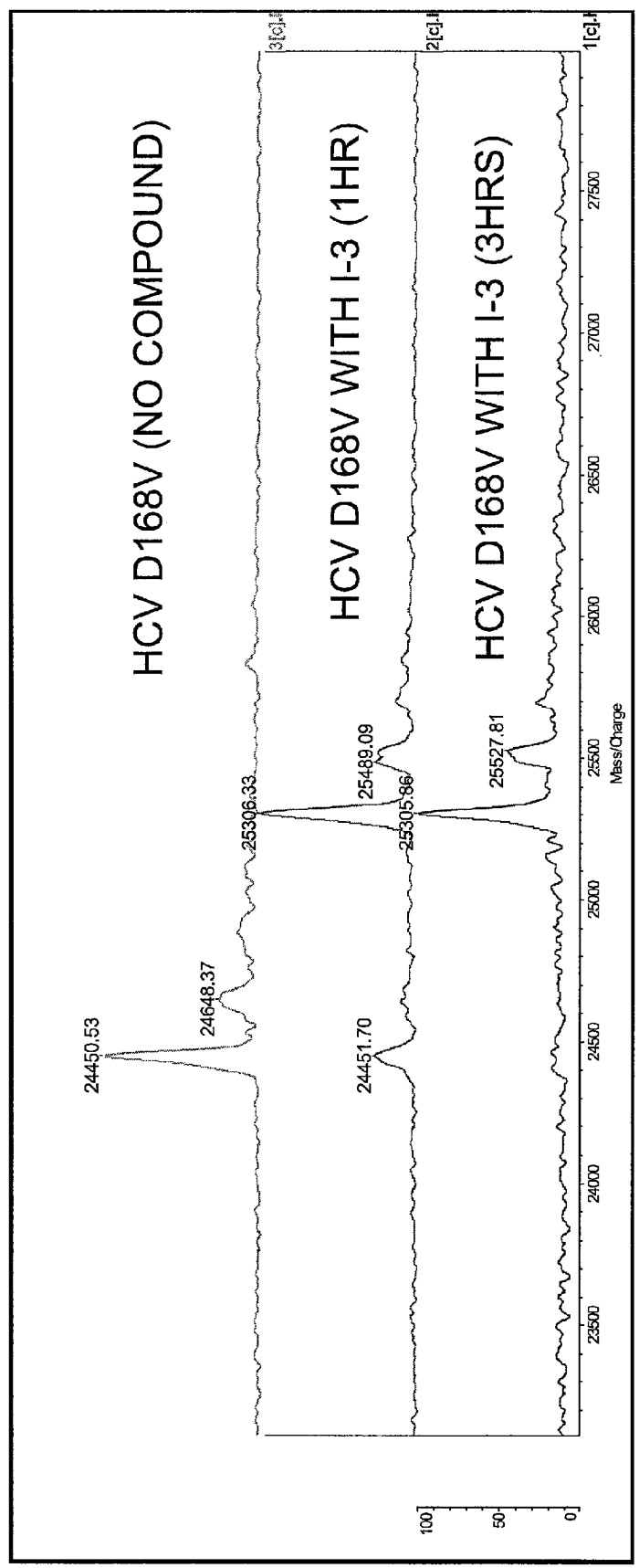
FIG. 5 depicts a mass spectroscopic analysis of HCV NS3/4A mutant D168V in the presence of test compound (I-3).
Figure 6:
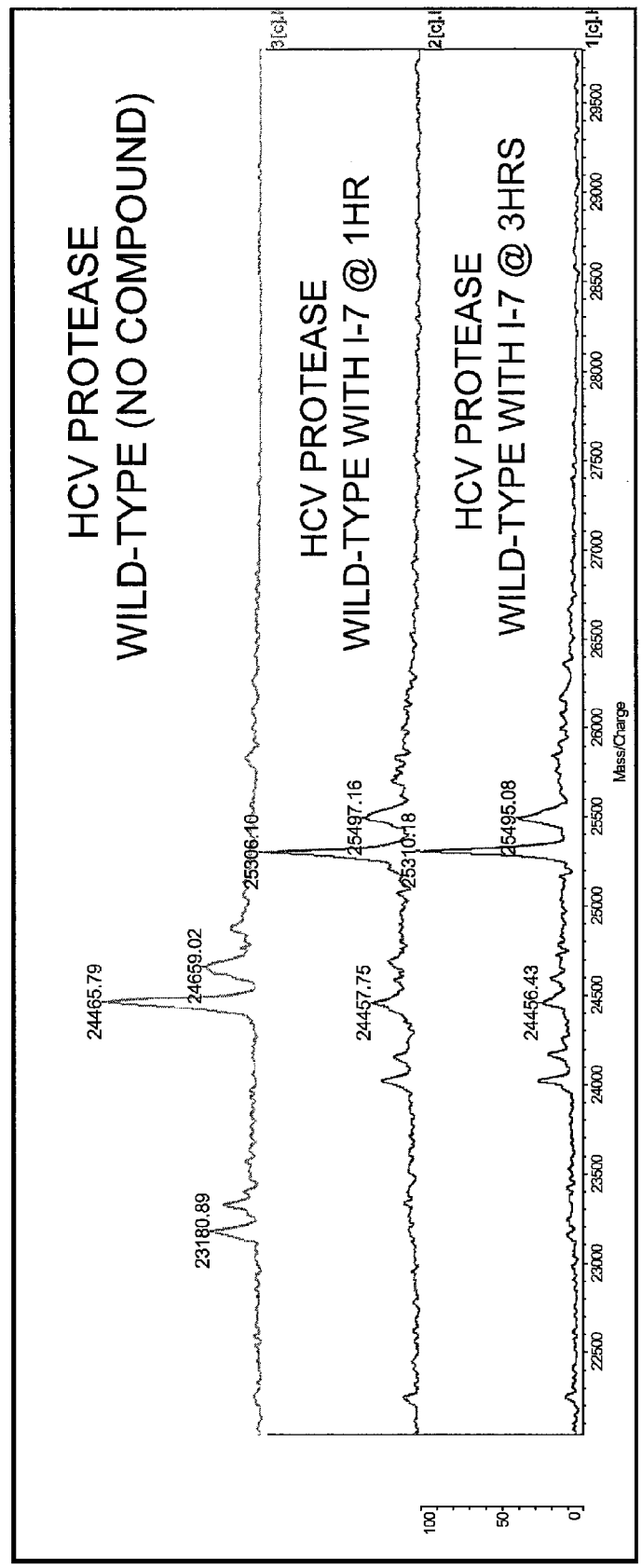
FIG. 6 depicts a mass spectroscopic analysis of HCV NS3/4A wild type in the presence of test compound (I-7).
Figure 7:
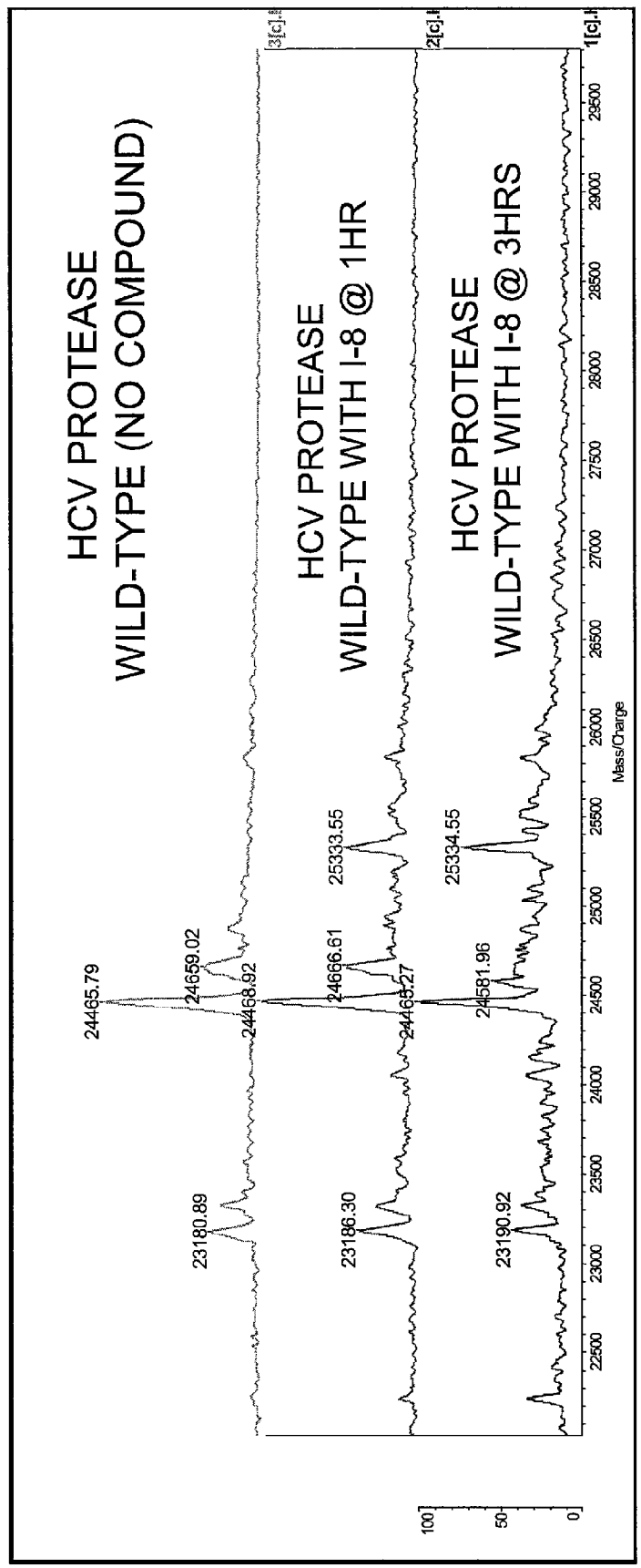
FIG. 7 depicts a mass spectroscopic analysis of HCV NS3/4A wild type in the presence of test compound (I-8).
Figure 8:
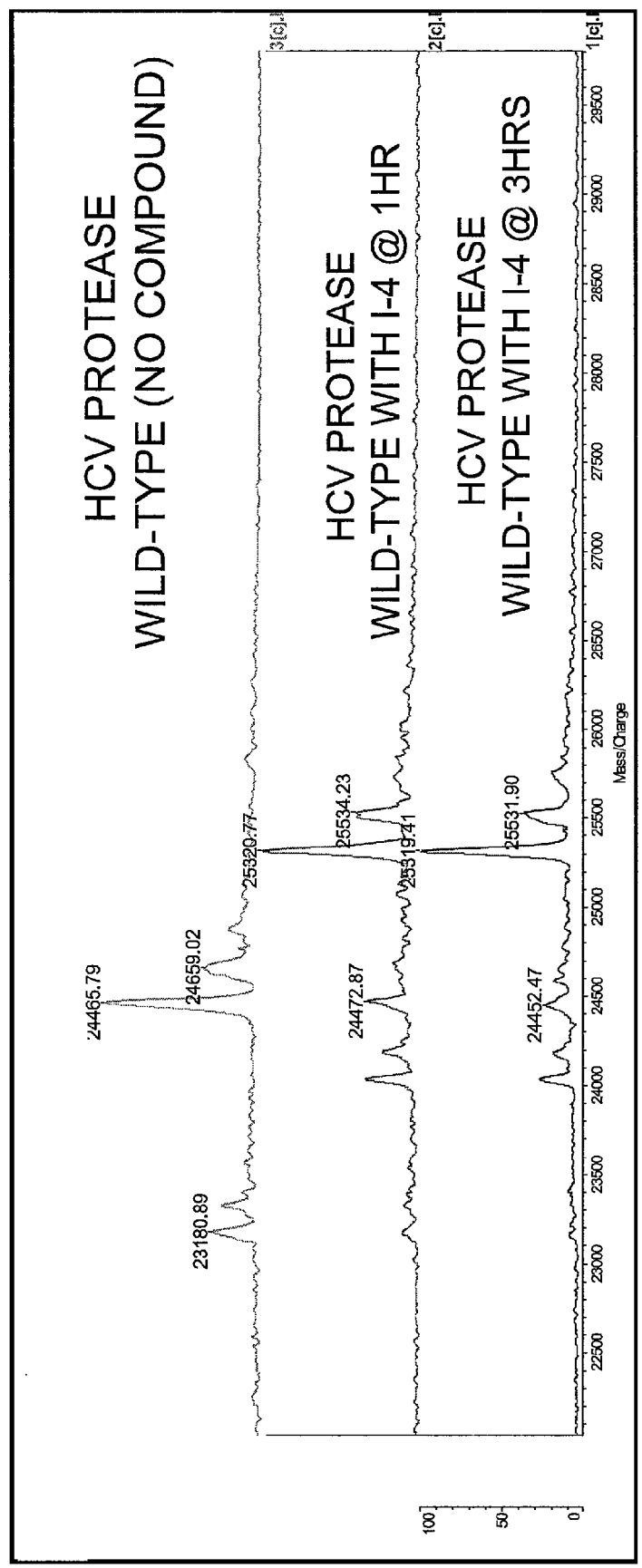
FIG. 8 depicts a mass spectroscopic analysis of HCV NS3/4A wild type in the presence of test compound (I-4).
Figure 9:
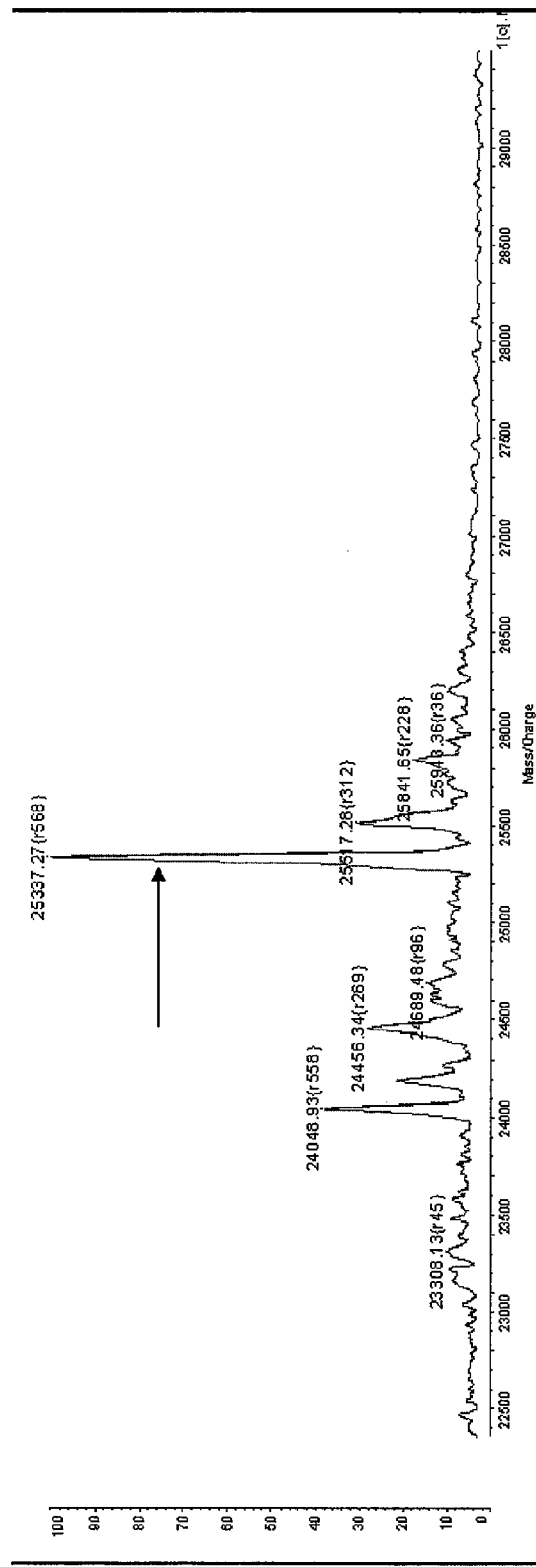
FIG. 9 depicts a mass spectroscopic analysis of HCV NS3/4A wild type in the presence of test compound I-9.
Figure 10:
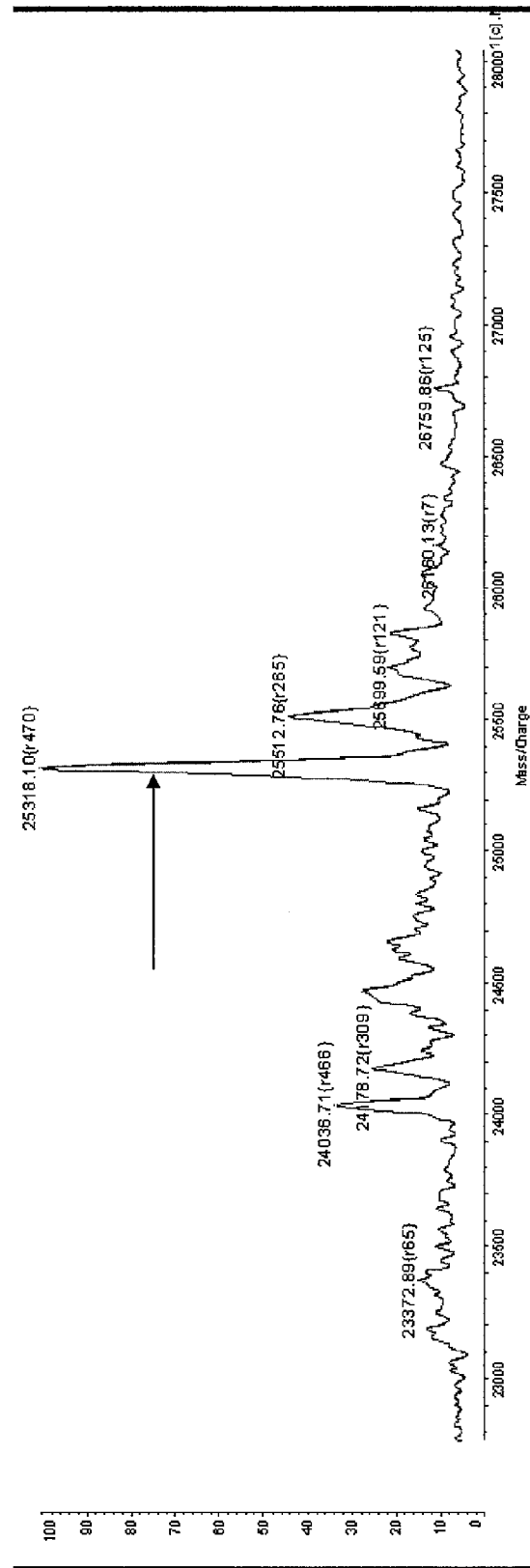
FIG. 10 depicts a mass spectroscopic analysis of HCV NS3/4A wild type in the presence of test compound I-10.

HCV(D168V): As depicted in FIG. 5, for the HCV (D168V) mutant there is complete conversion after 3 hours reaction time. Again the mass difference between the new species (25,305) and the unreacted mutant (24,450) is consistent with the mass of compound I-3.

As depicted in FIGS. 6, 7, 8, 9, and 10, mass spectrometric analysis of HCV wild type in the presence of test compounds I-7, I-8, I-4, I-9, and I-12 was performed, and the appropriate mass spec shifts expected from covalent modification of HCV with each respective compound were observed.

Example 27

Mass spectrometric analysis of HCV wild type (genotype 1b) in the presence of test compounds I-73 and I-75 was performed using the following protocol: HCV NS3/4A wild type (wt) was incubated for 1 hr at a 10× fold access of test compound to protein. 2 ul aliquots of the samples were diluted with 10 ul of 0.1% TFA prior to micro C4 ZipTipping directly onto the MALDI target using Sinapinic acid as the desorption matrix (10 mg/ml in 0.1% TFA:Acetonitrile 50:50). For intact protein mass measurement the instrument was set in Linear mode using a pulsed extraction setting of 24,500 and apomyoglobin as the standard to calibrate the instrument.

As depicted in FIG. 13, after 1 hour reaction there was near complete conversion to a new mass. The first mass peak of 25256 Da showed a mass increase of 789 Da which is consistent with the mass of I-73 (790 Da). Similarly, for compound I-73 covalent modification was observed with the D168A mutant.

As depicted in FIG. 14, after 1 hour reaction there was conversion to a new peak at MH+ of 25282 which is 815 Da heavier and is consistent with the mass of I-75 (817 Da). Substantial conversion was also observed with compound I-75 against the D168A mutant when run for 1 hr and longer.

Compound I-50 was tested in a similar fashion, and after 1 hour reaction time, measurable covalent modification of HCV NS3/4A wt was observed.

Example 28

Mass spectrometric analysis of HCV NS3/4A genotypes 1a, 1b, 2a, and 3a in the presence of test compound I-96 was performed using the following protocol: HCV NS3/4A was incubated for 3 hr at a 10× fold access of test compound to protein. 2 ul aliquots of the samples were diluted with 10 ul of 0.1% TFA prior to micro C4 ZipTipping directly onto the MALDI target using Sinapinic acid as the desorption matrix (10 mg/ml in 01% TFA:Acetonitrile 50:50). For intact protein mass measurement the instrument was set in Linear mode using a pulsed extraction setting of 24,500 and apomyoglobin as the standard to calibrate the instrument. After 3 hours reaction, measurable covalent modification of each HCV NS3/4A genotype was observed.

Compound I-27 was tested in a similar fashion with HCV NS3/4A wt (genotype 1b), and after 3 hours reaction time, near complete covalent modification of HCV NS3/4A wt was observed.

Example 29

Modification of Cys159 of Wild-Type HCV Protease using a Tryptic Digest Strategy HCV was incubated with test compound I-3 for 3 hrs prior to tryptic digestion. Todoacetamide was used as the alkylating agent after compound incubation. For tryptic digests a 2 ul aliquot (0.06 ug/ul) was diluted with 10 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

For tryptic digests the instrument was set in Reflectron mode with a pulsed extraction setting of 1800. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

The modification appeared on the tryptic peptide AAVCTR. The mass of the modified peptide is in agreement with the mass of the peptide (MH$^+$ 620.32)+I-3 (852.31)= 1472.63. No other modified peptides were observed in the various digests. CID analysis of the compound at 853.20 shows a signature fragment at 252. See FIGS. 12-12A.

Example 30

Cell Culture

Huh-luc/neo-ET, Huh7-Lunet were obtained from ReBLikon Gmbh (Heidelberg, Germany). Cells were grown in Dulbecco modified Eagle medium (DMEM; Invitrogen) supplemented with 2 mM L-glutamine, nonessential amino acids, 100 U of penicillin/ml, 100 μg of streptomycin/mL, and 10% fetal bovine serum. G418 (Geneticin; Invitrogen) was added at a final concentration of 400 ug//mL. Huh7-Lunet were grown in the absence of G418.

Example 31

Mutant Constructs

Constructs containing clinically relevant mutations were generated by performing site-directed mutagenesis on the pFK-I389-luc-ubi-neo-NS3-3'ET plasmid (ReBLikon Gmbh (Heidelberg, Germany)). using the QuickChange II Site-Directed Mutagenesis Kit (Stratagene, La Jolla, Calif.) according to manufacturer's directions and with the primers described in Table 7, below.

TABLE 7

Primer sequence used to establish Mutant Replicon cell lines.

| | | |
|---|---|---|
| NS3-A156S-F | GCTGTGGGCATCTTTCGGTCTGCCGT GTGCACCCGAGGG | SEQ ID NO: 66 |
| NS3-A156S-R | CCCTCGGGTGCACACGGCAGACCGAA AGATGCCCACAGC | SEQ ID NO: 67 |
| NS3-A156T-F | GCTGTGGGCATCTTTCGGACTGCCGT GTGCACCCGAGGG | SEQ ID NO: 68 |
| NS3-A156T-R | CCCTCGGGTGCACACGGCAGTCCGAA AGATGCCCACAGC | SEQ ID NO: 69 |
| NS3-D168A-F | GGGGTTGCGAAGGCGGTGGCCTTTGT ACCCGTCGAGTCT | SEQ ID NO: 70 |
| NS3-D168A-R | AGACTCGACGGGTACAAAGGCCACCG CCTTCGCAACCCC | SEQ ID NO: 71 |
| NS3-D168V-F | GGGGTTGCGAAGGCGGTGGTCTTTGT ACCCGTCGAGTCT | SEQ ID NO: 72 |
| NS3-D168V-R | AGACTCGACGGGTACAAAGACCACCG CCTTCGCAACCCC | SEQ ID NO: 73 |
| NS3-C159S-F | ATCTTTCGGGCTGCCGTGAGCACCCG AGGGGTTGCGAAG | SEQ ID NO: 74 |
| NS3-C159S-R | CTTCGCAACCCCTCGGGTGCTCACGG CAGCCCGAAAGAT | SEQ ID NO: 75 |
| NS3-R155K-F | CACGCTGTGGGCATCTTTAAGGCTGC CGTGTGCACCCGA | SEQ ID NO: 76 |
| NS3-R155K-R | TCGGGTGCACACGGCAGCCTTAAAGA TGCCCACAGCGTG | SEQ ID NO: 77 |

Example 32

In Vitro Transcription

In vitro transcripts of HCV positive strands were generated by using the protocol described by Lohmann V et al., J. Virol., 77:3007-3019, 2003. For transcription of positive-strand HCV RNAs, plasmid DNA (pFK 1341 PI-Luc/NS3-3'/ET, obtained from ReBLikon Gmbh (Heidelberg, Germany)), was digested with AseI followed by ScaI. After restriction digest, DNA was extracted with phenol and chloroform, precipitated with ethanol, and dissolved in RNase-free water. In vitro transcription reactions contained 80 mM HEPES (pH 7.5), 12 mM $MgCl_2$, 2 mM spermidine, 40 mM dithiothreitol, a 3.125 mM concentration of each nucleoside triphosphate, 1 U of RNasin. 5 ug of restricted plasmid DNA and 80 U of T7 RNA polymerase (Promega) was used. After 2 h at 37° C., an additional 40 U of T7 polymerase was added, and the reaction was incubated for another 2 h. Transcription was terminated by the addition of 1 U of RNase-free DNase (Promega) per ug of plasmid DNA, followed by incubation for 30 min at 37° C. After extraction with acidic phenol and chloroform, RNA was precipitated with isopropanol and dissolved in RNase-free water. The concentration was determined by measurement of the optical density at 260 nm (OD260), and RNA integrity was checked by denaturing agarose gel electrophoresis.

Example 33

Transfection of HCV Full Length Genome and Selection of Stable Cell Lines $7 \times 10^4$ Huh7-Lunet cells were seeded over night in a 12 well plate, the next day 1 ug of RNA/well was transfected using Mirus Tx (Madison, Wis.) kit. Transfection was performed according to manufacturer's instructions, and 24 hours after transfection cells were either subjected to Luciferase assay or subjected to G418 (400 ug/ml) selection in order to establish stable cell lines.

Example 34

Inhibition of Protease Self Cleavage

Huh-7-Luc-Neo-ET cells were plated in Replicon Assay Medium (RPMI supplemented with 5% FBS, 1× non-essential amino acids and pen/strep) at a density of $1 \times 10^5$ cells/well in 12 well plates. Eight hours later the media was removed and replaced with 1 ml media containing test compound (5 wells per compound) and 0.02% DMSO and the cells were returned to the incubator overnight. Sixteen hours later 1 well from each compound and 1 untreated well were washed with PBS, then lysed and scraped into 30 ul of Cell Extraction Buffer (Biosource, Camarillo, Calif.) plus Complete Protease Inhibitor (Roche, Indianapolis, Ind.). The remaining wells were rinsed 2× with PBS then fed with Replicon Media and returned to the incubator. Cells were washed once every hour by removing the old media and replacing it with fresh media and were lysed and collected at 4, 12, 24, and 48 hours following the first collection.

Cell lysates were separated by SDS-Page (4-20%) and transferred to Immobilon-P PVDF membrane (Millipore Corporation, Mass.) and blotted with polyclonal anti NS3 antibody (Bioenza, Calif.). Blots were scanned on an Odyssey infrared scanner from Licor and the FL band and cleavage products were quantified separately using the Licor software provided with the scanner. The cleavage product was calculated as a percentage of the total NS3 in each sample and then normalized to the DMSO control so that the DMSO control reflects 100% activity.

Results and Discussion

When protease activity is inhibited, self-cleavage is abolished and the only protein species detectable is the holoenzyme. After 16 hours of continuous exposure of the replicon cells to NS3 inhibitor compound, the self-cleavage products were undetectable in the treated samples, but readily detectable in the not treated control replicon cells. Prolonged duration of action was demonstrated by exposing the replicon cells to a protease inhibitor for 16 hours, at which time the compound was removed, and the replicon cells were repeatedly washed for several more hours. Covalent irreversible NS3 inhibitors demonstrated sustained inhibition of NS3 internal self-cleavage activity for up to 48 hours, whereas the protease self-cleavage activity rapidly returned when using reversible compounds (FIGS. 17-17A and FIG. 18).

Specifically, FIGS. 15 and 16 depict luciferase activity, using a replicon assay, in the presence of varying concentrations of two HCV protease inhibitors, Compound I-R and Compound I-50, at 24 h, 48 h and 96 h. Compound I-R is a non-covalent inhibitor whereas Compound I-50 is an irreversible covalent inhibitor. Despite differences in the mechanism of action of the two compounds on the protease, the replicon assay shows similar results, due to the indirect nature of the assay readout.

FIGS. 17-17A depict two irreversible covalent inhibitors (compound I-96 and compound I-102) of NS3 protease demonstrate prolonged inhibition of NS3 protease activity in the wild-type replicon cells, as measured by self-cleavage, after the compounds are removed. Compounds were incubated with replicon cells for 16 hours and then removed (time 0). Even up to 48 hours after removal of covalent irreversible NS3 inhibitors, NS3 self-cleaving activity is inhibited by at least 50%, whereas a reversible drug, VX-950, shows virtually complete return of activity in as little as 4 hours after drug removal.

FIG. 18 depicts another covalent inhibitor of NS3 protease, compound I-54, demonstrates prolonged inhibition of NS3 protease activity in the wild-type replicon cells, as measured by self-cleavage, up to 24 hours after the compound is removed. The irreversible covalent inhibitor compound I-54 demonstrates virtually complete inhibition up to 24 hours after compound removal whereas the reversible drug, VX-950, shows complete return of activity in as little as 4 hours after drug removal.

FIG. 19 depicts a covalent protease inhibitor, compound I-54, demonstrates prolonged inhibition of NS3 protease activity in modified replicon system where the NS3 protease contains a clinically observed mutation that alters an amino acid from arginine to lysine at position 155 (R155K). This mutation results in clinical drug resistance to protease inhibitors. FIG. 19 depicts that, even with this mutation, irreversible covalent drugs can inhibit activity from the mutant protease for at least 24 hours after compound removal.

Example 35

Luciferase Assay

The compounds were assayed to evaluate the antiviral activity and cytotoxicity of compounds using replicon-derived luciferase activity. This assay used the cell line ET (luc-ubi-neo/ET), which is a human Huh7 hepatoma cell line that contains an HCV RNA replicon with a stable luciferase (Luc) reporter and cell culture-adaptive mutations. The ET cell line was grown in a 5% $CO_2$ incubator at 37° C. in Dulbecco's modified essential media (DMEM) supplemented with 2 mM L-glutamine, nonessential amino acids, 100 U of penicillin/ml, 100 μg of streptomycin/mL, and 10% fetal bovine serum. G418 (Geneticin; Invitrogen) was added at a final concentration of 400 ug//mL.

All cell culture reagents were obtained from Invitrogen (Carlsbad). Cells were trypsinized (1% trypsin:EDTA) and plated out at $5 \times 10^3$ cells/well in white 96-well assay plates (Costar) dedicated to cell number (cytotoxicity) or antiviral activity assessments. Test compounds were added at six 3-fold concentrations each and the assay was run in DMEM, 5% FBS, 1% pen-strep, 1% glutamine, 1% non essential amino acid. Human interferon alpha-2b (PBL Biolabs, New Brunswick, N.J.) was included in each run as a positive control compound. Cells were processed 72 hr post test compound addition when the cells were still subconfluent. Antiviral activity was measured by analyzing replicon-derived luciferase activity using the Steady-Glo Luciferase Assay System (Promega, Madison, Wis.) according to manufacturer's instruction. The number of cells in each well was determined by Cell Titer Blue Assay (Promega). Compound profile was derived by calculating applicable $EC_{50}$ (effective concentration inhibiting virus replication by 50%), $EC_{90}$ (effective concentration inhibiting virus replication by 90%), $IC_{50}$ (concentration decreasing cell viability by 50%) and $SI_{50}$ (selective index: $EC_{50}/IC_{50}$) values.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

---

We claim:

1. A compound of formula I:

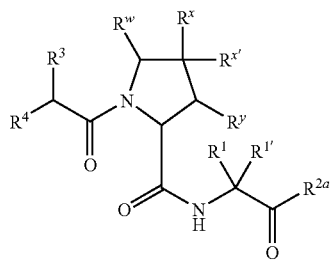

I or a pharmaceutically acceptable salt thereof, wherein:
$R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
$R^{2a}$ is —OH or —NHSO$_2$R$^2$;
$R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or:
two R on the same nitrogen atom are taken together with the nitrogen to form a 4-7 membered heterocyclic ring having 1-2 heteroatoms independently selected from nitrogen, oxygen, or sulfur;
$R^3$ is selected from the group consisting of:

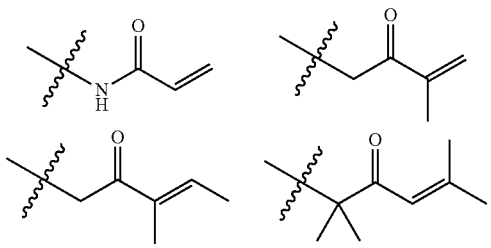

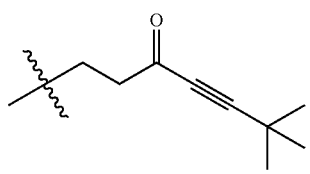

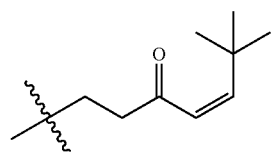

-continued

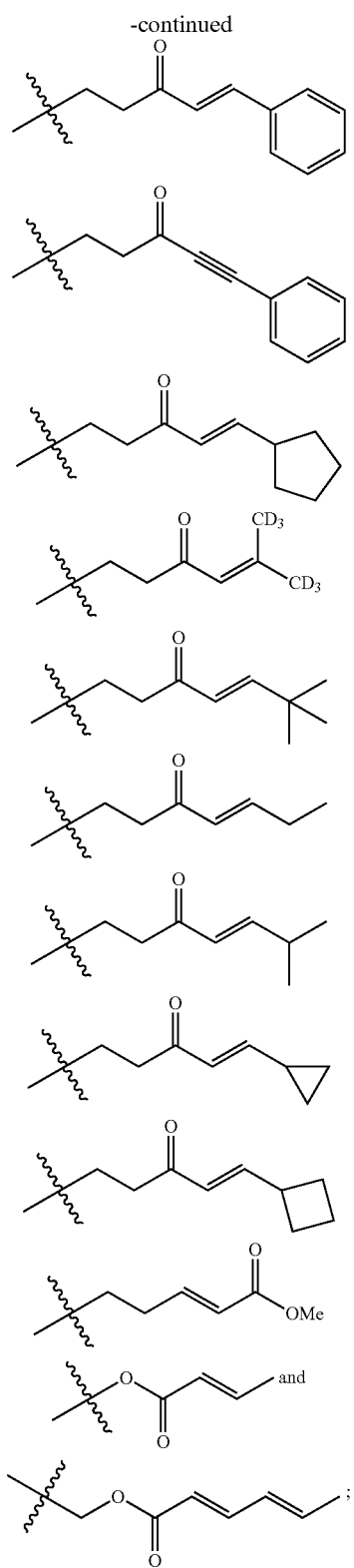

$R^w$ is hydrogen or an optionally substituted group selected from $C_{1-6}$ aliphatic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur: or $R^w$ and $R^x$ are taken together to form an optionally substituted $C_{3-7}$ membered ring having 0-2 heteroatoms independently selected from nitrogen, oxygen or sulfur, or:

$R^w$ and $R^y$ are taken together to form an optionally substituted $C_{3-7}$ membered ring having 0-2 heteroatoms independently selected from nitrogen, oxygen or sulfur;

$R^x$ is -T-$R^z$, wherein:
T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and $R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^{x'}$ is hydrogen, or $R^{x'}$ and $R^x$ are taken together with their intervening atoms to form an optionally substituted spiro-fused 5-7 membered ring having 0-2 heteroatoms independently selected from nitrogen, oxygen, or sulfur;

$R^y$ is hydrogen, or $R^x$ and $R^y$ are taken together to form an optionally substituted $C_{3-7}$ membered ring having 0-2 heteroatoms independently selected from nitrogen, oxygen or sulfur;

$R^4$ is H, —NHC(O)$R^5$, —NHC(O)O$R^6$,

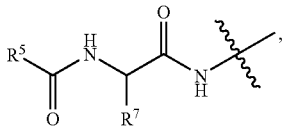

a natural or unnatural amino acid side-chain group; or $R^4$ and Rx are taken together with their intervening atoms to form an optionally substituted, saturated or unsaturated 16-22 membered ring having 2-6 heteroatoms independently selected from nitrogen, oxygen, or sulfur;

each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and $R^7$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

wherein when $R^3$ is

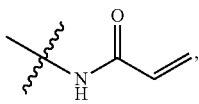

$R^4$ is an unnatural amino acid side-chain group of threonine substituted with one, two, or three methyl groups.

2. The compound according to claim 1, wherein said compound is of formula II-a or II-b:

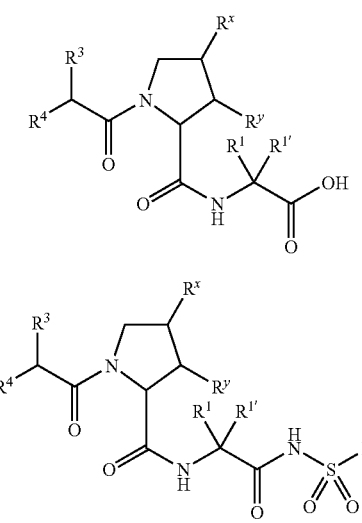

or a pharmaceutically acceptable salt thereof, wherein:
  $R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
  $R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
  each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
  $R^x$ is -T-$R^z$, wherein:
    T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and
    $R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^y$ is hydrogen or $R^x$ and $R^y$ are taken together to form an optionally substituted $C_{3-7}$ membered carbocycle;
  $R^4$ is H, —NHC(O)$R^5$, —NHC(O)O$R^6$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur;
  each $R^5$ is independently —N(R)$_2$ or an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and
  $R^6$ is an optionally substituted group selected from $C_{1-6}$ aliphatic, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

3. The compound according to claim 1, wherein said compound is of formula III-a or III-b:

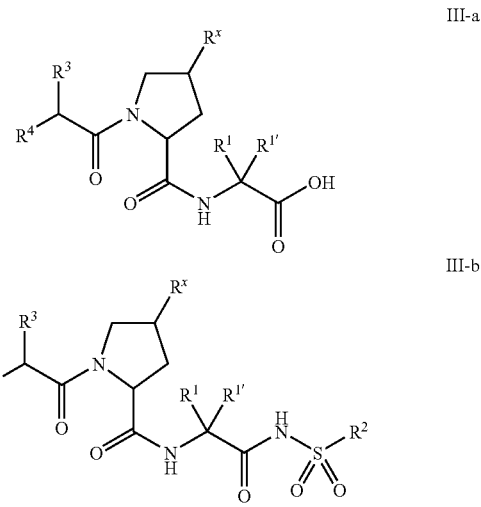

or a pharmaceutically acceptable salt thereof, wherein:
  $R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
  $R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
  each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
  $R^x$ is -T-$R^z$, wherein:
    T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and R$^z$ is hydrogen or an optionally substituted group selected from C$_{1-6}$ aliphatic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

R$^4$ is H, —NHC(O)OR$^6$, a natural or unnatural amino acid side-chain group; or R$^4$ and Rx are taken together with their intervening atoms to form an optionally substituted, saturated or unsaturated 16-22 membered ring having 2-6 heteroatoms independently selected from nitrogen, oxygen, or sulfur; and R$^6$ is an optionally substituted group selected from C$_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

4. The compound according to claim 1, wherein said compound is of formula IV-a or IV-b:

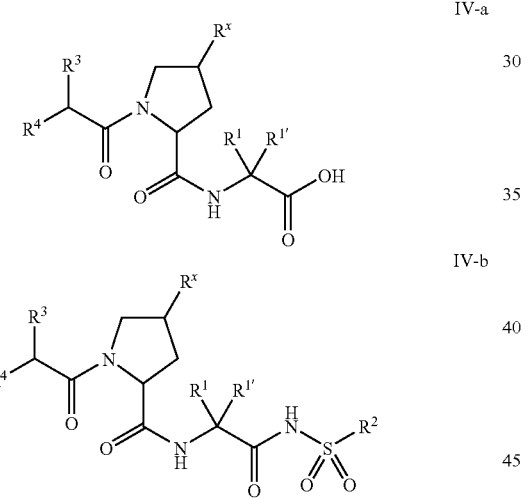

or a pharmaceutically acceptable salt thereof, wherein:

R$^1$ and R$^{1'}$ are taken together to form an optionally substituted 3-7 membered carbocyclic ring;

R$^2$ is an optionally substituted group selected from C$_{3-7}$ cycloalkyl, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

each R is independently hydrogen, optionally substituted C$_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;

R$^x$ is -T-R$^z$, wherein:

T is a covalent bond or a C$_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and R$^z$ is an optionally substituted group selected from 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

R$^4$ is H, —NHC(O)OR$^6$, a natural or unnatural amino acid side-chain group; or R$^4$ and R$^x$ are taken together with their intervening atoms to form an optionally substituted, saturated or unsaturated 16-22 membered ring having 2-6 heteroatoms independently selected from nitrogen, oxygen, or sulfur; and R$^6$ is an optionally substituted group selected from C$_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

5. The compound according to claim 1, wherein said compound is of formula V-a or V-b:

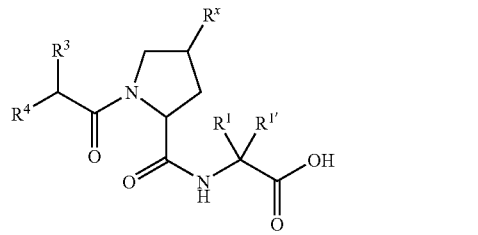

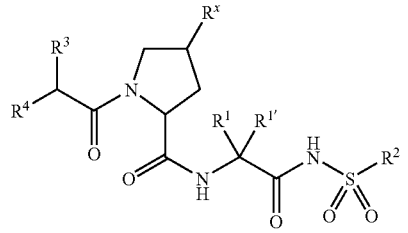

or a pharmaceutically acceptable salt thereof, wherein:

R$^1$ and R$^{1'}$ are independently hydrogen or optionally substituted C$_{1-6}$ aliphatic, or R$^1$ and R$^{1'}$ are taken together to form an optionally substituted 3-7 membered carbocyclic ring;

R$^2$ is —N(R)$_2$;

each R is independently hydrogen, optionally substituted C$_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;

R$^x$ is -T-R$^z$, wherein:

T is a covalent bond or a C$_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and R$^z$ is hydrogen or an optionally substituted group selected from C$_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur;

$R^4$ is H, —NHC(O)OR$^6$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur; and $R^6$ is an optionally substituted group selected from $C_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

6. The compound according to claim 1, wherein said compound is of formula VI-a or VI-b:

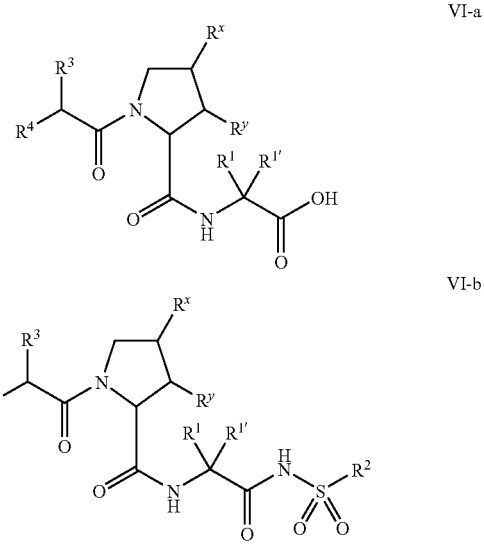

or a pharmaceutically acceptable salt thereof, wherein:
$R^1$ and $R^{1'}$ are taken together to form an optionally substituted 3-7 membered carbocyclic ring;
$R^2$ is an optionally substituted group selected from $C_{3-7}$ cycloalkyl, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
$R^x$ and $R^y$ are taken together to form an optionally substituted $C_{3-7}$ membered carbocycle;
$R^4$ is H, —NHC(O)R$^5$, a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur; and
$R^5$ is —N(R)$_2$.

7. The compound according to claim 1, wherein said compound is of formula VII-a or VII-b:

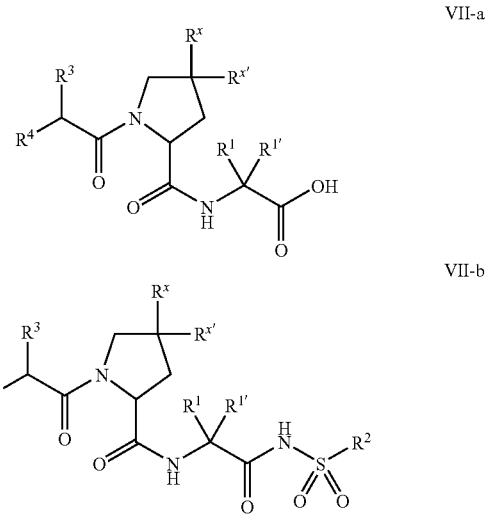

or a pharmaceutically acceptable salt thereof, wherein:
$R^1$ and $R^{1'}$ are independently hydrogen or optionally substituted $C_{1-6}$ aliphatic;
$R^2$ is an optionally substituted group selected from $C_{3-7}$ cycloalkyl, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
each R is independently hydrogen, optionally substituted $C_{1-6}$ aliphatic, or two R on the same nitrogen atom are taken together with the nitrogen to form a 4-7 membered heterocyclic ring having 1-2 heteroatoms independently selected from nitrogen, oxygen, or sulfur;
$R^{x'}$ and $R^x$ are taken together with their intervening atoms to form an optionally substituted spiro-fused 5-7 membered ring having 0-2 heteroatoms independently selected from nitrogen, oxygen, or sulfur;
$R^4$ is H,

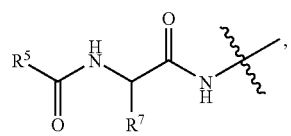

a natural or unnatural amino acid side-chain group; or $R^4$ and $R^x$ are taken together with their intervening atoms to form an optionally substituted, saturated or unsaturated 16-22 membered ring having 2-6 heteroatoms independently selected from nitrogen, oxygen, or sulfur;
$R^5$ is an optionally substituted group selected from $C_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and
$R^7$ is an optionally substituted group selected from $C_{1-6}$ aliphatic, bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur.

8. The compound according to claim 1, wherein said compound is of formula VII-a or VII-b:

VIII-a

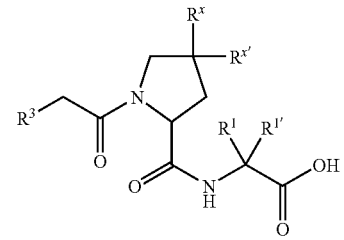

VIII-b

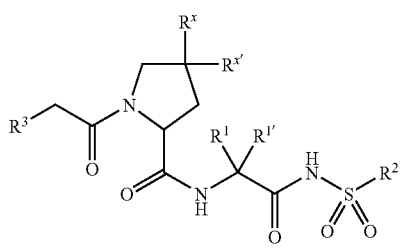

or a pharmaceutically acceptable salt thereof, wherein:
  $R^1$ and $R^{1'}$ are independently hydrogen or optionally substituted $C_{1-6}$ aliphatic, or $R^1$ and $R^{1'}$ are taken together to form an optionally substituted 3-7 membered carbocyclic ring;
  $R^2$ is —N(R)$_2$ or an optionally substituted group selected from $C_{3-7}$ cycloalkyl, a bridged bicyclic, 6-10 membered aryl, 5-10 membered heteroaryl having 1-4 heteroatoms independently selected from nitrogen, oxygen, or sulfur, or 4-7 membered heterocyclyl having 1-2 heteroatoms independently selected from nitrogen, oxygen, or sulfur;
  each R is independently hydrogen, optionally substituted $C_{1-6}$ aliphatic, or:
    two R on the same nitrogen atom are taken together with the nitrogen to form a 4-7 membered heterocyclic ring having 1-2 heteroatoms independently selected from nitrogen, oxygen, or sulfur;
  $R^x$ is -T-$R^z$, wherein:
    T is a covalent bond or a $C_{1-6}$ bivalent hydrocarbon chain wherein one or two methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, or —SO$_2$N(R)—; and
    $R^z$ is hydrogen or an optionally substituted group selected from $C_{1-6}$ aliphatic, a bridged bicyclic, 6-10 membered monocyclic or bicyclic aryl, 5-10 membered monocyclic or bicyclic heteroaryl having 1-4 heteroatoms independently selected from nitrogen, oxygen, or sulfur, or 4-7 membered heterocyclyl having 1-2 heteroatoms independently selected from nitrogen, oxygen, or sulfur; and
  $R^{x'}$ is hydrogen, or $R^{x'}$ and $R^x$ are taken together with their intervening atoms to form an optionally substituted spiro-fused 5-7 membered ring having 0-2 heteroatoms independently selected from nitrogen, oxygen, or sulfur.

9. A compound selected from the group consisting of:

I-130

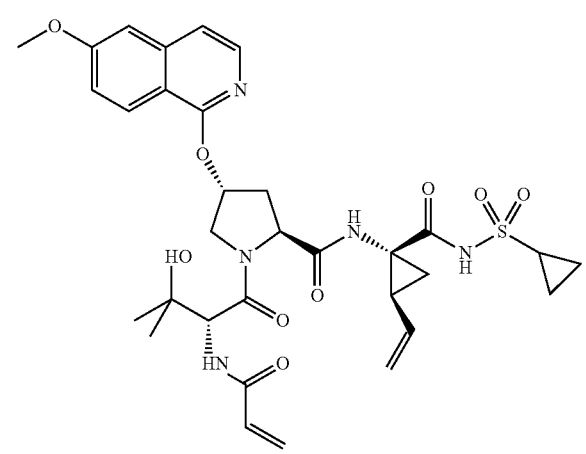

I-131

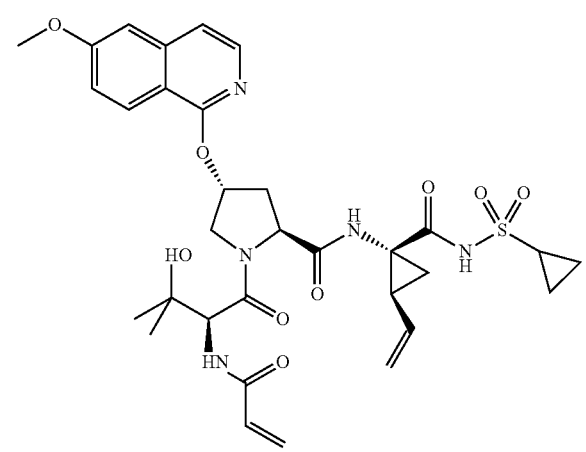

I-132

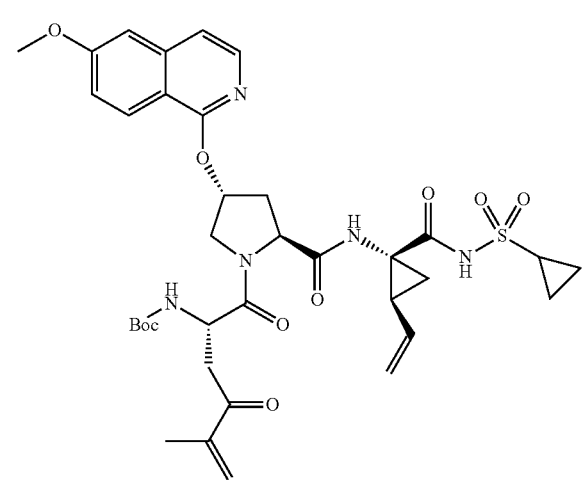

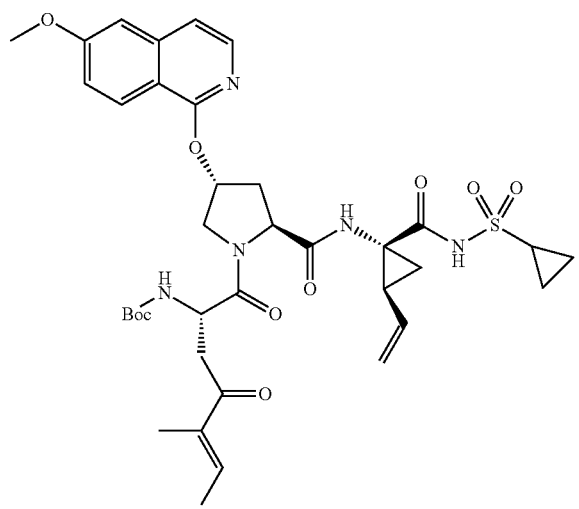
I-133
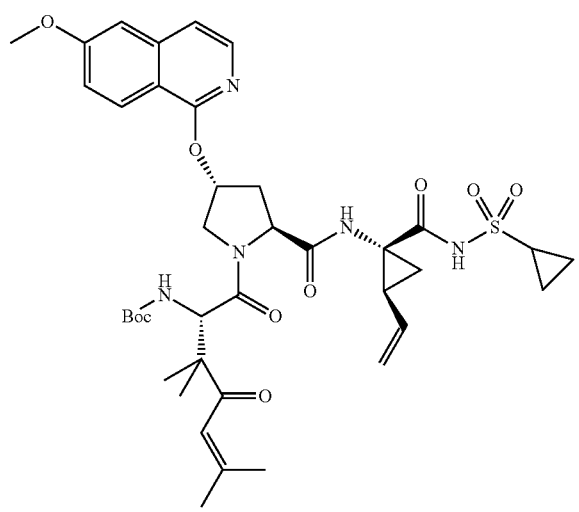
I-134
I-135
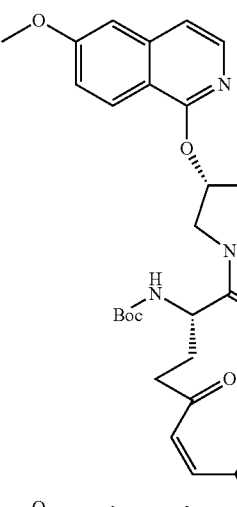
I-136
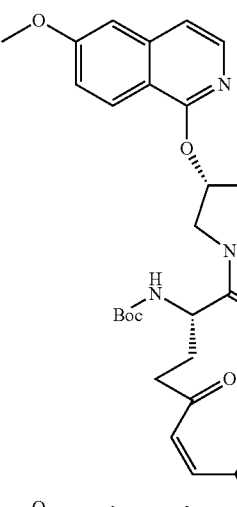
I-137
I-138

405
-continued
I-139
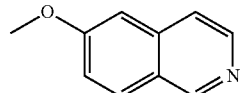
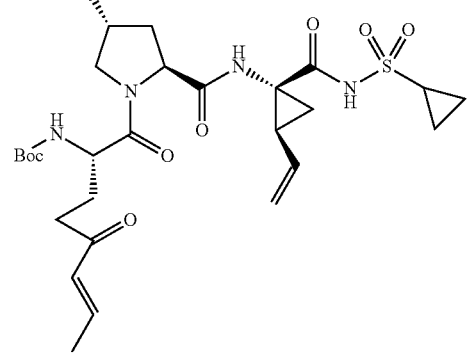
I-140
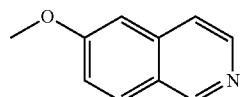
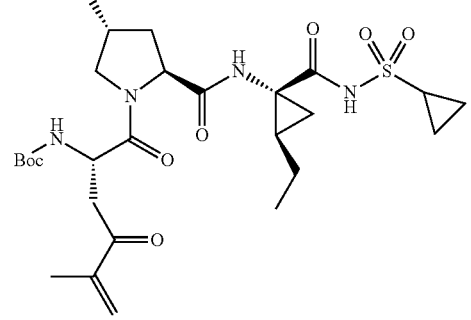
I-141
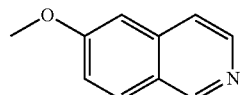
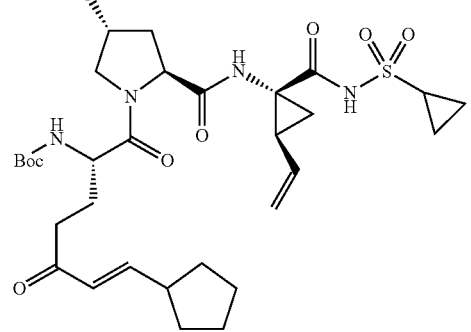
406
-continued
I-142
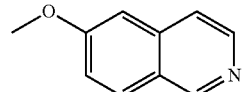
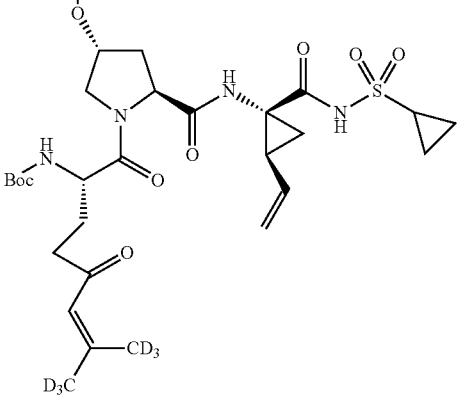
I-143
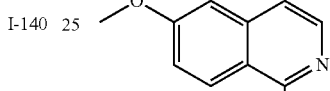
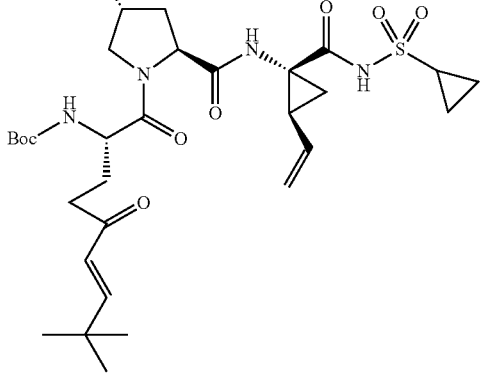
I-144
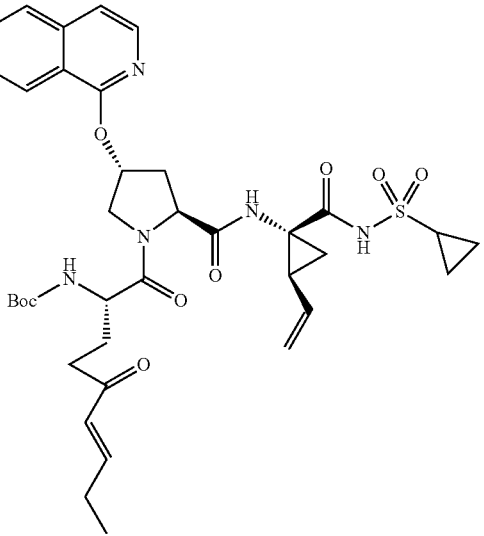

-continued

I-145

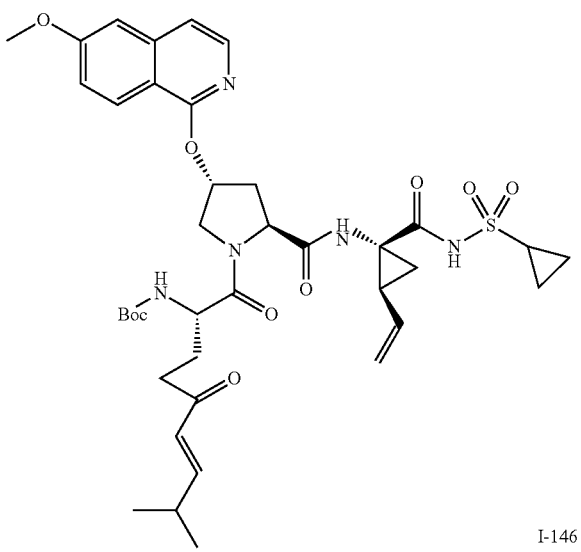

I-146

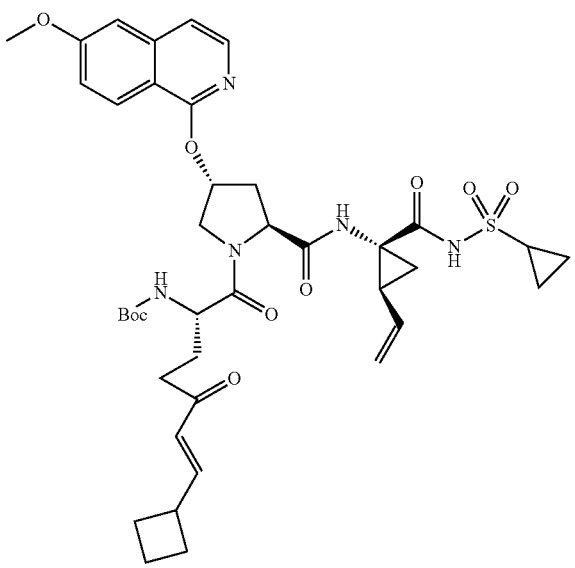

I-147

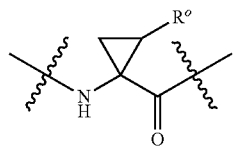

or a pharmaceutically acceptable salt thereof.

10. A composition comprising a compound according to claim 1, and a pharmaceutically acceptable adjuvant, carrier, or vehicle.

11. The composition according to claim 10, in combination with an additional therapeutic agent.

12. The composition according to claim 11, wherein the additional therapeutic agent is an antiviral agent.

13. A method for inhibiting HCV protease, or a mutant thereof, activity comprising administering to a patient in need thereof a compound according to claim 1.

14. The method according to claim 13, wherein the HCV protease, or a mutant thereof, activity is inhibited irreversibly.

15. The method according to claim 14, wherein the HCV protease, or a mutant thereof, activity is inhibited irreversibly by covalently modifying a cysteine residue conserved at an equivalent position to Cys159 of HCV protease subtype 1b.

16. The method according to claim 14, wherein the HCV protease, or a mutant thereof, activity is inhibited irreversibly by covalently modifying Cys16.

17. A method for treating a hepatitis C viral infection, comprising administering to a patient in need thereof a compound according to claim 1.

18. The method of claim 17, wherein the step of administering occurs once daily.

19. The method of claim 17, wherein the compound irreversibly inhibits HCV protease by covalently modifying a cysteine residue conserved at an equivalent position to Cys159 of HCV protease subtype 1b.

20. The method of claim 19, wherein the HCV protease genotype or subtype is selected from the group consisting of 1a, 1b, 1c, 2a, 2b, 2c, 2l, 2k, 3a, 3b, 3k, 4a, 4d, 4f, 5a, 6a, 6b, 6c, 6d, 6e, 6f, 6g, 6h, 6l, 6j, 6k, 6l, 6m, 6n, 6o, 6p, 6q, 6t, and 7a.

21. The method of claim 20, wherein the HCV protease genotype or subtype is 1a, 1b, 2a, or 3a.

22. The method of claim 17, wherein the compound irreversibly inhibits HCV protease by covalently modifying Cys16 of HCV protease.

23. The compound according to claim 1, wherein $R^w$ is hydrogen, and $R^1$ and $R^{1'}$ are taken together to form:

wherein $R^o$ is an optionally substituted group selected from $C_{1-6}$ aliphatic.

24. The compound according to claim 23, wherein $R^o$ is vinyl.

25. The compound according to claim 23, wherein $R^o$ is ethyl.

26. The compound according to claim 1, wherein $R^{2a}$ is —NHSO$_2$R$^2$ and R$^2$ is cyclopropyl.

27. The compound according to claim 1, wherein $R^w$, $R^{x'}$, and $R^y$ are hydrogen, T is —O—, and $R^z$ is

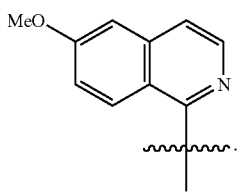

28. The compound according to claim 1, wherein $R^4$ is —NHC(O)OR$^6$ and $R^6$ is $C_{1-6}$ aliphatic.

29. The compound according to claim 1, wherein $R^4$ is an unnatural amino acid side-chain group of threonine substituted with one, two, or three methyl groups.

30. A covalent adduct formed by reacting a compound of claim 1 with HCV protease.

31. The covalent adduct of claim 30, wherein the adduct is formed via a covalent bond between substituent $R^3$ and a cysteine sulfhydryl group of HCV protease, which cysteine is conserved at an equivalent position to Cys159 of the HCV protease subtype Ib polypeptide chain.

32. The covalent adduct of claim 30, wherein the adduct is formed via a covalent bond between substituent $R^3$ and a cysteine sulfhydryl group of HCV protease, which cysteine is present at position 16 of the HCV protease polypeptide chain.

33. A method for inhibiting HCV protease, or a mutant thereof, activity in a biological sample comprising the step of contacting said biological sample with a compound according to claim 1.

34. The method according to claim 33, wherein the HCV protease, or a mutant thereof, activity is inhibited irreversibly.

35. The method according to claim 34, wherein the HCV protease, or a mutant thereof, activity is inhibited irreversibly by covalently modifying a cysteine residue conserved at an equivalent position to Cys159 of HCV protease subtype 1b.

36. The method according to claim 34, wherein the HCV protease, or a mutant thereof, activity is inhibited irreversibly by covalently modifying Cys16.

* * * * *

SEQUENCE LISTING

```
<160> NUMBER OF SEQ ID NOS: 77

<210> SEQ ID NO 1
<211> LENGTH: 20
<212> TYPE: PRT
<213> ORGANISM: Hepatitis C virus

<400> SEQUENCE: 1

Gly His Ala Val Gly Leu Phe Arg Ala Ala Val Cys Thr Arg Gly Val
1               5                   10                  15

Ala Lys Ala Val
            20

<210> SEQ ID NO 2
<211> LENGTH: 20
<212> TYPE: PRT
<213> ORGANISM: Hepatitis C virus

<400> SEQUENCE: 2

Gly His Ala Val Gly Ile Phe Arg Ala Ala Val Cys Thr Arg Gly Val
1               5                   10                  15

Ala Lys Ala Val
            20

<210> SEQ ID NO 3
<211> LENGTH: 20
<212> TYPE: PRT
<213> ORGANISM: Hepatitis C virus

<400> SEQUENCE: 3

Gly His Ala Val Gly Ile Phe Arg Ala Ala Val Cys Thr Arg Gly Val
1               5                   10                  15

Ala Lys Ala Val
            20

<210> SEQ ID NO 4
<211> LENGTH: 20
<212> TYPE: PRT
<213> ORGANISM: Hepatitis C virus

<400> SEQUENCE: 4

Gly His Ala Val Gly Leu Phe Arg Ala Ala Val Cys Thr Arg Gly Val
1               5                   10                  15

Ala Lys Ala Val
            20

<210> SEQ ID NO 5
<211> LENGTH: 20
```

```
<212> TYPE: PRT
<213> ORGANISM: Hepatitis C virus

<400> SEQUENCE: 5

Gly His Ala Val Gly Ile Phe Arg Ala Ala Val Cys Thr Arg Gly Val
1               5                   10                  15

Ala Lys Ala Val
            20

<210> SEQ ID NO 6
<211> LENGTH: 20
<212> TYPE: PRT
<213> ORGANISM: Hepatitis C virus

<400> SEQUENCE: 6

Gly His Val Val Gly Ile Phe Arg Ala Ala Val Cys Thr Arg Gly Val
1               5                   10                  15

Ala Lys Ala Val
            20

<210> SEQ ID NO 7
<211> LENGTH: 20
<212> TYPE: PRT
<213> ORGANISM: Hepatitis C virus

<400> SEQUENCE: 7

Gly His Ala Val Gly Ile Phe Arg Ala Ala Val Cys Thr Arg Gly Val
1               5                   10                  15

Ala Lys Ala Val
            20

<210> SEQ ID NO 8
<211> LENGTH: 20
<212> TYPE: PRT
<213> ORGANISM: Hepatitis C virus

<400> SEQUENCE: 8

Gly His Ala Val Gly Ile Phe Arg Ala Ala Val Cys Thr Arg Gly Val
1               5                   10                  15

Ala Lys Ala Val
            20

<210> SEQ ID NO 9
<211> LENGTH: 20
<212> TYPE: PRT
<213> ORGANISM: Hepatitis C virus

<400> SEQUENCE: 9

Gly His Val Ala Gly Ile Phe Arg Ala Ala Val Cys Thr Arg Gly Val
1               5                   10                  15

Ala Lys Ala Val
            20

<210> SEQ ID NO 10
<211> LENGTH: 20
<212> TYPE: PRT
<213> ORGANISM: Hepatitis C virus

<400> SEQUENCE: 10

Gly His Ala Val Gly Ile Phe Arg Ala Ala Val Cys Ser Arg Gly Val
1               5                   10                  15

Ala Lys Ser Ile
            20
```

```
<210> SEQ ID NO 11
<211> LENGTH: 20
<212> TYPE: PRT
<213> ORGANISM: Hepatitis C virus

<400> SEQUENCE: 11

Gly His Ala Val Gly Ile Phe Arg Ala Ala Val Cys Ser Arg Gly Val
1               5                   10                  15

Ala Lys Ser Ile
            20

<210> SEQ ID NO 12
<211> LENGTH: 20
<212> TYPE: PRT
<213> ORGANISM: Hepatitis C virus

<400> SEQUENCE: 12

Gly His Ala Val Gly Ile Phe Arg Ala Ala Val Cys Ser Arg Gly Val
1               5                   10                  15

Ala Lys Ser Ile
            20

<210> SEQ ID NO 13
<211> LENGTH: 20
<212> TYPE: PRT
<213> ORGANISM: Hepatitis C virus

<400> SEQUENCE: 13

Gly His Ala Val Gly Leu Phe Arg Ala Ala Val Cys Ala Arg Gly Val
1               5                   10                  15

Ala Lys Ser Ile
            20

<210> SEQ ID NO 14
<211> LENGTH: 20
<212> TYPE: PRT
<213> ORGANISM: Hepatitis C virus

<400> SEQUENCE: 14

Gly His Ala Val Gly Leu Phe Arg Ala Ala Val Cys Ala Arg Gly Val
1               5                   10                  15

Ala Lys Ser Ile
            20

<210> SEQ ID NO 15
<211> LENGTH: 20
<212> TYPE: PRT
<213> ORGANISM: Hepatitis C virus

<400> SEQUENCE: 15

Gly His Ala Val Gly Ile Phe Arg Ala Ala Val Cys Ser Arg Gly Val
1               5                   10                  15

Ala Lys Ser Ile
            20

<210> SEQ ID NO 16
<211> LENGTH: 20
<212> TYPE: PRT
<213> ORGANISM: Hepatitis C virus

<400> SEQUENCE: 16

Ala His Ala Val Gly Ile Phe Arg Ala Ala Val Cys Ser Arg Gly Val
```

```
1               5                  10                 15

Ala Lys Ser Ile
            20

<210> SEQ ID NO 17
<211> LENGTH: 20
<212> TYPE: PRT
<213> ORGANISM: Hepatitis C virus

<400> SEQUENCE: 17

Gly His Ala Val Gly Ile Phe Arg Ala Ala Ile Cys Thr Arg Gly Ala
1               5                  10                 15

Ala Lys Ser Ile
            20

<210> SEQ ID NO 18
<211> LENGTH: 20
<212> TYPE: PRT
<213> ORGANISM: Hepatitis C virus

<400> SEQUENCE: 18

Gly His Val Ala Gly Ile Phe Arg Ala Ala Val Cys Thr Arg Gly Val
1               5                  10                 15

Ala Lys Ala Leu
            20

<210> SEQ ID NO 19
<211> LENGTH: 20
<212> TYPE: PRT
<213> ORGANISM: Hepatitis C virus

<400> SEQUENCE: 19

Gly His Val Ala Gly Ile Phe Arg Ala Ala Val Cys Thr Arg Gly Val
1               5                  10                 15

Ala Lys Ala Leu
            20

<210> SEQ ID NO 20
<211> LENGTH: 20
<212> TYPE: PRT
<213> ORGANISM: Hepatitis C virus

<400> SEQUENCE: 20

Gly His Val Ala Gly Ile Phe Arg Ala Ala Val Cys Thr Arg Gly Val
1               5                  10                 15

Ala Lys Ala Leu
            20

<210> SEQ ID NO 21
<211> LENGTH: 20
<212> TYPE: PRT
<213> ORGANISM: Hepatitis C virus

<400> SEQUENCE: 21

Gly His Val Met Gly Ile Phe Ile Ala Val Val Cys Thr Arg Gly Val
1               5                  10                 15

Ala Lys Ala Leu
            20

<210> SEQ ID NO 22
<211> LENGTH: 20
<212> TYPE: PRT
<213> ORGANISM: Hepatitis C virus
```

```
<400> SEQUENCE: 22

Gly His Val Val Gly Ile Phe Arg Ala Ala Val Cys Thr Arg Gly Val
1               5                   10                  15

Ala Lys Ala Leu
            20

<210> SEQ ID NO 23
<211> LENGTH: 20
<212> TYPE: PRT
<213> ORGANISM: Hepatitis C virus

<400> SEQUENCE: 23

Gly His Val Ala Gly Ile Phe Arg Ala Ala Val Cys Thr Arg Gly Val
1               5                   10                  15

Ala Lys Ala Leu
            20

<210> SEQ ID NO 24
<211> LENGTH: 20
<212> TYPE: PRT
<213> ORGANISM: Hepatitis C virus

<400> SEQUENCE: 24

Gly His Ala Ala Gly Ile Phe Arg Ala Ala Val Cys Thr Arg Gly Val
1               5                   10                  15

Ala Lys Ala Val
            20

<210> SEQ ID NO 25
<211> LENGTH: 20
<212> TYPE: PRT
<213> ORGANISM: Hepatitis C virus

<400> SEQUENCE: 25

Gly His Ala Ala Gly Leu Phe Arg Ala Ala Val Cys Thr Arg Gly Val
1               5                   10                  15

Ala Lys Ala Val
            20

<210> SEQ ID NO 26
<211> LENGTH: 20
<212> TYPE: PRT
<213> ORGANISM: Hepatitis C virus

<400> SEQUENCE: 26

Gly His Ala Ala Gly Leu Phe Arg Ala Ala Val Cys Thr Arg Gly Val
1               5                   10                  15

Ala Lys Ala Val
            20

<210> SEQ ID NO 27
<211> LENGTH: 20
<212> TYPE: PRT
<213> ORGANISM: Hepatitis C virus

<400> SEQUENCE: 27

Gly His Ala Ala Gly Ile Phe Arg Ala Ala Val Cys Thr Arg Gly Val
1               5                   10                  15

Ala Lys Ala Val
            20
```

```
<210> SEQ ID NO 28
<211> LENGTH: 20
<212> TYPE: PRT
<213> ORGANISM: Hepatitis C virus

<400> SEQUENCE: 28

Gly His Ala Ala Gly Ile Phe Arg Ala Ala Val Cys Thr Arg Gly Val
1               5                   10                  15

Ala Lys Thr Val
            20

<210> SEQ ID NO 29
<211> LENGTH: 20
<212> TYPE: PRT
<213> ORGANISM: Hepatitis C virus

<400> SEQUENCE: 29

Gly His Ala Val Gly Ile Phe Arg Ala Ala Val Cys Thr Arg Gly Val
1               5                   10                  15

Ala Lys Ala Val
            20

<210> SEQ ID NO 30
<211> LENGTH: 20
<212> TYPE: PRT
<213> ORGANISM: Hepatitis C virus

<400> SEQUENCE: 30

Gly His Ala Val Gly Ile Phe Arg Ala Ala Val Cys Thr Arg Gly Val
1               5                   10                  15

Ala Lys Ala Val
            20

<210> SEQ ID NO 31
<211> LENGTH: 20
<212> TYPE: PRT
<213> ORGANISM: Hepatitis C virus

<400> SEQUENCE: 31

Gly His Val Val Gly Val Phe Arg Ala Ala Val Cys Thr Arg Gly Val
1               5                   10                  15

Ala Lys Ala Leu
            20

<210> SEQ ID NO 32
<211> LENGTH: 20
<212> TYPE: PRT
<213> ORGANISM: Hepatitis C virus

<400> SEQUENCE: 32

Gly His Val Val Gly Val Phe Arg Ala Ala Val Cys Thr Arg Gly Val
1               5                   10                  15

Ala Lys Ala Leu
            20

<210> SEQ ID NO 33
<211> LENGTH: 20
<212> TYPE: PRT
<213> ORGANISM: Hepatitis C virus

<400> SEQUENCE: 33

Gly His Val Val Gly Leu Phe Arg Ala Ala Val Cys Thr Arg Gly Val
1               5                   10                  15
```

Ala Lys Ser Leu
            20

<210> SEQ ID NO 34
<211> LENGTH: 20
<212> TYPE: PRT
<213> ORGANISM: Hepatitis C virus

<400> SEQUENCE: 34

Gly His Val Val Gly Leu Phe Arg Ala Ala Val Cys Thr Arg Gly Val
1               5                   10                  15

Ala Lys Ser Leu
            20

<210> SEQ ID NO 35
<211> LENGTH: 20
<212> TYPE: PRT
<213> ORGANISM: Hepatitis C virus

<400> SEQUENCE: 35

Gly His Val Val Gly Leu Phe Arg Ala Ala Val Cys Thr Arg Gly Val
1               5                   10                  15

Ala Lys Ser Leu
            20

<210> SEQ ID NO 36
<211> LENGTH: 20
<212> TYPE: PRT
<213> ORGANISM: Hepatitis C virus

<400> SEQUENCE: 36

Gly His Val Val Gly Leu Phe Arg Ala Ala Val Cys Thr Arg Gly Val
1               5                   10                  15

Ala Lys Ala Leu
            20

<210> SEQ ID NO 37
<211> LENGTH: 20
<212> TYPE: PRT
<213> ORGANISM: Hepatitis C virus

<400> SEQUENCE: 37

Gly His Val Val Gly Leu Phe Arg Ala Ala Val Cys Thr Arg Gly Val
1               5                   10                  15

Ala Lys Ala Leu
            20

<210> SEQ ID NO 38
<211> LENGTH: 20
<212> TYPE: PRT
<213> ORGANISM: Hepatitis C virus

<400> SEQUENCE: 38

Asp His Val Val Gly Leu Phe Arg Ala Ala Val Cys Thr Arg Gly Val
1               5                   10                  15

Ala Lys Ala Leu
            20

<210> SEQ ID NO 39
<211> LENGTH: 20
<212> TYPE: PRT
<213> ORGANISM: Hepatitis C virus

<400> SEQUENCE: 39

```
Gly His Val Val Gly Leu Phe Arg Ala Ala Val Cys Thr Arg Gly Val
1               5                   10                  15

Ala Lys Ala Ile
            20

<210> SEQ ID NO 40
<211> LENGTH: 20
<212> TYPE: PRT
<213> ORGANISM: Hepatitis C virus

<400> SEQUENCE: 40

Gly His Ala Val Gly Ile Phe Arg Ala Ala Val Cys Thr Arg Gly Val
1               5                   10                  15

Ala Lys Ala Ile
            20

<210> SEQ ID NO 41
<211> LENGTH: 20
<212> TYPE: PRT
<213> ORGANISM: Hepatitis C virus

<400> SEQUENCE: 41

Gly His Ala Val Gly Ile Phe Arg Ala Ala Val Cys Thr Arg Gly Val
1               5                   10                  15

Ala Lys Ala Ile
            20

<210> SEQ ID NO 42
<211> LENGTH: 20
<212> TYPE: PRT
<213> ORGANISM: Hepatitis C virus

<400> SEQUENCE: 42

Gly His Val Val Gly Leu Phe Arg Ala Ala Val Cys Thr Arg Gly Val
1               5                   10                  15

Ala Lys Ala Leu
            20

<210> SEQ ID NO 43
<211> LENGTH: 20
<212> TYPE: PRT
<213> ORGANISM: Hepatitis C virus

<400> SEQUENCE: 43

Gly His Val Val Gly Leu Phe Arg Ala Ala Val Cys Thr Arg Gly Val
1               5                   10                  15

Ala Lys Ala Leu
            20

<210> SEQ ID NO 44
<211> LENGTH: 20
<212> TYPE: PRT
<213> ORGANISM: Hepatitis C virus

<400> SEQUENCE: 44

Gly His Val Ala Gly Ile Phe Arg Ala Ala Val Cys Thr Arg Gly Val
1               5                   10                  15

Ala Lys Ser Leu
            20

<210> SEQ ID NO 45
<211> LENGTH: 20
```

```
<212> TYPE: PRT
<213> ORGANISM: Hepatitis C virus

<400> SEQUENCE: 45

Gly His Val Ala Gly Ile Phe Arg Ala Ala Val Cys Thr Arg Gly Val
1               5                   10                  15

Ala Lys Ser Leu
            20

<210> SEQ ID NO 46
<211> LENGTH: 20
<212> TYPE: PRT
<213> ORGANISM: Hepatitis C virus

<400> SEQUENCE: 46

Gly His Val Ala Gly Ile Phe Arg Ala Ala Val Cys Thr Arg Gly Val
1               5                   10                  15

Ala Lys Ser Leu
            20

<210> SEQ ID NO 47
<211> LENGTH: 20
<212> TYPE: PRT
<213> ORGANISM: Hepatitis C virus

<400> SEQUENCE: 47

Gly His Val Ala Gly Ile Phe Arg Ala Ala Val Cys Thr Arg Gly Val
1               5                   10                  15

Ala Lys Ser Leu
            20

<210> SEQ ID NO 48
<211> LENGTH: 20
<212> TYPE: PRT
<213> ORGANISM: Hepatitis C virus

<400> SEQUENCE: 48

Gly His Val Ala Gly Ile Phe Arg Ala Ala Val Cys Thr Arg Gly Val
1               5                   10                  15

Ala Lys Ser Leu
            20

<210> SEQ ID NO 49
<211> LENGTH: 20
<212> TYPE: PRT
<213> ORGANISM: Hepatitis C virus

<400> SEQUENCE: 49

Gly His Val Ala Gly Ile Phe Arg Ala Ala Val Cys Thr Arg Gly Val
1               5                   10                  15

Ala Lys Ser Leu
            20

<210> SEQ ID NO 50
<211> LENGTH: 20
<212> TYPE: PRT
<213> ORGANISM: Hepatitis C virus

<400> SEQUENCE: 50

Gly His Val Ala Gly Ile Phe Arg Ala Ala Val Cys Thr Arg Gly Val
1               5                   10                  15

Ala Lys Ser Leu
            20
```

<210> SEQ ID NO 51
<211> LENGTH: 20
<212> TYPE: PRT
<213> ORGANISM: Hepatitis C virus

<400> SEQUENCE: 51

Gly His Val Ala Gly Ile Phe Arg Ala Ala Val Cys Thr Arg Gly Val
1               5                   10                  15

Ala Lys Ser Leu
            20

<210> SEQ ID NO 52
<211> LENGTH: 20
<212> TYPE: PRT
<213> ORGANISM: Hepatitis C virus

<400> SEQUENCE: 52

Gly His Ala Val Gly Val Phe Arg Ala Ala Val Cys Thr Arg Gly Val
1               5                   10                  15

Ala Lys Ser Leu
            20

<210> SEQ ID NO 53
<211> LENGTH: 20
<212> TYPE: PRT
<213> ORGANISM: Hepatitis C virus

<400> SEQUENCE: 53

Gly His Ala Val Gly Val Phe Arg Ala Ala Val Cys Thr Arg Gly Val
1               5                   10                  15

Ala Lys Ser Leu
            20

<210> SEQ ID NO 54
<211> LENGTH: 20
<212> TYPE: PRT
<213> ORGANISM: Hepatitis C virus

<400> SEQUENCE: 54

Gly His Val Val Gly Ile Phe Arg Ala Ala Val Cys Thr Arg Gly Val
1               5                   10                  15

Ala Lys Ser Leu
            20

<210> SEQ ID NO 55
<211> LENGTH: 20
<212> TYPE: PRT
<213> ORGANISM: Hepatitis C virus

<400> SEQUENCE: 55

Gly His Val Val Gly Ile Phe Arg Ala Ala Val Cys Thr Arg Gly Val
1               5                   10                  15

Ala Lys Ser Leu
            20

<210> SEQ ID NO 56
<211> LENGTH: 20
<212> TYPE: PRT
<213> ORGANISM: Hepatitis C virus

<400> SEQUENCE: 56

Gly His Ala Val Gly Leu Phe Arg Ala Ala Val Cys Thr Arg Gly Val

Ala Lys Ala Ile
            20

<210> SEQ ID NO 57
<211> LENGTH: 20
<212> TYPE: PRT
<213> ORGANISM: Hepatitis C virus

<400> SEQUENCE: 57

Gly His Val Val Gly Leu Phe Arg Ala Ala Val Cys Thr Arg Gly Val
1               5                   10                  15

Ala Lys Ala Ile
            20

<210> SEQ ID NO 58
<211> LENGTH: 20
<212> TYPE: PRT
<213> ORGANISM: Hepatitis C virus

<400> SEQUENCE: 58

Gly His Ala Val Gly Leu Phe Arg Ala Ala Val Cys Thr Arg Gly Val
1               5                   10                  15

Ala Lys Ala Ile
            20

<210> SEQ ID NO 59
<211> LENGTH: 20
<212> TYPE: PRT
<213> ORGANISM: Hepatitis C virus

<400> SEQUENCE: 59

Gly His Val Val Gly Leu Phe Arg Ala Ala Val Cys Thr Arg Gly Val
1               5                   10                  15

Ala Lys Ala Ile
            20

<210> SEQ ID NO 60
<211> LENGTH: 20
<212> TYPE: PRT
<213> ORGANISM: Hepatitis C virus

<400> SEQUENCE: 60

Gly His Val Val Gly Leu Phe Arg Ala Ala Val Cys Thr Arg Gly Val
1               5                   10                  15

Ala Lys Ala Ile
            20

<210> SEQ ID NO 61
<211> LENGTH: 20
<212> TYPE: PRT
<213> ORGANISM: Hepatitis C virus

<400> SEQUENCE: 61

Gly His Val Val Gly Leu Phe Arg Ala Ala Val Cys Thr Arg Gly Val
1               5                   10                  15

Ala Lys Ala Ile
            20

<210> SEQ ID NO 62
<211> LENGTH: 20
<212> TYPE: PRT
<213> ORGANISM: Hepatitis C virus -continued

<400> SEQUENCE: 62

Ser His Cys Val Gly Ile Phe Arg Ala Ala Val Cys Thr Arg Gly Val
1               5                   10                  15

Ala Lys Ala Val
            20

<210> SEQ ID NO 63
<211> LENGTH: 21
<212> TYPE: DNA
<213> ORGANISM: Artificial sequence
<220> FEATURE:
<223> OTHER INFORMATION: Synthetic; designed from HCV protease NS3

<400> SEQUENCE: 63
acgcagaaag cgtctagcca t                                        21

<210> SEQ ID NO 64
<211> LENGTH: 19
<212> TYPE: DNA
<213> ORGANISM: Artificial sequence
<220> FEATURE:
<223> OTHER INFORMATION: Synthetic; designed from HCV protease NS3

<400> SEQUENCE: 64
tactcaccgg ttccgcaga                                           19

<210> SEQ ID NO 65
<211> LENGTH: 23
<212> TYPE: DNA
<213> ORGANISM: Artificial sequence
<220> FEATURE:
<223> OTHER INFORMATION: Synthetic; designed from HCV protease NS3
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (23)..(23)
<223> OTHER INFORMATION: Carboxytetramethylrhodamine
<220> FEATURE:
<221> NAME/KEY: modified_base
<222> LOCATION: (23)..(23)

<400> SEQUENCE: 65
cctggaggct gcacgacact cat                                      23

<210> SEQ ID NO 66
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 66
gctgtgggca tctttcggtc tgccgtgtgc acccgaggg                     39

<210> SEQ ID NO 67
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 67
ccctcgggtg cacacggcag accgaaagat gcccacagc                     39

```
<210> SEQ ID NO 68
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 68
gctgtgggca tctttcggac tgccgtgtgc acccgaggg                              39

<210> SEQ ID NO 69
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 69
ccctcgggtg cacacggcag tccgaaagat gcccacagc                              39

<210> SEQ ID NO 70
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 70
ggggttgcga aggcggtggc ctttgtaccc gtcgagtct                              39

<210> SEQ ID NO 71
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 71
agactcgacg ggtacaaagg ccaccgcctt cgcaacccc                              39

<210> SEQ ID NO 72
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 72
ggggttgcga aggcggtggt ctttgtaccc gtcgagtct                              39

<210> SEQ ID NO 73
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 73
agactcgacg ggtacaaaga ccaccgcctt cgcaacccc                              39

<210> SEQ ID NO 74
<211> LENGTH: 39
<212> TYPE: DNA
<213> ORGANISM: Artificial sequence
<220> FEATURE:
<223> OTHER INFORMATION: Synthetic; designed from HCV protease NS3
```

```
<400> SEQUENCE: 74
atctttcggg ctgccgtgag cacccgaggg gttgcgaag                              39

<210> SEQ ID NO 75
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 75
cttcgcaacc cctcgggtgc tcacggcagc ccgaaagat                              39

<210> SEQ ID NO 76
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 76
cacgctgtgg gcatctttaa ggctgccgtg tgcacccga                              39

<210> SEQ ID NO 77
<211> LENGTH: 39
<212> TYPE: DNA
<213> ORGANISM: Artificial sequence
<220> FEATURE:
<223> OTHER INFORMATION: Synthetic; designed from HCV protease NS3

<400> SEQUENCE: 77
tcgggtgcac acggcagcct taaagatgcc cacagcgtg                              39
```